(12) United States Patent
Kalluri

(10) Patent No.: US 7,387,779 B2
(45) Date of Patent: Jun. 17, 2008

(54) ANTI-ANGIOGENIC PROTEINS AND FRAGMENTS AND METHODS OF USE THEREOF

(75) Inventor: Raghuram Kalluri, Boston, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 10/032,221

(22) Filed: Dec. 21, 2001

(65) Prior Publication Data

US 2003/0144481 A1 Jul. 31, 2003

Related U.S. Application Data

(63) Continuation-in-part of application No. PCT/US01/00565, filed on Jan. 8, 2001, which is a continuation-in-part of application No. 09/625,191, filed on Jul. 21, 2000, now Pat. No. 6,962,974, and a continuation-in-part of application No. 09/543,371, filed on Apr. 4, 2000, now abandoned, and a continuation-in-part of application No. 09/479,118, filed on Jan. 7, 2000, now abandoned, said application No. 09/625,191 is a continuation-in-part of application No. 09/543,371, which is a continuation-in-part of application No. 09/335,224, filed on Jun. 17, 1999, now Pat. No. 6,759,047, said application No. 09/479,118 is a continuation-in-part of application No. 09/335,224.

(60) Provisional application No. 60/089,689, filed on Jun. 17, 1998, provisional application No. 60/126,175, filed on Mar. 25, 1999.

(51) Int. Cl.
*A61K 38/04* (2006.01)
*A61K 39/00* (2006.01)

(52) U.S. Cl. .................... 424/185.1; 530/324; 530/325; 530/326

(58) Field of Classification Search ................. 530/324, 530/326; 514/12, 13; 424/185.1
See application file for complete search history.

(56) References Cited

U.S. PATENT DOCUMENTS

| | | | |
|---|---|---|---|
| 5,114,840 A | | 5/1992 | Tryggvason et al. |
| 5,326,875 A | * | 7/1994 | Talaga et al. |
| 5,424,408 A | | 6/1995 | Reeders et al. |
| 5,567,609 A | | 10/1996 | Sarras, Jr. et al. |
| 5,593,900 A | | 1/1997 | Tryggvason et al. |
| 5,691,182 A | | 11/1997 | Sarras, Jr. et al. |
| 5,731,192 A | | 3/1998 | Reeders et al. |
| 5,753,230 A | | 5/1998 | Brooks et al. |
| 5,766,591 A | | 6/1998 | Brooks et al. |
| 5,807,821 A | * | 9/1998 | Lampe |
| 5,856,184 A | | 1/1999 | Sarras, Jr. et al. |
| 5,858,670 A | * | 1/1999 | Lam et al. |
| 5,973,120 A | | 10/1999 | Reeders et al. |
| 6,007,980 A | | 12/1999 | Reeders et al. |
| 6,017,926 A | | 1/2000 | Askew et al. |
| 6,361,994 B1 | | 3/2002 | Hudson et al. |
| 6,440,729 B1 | | 8/2002 | Hudson et al. |
| 6,962,974 B1 | * | 11/2005 | Kalluri ........................ 530/350 |
| 7,122,517 B2 | | 10/2006 | Hudson et al. |

FOREIGN PATENT DOCUMENTS

| | | |
|---|---|---|
| WO | WO 89/03392 | 4/1989 |
| WO | WO 91/08755 | 6/1991 |
| WO | WO 91/09113 | 6/1991 |
| WO | WO 96/00582 | 1/1996 |
| WO | WO 97/06791 | 2/1997 |
| WO | WO 97/45137 | 12/1997 |
| WO | WO 99/02551 | 1/1999 |
| WO | WO 99/16465 | 4/1999 |
| WO | WO 99/49885 | 10/1999 |
| WO | WO 99/50281 | 10/1999 |
| WO | WO 99/65940 | 12/1999 |
| WO | WO 00/11475 | 3/2000 |
| WO | WO 00/31248 | 6/2000 |
| WO | WO 00/59532 | 10/2000 |
| WO | WO 01/51523 A | 7/2001 |

OTHER PUBLICATIONS

Kuntz. Structure-based strategies for drug design and discovery. Science. 1992 257(5073):1078-1082.*
Miller et al Ligand binding to proteins: the binding landscape model. Protein Sci. Oct. 1997;6(10):2166-79.*
Burgess et al Possible dissociation of the heparin-binding and mitogenic activities of heparin-binding growth factor-1 from its receptor-binding activities by site-directed mutagenesis of a single lysine residue. J Cell Biol. 111:2129-2138, 1990.*
Wang et al A single amino acid determines lysophospholipid specificity of the S1P1 (EDG1) and LPA1 (EDG2) phospholipid growth factor receptors. J Biol Chem. Dec. 28, 2001;276(52):49213-20.*
Bowie Ju, et al Deciphering the message in protein sequences: tolerance to amino acid substitutions. Science. 247(4948):1306-1310, 1990.*
Boudreau, N. et al., "Suppression of ICE and Apoptosis in Mammary Epithelial Cells by Extracellular Matrix," *Science* 267:891-893 (1995).
Briesewitz, R. et al., "Expression of Native and Truncated Forms of the Human Integrin $\alpha_1$ Subunit," *J. Biol. Chem.* 268(4):2989-2996 (1993).
Brinker, J.M. et al., GenBank Acc. No. M11315, Nov. 1, 1994.
Brooks, P.C. et al., "Requirement of Vascular Integrin $\alpha_v\beta_3$ for Angiogenesis," *Science* 264: 569-571 (1994).
Butkowski, R.J. et al., "Properties of the Globular Domain of Type IV Collagen and Its Relationship to the Goodpasture Antigen," *J. Biol. Chem.* 260(6):3739-3747 (1985).
Chan, B.M.C. et al., "In Vitro and in Vivo Consequences of VLA-2 Expression on Rhabdomyosarcoma Cells," *Science* 251:1600-1602 (1991).

(Continued)

*Primary Examiner*—Maher M. Haddad
(74) *Attorney, Agent, or Firm*—Nixon Peabody, LLP

(57) ABSTRACT

Proteins with anti-angiogenic properties are disclosed, and fragments thereof, and methods of using those proteins and fragments to inhibit or promote angiogenesis.

9 Claims, 58 Drawing Sheets-

OTHER PUBLICATIONS

Colorado, P.C. et al., "Arresten: Angiogenesis and Renal Cell Carcinoma Tumor Inhibiting Matrix Protein", *J. Amer. Soc. Nephrol.* 10:489A (1999).

Colorado, P.C. et al., "Anti-Angiogenic Cues From Vascular Basement Membrane Collagen", *Cancer Res.* 60:2520-2526 (2000).

Dickeson, S.K. et al., "Determinants of Ligand Binding Specificity of the $\alpha_1\beta_1$ and $\alpha_2\beta_1$ Integrins," *J. Biol. Chem.* 274:32182-32191 (1999).

Fleischmajer, R. et al., "There Is Binding of Collagen IV to $\beta$1 Integrin during Early Skin Basement Membrane Assembly," *Ann. N.Y. Acad. Sci.* 857:212-227 (1998).

Gehlsen, K.R. et al., "Subunit Structure of a Laminin-binding Integrin and Localization of Its Binding Site on Laminin," *J. Biol. Chem.* 264(32):19034-19038 (1989).

Gunwar, S. et al., "Properties of the Collagenous Domain of the $\alpha$3(IV) Chain, the Goodpasture Antigen, of Lens Basement Membrane Collagen," *J. Biol. Chem.* 266(21):14088-14094 (1991).

Gunwar, S. et al., "Glomerular Basemen Membrane," *J. Biol. Chem.* 273(15):8767-8775 (1998).

Han, J. et al., "A Cell Binding Domain from the $\alpha$3 Chain of Type IV Collagen Inhibits Proliferation of Melanoma Cells," *J. Biol. Chem.* 272(33):20395-20401 (1997).

Hostikka, S.L. and Tryggvason, K., "The Complete Primary Structure of the $\alpha$2 Chain of Human Type IV Collagen and Comparison with the $\alpha$1(IV) Chain," *J. Biol. Chem.* 263(36):19488-19493 (1988).

Hynes, R.O., "Integrins: Versatility, Modulation, and Signaling in Cell Adhesion," *Cell* 69:11-25 (1992).

Ivaska, J. et al., "A Peptide Inhibiting the Collagen Binding Function of Integrin $\alpha_2$I Domain," *J. Biol. Chem.* 274(6): 3513-3521 (1999).

Kalluri, R. and D. Cosgrove, "Assembly of Type IV Collagen," *J. Biol. Chem.* 275(17): 12719-12724 (2000).

Kalluri, R. et al., "The $\alpha$3 chain of type IV collagen induces autoimmune Goodpasture syndrome," *Proc. Natl. Acad. Sci. USA* 91:6201-6205 (1994).

Kalluri, R. et al., "The Goodpasture Autoantigen," *J. Biol. Chem.* 271(15):9062-9068 (1996).

Kalluri, R. et al., "Isoform Switching of Type IV Collagen Is Developmentally Arrested in X-Linked Alport Syndrome Leading to Increased Susceptibility of Renal Basement Membranes to Endoproteolysis," *J. Clin. Invest.* 99(10):2470-2478 (1997).

Kalluri, R. and V.P. Sukhatme, "Fibrosis and Angiogenesis", *Curr. Opin. Nephrol. Hypert.* 9:413-418 (2000).

Kalluri, R. et al., "Reactive Oxygen Species Expose Cryptic Epitopes Associated with Autoimmune Goodpasture Syndrome," *J. Biol. Chem.* 275(26): 20027-20032 (2000).

Kamphaus, G.D. et al., "Canstain: A Novel Matrix Derived Inhibitor of Angiogenesis and Renal Cell Carcinoma Tumor Growth", *J. Amer. Soc. Nephrol.* 10:495A (1999).

Kamphaus, G.D. et al., "Canstatin, a Novel Matrix-derived Inhibitor of Angiogenesis and Tumor Growth," *J. Biol. Chem.* 275(2):1209-1215 (2000).

Kefalides, N.A. et al., "Suppression of Tumor Cell Growth By Type IV Collagen and a Peptide From the NC1 Domain of the $\alpha$3(IV) Chain", *Medicina* 59:553(1999).

Kern, A. et al., "The Role of the I Domain in Ligand Binding of the Human Integrin $\alpha_1\beta_1$," *J. Biol. Chem.* 269(36):22811-22816 (1994).

Killen, P.D. et al., GenBank Acc. No. M24766, Nov. 1, 1994.

Kramer, R.H. and Marks, N., "Identification of Integrin Collagen Receptors on Human Melanoma Cells," *J. Biol. Chem.* 264(8):4684-4688 (1989).

Langeveld, J.P.M. et al., "Structural Heterogeneity of the Noncollagenous Domain of Basement Membrane Collagen," *J. Biol. Chem.* 263(21):10481-10488 (1988).

Liotta, L.A., "Cancer Cell Invasion and Metastasis," *Scientific American* 54-64 (Feb. 1992).

Lochter, A. et al., "$\alpha$1 and $\alpha$2 Integrins Mediate Invasive Activity of Mouse Mammary Carcinoma Cells through Regulation of Stromelysin-1 Expression," *Mol. Biol. Cell* 10:271-282 (1999).

Maeshima, Y. et al., "Two RGD-Independent $\alpha_v\beta_3$ Integrin Binding Sites on Tumstatin Regulate Distinct Anti-tumor Properties", *J. Biol. Chem.* 275(31)23745-23750 (2000).

Maeshima, Y et al., "Distinct Antitumor Properties of a Type IV Collagen Domain Derived from Basement Membrane", *J. Biol. Chem.* 275(28):21340-21348 (2000).

Maeshima, Y. et al.,. "Tumstatin, an Endothelial Cell-Specific Inhibitor of Protein Synthesis," *Science* 295: 140-143 (2002).

Maragoudakis, M.E. et al., "Basement membrane biosynthesis as a target for developing inhibitors of angiogenesis with anti-tumor properties," *Kidney International* 43:147-150 (1993).

Mariyama, M. et al., "The $\alpha$4(IV) Chain of Basement Membrane Collagen," *J. Biol. Chem.* 267(2):1253-1258 (1992).

Mariyama, M. et al., "Colocalization of the Genes for the $\alpha$3(IV) and $\alpha$4(IV) Chains of Type IV Collagen to Chromosome 2 Bands q35-q37," *Genomics* 13:809-813 (1992).

Mariyama, M. et al., GenBank Acc. No. X80031, Oct. 5, 1998.

Miles, A.J. et al., "Promotion of Cell Adhesion by Single-stranded and Triple-helical Peptide Models of Basement Membrane Collagen $\alpha$1(IV)531-543," *J. Biol. Chem.* 269(49): 30939-30945 (1994).

Miles, A.J. et al., "A Peptide Model of Basement Membrane Collagen $\alpha$1(IV) 531-543 Binds the $\alpha_3\beta_1$ Integrin," *J. Biol. Chem.* 270(49): 29047-29050 (1995).

Monboisse, J.C. et al., "The $\alpha$3 Chain of Type IV Collagen Prevents Activation of Human Polymorphonuclear Leukocytes," *J. Biol. Chem.* 269(41):25475-25482 (1994).

Mooney, A. et al., "Type IV Collagen and Laminin Regulate Glomerular Mesangial Cell Susceptibility to Apoptosis Via $\beta_1$ Integrin-Mediated Survival Signals," *Amer. J. Pathol.* 155(2):599-606 (1999).

Morrison, K.E. et al., "Sequence and Localization of a Partial cDNA Encoding the Human $\alpha$3 Chain of Type IV Collagen," *Am. J. Hum. Genet.* 49:545-554 (1991).

Neilson, E.G. et al., "Specificity of Goodpasture Autoantibodies for the Recombinant Noncollagenous Domains of Human Type IV Collagen," *J. Biol. Chem.* 268(12):8402-8405 (1993).

Nickols, A. et al., "Antiangiogenic and anticancer Activities of Antagonists if Integrin $\alpha_v\beta_3$", *Proc. Ann. Mtg. Amer. Assoc. Cancer Res.* 38:206 (1997).

Petitclerc, E. et al., "New Functions for Non-collagenous Domains of Human Collagen Type IV," *J. Biol. Chem.* 275(11):8051-8061 (2000).

Prestayko, A. W. et al., "Type IV Collagen domains inhibit adhesion and migration of tumor cells and block angiogenesis," *Proceedings of the American Association for Cancer Research* 39:45 (Mar. 1998).

Prockop, D.J. and Kivirikko, K.I., "COLLAGENS: Molecular Biology, Diseases, and Potentials for Therapy," *Annu. Rev. Biochem.* 64:403-434 (1995).

Quinones, S. et al., GenBank Acc. No. M92993, Sep. 23, 1994.

Sado, Y. et al., "Induction of anti-GBM nephritis in rats by recombinant $\alpha$3(IV)NC1 and $\alpha$4(IV)NC1 of type IV collagen," *Kidney International* 53:664-671 (1998).

Sarras Jr., M.P. et al., "Extracellular Matrix (Mesoglea) of *Hydra vulgaris,*" *Developmental Biology* 148:481-494 (1991).

Saus, J. et al., "Identification of the Goodpasture Antigen as the $\alpha$3(IV) Chain of Collagen IV," *J. Biol. Chem.* 283(26):13374-13380 (1988).

Senger, D.R. et al., "Angiogenesis promoted by vascular endothelial growth factor: Regulation through $\alpha_1\beta_1$ and $\alpha_2\beta_1$ integrins," *Proc. Natl. Acad. Sci USA* 94:13612-13617 (1997).

Shahan, T.A. et al., "Identification of CD47/Integrin-associated Protein and $\alpha_V\beta_3$ as Two Receptors for the $\alpha$3(IV) Chain of Type IV Collagen on Tumor Cells," *Cancer Res.* 59:4584-4590 (1999).

Timpl, R. et al., "A Network Model for the Organization of Type IV Collagen Molecules in Basement Membranes," *Eur. J. Biochem.* 120:203-211 (1981).

Turner, N. et al., GenBank Acc. No. M81379, Oct. 30, 1994.

Varner, J.A. et al., "Review: The Integrin $\alpha_v\beta_3$: Angiogenesis and Apoptosis," *Cell Adhesion and Communication* 3:367-374 (1995).

Varner, J.A., "The role of vascular cell integrins $\alpha_v\beta_3$ and $\alpha_v\beta_5$ in angiogenesis", *Regulation of Angiogenesis,* Biurkhauser Verlag, Basel, Switzerland, 361-390 (1997).

Vuorio, E. and de Crombrugghe, B., "The Family of Collagen Genes," *Annu. Rev. Biochem.* 59:837-872 (1990).

Witkowski, C.M. and Kramer, J.M. "Site-Directed Mutations of Evolutionarily Conserved Sites on Type IV Collagen In C. Elegans," Early 1997 International Worm Meeting Abstract 650 (1997).

Zhou, J. et al., "Deletion of the Paired α5(IV) and α6(IV) Collagen Genes in Inherited Smooth Muscle Tumors," *Science* 261:1167-1169 (1993).

Maeshima Y, et al.: Two RGD-independent alpha v beta 3 Integrin binding sites on Tumstatin regulate Distinct anti-tumor properties; *Journal of Biological Chemistry*, American Society of Biological Chemists, Baltimore MD, US. vol. 275, No. 31, Aug. 4, 2000, pp. 23745-23750, XP002177918, ISSN: 0021-9258.

Kaytes, et al., "Homologies between the non-collagenous C-terminal (NC1) globular domains of the α1 and α2 subunits of type-IV collagen," Gene, 54 (1987) pp. 141-146.

Neilson, et al., "Specificity of Goodpasture Autoantibodies for the Recombinant Noncollagenous Domains of Human Type IV Collagen," J. Biol. Chem. (1993), vol. 268, No. 12, pp. 8402-8405.

* cited by examiner

FIG. 1A pET22b(+) forward primer:
 5'-CGGGATCCT <u>TCT GTT GAT CAC GGC TTC</u>-3' (SEQ ID NO:3)
pET22b(+) reverse primer:
 5'-CCCAAGCTT <u>TGT TCT TCT CAT ACA GAC</u>-3' (SEQ ID NO:4)
pPICZαA forward primer:
 5'-TTCGGAATTC <u>TCT GTT GAT CAC GGC TTC</u>-3' (SEQ ID NO:15)
pPICZαA reverse primer:
 5'-TGCTCTAGAGG <u>TGT TCT TCT CAT ACA GAC TTG GCA</u>-3' (SEQ ID NO:16)

```
            5          10         15         20         25         30         35         40         45
    tct    gtt    gat    cac    ggc    ttc    ctt    gtg    acc    agg    cat    agt    caa    aca    ata
           50         55         60         65         70         75         80         85         90
    gat    gac    cca    cag    tgt    cct    tct    ggg    acc    aaa    att    ctt    tac    cac    ggg
           95        100        105        110        115        120        125        130        135
    tac    tct    ttg    ctc    tac    gtg    caa    ggc    aat    gaa    cgg    gcc    cat    gga    cag
          140        145        150        155        160        165        170        175        180
    gac    ttg    ggc    acg    gcc    ggc    agc    tgc    ctg    cgc    aag    ttc    agc    aca    atg
          185        190        195        200        205        210        215        220        225
    ccc    ttc    ctg    ttc    tgc    aat    att    aac    aac    gtg    tgc    aac    ttt    gca    tca
          230        235        240        245        250        255        260        265        270
    cga    aat    gac    tac    tcg    tac    tgg    ctg    tcc    acc    cct    gag    ccc    atg    ccc
          275        280        285        290        295        300        305        310        315
    atg    tca    atg    gca    ccc    atc    acg    ggg    gaa    aac    ata    aga    cca    ttt    att
          320        325        330        335        340        345        350        355        360
    agt    agg    tgt    gct    gtg    tgt    gag    gcg    cct    gcc    atg    gtg    atg    gcc    gtg
          365        370        375        380        385        390        395        400        405
    cac    agc    cag    acc    att    cag    atc    cca    ccg    tgc    ccc    agc    ggg    tgg    tcc
          410        415        420        425        430        435        440        445        450
    tcg    ctg    tgg    atc    ggc    tac    tct    ttt    gtg    atg    cac    acc    agc    gct    ggt
          455        460        465        470        475        480        485        490        495
    gca    gaa    ggc    tct    ggc    caa    gcc    ctg    gcg    tcc    ccc    ggc    tcc    tgc    ctg
          500        505        510        515        520        525        530        535        540
    gag    gag    ttt    aga    agt    gcg    cca    ttc    atc    gag    tgt    cac    ggc    cgt    ggg
          545        550        555        560        565        570        575        580        585
    acc    tgc    aat    tac    tac    gca    aac    gct    tac    agc    ttt    tgg    ctc    gcc    acc
          590        595        600        605        610        615        620        625        630
    ata    gag    agg    agc    gag    atg    ttc    aag    aag    cct    acg    ccg    tcc    acc    ttg
          635        640        645        650        655        660        665        670        675
    aag    gca    ggg    gag    ctg    cgc    acg    cac    gtc    agc    cgc    <u>tgc    caa    gtc    tgt</u>
          680        685        690
    <u>atg    aga    aga    aca</u>    taa        (SEQ ID NO:1)
```

FIG. 1B

```
      5       10      15      20      25      30      35      40      45
SVD   HGF   LVT   RHS   QTI   DDP   QCP   SGT   KIL   YHG   YSL   LYV   QGN   ERA   HGQ
     50      55      60      65      70      75      80      85      90
DLG   TAG   SCL   RKF   STM   PFL   FCN   INN   VCN   FAS   RND   YSY   WLS   TPE   PMP
     95     100     105     110     115     120     125     130     135
MSM   API   TGE   NIR   PFI   SRC   AVC   EAP   AMV   MAV   HSQ   TIQ   IPP   CPS   GWS
    140     145     150     155     160     165     170     175     180
SLW   IGY   SFV   MHT   SAG   AEG   SGQ   ALA   SPG   SCL   EEF   RSA   PFI   ECH   GRG
    185     190     195     200     205     210     215     220     225
TCN   YYA   NAY   SFW   LAT   IER   SEM   FKK   PTP   STL   KAG   ELR   THV   SRC   QVC
    229
MRR   T          (SEQ ID NO:2)
```

Forward primer: 5'-cgggatccttctgttgatcacggcttc-3'
Reverse primer: 5'-cccaagctttgttcttctcatacagac-3'

Control

Arresten 2 µg/ml

Endostatin 20 µg/ml

FIG. 11A pET22b(+) forward primer:
    5'-CGGGATCCT <u>GTC AGC ATC GGC TAC CTC</u>-3'   (SEQ ID NO:7)
pET22b(+) reverse primer:
    5'-CCCAAGCTT <u>CAG GTT CTT CAT GCA CAC</u>-3'   (SEQ ID NO:8)
pPICZαA forward primer:
    5'-TTCGGAATTC <u>GTC AGC ATC GGC TAC CTC CTG</u>-3'   (SEQ ID NO:17)
pPICZαA reverse primer:
    5'-GGGGTACCCC <u>CAG GTT CTT CAT GCA CAC CTG G</u>-3'   (SEQ ID NO:18)

```
         5        10        15        20        25        30        35        40        45
       gtc       agc       atc       ggc       tac       ctc       ctg       gtg       aag       cac       agc       cag       acg       gac       cag
        50        55        60        65        70        75        80        85        90
       gag       ccc       atg       tgc       ccg       gtg       ggc       atg       aac       aaa       ctc       tgg       agt       gga       tac
        95       100       105       110       115       120       125       130       135
       agc       ctg       ctg       tac       ttc       gag       ggc       cag       gag       aag       gcg       cac       aac       cag       gac
       140       145       150       155       160       165       170       175       180
       ctg       ggg       ctg       gcg       ggc       tcc       tgc       ctg       gcg       cgg       ttc       agc       acc       atg       ccc
       185       190       195       200       205       210       215       220       225
       ttc       ctg       tac       tgc       aac       cct       ggt       gat       gtc       tgc       tac       tat       gcc       agc       cgg
       230       235       240       245       250       255       260       265       270
       aac       gac       aag       tcc       tac       tgg       ctc       tct       acc       act       gcg       ccg       ctg       ccc       atg
       275       280       285       290       295       300       305       310       315
       atg       ccc       gtg       gcc       gag       gac       gag       atc       aag       ccc       tac       atc       agc       cgc       tgt
       320       325       330       335       340       345       350       355       360
       tct       gtg       tgt       gag       gcc       ccg       gcc       atc       gcc       atc       gcg       gtc       cac       agt       cag
       365       370       375       380       385       390       395       400       405
       gat       gtc       tcc       atc       cca       cac       tgc       cca       gct       ggg       tgg       cgg       agt       ttg       tgg
       410       415       420       425       430       435       440       445       450
       atc       gga       tat       tcc       ttc       ctc       atg       cac       acg       gcg       gcg       gga       gac       gaa       ggc
       455       460       465       470       475       480       485       490       495
       ggt       ggc       caa       tca       ctg       gtg       tca       ccg       ggc       agc       tgt       cta       gag       gac       ttc
       500       505       510       515       520       525       530       535       540
       cgc       gcc       aca       cca       ttc       atc       gaa       tgc       aat       gga       ggc       cgc       ggc       acc       tgc
       545       550       555       560       565       570       575       580       585
       cac       tac       tac       gcc       aac       aag       tac       agc       ttc       tgg       ctg       acc       acc       att       ccc
       590       595       600       605       610       615       620       625       630
       gag       cag       agc       ttc       cag       ggc       tcg       ccc       tcc       gcc       gac       acg       ctc       aag       gcc
       635       640       645       650       655       660       665       670       675
       ggc       ctc       atc       cgc       aca       cac       atc       agc       cgc       tgc       cag       gtg       tgc       atg       aag
       680
       aac       ctg       tga         (SEQ ID NO:5)
```

FIG. 11B

```
         5      10      15      20      25      30      35      40      45
VSI  GYL  LVK  HSQ  TDQ  EPM  CPV  GMN  KLW  SGY  SLL  YFE  GQE  KAH  NQD
        50      55      60      65      70      75      80      85      90
LGL  AGS  CLA  RFS  TMP  FLY  CNP  GDV  CYY  ASR  NDK  SYW  LST  TAP  LPM
        95     100     105     110     115     120     125     130     135
MPV  AED  EIK  PYI  SRC  SVC  EAP  AIA  IAV  HSQ  DVS  IPH  CPA  GWR  SLW
       140     145     150     155     160     165     170     175     180
IGY  SFL  MHT  AAG  DEG  GGQ  SLV  SPG  SCL  EDF  RAT  PFI  ECN  GGR  GTC
       185     190     195     200     205     210     215     220     225
HYY  ANK  YSF  WLT  TIP  EQS  FQG  SPS  ADT  LKA  GLI  RTH  ISR  CQV  CMK
227
NL      (SEQ ID NO:6)
```

Forward primer: 5'-cgggatcctgtcagcatcggctacctc-3'

Reverse primer: 5'-cccaagcttcaggttcttcatgcacac-3'

☒ 786-0
☒ PC-3
☐ HEK 293

☐ HEK 293
☒ PC-3

FIG. 18A pET22b(+) forward primer:
    5'-CGG GAT CCG <u>GGT TTG AAA GGA AAA CGT</u>-3'  (SEQ ID NO:11)
pET22b(+) reverse primer:
    5'-CCC AAG CTT <u>TCA GTG TCT TTT CTT CAT</u>-3'  (SEQ ID NO:12)

```
         5          10         15         20         25         30         35         40         45
       ggt        ttg        aaa        gga        aaa        cgt        gga        gac        agt        gga        tca        cct        gca        acc        tgg
         50         55         60         65         70         75         80         85         90
       aca        acg        aga        ggc        ttt        gtc        ttc        acc        cga        cac        agt        caa        acc        aca        gca
         95        100        105        110        115        120        125        130        135
       att        cct        tca        tgt        cca        gag        ggg        aca        gtg        cca        ctc        tac        agt        ggg        ttt
        140        145        150        155        160        165        170        175        180
       tct        ttt        ctt        ttt        gta        caa        gga        aat        caa        cga        gcc        cac        gga        caa        gac
        185        190        195        200        205        210        215        220        225
       ctt        gga        act        ctt        ggc        agc        tgc        ctg        cag        cga        ttt        acc        aca        atg        cca
        230        235        240        245        250        255        260        265        270
       ttc        tta        ttc        tgc        aat        gtc        aat        gat        gta        tgt        aat        ttt        gca        tct        cga
        275        280        285        290        295        300        305        310        315
       aat        gat        tat        tca        tac        tgg        ctg        tca        aca        cca        gct        ctg        atg        cca        atg
        320        325        330        335        340        345        350        355        360
       aac        atg        gct        ccc        att        act        ggc        aga        gcc        ctt        gag        cct        tat        ata        agc
        365        370        375        380        385        390        395        400        405
       aga        tgc        act        gtt        tgt        gaa        ggt        cct        gcg        atc        gcc        ata        gcc        gtt        cac
        410        415        420        425        430        435        440        445        450
       agc        caa        acc        act        gac        att        cct        cca        tgt        cct        cac        ggc        tgg        att        tct
        455        460        465        470        475        480        485        490        495
       ctc        tgg        aaa        gga        ttt        tca        ttc        atc        atg        ttc        aca        agt        gca        ggt        tct
        500        505        510        515        520        525        530        535        540
       gag        ggc        acc        ggg        caa        gca        ctg        gcc        tcc        cct        ggc        tcc        tgc        ctg        gaa
        545        550        555        560        565        570        575        580        585
       gaa        ttc        cga        gcc        agc        cca        ttt        cta        gaa        tgt        cat        gga        aga        gga        acg
        590        595        600        605        610        615        620        625        630
       tgc        aac        tac        tat        tca        aat        tcc        tac        agt        ttc        tgg        ctg        gct        tca        tta
        635        640        645        650        655        660        665        670        675
       aac        cca        gaa        aga        atg        ttc        aga        aag        cct        att        cca        tca        act        gtg        aaa
        680        685        690        695        700        705        710        715        720
       gct        ggg        gaa        tta        gaa        aaa        ata        ata        agt        cgc        tgt        cag        gtg        tgc        atg
        725        730        735
       aag        aaa        aga        cac        tga          (SEQ ID NO:9)
``` pET22b-α3(IV) NC1 = nucleotides 1 through 732
Tumstatin 333 = nucleotides 1 through 372
Tumstatin 334 - nucleotide 373 through 732

FIG. 18B

```
         *
          5      10      15      20      25      30      35      40      45
        GLK     GKR     GDS     GSP     ATW     TTR     GFV     FTR     HSQ     TTA     IPS     CPE     GTV     PLY     SGF 50      55      60      65      70      75      80      85      90
        SFL     FVQ     GNQ     RAH     GQD     LGT     LGS     CLQ     RFT     TMP     FLF     CNV     NDV     CNF     ASR
                                                                                *+
               95     100     105     110     115     120     125     130     135
        NDY     SYW     LST     PAL     MPM     NMA     PIT     GRA     LEP     YIS     RCT     VCE     GPA     IAI     AVH 140     145     150     155     160     165     170     175     180
        SQT     TDI     PPC     PHG     WIS     LWK     GFS     FIM     FTS     AGS     EGT     GQA     LAS     PGS     CLE 185     190     195     200     205     210     215     220     225
        EFR     ASP     FLE     CHG     RGT     CNY     YSN     SYS     FWL     ASL     NPE     RMF     RKP     IPS     TVK
                                                 +
              230     235     240     244
        AGE     LEK     IIS     RCQ     VCM     KKR     H           (SEQ ID NO:10)
``` pET22b α3(IV) NC1 = residues 1 through 244
Tumstatin 333 = residues 1 through 124
Tumstatin 334 = residues 125 through 244

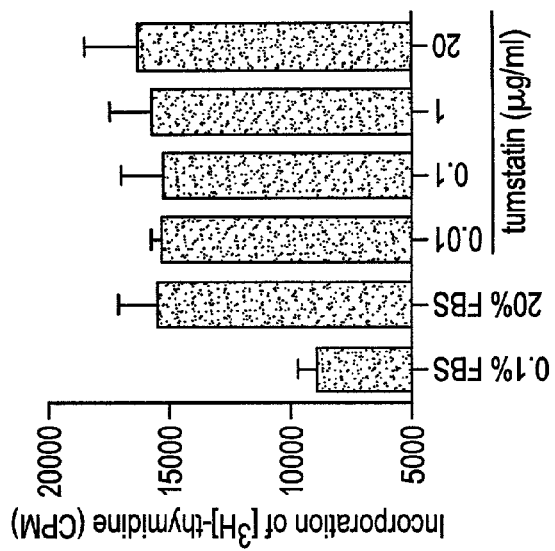
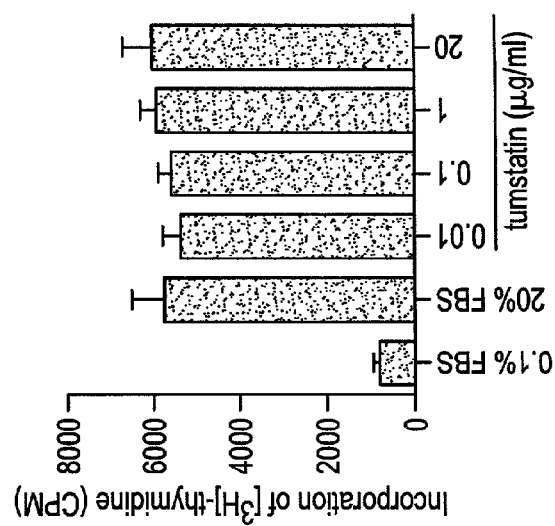
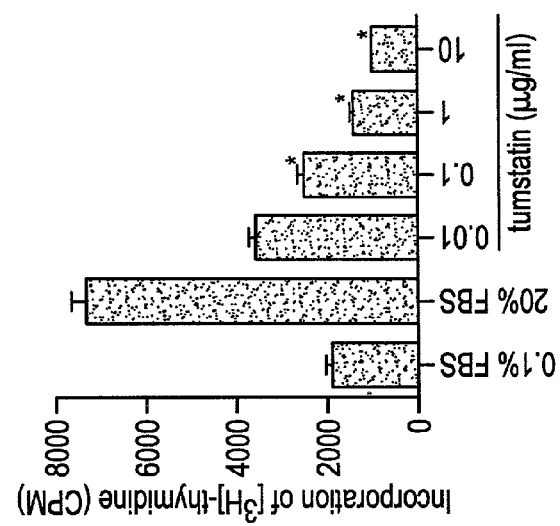
FIG. 21A
FIG. 21B
FIG. 21C

FIG. 42

```
         T1                                    GP-A
GLKGKRGDSGSPATWTTRGFVFTRHSQTTAIPSCPEGTVPLYSG

T2                    T3
FSFLFVQGNQRAHGQDLGTLGSCLQRFTTMPFLFCNVNDVCNFAS

T4           T5               T6
RNDYSYWLSTPALMPMNMAPITGRALEPYISRCTVCEGPAIAIAVH

GP-B
SQTTDIPPCPHGWISLWKGFSFIMFTSAGSEGTGQALASPGSCLE
EFRASPFLECHGRGTCNYYSNSYSFWLASLNPERMFRKPIPSTVK
AGELEKIISRCQVCMKKRH
```

Fig. 58
Fig. 58A
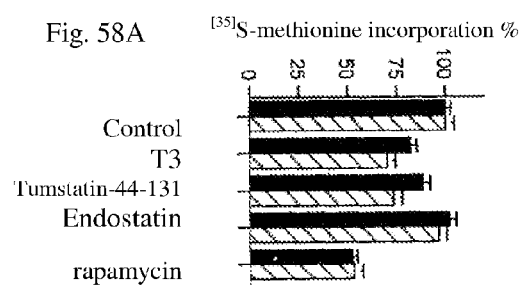
Fig. 58B
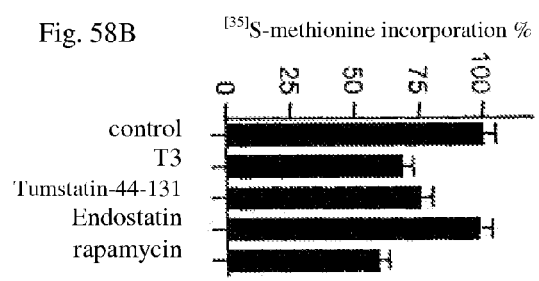
Fig. 58C
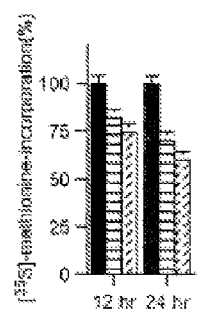
Fig. 58D
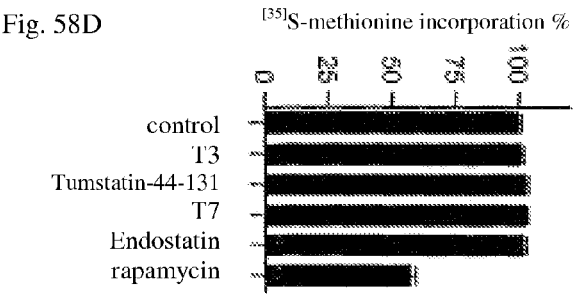
Fig. 58E
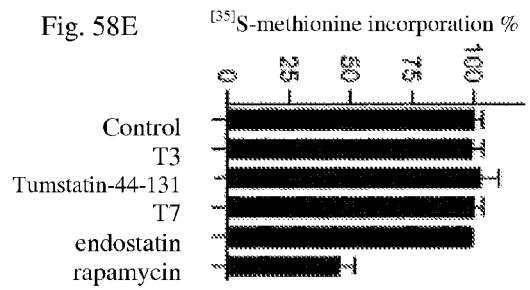
Fig. 58F
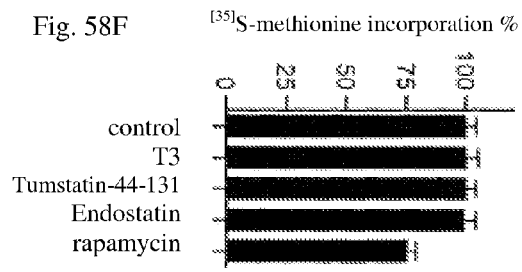

Fig. 58 (con't)
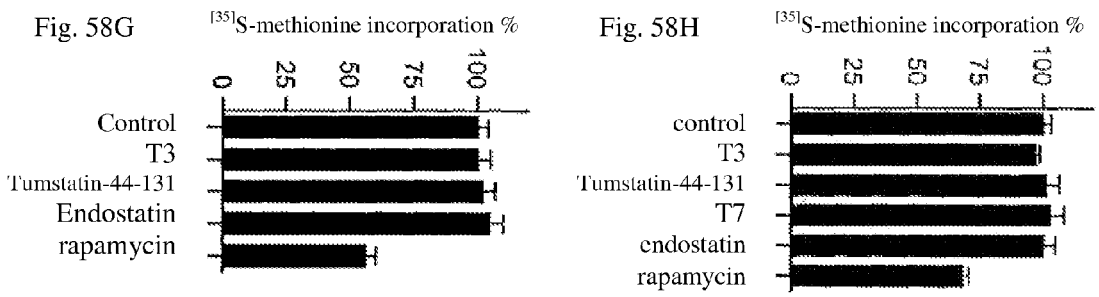
Fig. 59
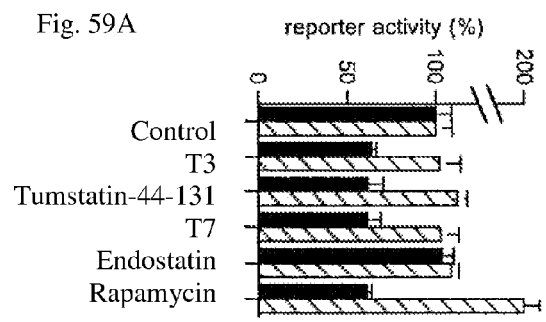
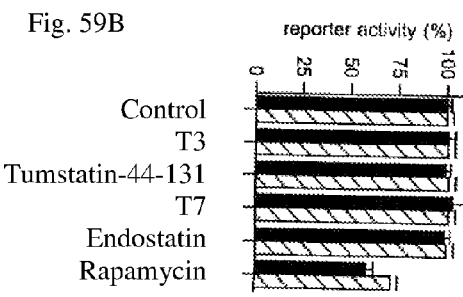

Fig. 60
Fig. 60A
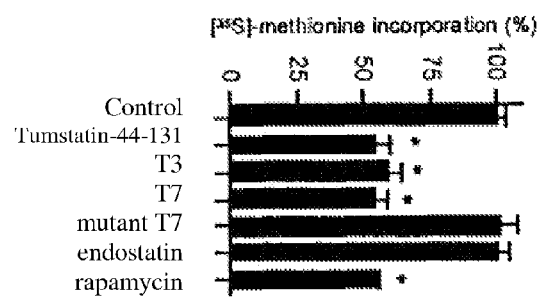
Fig. 60B
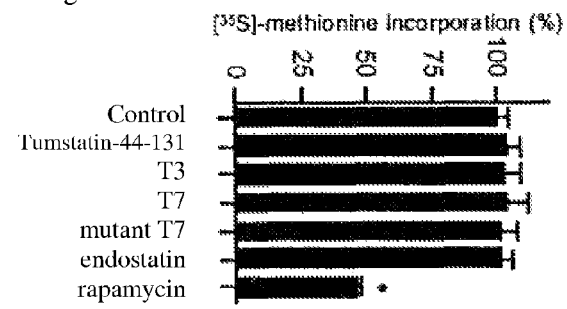
Fig. 60C
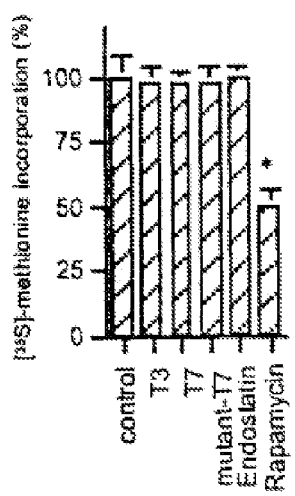
Fig. 60D
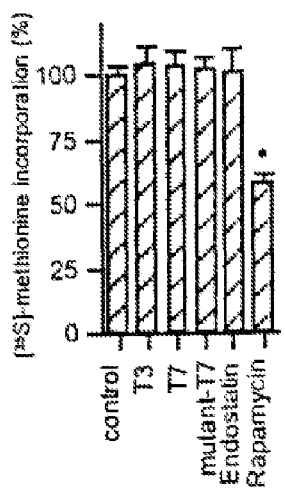

Fig. 60 (con't)

ANTI-ANGIOGENIC PROTEINS AND FRAGMENTS AND METHODS OF USE THEREOF

RELATED APPLICATIONS

This application is a continuation-in-part of International Application No. PCT/US01/00565, which designated the United States and was filed on Jan. 8, 2001, to be published in English, which is a continuation-in-part of application Ser. No. 09/625,191, filed Jul. 21, 2000, now U.S. Pat. No. 6,962,974, U.S. Ser. No. 09/543,371, filed Apr. 4, 2000, now abandoned and U.S. Ser. No. 09/479,118, filed Jan. 7, 2000 now abandoned, U.S. Ser. No. 09/625,191 is in turn a Continuation-In-Part of U.S. Ser. No. 09/543,371, which, with U.S. Ser. No. 09/479,118, is a Continuation-In-Part of U.S. Ser. No. 09/335,224, filed Jun. 17, 1999, now U.S. Pat. No. 6,759,047, which in turn claims the benefit of U.S. provisional application No. 60/089,689, filed Jun. 17, 1998 and U.S. provisional application No. 60/126,175, filed Mar. 25, 1999. The entire teachings of all these applications are incorporated herein by reference.

GOVERNMENT INTERESTS

The invention was supported, in whole or in part, by grants DK-51711, DK-55001, from the National Institutes of Health. The Government has certain rights in the invention.

BACKGROUND OF THE INVENTION

Basement membranes are thin layers of specialized extracellular matrix that provide supporting structure on which epithelial and endothelial cells grow, and that surround muscle or fat (Paulsson, M., 1992, Crit. Rev. Biochem. Mol. Biol. 27:93-127). Basement membranes are always associated with cells, and it has been well documented that basement membranes not only provide mechanical support, but also influence cellular behavior such as differentiation and proliferation. Vascular basement membranes are composed of macromolecules such as collagen, laminin, heparan sulfate proteoglycans, fibronectin and entactin (Timpl, R., 1996, Curr. Opin. Cell. Biol. 8:618-24). Functionally, collagen promotes cell adhesion, migration, differentiation and growth (Paulsson, M., 1992, Crit. Rev. Biochem. Mol. Biol. 27:93-127), and via these functions is presumed to play a crucial role in endothelial cell proliferation and behavior during angiogenesis, which is the process of formation of new blood vessels from pre-existing ones (Madri, J. A. et al., 1986, J. Histochem. Cytochem. 34:85-91; Folkman, J., 1972, Ann. Surg. 175:409-16). Angiogenesis is a complex process, and requires sprouting and migration of endothelial cells, proliferation of those cells, and their differentiation into tube-like structures and the production of a basement membrane matrix around the developing blood vessel. Additionally angiogenesis is a process critical for normal physiological events such as wound repair and endometrium remodeling (Folkman, J. et al., 1995, J. Biol. Chem. 267:10931-34). It is now well documented that angiogenesis is required for metastasis and growth of solid tumors beyond a few mm$^3$ in size (Folkman, J., 1972, Ann. Surg. 175:409-16; Folkman, J., 1995, Nat. Med. 1:27-31). Expansion of tumor mass occurs not only by perfusion of blood through the tumor, but also by paracrine stimulation of tumor cells by several growth factors and matrix proteins produced by the new capillary endothelium (Folkman, J., 1995, Nat. Med. 1:27-31). Recently, a number of angiogenesis inhibitors have been identified, namely angiostatin (O'Reilly, M. S. et al., 1994, Cell 79:315-28), endostatin (O'Reilly, M. S. et al., 1997, Cell 88:277-85), restin (Ramchandran, R. et al., 1999, Biochem. Biophys. Res. Commun. 255:735-9) and pigment epithelilum-derived factor (PEDF) (Dawson, D. W. et al., 1999, Science 285:245-8).

Type IV collagen is expressed as six distinct α-chains, α1 through α6 (Prockop, D. J. et al., 1995, Annu. Rev. Biochem. 64:403-34), and assembled into triple helices. It further forms a network to provide a scaffold for other macromolecules in basement membranes. These α-chains are composed of three domains, the N-terminal 7S domain, the middle triple helical domain, and the C-terminal globular non-collagenous (NC1) domain (Timpl, R. et al., 1981, Eur. J. Biochem. 120:203-11). Several studies have shown that inhibitors of collagen metabolism have anti-angiogenic properties, supporting the notion that basement membrane collagen synthesis and deposition is crucial for blood vessel formation and survival (Maragoudakis, M. E. et al., 1994, Kidney Int. 43:147-50; Haralabopoulos, G. C. et al., 1994, Lab. Invest. 71:575-82). However, the precise role of collagen in basement membrane organization and angiogenesis is still not well understood.

Integrins are a family of important cell surface adhesion receptors which function as adhesive molecules for many compounds. They are involved in cell-cell or cell-extracellular matrix interactions, and both mediate cells' interactions with the extracellular matrix, and cause cells to bind with it. Integrins are αβ heterodimers, consisting of two non-covalently bound transmembrane glycoprotein subunits, the α subunit and the β subunit. All α subunits exhibit shared homology with each other, as do all of the β subunits. There are currently sixteen α subunits identified ($\alpha_1$ through $\alpha_9$, $\alpha_D$, $\alpha_L$, $\alpha_M$, $\alpha_v$, $\alpha_X$, $\alpha_{IIb}$ and $\alpha_{IELb}$), and eight β subunits ($\beta_1$ through $\beta_8$), which form 22 different known combinations ($\beta_1$ and $\alpha_1$ through $\alpha_{.9}$; $\beta_1$ and $\alpha_v$; $\beta_2$ and $\alpha_D$, $\alpha_L$, $\alpha_M$ and $.\alpha_X$; $\beta_3$ and $\alpha_v$ and $\alpha_X$; $\beta_4$ and $\alpha_6$; $\beta_5$ and $\alpha_v$; $\beta_6$ and $\alpha_v$; $\beta_7$ and $\alpha_4$ and $\alpha_{IELb}$; $\beta_8$ and $\alpha_v$). The pool of the available integrin subunits can be further increased by alternative splicing of the mRNA of some of the integrin subunits.

Integrins generally bind their ligands when the concentration of integrins at a particular spot on the cell surface is above a certain minimum threshold, forming a focal contact, or hemidesmosome. This combination of low binding affinity and formation of focal contacts enables integrins to bind both weakly and strongly, depending on the concentrations of integrin molecules.

SUMMARY OF THE INVENTION

The present invention relates to anti-angiogenic proteins, and their biologically-active fragments. The fragments described herein demonstrate that anti-angiogenic proteins can be subdivided into regions with discrete activities, for example, anti-angiogenic and anti-tumor cell activities, and that these discrete activities may only be apparent upon subdivision of the larger protein molecule. In the case of the α3(IV) NC1 domain of Type IV collagen, these activities are also outside the region of the Goodpasture epitope.

As shown herein, these active fragments have a high specificity for endothelial cells, and in particular, endothelial cells expressing the $\alpha_v\beta_3$ integrin, and these fragments inhibit protein synthesis in such cells. The binding of the active fragments to $\alpha_v\beta_3$ integrin on endothelial cells induces a negative signal which results in the inhibition of protein synthesis in those cells. This is shown to be distinct from the inhibition of protein synthesis that is caused by rapamycin, which affects protein synthesis in all cell types, not just endothelial cells. Such specificity may be useful in inhibiting protein synthesis in situations where protein synthesis is undesirable, e.g., the proteins and peptides described herein can be used as immunosuppressive agents.

In particular, the invention described herein relates to an isolated fragment of SEQ ID NO:10, having the ability to inhibit tumor growth. The fragment can be T7 (SEQ ID NO:37), T7-mutant (SEQ ID NO:38), T8 (SEQ ID NO:39), T8-3 (SEQ ID NO:40), TP3 (SEQ ID NO:41) or P2 (SEQ ID NO:42). Such fragments can be reduced, alkylated, or oxidized. Such fragments can also have one or more of the cysteine residues substituted for another amino acid.

The invention also relates to an isolated mutated fragment of SEQ ID NO:10, where one to five amino acids have been substituted, and where the mutated fragment has the ability to inhibit tumor growth. The fragment can be T7-mutant (SEQ ID NO:38), T8 (SEQ ID NO:39), T8-3 (SEQ ID NO:40), TP3 (SEQ ID NO:41) or P2 (SEQ ID NO:42). Such fragments can also be reduced, alkylated, or oxidized. Such fragments can also have one or more of the cysteine residues substituted for another amino acid.

The invention further relates to an isolated fragment of SEQ ID NO:10, which has the ability to inhibit angiogenesis. The fragment can be T7 (SEQ ID NO:37), T7-mutant (SEQ ID NO:38), T8 (SEQ ID NO:39), T8-3 (SEQ ID NO:40), TP3 (SEQ ID NO:41) or P2 (SEQ ID NO:42). Such fragments can be reduced, alkylated, or oxidized. Such fragments can also have one or more of the cysteine residues substituted for another amino acid.

The invention also relates to an isolated mutated fragment of SEQ ID NO:10, where one to five amino acids have been substituted, and where the mutated fragment has the ability to inhibit angiogenesis. The fragment can be T7-mutant (SEQ ID NO:38), T8 (SEQ ID NO:39), T8-3 (SEQ ID NO:40), TP3 SEQ ID NO:41) or P2 (SEQ ID NO:42). Such fragments can also be reduced, alkylated, or oxidized. Such fragments can also have one or more of the cysteine residues substituted for another amino acid.

The invention further relates to an isolated fragment of SEQ ID NO:10, which has the ability to inhibit protein synthesis in endothelial cells. The fragment can be T7 (SEQ ID NO:37), T7-mutant (SEQ ID NO:38), T8 (SEQ ID NO:39), T8-3 (SEQ ID NO:40), TP3 (SEQ ID NO:41) or P2 (SEQ ID NO:42). Such fragments can be reduced, alkylated, or oxidized. Such fragments can also have one or more of the cysteine residues substituted for another amino acid. The protein synthesis can be cap-dependent protein synthesis. The cells can express the $\alpha_v\beta_3$ integrin.

The invention also relates to an isolated mutated fragment of SEQ ID NO:10, where one to five amino acids have been substituted, and where the mutated fragment has the ability to inhibit protein synthesis in endothelial cells. The fragment can be T7-mutant (SEQ ID NO:38), T8 (SEQ ID NO:39), T8-3 (SEQ ID NO:40), TP3 (SEQ ID NO:41) or P2 (SEQ ID NO:42). Such fragments can also be reduced, alkylated, or oxidized. Such fragments can also have one or more of the cysteine residues substituted for another amino acid. The protein synthesis can be cap-dependent protein synthesis. The cells can express the $\alpha_v\beta_3$ integrin.

In an additional aspect, the invention relates to a method for inhibiting angiogenic activity in mammalian tissue, where the method includes contacting the tissue with a composition containing an isolated fragment selected from the group consisting of: (a) SEQ ID NO:10; (b) amino acid 1 through amino acid 244 of SEQ ID NO:10; (c) amino acid 1 through amino acid 124 of SEQ ID NO:10; (d) SEQ ID NO:20; (e) SEQ ID NO:21; (f) SEQ ID NO:22; (g) SEQ ID NO:23; (h) SEQ ID NO:25; (i) SEQ ID NO:26; (j) SEQ ID NO:29; (k) SEQ ID NO:30; (l) SEQ ID NO:33; (m) SEQ ID NO:34; (n) SEQ ID NO:37; (o) SEQ ID NO:38; (p) SEQ ID NO:39; (q) SEQ ID NO:40; (r) SEQ ID NO:41; and/or (s) SEQ ID NO:42. Such fragments can also be reduced, alkylated, or oxidized. Such fragments can also have one or more of the cysteine residues substituted for another amino acid.

In an additional aspect, the invention relates to a method for inhibiting tumor growth in mammalian tissue, where the method includes contacting the tissue with a composition containing an isolated fragment selected from the group consisting of: (a) SEQ ID NO:10; (b) amino acid 1 through amino acid 244 of SEQ ID NO:10; (c) amino acid 1 through amino acid 124 of SEQ ID NO:10; (d) SEQ ID NO:20; (e) SEQ ID NO:21; (f) SEQ ID NO:22; (g) SEQ ID NO:23; (h) SEQ ID NO:25; (i) SEQ ID NO:26; (j) SEQ ID NO:29; (k) SEQ ID NO:30; (l) SEQ ID NO:33; (m) SEQ ID NO:34; (n) SEQ ID NO:37; (o) SEQ ID NO:38; (p) SEQ ID NO:39; (q) SEQ ID NO:40; (r) SEQ ID NO:41; and/or (s) SEQ ID NO:42. Such fragments can also be reduced, alkylated, or oxidized. Such fragments can also have one or more of the cysteine residues substituted for another amino acid.

In an additional aspect, the invention relates to a method for inhibiting protein synthesis in one or more mammalian cells, where the method includes contacting the cells with a composition containing an isolated fragment selected from the group consisting of: (a) SEQ ID NO:10; (b) amino acid 1 through amino acid 244 of SEQ ID NO:10; (c) amino acid 1 through amino acid 124 of SEQ ID NO:10; (d) SEQ ID NO:20; (e) SEQ ID NO:21; (f) SEQ ID NO:22; (g) SEQ ID NO:23; (h) SEQ ID NO:25; (i) SEQ ID NO:26; (j) SEQ ID NO:29; (k) SEQ ID NO:30; (l) SEQ ID NO:33; (m) SEQ ID NO:34; (n) SEQ ID NO:37; (o) SEQ ID NO:38; (p) SEQ ID NO:39; (q) SEQ ID NO:40; (r) SEQ ID NO:41; and/or (s) SEQ ID NO:42. Such fragments can also be reduced, alkylated, or oxidized. Such fragments can also have one or more of the cysteine residues substituted for another amino acid. The protein synthesis can be cap-dependent protein synthesis. The cells can be endothelial cells. The cells can express the $\alpha_v\beta_3$ integrin.

In another aspect, the invention features a method for inhibiting protein synthesis in one or more mammalian cells, tumor growth, and/or angiogenesis in mammalian tissue, where the method includes contacting the one or more cells with a composition including an isolated fragment such as (a) SEQ ID NO:2, (b) SEQ ID NO:6, or (c) SEQ ID NO:10. The protein synthesis can be cap-dependent protein synthesis. The mammalian cells can express the $\alpha_v\beta_3$ integrin.

The invention also features an isolated peptide of the formula:

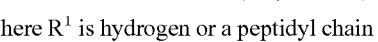

$$R^1X^1LFX^2NVNX^3VX^4NFR^2 \text{(SEQ ID NO:45)},$$

where $R^1$ is hydrogen or a peptidyl chain of 1 to 17 amino acids, $R^2$ is hydrogen or a peptidyl chain of 1 to 12 amino acids, and $X^1$, $X^2$ and $X^3$ are individually an amino acid, where said peptide inhibits tumor growth. $X^1$ can be an amino acid with a basic side chain or an amino acid with an aromatic side chain. $X^1$ can be phenylalanaine, tyrosine, tryptophan, lysine, arginine, histidine, glutamine or asparagine. $X^1$ can also be lysine or phenylalanine. $X^2$, $X^3$ and $X^4$ can be independently an amino acid with a hydrophilic side chain or an amino acid with a basic side chain. $X^2$, $X^3$ and $X^4$ can be independently cysteine, serine, threonine, aspartic acid or glutamine. $X^2$ and $X^4$ can be independently cysteine, serine or aspartic acid and $X^3$ is cysteine or aspartic acid. $X^1$ can be phenylalanine, tyrosine, tryptophan, lysine, arginine, histidine, glutamine or asparagine, $X^2$, $X^3$ and $X^4$ can be independently cysteine, serine, threonine, aspartic acid or glutamine. $R^1$ can be one amino acid or a peptidyl chain of 2, 3, 4, 5, 6, 7, or 8 amino acid residues. The amino acid or peptidyl chain represented by $R^1$ can be selected from the group consisting of: (a) P, (b) MP, (c) TMP, (d) TTMP (SEQ ID NO:46), (e) FTTMP (SEQ ID NO:47), (f) RFTTMP (SEQ ID NO:48), (g) QRFTTMP (SEQ ID NO:49), (h) LQRFTTMP (SEQ ID NO:50), (i) KQRFTTMP (SEQ ID NO:51), and (j) a conservative variant of any of (a)-(i). $R^2$ can be one amino acid or a peptidyl chain of 2, 3, 4, 5, 6, 7, 8 or 9 amino acid residues. The amino acid or peptidyl chain represented by $R^2$ can be selected from the group consisting of: (a) A, (b) AS, (c) ASR, (d) ASRN (SEQ ID NO:52), (e) ASRND (SEQ ID NO:53), (f) ASRNDY (SEQ ID NO:54), (g) ASRNDYS (SEQ ID NO:55), (h) ASRNDYSY (SEQ ID NO:56), (i) ASRNDYSYW (SEQ ID NO:57), (j) ASRNDYSYWL (SEQ ID NO:58), and (k) a conservative variant of any of (a)-(j). Such an isolated peptide can be reduced, alkylated, or oxidized. Such an isolated peptide can be used in a method for inhibiting protein synthesis in one or more mammalian cells, tumor growth, and/or angiogenesis in mammalian tissue, where the method includes contacting the tissue with a composition comprising the isolated peptide. The isolated peptide can be combined with a pharmaceutically-acceptable carrier.

The invention also relates to an anti-angiogenic, isolated non-Goodpasture fragment of α3(IV) NC1 domain, which has one or more of the following characteristics: (a) the ability to bind $\alpha_v\beta_3$ integrin; (b) the ability to inhibit proliferation of endothelial cells; and (c) the ability to cause apoptosis of endothelial cells. The isolated non-Goodpasture fragment binds $\alpha_v\beta_3$ integrin by an RGD-independent mechanism, as described herein. Such an isolated fragment of the α3(IV) NC1 domain of Type IV collagen is described herein, and is designated "Tumstatin". "Tumstatin", as the term is used herein, comprises the amino acid sequence of SEQ ID NO:10. In addition, another isolated non-Goodpasture fragment, designated herein as "Tum-1", or "Tumstatin N53" (SEQ ID NO:22), consists of the amino acid sequence of amino acid residue 54 to amino acid 244 of full-length Tumstatin (SEQ ID NO:10). Other isolated fragments disclosed herein include "Tum-2" (SEQ ID NO:23), "Tum-3" (SEQ ID NO:24), "Tum-4" (SEQ ID NO:25), and "Tum-5" (SEQ ID NO:26), which consist of the amino acid sequence of residues 1 to 132 (Tum-2), residues 133 to 244 (Tum-3), residues 181 to 244 (Tum-4), and residues 54 to 132 (Tum-5) of full-length Tumstatin (SEQ ID NO:10), respectively. Peptide fragments are also disclosed herein, including "T1" (SEQ ID NO:27), "T2" (SEQ ID NO:28), "T3" (SEQ ID NO:29), "T4" (SEQ ID NO:30), "T5" (SEQ ID NO:31), "T6" (SEQ ID NO:32) and "T7" (SEQ ID NO:37), which consist of amino acid residues 1 to 20 (T1), 53 to 72 (T2), 68 to 87 (T3), 83 to 102 (T4), 98 to 116 (T5), 113 to 131 (T6) and 73 to 97 (T7), respectively, of full-length Tumstatin (SEQ ID NO:10). Yet another peptide fragment of full-length Tumstatin is designated herein as "Tumstatin-44-131" (SEQ ID NO:33) and consists of amino acid residues 44 to 131 of full-length Tumstatin (SEQ ID NO:10). Another fragment of full-length Tumstatin is designated herein as "Tum-5-125-C-A" (SEQ ID NO:34), and consists of Tumstatin-44-131, where the cysteine at position 125 (of full-length Tumstatin) is mutated via site-directed mutagenesis to alanine. Fragments of Tumstatin which are reduced, e.g., alkaline reduced, are also described herein to possess anti-angiogenic properties. Two other fragments are "Tumstatin 333" (SEQ ID NO:20) and "Tumstatin 334" (SEQ ID NO:21), which consist of residues 1 through 124 (Tumstatin 333) and residues 125 through 244 of full-length Tumstatin (SEQ ID NO:10), respectively. Other fragments of Tumstatin include T7-mutant (SEQ ID NO:38, in which methionine has been substituted for the leucine residue at position 77 of the full-length Tumstatin molecule, and isoleucine has been substituted for valine at position 81, and asparagine has been substituted for aspartic acid at position 83), T8 (SEQ ID NO:39, in which lysine has been substituted for the leucine residue at position 68 of the full-length Tumstatin molecule), T8-3 (SEQ ID NO:40, in which lysine has been substituted for the leucine residue at position 68 of the full-length Tumstatin molecule, and serine has been substituted for the cysteine residues at positions 79 and 85), TP3 (SEQ ID NO:41, in which lysine has been substituted for the phenylalanine residue at position 76 of the full-length Tumstatin molecule, and cysteine has been substituted for the aspartic acid at position 83), and P2 (SEQ ID NO:42, in which lysine has been substituted for the leucine residue at position 68 of the full-length Tumstatin molecule, and aspartic acid has been substituted for the cysteine residues at positions 79 and 85).

The invention also features an anti-tumor, isolated non-Goodpasture fragment of α3(IV) NC1 domain, which has one or more of the following characteristics: (a) the ability to bind $\alpha_v\beta_3$ integrin, (b) the ability to bind endothelial cells, (c) the ability to inhibit proliferation of tumor cells, and (d) the inability to inhibit proliferation of endothelial cells. The isolated non-Goodpasture fragment can bind $\alpha_v\beta_3$ integrin by an RGD-independent mechanism, as described herein. One isolated non-Goodpasture fragment comprises the amino acid sequence of amino acid residue 185 to amino acid 203 of full-length Tumstatin (SEQ ID NO:10). Another peptide fragment of full-length Tumstatin is designated herein as "T3," and consists of amino acid residues 68 to 87 of full-length Tumstatin (SEQ ID NO:10). Yet another peptide fragment of full-length Tumstatin is designated herein as "Tumstatin-44-131," and consists of amino acid residues 44 to 131 of full-length Tumstatin (SEQ ID NO:10). Another fragment of full-length Tumstatin is designated herein as "Tum-5-125-C-A" (SEQ ID NO:34), and consists of Tumstatin-44-131 (SEQ ID NO:33), where the cysteine at position 125 (of full-length Tumstatin) is mutated via site-directed mutagenesis to alanine. Fragments of Tumstatin which are reduced, e.g., alkaline reduced, are also described herein to possess anti-angiogenic properties. Other fragments of Tumstatin include T7-mutant, T8, T8-3, TP3, and P2.

The present invention also relates to receptors, binding proteins, e.g., that interact with (e.g., bind to) anti-angiogenic proteins and peptides, thereby providing targets for assessing anti-angiogenic proteins, peptides and compounds. These receptors and their subunits mediate angiogenesis, tumor growth and metasasis, and endothelial cell proliferation and migration and endothelial cell tube formation. These receptors also mediate cell apoptosis.

In particular, the invention relates to the integrin subunits $\alpha_1$, $\alpha_2$, $\alpha_3$, $\alpha_v$, $\beta_1$ and $\beta_3$, which have been found to bind to Arresten, which is the α1 chain of the NC1 domain of Type IV collagen, the integrin subunits $\alpha_1$, $\alpha_2$ and $\beta_1$, which have been found to bind to Canstatin, which is the α2 chain of the NC1 domain of Type IV collagen, and integrin subunits $\alpha_5$, $\alpha_6$, $\alpha_v$, $\beta_1$ and $\beta_3$, which have been found to bind to Tumstatin, the α3 chain of the NC1 domain of Type IV collagen. Angiogenesis and proliferation of endothelial cells mediated by integrin binding may be inhibited by either administering Arresten, Canstatin or Tumstatin, or administering another protein, peptide or compound that binds to the above-listed integrin subunits, which serve as receptors for Arresten, Canstatin and Tumstatin. Apoptosis of endothelial cells mediated by integrin binding may also be inhibited by either administering Arresten, Canstatin or Tumstatin, or administering another protein, peptide or compound that binds to the above-listed integrin subunits, which serve as receptors for Arresten, Canstatin and Tumstatin. Such compounds can include antibodies, fragments or portions of Arresten, Canstatin or Tumstatin, or proteins or peptides comprising those regions of Arresten, Canstatin or Tumstatin which bind to the above-listed integrin subunits.

The invention also relates to methods of enhancing, promoting or inducing angiogenesis and cell proliferation by administering proteins, peptides or compounds that mimic the integrin subunits that serve as receptors for Arresten, Canstatin or Tumstatin. Such proteins, peptides or compounds include integrin protein composed of the selected subunits, which serves to interact with (e.g., bind to) available Arresten, Canstatin or Tumstatin, and biologically active (e.g., anti-angiogenic) fragments, mutants, analogs, homologs and derivatives thereof, as well as multimers (e.g., dimers) and fusion proteins (also referred to herein as chimeric proteins) thereof. Such proteins, peptides or compounds also include heparan sulfate proteoglycan, which binds Arresten with a $Kd_1$ value of $8.5 \times 10^{-1}$ M and $Bmax_1$ of $3 \times 10^6$ sites per cell. As referred to herein, "available" can mean soluble or circulatory proteins that can contact or interact with (e.g., bind to) the integrins or a subunit or fragment thereof. Angiogenesis and cell proliferation can also be enhanced by administering antibodies to Arresten, Canstatin or Tumstatin, or biologically active (e.g., anti-angiogenic) fragments, mutants, analogs, homologs and derivatives thereof, as well as multimers (e.g., dimers) and fusion proteins (also referred to herein as chimeric proteins) thereof. Such antibodies bind these molecules, thereby preventing them from interacting with their respective integrin receptors and inhibiting angiogenic activity.

The invention also includes kits for identifying anti-angiogenic proteins, peptides and compounds which inhibit angiogenesis in a manner similar to Arresten, Canstatin and Tumstatin, and anti-angiogenic variants and fragments thereof. Such kits comprise appropriate (e.g., $\alpha_1$, $\alpha_2$, $\beta_3$, etc.) subunits of integrin, and such other components necessary to perform one of the assays described in the Examples below. Exceptional assays to be performed with such a kit would include the Cell Adhesion Assay, described in Examples 12 and 28 below, and the Competition Proliferation Assay, described in Example 26 below.

The invention relates to methods of inhibiting angiogenesis, tumor growth, or tumor metastasis in a tissue (e.g., mammalian or human tissue), wherein the tissue is contacted with one or more a chains (e.g., α1 through α6) of the NC1 domain of Type IV collagen, and wherein the angiogenesis, tumor growth or tumor metastasis is mediated by one or more integrins or integrin subunits.

More specifically, the invention features a method of inhibiting angiogenesis in a tissue, where the angiogenesis is mediated by one or more endothelial cell integrins (e.g., $\alpha_1\beta_1$, $\alpha_2\beta_1$, $\alpha_3\beta_1$, $\alpha_v\beta_3$) or one or more endothelial cell integrin subunits (e.g., $\alpha_1$, $\alpha_2$, $\alpha_3$, $\alpha_v$, $\beta_1$, $\beta_3$). The method comprises contacting the endothelial cells with Arresten or a fragment, mutant, homolog, analog or allelic variant thereof. The angiogenesis can be inhibited by inhibiting one or more of the following: endothelial cell proliferation, endothelial cell migration, or endothelial cell tube formation.

The invention also features a method of inhibiting tumor growth or metastasis in a tissue, where the tumor growth or metastasis is mediated by one or more endothelial cell integrins (e.g., $\alpha_1\beta_1$, $\alpha_2\beta_1$, $\alpha_3\beta_1$, $\alpha_v\beta_3$) or one or more endothelial cell integrin subunits (e.g., $\alpha_1$, $\alpha_2$, $\alpha_3$, $\alpha_v$, $\beta_1$, $\beta_3$); the method comprises contacting the endothelial cells with Arresten or a fragment, mutant, homolog, analog or allelic variant thereof. The tumor growth can be inhibited by inhibiting one or more of the following: endothelial cell proliferation, endothelial cell migration, or endothelial cell tube formation.

In addition, the invention features a method of promoting or inducing endothelial cell apoptosis in a tissue, where the endothelial cell apoptosis is mediated by one or more endothelial cell integrins (e.g., $\alpha_1\beta_1$, $\alpha_2\beta_1$, $\alpha_2\beta_1$, $\alpha_v\beta_3$) or one or more endothelial cell integrin subunits (e.g., $\alpha_1$, $\alpha_2$, $\alpha_3$, $\alpha_v$, $\beta_1$, $\beta_3$); the method comprises contacting the endothelial cells with Arresten or a fragment, mutant, homolog, analog or allelic variant thereof. The apoptosis can be promoted or induced by inhibiting one or more of the following: endothelial cell proliferation, endothelial cell migration, or endothelial cell tube formation.

The invention features a method of inhibiting angiogenesis in a tissue, where the angiogenesis is mediated by one or more endothelial cell integrins (e.g., $\alpha_1\beta_1$, $\alpha_2\beta_1$) or one or more endothelial cell integrin subunits (e.g., $\alpha_1$, $\alpha_2$, $\beta_1$); the method comprises contacting the endothelial cells with Canstatin or a fragment, mutant, homolog, analog or allelic variant thereof. The angiogenesis can be inhibited by inhibiting one or more of the following: endothelial cell proliferation, endothelial cell migration, or endothelial cell tube formation.

The invention also features a method of inhibiting tumor growth or metastasis in a tissue, where the tumor growth or metastasis is mediated by one or more endothelial cell integrins (e.g., $\alpha_1\beta_1$, $\alpha_2\beta_1$) or one or more endothelial cell integrin subunits (e.g., $\alpha_1$, $\alpha_2$, $\beta_1$); the method comprises contacting the endothelial cells with Canstatin or a fragment, mutant, homolog, analog or allelic variant thereof. The tumor growth can be inhibited by inhibiting one or more of the following: endothelial cell proliferation, endothelial cell migration, or endothelial cell tube formation.

In addition, the invention features a method of promoting or inducing endothelial cell apoptosis in a tissue, where the endothelial cell apoptosis is mediated by one or more endothelial cell integrins (e.g., $\alpha_1\beta_1$, $\alpha_2\beta_1$) or one or more endothelial cell integrin subunits (e.g., $\alpha_1$, $\alpha_2$, $\beta_1$); the method comprises contacting the endothelial cells with Canstatin or a fragment, mutant, homolog, analog or allelic variant thereof. The apoptosis can be promoted or induced by inhibiting one or more of the following: endothelial cell proliferation, endothelial cell migration, or endothelial cell tube formation.

The invention features a method of inhibiting angiogenesis in a tissue, where the angiogenesis is mediated by one or more endothelial cell integrins (e.g., $\alpha_5\beta_3$, $\alpha_6\beta_1$, $\alpha_v\beta_3$) or one or more endothelial cell integrin subunits (e.g., $\alpha_5$, $\alpha_6$, $\alpha_v$, $\beta_1$, $\beta_3$); the method comprises contacting the endothelial cells with Tumstatin or a fragment, mutant, homolog, analog or allelic variant thereof. The angiogenesis can be inhibited by inhibiting one or more of the following: endothelial cell proliferation, endothelial cell migration, or endothelial cell tube formation.

The invention also features a method of inhibiting tumor growth or metastasis in a tissue, where the tumor growth or metastasis is mediated by one or more endothelial cell integrins (e.g., $\alpha_5\beta_3$, $\alpha_6\beta_1$, $\alpha_v\beta_3$) or one or more endothelial cell integrin subunits (e.g., $\alpha_5$, $\alpha_6$, $\alpha_v$, $\beta_1$, $\beta_3$); the method comprises contacting the endothelial cells with Tumstatin or a fragment, mutant, homolog, analog or allelic variant thereof. The tumor growth can be inhibited by inhibiting one or more of the following: endothelial cell proliferation, endothelial cell migration, or endothelial cell tube formation.

In addition, the invention features a method of promoting or inducing endothelial cell apoptosis in a tissue, where the endothelial cell apoptosis is mediated by one or more endothelial cell integrins (e.g., $\alpha_5\beta_3$, $\alpha_6\beta_1$, $\alpha_v\beta_3$) or one or more endothelial cell integrin subunits (e.g., $\alpha_5$, $\alpha_6$, $\alpha_v$, $\beta_1$, $\beta_3$); the method comprises contacting the endothelial cells with Tumstatin or a fragment, mutant, homolog, analog or allelic variant thereof. The apoptosis can be promoted or induced by inhibiting one or more of the following: endothelial cell proliferation, endothelial cell migration, or endothelial cell tube formation.

The invention further features a method of inhibiting angiogenesis or cell proliferation in a tissue, comprising contacting the tissue with one or more of the following: an antibody or peptide that specifically binds the $\alpha_1$ subunit of integrin; an antibody or peptide that specifically binds the $\alpha_2$ subunit of integrin; an antibody or peptide that specifically binds the $\alpha_3$ subunit of integrin; an antibody or peptide that specifically binds the $\alpha_5$ subunit of integrin; an antibody or peptide that specifically binds the $\alpha_6$ subunit of integrin; an antibody or peptide that specifically binds the $\alpha_v$ subunit of integrin; an antibody or peptide that specifically binds the $\beta_1$ subunit of integrin; or an antibody or peptide that specifically binds the $\beta_3$ subunit of integrin. This method may be used to treat a condition characterized by angiogenesis or cell proliferation.

Additionally, the invention features a method of promoting or inducing angiogenesis or cell proliferation in a tissue, comprising contacting the tissue with one or more of the following: the $\alpha_1$ subunit of integrin; the $\alpha_2$ subunit of integrin; the $\alpha_3$ subunit of integrin; the $\alpha_5$ subunit of integrin; the $\alpha_6$ subunit of integrin; the $\alpha_v$ subunit of integrin; the $\beta_1$ subunit of integrin; or the $\beta_3$ subunit of integrin. The one or more of the subunits of integrin can be in soluble form, and they can also be monomers, dimers, trimers, tetramers, or multimers.

The invention also features a method of inhibiting a proliferative disease in a vertebrate, where the disease is characterized by angiogenesis that is mediated by receptors to Arresten (e.g., $\alpha_1\beta_1$ integrins, $\alpha_2\beta_1$ integrins, $\alpha_3\beta_3$, integrins, $\alpha_v\beta_3$ integrins); the method comprises inhibiting Arresten receptor-mediated angiogenesis, thereby inhibiting the proliferative disease. The inhibition of Arresten receptor-mediated angiogenesis can result in the inhibition of tumor growth, metastasis, or the regression of an established tumor. The inhibition of the Arresten receptor-mediated angiogenesis can be accomplished by contacting the proliferating cells with a molecule that inhibits Arresten receptor-mediated angiogenesis, e.g., an antibody (e.g., polyclonal or monoclonal antibody), antibody fragment or a peptide that specifically binds to the Arresten receptor.

The invention additionally features a method of promoting angiogenesis in a tissue, comprising contacting the tissue with a composition comprising one or more soluble receptors that bind Arresten.

In another aspect, the invention features a method of inhibiting a proliferative disease in a vertebrate, where the disease is characterized by angiogenesis that is mediated by receptors to Canstatin (e.g., $\alpha_1\beta_1$ integrins, $\alpha_2\beta_1$ integrins); the method comprises inhibiting Canstatin receptor-mediated angiogenesis, thereby inhibiting the proliferative disease. The inhibition of Canstatin receptor-mediated angiogenesis can result in the inhibition of tumor growth, metastasis, or the regression of an established tumor. The inhibition of the Canstatin receptor-mediated angiogenesis can be accomplished by contacting the proliferating cells with a molecule that inhibits Canstatin receptor-mediated angiogenesis, e.g., an antibody (e.g., polyclonal or monoclonal antibody), antibody fragment or a peptide that specifically binds to the Canstatin receptor.

The invention additionally features a method of promoting angiogenesis in a tissue, comprising contacting the tissue with a composition comprising one or more soluble receptors that bind Canstatin.

In another aspect, the invention features a method of inhibiting a proliferative disease in a vertebrate, where the disease is characterized by angiogenesis that is mediated by receptors to Tumstatin (e.g., $\alpha_5\beta_1$ integrins, $\alpha_6\beta_1$ integrins, $\alpha_v\beta_3$ integrins); the method comprises inhibiting Tumstatin receptor-mediated angiogenesis, thereby inhibiting the proliferative disease. The inhibition of Tumstatin receptor-mediated angiogenesis can result in the inhibition of tumor growth, metastasis, or the regression of an established tumor. The inhibition of the Tumstatin receptor-mediated angiogenesis can be accomplished by contacting the proliferating cells with a molecule that inhibits Tumstatin receptor-mediated angiogenesis, e.g., an antibody (e.g., polyclonal or monoclonal antibody), antibody fragment or a peptide that specifically binds to the Tumstatin receptor.

The invention additionally features a method of promoting angiogenesis in a tissue, comprising contacting the tissue with a composition comprising one or more soluble receptors that bind Tumstatin.

In another aspect, the invention features a method of inhibiting angiogenesis in a tissue, comprising contacting the tissue with a molecule that decreases FLIP levels in the tissue.

The invention also features a composition comprising, as a biologically active ingredient, one or more molecules (e.g., antibodies, antibody fragments, peptides) that specifically bind to one or more Arresten receptors or Arresten receptor subunits (e.g., $\alpha_1\beta_1$ integrin, $\alpha_2\beta_1$ integrin, $\alpha_3\beta_1$ integrin, $\alpha_v\beta_3$ integrin, $\alpha_1$ integrin subunit, $\alpha_2$ integrin subunit, $\alpha_3$ integrin subunit, $\alpha_v$ integrin subunit, $\beta_1$ integrin subunit, $\beta_3$ integrin subunit). The composition may optionally include a pharmaceutically-acceptable carrier. The composition can be used in a method to inhibit a disease characterized by angiogenic activity, where the method comprises administering the composition to a patient with the disease. The disease may be characterized by angiogenic activity, and the composition can be administered to a patient in conjunction with radiation therapy, chemotherapy or immunotherapy.

In another aspect, the invention features a composition comprising, as a biologically active ingredient, one or more Arresten receptors or Arresten receptor subunits (e.g., $\alpha_1\beta_1$ integrin, $\alpha_2\beta_1$ integrin, $\alpha_3\beta_1$ integrin, $\alpha_v\beta_3$ integrin, $\alpha_1$, integrin subunit, $\alpha_2$ integrin subunit, $\alpha_3$ integrin subunit, $\alpha_v$ integrin subunit, $\beta_1$ integrin subunit, $\beta_3$ integrin subunit). The composition may optionally include a pharmaceutically-acceptable carrier. The composition can be used in a method to promote or induce angiogenesis, where the method comprises administering the composition to a patient with the disease. The disease may be characterized by angiogenic activity, and the composition can be administered to a patient in conjunction with radiation therapy, chemotherapy or immunotherapy.

The invention also features a composition comprising, as a biologically active ingredient, one or more molecules (e.g., antibodies, antibody fragments, peptides) that specifically bind to one or more Canstatin receptors or Canstatin receptor subunits (e.g., $\alpha_1\beta_1$ integrin, $\alpha_2\beta_1$ integrin, $\alpha_3\beta_1$ integrin, $\alpha_v\beta_3$ integrin, $\alpha_1$, integrin subunit, $\alpha_2$ integrin subunit, $\alpha_3$ integrin subunit, $\alpha_v$ integrin subunit, $\beta_1$ integrin subunit, $\beta_3$ integrin subunit). The composition may optionally include a pharmaceutically-acceptable carrier. The composition can be used in a method to inhibit a disease characterized by angiogenic activity, where the method comprises administering the composition to a patient with the disease. The disease may be characterized by angiogenic activity, and the composition can be administered to a patient in conjunction with radiation therapy, chemotherapy or immunotherapy.

In another aspect, the invention features a composition comprising, as a biologically active ingredient, one or more Canstatin receptors or Canstatin receptor subunits (e.g., $\alpha_1\beta_1$ integrin, $\alpha_2\beta_1$ integrin, $\alpha_3\beta_1$ integrin, $\alpha_v\beta_3$ integrin, $\alpha_1$ integrin subunit, $\alpha_2$ integrin subunit, $\alpha_3$ integrin subunit, $\alpha_v$ integrin subunit, $\beta_1$ integrin subunit, $\beta_3$ integrin subunit). The composition may optionally include a pharmaceutically-acceptable carrier. The composition can be used in a method to promote or induce angiogenesis, where the method comprises administering the composition to a patient with the disease. The disease may be characterized by angiogenic activity, and the composition can be administered to a patient in conjunction with radiation therapy, chemotherapy or immunotherapy.

The invention also features a composition comprising, as a biologically active ingredient, one or more molecules (e.g., antibodies, antibody fragments, peptides) that specifically bind to one or more Tumstatin receptors or Tumstatin receptor subunits (e.g., $\alpha_5\beta_1$ integrin, $\alpha_6\beta_1$ integrin, $\alpha_v\beta_3$ integrin, $\alpha_5$ integrin subunit, $\alpha_6$ integrin subunit, $\alpha_v$ integrin subunit, $\beta_1$ integrin subunit, $\beta_3$ integrin subunit). The composition may optionally include a pharmaceutically-acceptable carrier. The composition can be used in a method to inhibit a disease characterized by angiogenic activity, where the method comprises administering the composition to a patient with the disease. The disease may be characterized by angiogenic activity, and the composition can be administered to a patient in conjunction with radiation therapy, chemotherapy or immunotherapy.

In another aspect, the invention features a composition comprising, as a biologically active ingredient, one or more Tumstatin receptors or Tumstatin receptor subunits (e.g., $\alpha_5\beta_1$ integrin, $\alpha_6\beta_1$ integrin, $\alpha_v\beta_3$ integrin, $\alpha_5$ integrin subunit, $\alpha_6$ integrin subunit, $\alpha_v$ integrin subunit, $\beta_1$ integrin subunit, $\beta_3$ integrin subunit). The composition may optionally include a pharmaceutically-acceptable carrier. The composition can be used in a method to promote or induce angiogenesis, where the method comprises administering the composition to a patient with the disease. The disease may be characterized by angiogenic activity, and the composition can be administered to a patient in conjunction with radiation therapy, chemotherapy or immunotherapy.

In further aspects, the invention features a method of determining if a cell (e.g., a cancer cell) will be susceptible to the action of Arresten, comprising the steps of: (a) providing a sample (e.g., from a mammal) containing the cell, (b) reacting the sample with one or more antibodies (e.g., antibodies to $\alpha_1\beta_1$ integrin, $\alpha_2\beta_1$ integrin, $\alpha_3\beta_1$ integrin, $\alpha_v\beta_3$ integrin, the $\alpha_1$ integrin subunit, the $\alpha_2$ integrin subunit, the $\alpha_3$ integrin subunit, the $\alpha_v$ integrin subunit, the $\beta_1$ integrin subunit, the $\beta_3$ integrin subunit) for sufficient time and under conditions suitable for binding of the one or more antibodies to the cell; and where if the cell is susceptible to the action of Arresten a cell-antibody complex is formed; and then (c) detecting the presence of the cell-antibody complex; so that the presence of the cell-antibody complex in the sample is indicative of the cell's susceptibility to the action of Arresten. The mammal may have a condition characterized at least in part by undesired angiogenesis.

In further aspects, the invention features a method of determining if a cell (e.g., a cancer cell) will be susceptible to the action of Canstatin, comprising the steps of: (a) providing a sample (e.g., from a mammal) containing the cell, (b) reacting the sample with one or more antibodies (e.g., antibodies to $\alpha_1\beta_1$ integrin, $\alpha_2\beta_1$ integrin, the $\alpha_1$ integrin subunit, the $\alpha_2$ integrin subunit, the $\beta_1$ integrin subunit) for sufficient time and under conditions suitable for binding of the one or more antibodies to the cell; and where if the cell is susceptible to the action of Canstatin a cell-antibody complex is formed; and then (c) detecting the presence of the cell-antibody complex; so that the presence of the cell-antibody complex in the sample is indicative of the cell's susceptibility to the action of Canstatin. The mammal may have a condition characterized at least in part by undesired angiogenesis.

In further aspects, the invention features a method of determining if a cell (e.g., a cancer cell) will be susceptible to the action of Tumstatin, comprising the steps of: (a) providing a sample (e.g., from a mammal) containing the cell, (b) reacting the sample with one or more antibodies (e.g., antibodies to $\alpha_5\beta_1$ integrin, $\alpha_6\beta_1$ integrin, $\alpha_v\beta_3$ integrin, $\alpha_1$, integrin subunit, the $\alpha_5$ integrin subunit, the $\alpha_6$ integrin subunit, the $\alpha_v$ integrin subunit, the $\beta_1$ integrin subunit, the $\beta_3$ integrin subunit) for sufficient time and under conditions suitable for binding of the one or more antibodies to the cell; and where if the cell is susceptible to the action of Tumstatin a cell-antibody complex is formed; and then (c) detecting the presence of the cell-antibody complex; so that the presence of the cell-antibody complex in the sample is indicative of the cell's susceptibility to the action of Tumstatin. The mammal may have a condition characterized at least in part by undesired angiogenesis.

The present invention also relates to proteins comprising the NC1 domain of an a chain of Type IV collagen having anti-angiogenic properties. In particular, the present invention relates to the novel proteins Arresten, Canstatin and Tumstatin, and to biologically active (e.g., anti-angiogenic) fragments, mutants, analogs, homologs and derivatives thereof, as well as multimers (e.g., dimers) and fusion proteins (also referred to herein as chimeric proteins) thereof. These proteins all comprise the C-terminal fragment of the NC1 (non-collagenous 1) domain of Type IV collagen. More specifically, Arresten, Canstatin and Tumstatin are each a C-terminal fragment of the NC1 domain of the α1 chain, α2 chain and α3 chain, respectively, of Type IV collagen. In particular, Arresten, Canstatin and Tumstatin are monomeric proteins. All three arrest tumor growth in vivo, and also inhibit the formation of capillaries in several in vitro models, including the endothelial tube assay.

The present invention encompasses the integrin or integrin subunits (e.g., the $\alpha_1\beta_1$, $\alpha_1\beta_2$ and $\alpha_2\beta_1$ integrins) as the receptor for Arresten in endothelial cells, mediating anti-angiogenic activity, including endothelial cell apoptosis, in these cells. Arresten also specifically binds and inhibits the basement membrane-degrading activities of matrix metalloproteinases 2, 3 and 9; such degradative activity is an integral part of angiogensis.

The present invention also encompasses isolated and recombinantly-produced Arresten, which comprises the NC1 domain of the α1 chain of Type IV collagen, having anti-angiogenic activity, anti-angiogenic fragments of the isolated Arresten, multimers of the isolated Arresten and anti-angiogenic fragments, and polynucleotides encoding those anti-angiogenic proteins. Also encompassed are compositions comprising isolated Arresten, its anti-angiogenic fragments, or both, as biologically active components. In another embodiment, the invention features a method of treating a proliferative disease such as cancer, in a mammal where said disease is characterized by angiogenic activity, the method comprising administering to the mammal a composition containing anti-angiogenic Arresten or its fragments. The anti-angiogenic Arresten and its fragments can also be used to prevent cell migration or endothelial cell proliferation. Also featured are antibodies to the isolated anti-angiogenic Arresten and its fragments.

The present invention also encompasses the integrins or integrin subunits (e.g., $\alpha_1\beta_1$ and $\alpha_1\beta_2$ integrins) as the cell adhesion receptors for Canstatin in endothelial cells, mediating anti-angiogenic activity, including endothelial cell apoptosis, in these cells.

The present invention also encompasses isolated and recombinantly produced Canstatin, which comprises the NC1 domain of the α2 chain of Type IV collagen, having anti-angiogenic activity, anti-angiogenic fragments of the isolated Canstatin, multimers of the isolated Canstatin and anti-angiogenic fragments, and polynucleotides encoding those anti-angiogenic proteins. Also encompassed are compositions comprising isolated Canstatin, its anti-angiogenic fragments, or both, as biologically active ingredients. In another embodiment, the invention features a method of treating a proliferative disease such as cancer, in a mammal, where said disease is characterized by angiogenic activity, the method comprising administering to the mammal a composition containing anti-angiogenic Canstatin or its fragments. The anti-angiogenic Canstatin and its fragments can also be used to prevent cell migration or endothelial cell proliferation. Also featured are antibodies to the isolated anti-angiogenic Canstatin and its fragments.

The present invention also encompasses the integrins and integrin subunits (e.g., $\alpha_5\beta_1$, $\alpha_6\beta_1$ and $\alpha_v\beta_3$ integrins) as receptors of Tumstatin in endothelial cells, mediating anti-angiogenic activity, including endothelial cell apoptosis, in these cells.

The invention likewise also encompasses isolated and recombinantly-produced Tumstatin, comprising the NC1 domain of the α3 chain of Type IV collagen, having anti-angiogenic activity, anti-angiogenic fragments of the isolated Tumstatin, multimers of the isolated Tumstatin and anti-angiogenic fragments, and polynucleotides encoding those anti-angiogenic proteins. Also encompassed are compositions comprising isolated Tumstatin, its anti-angiogenic fragments, or both, as biologically active ingredients. In another embodiment, the invention features a method of treating a proliferative disease such as cancer in a mammal, where said disease is characterized by angiogenic activity, the method comprising administering to the mammal a composition containing anti-angiogenic Tumstatin or its fragments. The anti-angiogenic Tumstatin and its fragments can also be used to prevent cell migration or endothelial cell proliferation. Also featured are antibodies to the isolated anti-angiogenic Tumstatin and its fragments.

BRIEF DESCRIPTION OF THE DRAWINGS

FIGS. 1A and 1B are diagrams depicting the nucleotide (FIG. 1A, SEQ ID NO:1) and amino acid (FIG. 1B, SEQ ID NO:2) sequences of the α1 chain of human Type IV collagen. The locations of the pET22b(+) forward (SEQ ID NO:3) and reverse (SEQ ID NO:4) primers are indicated by double underlining, and the locations of the pPICZαA forward (SEQ ID NO:15) and reverse (SEQ ID NO:16) primers are indicated by single underlining.

FIGS. 4A, 4B and 4C show the effect of Arresten (0 μg/ml-50 μg/ml (FIGS. 4A and 4B) and 0 μg/ml-10 μg/ml (FIG. 4C)) on 786-O, PC-3, HPEC cells respectively. FIG. 4D shows the effect of 0.1-10 μg/ml endostatin on A-498 cells.

FIG. 5A shows untreated control cells.

FIG. 6 shows the effect of either Arresten (2 μg/ml or 20 μg/ml) and endostatin (2.5 μg/ml and 20 μg/ml) on the migration of ECV-304 endothelial cells.

FIG. 9A is a plot showing the increase in tumor volume from 700 mm$^3$ for 10 mg/kg Arresten-treated (□), BSA-treated (+), and control mice (●). FIG. 9B shows the increase in tumor volume from 100 mm$^3$ for 10 mg/kg Arresten-treated (□) and BSA-treated (+) tumors. FIG. 9C shows the increase in tumor volume from about 100 mm$^3$ for 10 mg/kg Arresten-treated (□), Endostatin-treated (▲), and control mice (●). FIG. 9D shows the increase for 200 mm$^3$ tumors when treated with Arresten (□) versus controls (●).

FIGS. 11A and 11B are diagrams depicting the nucleotide (FIG. 11A, SEQ ID NO:5) and amino acid (FIG. 11B, SEQ ID NO:6) sequences of the α2 chain of human Type IV collagen. The locations of the pET22b(+) forward (SEQ ID NO:7) and reverse (SEQ ID NO:8) primers are indicated by double underlining, and the location of the pPICZαA forward (SEQ ID NO:17) and reverse (SEQ ID NO:18) primers are indicated by single underlining.

FIGS. 18A and 18B are diagrams depicting the nucleotide (FIG. 18A, SEQ ID NO:9) and amino acid (FIG. 18B, SEQ ID NO:10) sequence of the α3 chain of human Type IV collagen. The locations of the pET22b(+) forward (SEQ ID NO:11) and reverse (SEQ ID NO:12) primers are indicated by double underlining. The beginning and end of the "Tumstatin 333" (SEQ ID NO:20) and "Tumstatin 334" (SEQ ID NO:21) fragments are also indicated ("*"=Tumstatin 333; "+"=Tumstatin 334).

FIGS. 21A, 21B and 21C are a set of three histograms showing $^3$H-thymidine incorporation (y-axis) for C-PAE cells (FIG. 21A), PC-3 cells (FIG. 21B) and 786-O cells (FIG. 21C) when treated with varying concentrations of Tumstatin (x-axis). All groups represent triplicate samples.

FIGS. 36A, 36B and 36C show the percent binding of C-PAE cells (y-axis) to plates coated with Tum-1 (FIG. 36A), Tum-2 (FIG. 36B) and Tum-4 (FIG. 36C) in the presence of control IgG, $\alpha v\beta_3$, $\alpha_v\beta_5$ and BSA.

FIG. 42 is a diagram of the Tumstatin protein sequence, with the locations of the T1, T2, T3, T4, T5 and T6 peptides indicated. GP-A=first Goodpasture epitope. GP-B=second Goodpasture epitope.

FIG. 43A shows proliferation of C-PAE cells (y-axis) treated with 10 μg/ml of peptide T2, T3, T4, T5 or T6 (x-axis). FIG. 43B shows proliferation of C-PAE cells (y-axis) treated with 0.1, 1.0 or 10 μg/ml T3 peptide. FIG. 43C shows cell growth of C-PAE cells (y-axis) when treated with T3 peptide that has been pre-incubated with varying concentrations (x-axis) of $\alpha_v\beta_3$ integrin. FIG. 43D shows cell viability (y-axis) of C-PAE cells as determined by MTT assay, after treatment of the cells with 10 μg/ml of peptides T2, T3, T4, T5 or T6. All columns represent the mean ±SEM of triplicate wells.

FIG. 44A shows binding (y-axis) of HUVEC cells to plates coated with Tum-5 peptide (10 μg/ml), in the presence of BSA (control), no antibody (control), mouse IgG (control) and $\alpha_v\beta_3$ integrin antibody (x-axis). FIG. 44B is a histogram showing attachment of C-PAE cells (y-axis) to 96-well plates that were coated with 10 μg/ml recombinant Tum-5 peptide (x-axis). FIG. 44C is a histogram showing binding of C-PAE cells (y-axis) to 96-well plates coated (x-axis) with Tum-5 and treated with 2.5 μg/ml peptides T2, T3, T4, T5 or T6, or Tum-4-coated plates treated with T3. PBS treatment served as control. FIG. 44D shows the effect on binding of C-PAE cells (y-axis) to Tum-5-coated plates of varying concentrations of T3 peptide (x-axis). PBS treatment served as a control. FIG. 44E shows the binding of C-PAE cells (y-axis) to T2, T3, T4, T5 or T6-coated plates (x-axis) in the presence of PBS (control), IgG (control), or $\alpha_v\beta_3$ integrin antibody. FIG. 44F shows binding of C-PAE cells (y-axis) to T3-coated plates when incubated with PBS (control), IgG (control), or $\alpha_v$ integrin antibody, $\beta_1$ integrin antibody, $\beta_3$ integrin antibody, $\alpha_v\beta_5$ integrin antibody, or BSA (control) (x-axis). FIG. 44G shows binding of C-PAE cells (y-axis) to plates coated with vitronectin (2.5 μg/ml) when incubated with PBS (control), BSA (control) or varying (0.1, 1.0, 10.0 μg/ml) concentrations of T3 peptide or varying (0.1, 1.0, 10.0 μg/ml) concentrations of T6 peptide (x-axis). Each column represents the mean ±the SEM of triplcate wells. The experiments were repeated three times. *P<0.05 by one-tailed Student's t-test.

FIG. 50A shows cell proliferation measured by BrdU assay (at $OD_{450}$, y-axis), with C-PAE cells treated with E. Coli-expressed Tumstatin-44-131 (black bars), or 293 cell-expressed full-length Tumstatin (white bars), at concentrations of 0, 0.125, 0.250, 0.500, 1.0 or 2.0 μM (x-axis). FIG. 50B shows cell proliferation as measured by methylene blue staining (at $OD_{655}$), with C-PAE cells treated with Pichia-expressed Tumstatin-44-131 at concentrations of 0, 0.1, 1.0, 5.0 and 10.0 μg/ml (x-axis). Unstimulated C-PAE cells served as the control.

FIG. 52A shows cell viability as measured at $OD_{562}$ (y-axis) in an MTT assay, for C-PAE cells treated with 0, 3, 6, 12, 25 and 50 µg/ml (x-axis) Tumstatin-44-131 (black bars) and Tumstatin-44-131 that was alkylated and reduced (white bars). FIG. 52B shows cell viability as measured at $OD_{562}$ (y-axis) in an MTT assay, for C-PAE cells treated with 0, 3, 6, 12, 25 and 50 µg/ml (x-axis) Tum-5-125-C-A. FIG. 52C shows cell viability as measured at $OD_{562}$ (y-axis) in an MTT assay, for PC-3 cells treated with 0, 3, 6, 12, 25 and 50 µg/ml (x-axis) Tumstatin-44-131. FIG. 52D shows cell viability as measured at $OD_{562}$ (y-axis) in an MTT assay, for DU-145 cells treated with 0, 3, 6, 12, 25 and 50 µg/ml (x-axis) Tumstatin-44-131.

FIG. 55A shows cell binding in the presence of 10 µg/ml peptides T1, T2, T3, T4, T5, T6, Tum-4, and FIG. 55B shows cell binding in the presence of 0.1, 2.0 or 10.0 µg/ml T3 peptide.

FIGS. 58A-58H are a series of eight histograms showing $^{35}$S-methionine incorporation (y-axes) in cells under various treatments (x-axes). The experiments were repeated three times and representative data are shown. Each column consists of the mean ±SEM of triplicates. In FIG. 58A, C-PAE cells were treated for either 12 hours (black bars) or 24 hours (cross-hatched bars) with T3 peptide (4.5 µM), Tumstatin-44-131 (4.5 µM), endostatin (4.5 µM) or rapamycin (100 ng/ml). In FIG. 58B, HUVECs were treated for 24 hours with T3 peptide (4.5 µM), Tumstatin-44-131 (4.5 µM), endostatin (4.5 µM) or rapamycin (100 ng/ml). In FIG. 58C, C-PAEs were serum-starved for 12 or 24 hours, and then incubated with medium containing 10% FCS for 24 hours in the presence of T3 peptide at 0 µM (control, black bars), 4.5 µM (bars with horizontal cross-hatching), or 22.7 µM (bars with slanted cross-hatching). In FIGS. 58D-H, PC-3 cells, (FIG. 58D), 786-O cells (FIG. 58E), NIH3T3 cells (FIG. 58F), HRE cells (FIG. 58G) and WM-164 cells (FIG. 58H) were treated for 24 hours with T3 peptide (4.5 µM), Tumstatin-44-131 (4.5 µM), T7 peptide (FIG. 58D, FIG. 58E, FIG. 58H), endostatin (4.5 µM) or rapamycin (100 ng/ml).

FIGS. 59A and 59B are a pair of histograms showing the reporter activity (y-axis) for translation of luciferase (LUC; cap-dependent translation; black bars) or chloramphenicol acetyltransferase (CAT; cap-independent translation; cross-hatched bars), under treatment by T3 peptide (4.5 µM), Tumstatin-44-131 (4.5 µM), T7 peptide (4.5 µM), endostatin (4.5 µM) or rapamycin (100 ng/ml). Luciferase and CAT activity relative to the control group is shown. These experiments were repeated three times and representative data are shown. Each column consists of mean ±SEM of triplicates.

FIGS. 60A-60H are a set of eight histograms. FIGS. 60A-60D show total protein synthesis in terms of $^{35}$S-methionine incorporation (y-axis) in endothelial cells (MLEC) (FIGS. 60A and 60B) and embryonic fibroblasts (MEF) (FIGS. 60C and 60D) from wild-type (FIGS. 60A and 60C) and $β_3$-integrin knockout (FIGS. 60B and 60D) littermate mice, where the cells were treated (x-axis) with Tumstatin-44-131 (4.5 µM), T3 (4.5 µM), T7 (4.5 µM), T7-mutant peptide (4.5 µM), endostatin (4.5 µM) or rapamycin (100 ng/ml). FIGS. 60E-60G show reporter activity of either luciferase (Luc; black bars) or chloramphenicol acetyltransferase (CAT; cross-hatched bars) as a percentage of control (y-axis) in endothelial cells (MLEC) (FIGS. 60E and 60F) and embryonic fibroblasts (MEF) (FIGS. 60G and 60H) from wild-type (FIGS. 60E and 60G) and $P_3$-integrin knockout (FIGS. 60F and 60H) littermate mice, where the cells were treated (x-axis) with Tumstatin-44-131 (4.5 µM), T3 (4.5 µM), T7 (4.5 µM), T7-mutant peptide (4.5 µM), endostatin (4.5 µM) or rapamycin (100 ng/ml). These experiments were repeated three times and the representative data are shown. Each column consists of mean ±SEM of triplicates.

FIG. 61A shows the relative density of pFAK/FAK (y-axis) under treatments of (x-axis) no attachment time to vitronectin-coated plates and in the absence of T3 peptide ("0–" bar), 30 minutes attachment time and no T3 peptide ("30–" bar), 30 minutes attachment time and 50 µg/ml T3 peptide ("30+" bar), 60 minutes attachment time and no T3 peptide ("60–" bar) and 60 minutes attachment time and 50 µg/ml T3 peptide ("60+" bar). FIG. 61B shows PI3-kinase activity (y-axis) under treatments of (x-axis) no attachment time to vitronectin-coated plates and in the absence of T3 peptide ("0–" bar), 30 minutes attachment time and no T3 peptide ("30–" bar), 30 minutes attachment time and 50 µg/ml T3 peptide ("30+" bar), 60 minutes attachment time and no T3 peptide ("60–" bar) and 60 minutes attachment time and 50 µg/ml T3 peptide ("60+" bar). FIG. 61C shows the relative density of pFAK/FAK (y-axis) under the same treatments as in FIG. 61A (x-axis). FIG. 61D shows mTOR-kinase activity (y-axis) under treatments of (x-axis) no mTOR transfection and no peptide treatment ("--" bar), mTOR transfection and no peptide treatment ("±" bar), mTOR transfection and treatment with Tumstatin-44-131 ("+Tum-5" bar) and mTOR transfection and treatment with peptide T3 ("+T3" bar). FIG. 61E shows the density of eIF4E-bound 4E-BP1 (y-axis) in C-PAE cells after treatment with no FBS, T3, Tumstatin-44-131, Rapamycin, Endostatin or FBS (x-axis). FIG. 61F shows the percent luciferase activity relative to CAT activity (y-axis) for C-PAEs that were either infected with adenoviral vectors containing cDNAs of control lacZ (shaded bars), constitutive active Akt (cross-hatched bars), or not infected at all (black bars). The cells were then serum starved, transfected with pcDNA-LUC-pol-CAT, and treated with T3 peptide in the presence of medium containing 10% FCS.

In FIG. 64A, the treatments were: the stock vehicle used for T7 (○), T7 daily (□), stock vehicle used for T8 (◇), T8 daily (X), TP3 daily (+), SP1 daily (Δ) and SP2 daily (●). In FIG. 64B, the treatments were: the stock vehicle for T8 (○), T8 daily (□); T8 twice weekly (◇) and T8 weekly (X).

FIGS. 65A and 65B show the results for the MDAMB-435 and PC3 xenograft models, respectively.

DETAILED DESCRIPTION OF THE INVENTION

Figure 2:
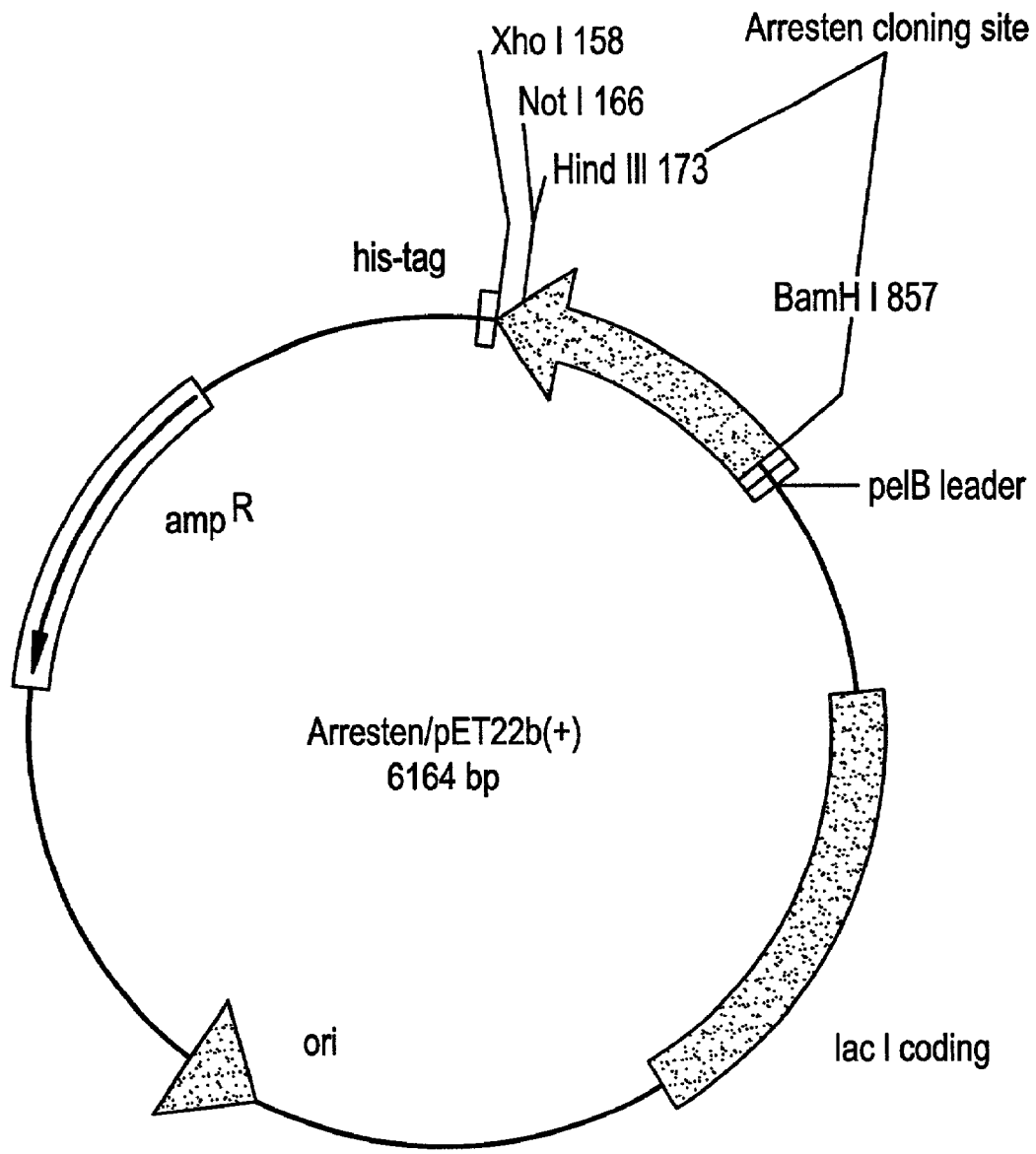
FIG. 2 is a schematic diagram representing the Arresten cloning vector pET22b(+). Forward (SEQ ID NO:3) and reverse (SEQ ID NO:4) primers and site into which Arresten was cloned are indicated.

A wide variety of diseases are the result of undesirable angiogenesis. Put another way, many diseases and undesirable conditions could be prevented or alleviated if it were possible to stop the growth and extension of capillary blood vessels under some conditions, at certain times, or in particular tissues. Basement membrane organization is dependent on the assembly of a type IV collagen network which is speculated to occur via the C-terminal globular non-collagenous (NC1) domain of type IV collagen (Timpl, R., 1996, Curr. Opin. Cell. Biol. 8:618-24; Timpl, R. et al., 1981, Eur. J. Biochem. 120:203-11). Type IV collagen is composed of six distinct gene products, namely, α1 through α6 (Prockop, D. J. et al., 1995, Annu. Rev. Biochem. 64:403-34). The α1 and α2 isoforms are ubiquitously present in human basement membranes (Paulsson, M., 1992, Crit. Rev. Biochem. Mol. Biol. 27:93-127), while the other four isoforms exhibit restricted distributions (Kalluri, R. et al., 1997, J. Clin. Invest. 99:2470-78).

The formation of new capillaries from pre-existing vessels, angiogenesis, is essential for the process of tumor growth and metastasis (Folkman, J. et al., 1992, J. Biol. Chem. 267:10931-34; Folkman, J. 1995, Nat. Med. 1:27-31; Hanahan, D. et al., 1996, Cell 86:353-64). Human and animal tumors are not vascularized at the beginning, however, and for a tumor to grow beyond few mm it must vascularize (Folkman, J. 1995, Nat. Med. 1:27-31; Hanahan, D. et al., 1996, Cell 86:353-64). The switch to an angiogenic phenotype requires both upregulation of angiogenic stimulators and downregulation of angiogenesis inhibitors (Folkman, J. 1995, Nat. Med. 1:27-31). Vascular endothelial growth factor (VEGF) and basic fibroblast growth factor (bFGF) are the most commonly expressed angiogenic factors in tumors. Vascularized tumors may overexpress one or more of these angiogenic factors which can synergistically promote tumor growth. Inhibition of a single angiogenic factor such as VEGF with a receptor antagonist is not enough to arrest tumor growth. A number of angiogenesis inhibitors have been recently identified, and certain factors such as IFN-α, platelet-factor-4 (Maione, T. E. et al., 1990, Science 247:77-9) and PEX (Brooks, P. C. et al., 1998, Cell 92:391-400) are not endogenously associated with tumor cells, whereas angiostatin (O'Reilly, M. S. et al., 1994, Cell 79:315-28) and endostatin (O'Reilly, M. S. et al., 1997, Cell 88:277-85) are tumor associated angiogenesis inhibitors generated by tumor tissue itself. Although treatment of tumor growth and metastasis with these endogenous angiogenesis inhibitors is very effective and an attractive idea, some potential problems associated with anti-angiogenic therapies must be considered. Delayed toxicity induced by chronic anti-angiogenic therapy as well as the possibility of impaired wound healing and reproductive angiogenesis occurring during treatment are to be considered seriously.

Integrins generally have a short C-terminal cytoplasmic domain linking the receptor to the cytoskeleton of the cell, and a long N-terminal extracellular domain for binding the ligand. Both the α and the β subunits are involved in ligand binding, and a wide array of potential ligands exists. Some common ligands include fibronectin, vitronectin, laminin, and various types of collagen. Some of these (e.g., fibronectin and laminin) are bound by multiple integrins. Collagen I is known to be bound by integrins $\alpha_1\beta_1$, $\alpha_2\beta_1$, and $\alpha_3\beta_1$ and collagen IV is bound by integrins $\alpha_2\beta_1$, and $\alpha_2\beta_1$. Epithelial cells are bound by integrins $\alpha_2\beta_1$, $\alpha_6\beta_1$, $\alpha_v\beta_3$ and $\alpha_6\beta_4$. Cytokine-activated endothelial cells are bound by $\alpha_4\beta_1$ and $\alpha_L\beta_2$, and vascular endothelium is bound by the $\alpha_M\beta_2$ integrin.

In the present invention, cell surface receptors that interact, e.g., specifically bind, anti-angiogenic proteins and peptides are disclosed, particularly the integrins and integrin subunits that bind the anti-angiogenic proteins Arresten, Canstatin and Tumstatin. These integrins provide targets for assessing new anti-angiogenic proteins, peptides and compounds, or more potent variants and fragments of currently-known anti-angiogenic proteins, peptides and compounds, especially more potent variants and fragments of Arresten, Canstatin and Tumstatin. Specifically, the invention relates to the integrin subunits $\alpha_1$, $\alpha_2$, $\alpha_3$, $\alpha_v$, $\beta_1$ and $\beta_3$, which have been found to bind to Arresten, which is the α1 chain of the NC1 domain of Type IV collagen. The invention also relates to the integrin subunits $\alpha_1$, $\alpha_2$ and $\beta_1$, which have been found to bind to Canstatin, which is the α2 chain of the NC1 domain of Type IV collagen. In addition, the invention relates to integrin subunits $\alpha_5$, $\alpha_6$, $\alpha_v$, $\beta_1$ and $\beta_3$, which have been found to bind to Tumstatin, the α3 chain of the NC1 domain of Type IV collagen. Other integrins or integrin subunits may also bind to Arresten, Canstatin or Tumstatin, and these may be identified by using the methods described herein (see, e.g., Examples 12, 26 and 28, below).

Angiogenesis and proliferation of endothelial cells may be inhibited, or endothelial cell apoptosis may be promoted or induced, by either administering Arresten, Canstatin or Tumstatin, or administering another protein, peptide or compound that binds to the above-listed integrin subunits, which serve as receptors for Arresten, Canstatin and Tumstatin. Such proteins, peptides and compounds include antibodies, fragments or portions of Arresten, Canstatin or Tumstatin, or proteins or peptides comprising those regions of Arresten, Canstatin or Tumstatin which specifically bind to the above-listed integrin subunits. "Specifically binds" means having high avidity and/or high affinity binding of a ligand (e.g., antigen) to a specific binding protein (e.g., antibody or receptor). For example, antibody binding to its epitope on this specific antigen is stronger than binding of the same antibody to any other epitope, particularly those which may be present in molecules in association with, or in the same sample, as the specific antigen of interest. Antibodies which bind specifically to a molecule of interest may be capable of binding other molecules at a weak, yet detectable, level (e.g., 10% or less of the binding shown to the molecule of interest). Such weak binding, or background binding, is readily discernible from the specific antibody binding to the molecule of interest, e.g. by use of appropriate controls.

Antibodies to particular peptides are commonly made, and the methods of producing antibodies to a given protein are well-known to those of ordinary skill in the art. See, e.g., Chapter 11 of Ausubel, F. M. et al., CURRENT PROTOCOLS IN MOLECULAR BIOLOGY, (John Wiley & Sons, Inc., 1987, with Supplements through 1999), especially pages 11.4.2-11.11.5 ("Preparation of Monoclonal Antibodies"), 11.12.1-11.13.4 ("Preparation of Polyclonal Antisera") and most especially pages 11.14.1-11.15.4 ("Preparation of Antipeptide Antibodies"). Custom antibodies can also be purchased commercially from a number of suppliers, e.g., from Berkeley Antibody Co., Richmond, Calif., USA. Methods of making antibodies to integrins and integrin subunits are also well known, and methods of making such antibodies are described in Gallatin, W. M. et al. (U.S. Pat. No. 5,817,515), and Kim, K. J. et al. (U.S. Pat. No. 5,652,110; No. 5,652,109; No. 5,578,704), the entire contents of all of which are incorporated herein by reference.

The integrins and integrin subunits described herein can be made recombinantly, and in soluble form. Methods of making soluble receptors and proteins are well-known in the art, and methods of making integrins and integrin receptors in soluble form are described in Briesewitz, R. et al. (1993, J. Biol. Chem. 268:2989-96), Kern, A. et al. (1994, J. Biol. Chem. 269:22811-6); and also in Gallatin, W. M. et al. (U.S. Pat. No. 5,728,533 and No. 5,831,029) and Duong, L. T. et al. (U.S. Pat. No. 5,895,754), the entire contents of all of which are incorporated herein by reference.

The invention also relates to methods of enhancing angiogenesis and cell proliferation, or inhibiting cell apoptosis, by administering proteins, peptides or compounds that mimic the integrin subunits that serve as receptors for Arresten, Canstatin or Tumstatin. Such proteins, peptides or compounds include integrin proteins composed of the selected subunits, which serves to bind available Arresten, Canstatin or Tumstatin, and biologically active (e.g., anti-angiogenic) fragments, mutants, analogs, homologs and derivatives thereof, as well as multimers (e.g., dimers) and fusion proteins (also referred to herein as chimeric proteins) thereof, thereby preventing them from interacting with their respective integrin receptors and inhibiting angiogenic activity. The proteins, peptides or compounds binding to Arresten, Canstatin or Tumstatin, or variants and fragments thereof can also include antibodies to Arresten, Canstatin and Tumstatin, or to the variants or fragments thereof. Such antibodies bind these molecules, thereby preventing them from interacting with their respective integrin receptors and inhibiting angiogenic activity.

In the present invention, Arresten, Canstatin and/or Tumstatin, or their fragments or mutants, may be used alone or in combination to inhibit angiogenesis, endothelial cell proliferation, endothelial cell migration, or endothelial cell tube formation in a tissue, or to induce or promote apoptosis in a tissue, e.g., Arresten and Canstatin can be combined in a pharmaceutical composition, Tum-4 and T7 can be combined in a composition, etc. The combination of Arresten, Canstatin and/or Tumstatin can be further combined with other collagen domains or NC1 chains, or other forms of therapy, e.g., radiotherapy, chemotherapy, immunotherapy, or other active molecules, e.g., endostatin, angiostatin, restin. These molecules decrease levels of the anti-apoptotic protein, FLIP (FLICE-Inhibitory Protein, or FADD-Like Interleukin-1β-Converting Enzyme-Inhibitory Protein). Angiogenesis is therefore inhibited by molecules that decrease levels of FLIP, thereby triggering caspase activation and delivering a terminal apoptotic signal.

The receptors to Arresten, Canstatin and Tumstatin described herein (e.g., the $\alpha_1\beta_1$, $\alpha_2\beta_1$, $\alpha_3\beta_1$, $\alpha_5\beta_1$, $\alpha_6\beta_1$, and $\alpha_v\beta_3$ integrins) and/or their subunits (e.g., $\alpha_1$, $\alpha_2$, $\alpha_3$, $\alpha_5$, $\alpha_6$, $\alpha_v$, $\beta_1$, $\beta_3$) can be used in combination to promote or induce angiogenesis. The antibodies to Arresten, Canstatin, and/or Tumstatin can also be combined into a single therapeutic regimen, as can the antibodies to the receptors to Arresten, Canstatin and Tumstatin, and their receptor subunits.

The invention also includes kits for identifying anti-angiogenic proteins, peptides and compounds which inhibit angiogenesis in a manner similar to Arresten, Canstatin and Tumstatin, and anti-angiogenic variants and fragments thereof. Such kits comprise appropriate (e.g., $\alpha_1$, $\alpha_2$, $\beta_3$, etc.) subunits of integrin, and such other ingredients necessary to perform one of the assays described in the Examples below. Exceptional assays to be performed with such a kit would include the Cell Adhesion Assay, described in Examples 12 and 28 below, and the Competition Proliferation Assay, described in Example 26 below. For instance, a kit for identifying proteins, peptides or compounds that behave in a manner similar to Tumstatin would include those ingredients and reagents necessary to perform the Cell Adhesion Assay of Example 28, such as antibodies to integrin subunits $\alpha 6$, $\beta_1$, $\alpha_v$, $\beta_3$ and IgG (which serves as a control). The kit can optionally include 96-well plates to be coated with the test compound and controls such as collagen Type IV or laminin-1 (or the plates can optionally be pre-coated). The kit can also optionally include BSA or other blocking agent, and cells (e.g., HUVEC cells) for attachment, as well as reagents for growing, trypsinizing, resuspending and staining the cells.

Once a potential anti-angiogenic compound has been identified, another kit can be used to demonstrate loss of anti-angiogenic activity by competition with the same integrin subunits used to identify the compound in the first place. Such a kit could be modeled on the Competition Proliferation Assay described in Example 26, below. The kit could include cells useful in the proliferation assay (described in the Examples, below), and the appropriate integrin subunits in protein form. The kit can also optionally include stains and other reagents necessary or useful in determining the effect of the integrin subunit protein in interfering with the anti-proliferative activity of the test compound.

In the present invention, proteins, and fragments, analogs, derivatives, homologs and mutants thereof with anti-angiogenic properties are described, along with methods of use of these proteins, analogs, derivatives, homologs and mutants to inhibit angiogenesis-mediated poliferative diseases. The proteins comprise the NC1 domain of the α chain of Type IV collagen, or portions of the domain, and specifically comprise monomers of the NC1 domain of the α1, α2 and α3 chains of Type IV collagen. These proteins, especially when in monomeric form, arrest tumor growth in in vivo models of cancer, and also inhibit the formation of capillaries in several in vitro models, including the endothelial tube assay.

These proteins may also include the junction region of the NC1 domain. The α1, α2, or α3 chains are preferred, as evidence suggests that the α4, α5, and α6 chains have reduced or non-detectable anti-angiogenic activity. In general, monomeric forms of the proteins are preferred, as evidence suggests that the hexameric forms also have little or reduced activity.

More particularly, the present invention describes a protein designated "Arresten," which is a protein of about 230 amino acids long, corresponding to the amino acids at the N-terminus of the α1 chain of the NC1 domain of human Type IV collagen (Hostikka, S. L. et al., 1988, J. Biol. Chem. 263:19488-93).

As disclosed herein, human Arresten can be produced in *E. Coli* using a bacterial expression plasmid, such as pET22b, which is capable of periplasmic transport, thus resulting in soluble protein. The protein is expressed as a 29 kDa fusion protein with a C-terminal six-histidine tag. The additional 3 kDa (beyond 26 kDa) arises from polylinker and histidine tag sequences. Arresten was also produced as a secreted soluble protein in 293 kidney cells using the pcDNA 3.1 eukaryotic vector. This 293-produced protein has no purification or detection tags.

Arresten causes endothelial cell apoptosis as early as two hours after treatment, and this effect was specific for endothelial cells with no significant cell death observed in tumor cells treated with high doses of Arresten. A representative CD-31 staining pattern showed a decrease in the vasculature of treated versus control mice. Tumor sections were stained for Proliferating Cell Nuclear Antigen (PCNA), fibronectin and Type IV collagen, and showed no difference in tumor cell proliferation, or content or architecture of Type IV collagen and fibronectin surrounding tumor cells.

*E. Coli*-produced Arresten inhibits proliferation of bFGF-stimulated endothelial cells in a dose-dependent manner, with an $ED_{50}$ of 0.25 µg/ml. No significant effect was observed on proliferation of renal carcinoma cells (786-O), prostate cancer cells (PC-3), or human prostate epithelial cells (HPEC). Endostatin inhibited proliferation of C-PAE cells at an $ED_{50}$ of 0.75 µg/ml, 3-fold higher than Arresten, and did not inhibit A-498 cancer cells.

The specific inhibition of endothelial cell proliferation and migration, as described herein, indicates that Arresten functions via a cell surface protein or receptor. Inhibition of matrix metalloproteinase, or MMP, suggests a direct role of Arresten in tumor growth and metastases, similar to batimastat (BB-94) and marimastat (BB-2516).

Figure 10A:
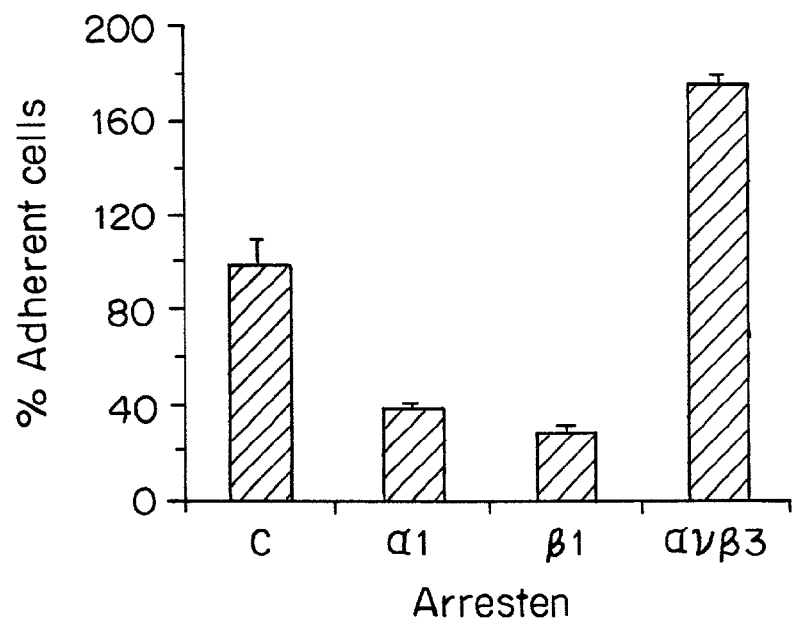
FIGS. 10A and 10B are a pair of histograms showing the amount of Caspase-3 activity as a function of absorbance at OD$_{405}$ (y-axis) for C-PAE cells (FIG. 10A) and PC-3 cells (FIG. 10B) under various treatments (x-axis). Each column represents the mean the standard error of the mean of triplicate well.
Figure 10B:
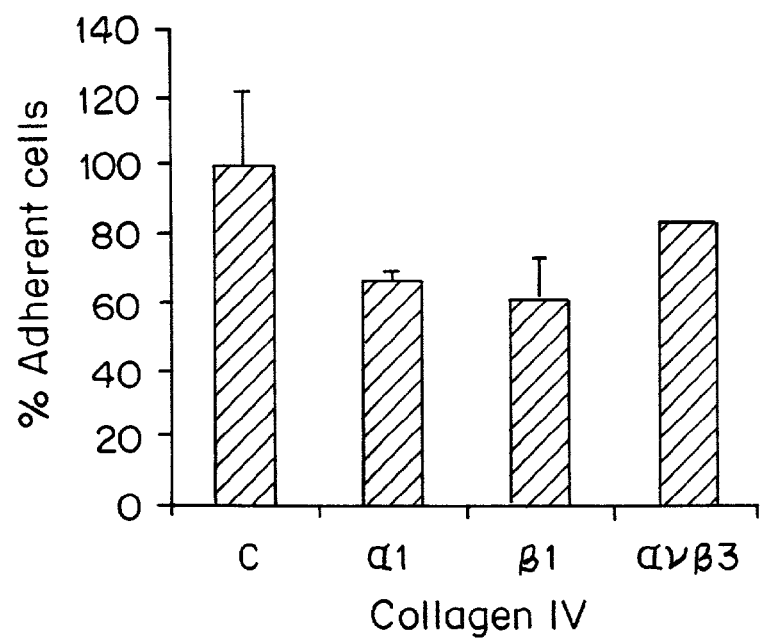

Recent studies have speculated that $\alpha_1\beta_1$ and $\alpha_2\beta_1$ integrins bind to type IV collagen isolated from the EHS Sarcoma tumour (Senger, D. R. et al., 1997, Proc. Natl. Acad. Sci. USA 94:13612-7). Because Arresten is a fragment of the α1 chain of type IV collagen, it was assessed for its capacity to mediate endothelial cell binding via $\alpha_1\beta_1/\alpha_2\beta_1$ integrins. It was shown to functionally block antibodies to the $\alpha_1$ and $\beta_1$ subunits, and to significantly diminish the binding of HUVEC cells to Arresten coated culture wells (FIG. 10A). Endothelial cell attachment to Arresten-coated plates was inhibited of 60% with $\alpha_1$ antibody and 70% with $\beta_1$ integrin antibody. These results are consistent with the results of binding assays using $^{125}I$ labeled Arresten. Arresten binds endothelial cells with a high affinity $Kd_1$ value of $8.5\times10^{-11}$ and a low affinity $Kd_2$ value of $4.6\times10^{-8}$. When plates were coated with collagen type IV, a moderate inhibition was observed of 30% with neutralizing antibodies to $\alpha_1$, 40% with $\beta_1$ antibodies and 15% with $\alpha_v\beta_3$ antibodies (FIG. 10B). The difference in cell adhesion between Arresten- and collagen IV-coated plates may be due to potential additional integrin binding sites on the whole collagen IV molecule, whereas Arresten provides a single and specific binding site for the $\alpha_1\beta_1$ integrin (see FIGS. 10A and 10B).

The tumour-suppressing activity of Arresten can be mediated by integrins, specifically $\alpha_1\beta_1$. Binding of Arresten to $\alpha_1\beta_1$ may downregulate the VEGF-induced proliferation and migration of endothelial cells, as suggested by VEGF dependency on $\alpha_1\beta_1$ integrin shown previously by others (Bloch, W. et al., 1997, J. Cell. Biol. 139:265-78). Collectively, these results indicate that Arresten may be exerting its effect at different stages in the angiogenic cascade. It had been shown that antibodies to the $\alpha_1$ and $\alpha_2$ integrin subunits can suppress angiogenesis in vivo (Senger, D. R. et al., WO 99/16465). Arresten may function by suppressing the activity of either VEGF and/or bFGF directly. A half-life for Arresten of 36 hours in rats suggests that the dose required for clinical use may be much less than for other protein inhibitors such as endostatin and angiostatin (O'Reilly, M. S. et al., 1994, Cell 79:315-28; O'Reilly, M. S., et al., 1997, Cell 88:277-85).

In the present invention, Canstatin, the NC1 domain of the α2 chain of Type IV collagen was used to inhibit angiogenesis, as assayed by inhibition of the proliferation and migration of endothelial cells, and by inhibition of endothelial tube formation. Canstatin inhibited endothelial cell proliferation and induced apoptosis of these cells with no inhibition of proliferation or apoptosis of non-endothelial cells. Canstatin-induced apoptosis is mediated by down-regulation of the anti-apoptotic protein, FLIP. CD-31 histological staining showed a decrease in the vasculature of treated vs. control mice. The specific inhibition of endothelial cell proliferation and migration by Canstatin also demonstrate its anti-angiogenic activity, and that it may function via a cell surface protein/receptor. Integrins are potential candidate molecules based on their extracellular matrix binding capacity and ability to modulate cell behavior such as migration and proliferation. In particular, $\alpha_v\beta_3$ integrin is a possible Canstatin receptor, due to its induction during angiogenesis, and its promiscuous binding capacity.

Figure 22:
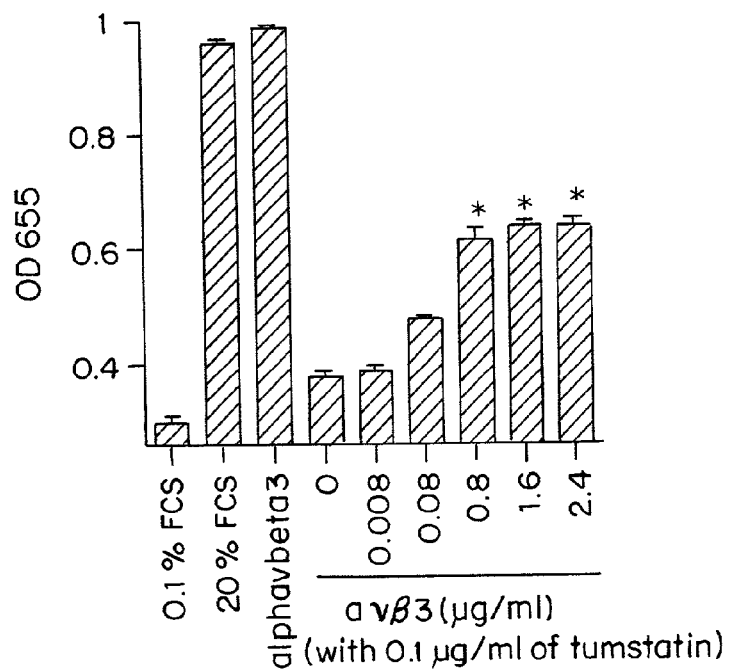
FIG. 22 is a histogram showing on the x-axis the effect of 0.1 µg/ml Tumstatin combined with increasing amounts of $\alpha_v\beta_3$ on the uptake of dye by C-PAE cells. Absorbance at $OD_{655}$ is shown on the y-axis. "0.1% FCS" represents the 0.1% FCS-treated (unstimulated) control, and "20% FCS" is the 20% FCS-treated (stimulated) control. The remaining bars represent a control of $\alpha_v\beta_3$ alone, and treatments with Tumstatin plus increasing concentrations of $\alpha_v\beta_3$. Each bar represents the mean ±the standard error of the mean for triplicate well. The experiments were repeated three times. An asterisk indicates that P<0.05 by the one-tailed Student's t-test.

In the present invention, Tumstatin, the NC1 domain of the α3 chain of type IV collagen (Timpl, R. et al., 1981, Eur. J. Biochem. 120:203-11; Turner, N. et al., 1992, J. Clin. Invest. 89:592-601), was used to modulate the proliferation of vascular endothelial cells and blood vessel formation using in vitro and in vivo models of angiogenesis and tumor growth. Tumstatin exerts its effect at different stages in the process of tumor angiogenesis. The specific inhibition of endothelial cells by Tumstatin strongly suggests that it functions via a cell surface protein or receptor. Recently, synthetic peptides 19 amino acids long, corresponding to the C-terminal portion of Tumstatin was reported to bind to $\alpha_v\beta_3$ integrin (Shahan, T. A. et al., 1999, Cancer Res. 59:4584-90). The results of the cell adhesion assays described in the Examples below indicate that Tumstatin binds to $\alpha_v\beta_3$ and $\alpha_6\beta_1$ integrins on endothelial cells. When Tumstatin is preincubated with $\alpha_v\beta_3$ integrin protein in order to inhibit its binding to $\alpha_v\beta_3$ integrin that is in turn bound to endothelial cells, the anti-proliferative effects of Tumstatin are significantly decreased (FIG. 22). This suggests that the anti-proliferative effects of Tumstatin are at least partially mediated through binding to $\alpha_v\beta_3$ integrin on the cell surface of proliferating endothelial cells. Because angiogenesis depends on specific endothelial cell adhesive events mediated by the $\alpha_v\beta_3$ integrin (Brooks, P. S. et al., 1994, Cell 79:1157-64; Brooks, P. S. et al., 1994, Science 264:569-71), Tumstatin may effect anti-angiogenesis by disrupting the interaction of proliferating endothelial cells with matrix components such as vitronectin and fibronectin. The normal interaction of proliferating endothelial cells with vitronectin and fibronectin is considered an important anti-apoptotic signal (Isik, F. F. et al., 1998, J. Cell. Physiol. 175:149-55). Tumstatin induces apoptosis in growth-stimulated endothelial cells, and this effect is most pronounced when Tumstatin is added to subconfluent monolayers, i.e., when cells are growing exponentially. Tumstatin may be selective for tumor vasculature in which endothelial cells are activated.

A fragment of "α3(IV) NC1 domain" means a fragment or portion of the amino acid sequence of the NC1 domain of the α3 chain of mammalian Collagen Type IV. An example of such a fragment would be a fragment of the amino acid sequence of SEQ ID NO:10.

The distribution of the α3 (IV) chain (Tumstatin) is limited to certain basement membranes, such as GBM, several basement membranes of the cochlea, ocular basement membrane such as anterior lens capsule, Descemet's membrane, ovarian and testicular basement membrane (Frojdman, K. et al., 1998, Differentiation 83:125-30) and alveolar capillary basement membrane (Kashtan, C. E., 1998, J. Am. Soc. Nephrol. 9:1736-50). This chain is absent, however, from kidney mesangium, vascular basement membranes and epidermal basement membranes of the skin, and vascular basement membrane of liver (Kashtan, C. E., supra). In the process of wound healing, α-chains of type IV collagen other than the α3 and α4 chains will assemble and form new capillaries, because those two chains are not the component of the basement membrane of "pre-existing," namely dermal vasculatures. Since α3 (IV) chain is not the original component in the skin of normal humans, the process of collagen assembly and angiogenesis in the lesion of wound healing may not be altered by the treatment using Tumstatin.

The α3 (IV) chain is expressed in human kidney vascular basement membrane as well as GBM (Kalluri, R. et al., 1997, J. Clin. Invest. 99:2470-8). These "pre-existing" vessels are speculated to be involved in the progression of primary renal tumors such as renal cell carcinoma. Tumstatin can be effective in the treatment of primary renal tumors by disrupting neovascularization mediated by the assembly of the α3 (IV) chain with the other α-chains. The number of patients diagnosed for renal cell carcinoma was about thirty thousand in the United States in 1996 (Mulders, P. et al., 1997, Cancer Res. 57:5189-95), and the prognosis for metastatic cases is highly unfavorable. Despite advances in radiation therapy and chemotherapy, the long term survival of treated patients has not been remarkably improved yet (Mulders, P. et al., supra). The lack of significant treatment options for renal cell carcinoma emphasizes the importance of developing novel therapeutic strategies. Considering this fact, targeting neovascularization of solid tumors has recently demonstrated promising results in several animal models (Baillie, C. T. et al., 1995, Br. J. Cancer 72:257-67; Burrows, F. J. et al., 1994, Pharmacol. Ther. 64:155-74; Thorpe, P. E. et al., 1995, Breast Cancer Res. Treat. 36:237-51). The effect of Tumstatin in inhibiting renal cell carcinoma growth in vivo demonstrates this molecule's potential as an effective anti-angiogenic therapy against this tumor type.

In the present invention, Tumstatin specifically inhibited serum-stimulated proliferation of calf pulmonary arterial cells in vitro in a dose-dependent manner, and had no effect on the proliferation of tumor cell lines PC-3, and 786-O in vitro. Although Tumstatin did not inhibit endothelial cell migration, it significantly suppressed tube formation of mouse aortic endothelial cells in vitro, and also induced endothelial cell apoptosis. Tumstatin inhibited in vivo neovascularization by 67% in a Matrigel plug assay, and at 6 mg/kg, suppressed tumor growth of human renal cell carcinoma (786-O) cells and prostate carcinoma (PC-3) cells in mouse xenograft models. Collectively, these results show that Tumstatin suppresses the formation of new blood vessels by inhibiting various steps in the angiogenic process.

In in vivo studies, Tumstatin inhibited angiogenesis in the Matrigel plug assay and suppressed the growth of PC-3 tumor and 786-O tumors in mouse xenograft model. The fact that Tumstatin inhibited the growth of large tumors is encouraging, especially considering the treatment of tumors in the clinical setting.

Because Tumstatin possesses the pathogenic epitope for Goodpasture syndrome, an autoimmune disease characterized by pulmonary hemorrhage and rapidly progressive glomerulonephritis (Butkowski, R. J. et al. 1987, J. Biol. Chem. 262:7874-77; Saus, J. et al., 1988, J. Biol. Chem. 263:13374-80; Kalluri, R. et al., 1991, J. Biol. Chem. 266:24018-24), it is possible that acute or chronic administration of Tumstatin may induce this autoimmune disease. Several groups have tried to map or predict the location of the Goodpasture auto-epitope on α3 (IV) NC1, and the N-terminal portion, middle portion, and C-terminal portion were reported to possess the epitope (Kalluri, R. et al., 1995, J. Am. Soc. Nephrol. 6:1178-85; Kalluri, R. et al., 1996, J. Biol. Chem. 271:9062-8; Levy, J. B. et al., 1997, J. Am. Soc. Nephrol. 8:1698-1705; Quinones, S. et al., 1992, J. Biol. Chem. 267:19780-4; Kefalides, N. A. et al., 1993, Kidney Int. 43:94-100; Netzer, K. O. et al., 1999, J. Biol. Chem. 274:11267-74). Recently it was reported that reactivity of the autoantibody was only to the N-terminus of the α3 (IV) NC1, and correlated with the renal survival rate. This was done by using recombinant chimeric constructs (Hellmark, T. et al., 1999, Kidney Int. 55:936-44). The disease-associated epitope was also identified to the first 40 amino acids of the N-terminal portion. Truncated Tumstatin was therefore synthesized, lacking the N-terminal 53 amino acid residues in order to remove the epitope for Goodpasture syndrome, and this molecule exhibits inhibitory effects on 786-O tumor growth in the mouse xenograft model. Additionally, this molecule did not bind autoantibodies from severe patients with Goodpasture syndrome. Tumstatin N-53 (also referred to herein as "Tum-1") also potently decreased the viability of endothelial cells. Surprisingly, this effect was higher in Tumstatin N-53 (Tum-1) than in the full-length molecule. These results show that the anti-angiogenic region of Tumstatin is conserved even when the N-terminal 53 amino acids are removed.

Besides Tum-1, other Tumstatin deletion mutants were also created, including Tum-2, Tum-3 and Tum-4. These are also described in Example 35, below. Tum-1, as stated above, comprises the C-terminal 191 amino acids, and is lacking the N-terminal 53 amino acids. "Tumstatin 333" comprises the N-terminal amino acids 1 to 124 of Tumstatin. Tum-3 comprises the C-terminal 112 amino acids. Tum-4 comprises the C-terminal 64 amino acids, which includes amino acids 185-203 (Han et al, 1997, J. Biol. Chem. 272:20395-401). The region of amino acids 54 to 132 of full-length Tumstatin was designated Tum-5. An extended version of Tum-5, designated herein as "Tumstatin-44-131", was created to increase the expression and solubility of Tum-5. Tumstatin-44-131 consists of Tum-5, with an extension at the N-terminal end of an additional nine amino acids. In addition, a mutant of Tumstatin-44-131 was created, designated herein as "Tum-5-125-C-A". This mutant consists of the sequence of Tumstatin-44-131, where the cysteine at position 125 (of full-length Tumstatin) is mutated via site-directed mutagenesis to alanine. Further deletion mutants were made of Tum-5, which comprised T1 and a set of partially overlapping peptides (T2, T3, T4, T5 and T6).

These mutants are illustrated in Table 1, below.

TABLE 1

Recombinant Tumstatin and deletion mutants of Tumstatin

| Protein | Residues | Size | SEQ ID NO: |
|---|---|---|---|
| Tumstatin | 1_____244 | 244 | 10 |
| Tumstatin 333 | 1_____124 | 124 | 20 |
| Tumstatin 334 | 125____244 | 119 | 21 |
| Tum-1 (Tumstatin N53) | 54_____244 | 191 | 22 |
| Tum-2 | 1_____132 | 132 | 23 |
| Tum-3 | 133____112 | 112 | 24 |
| Tum-4 | 181__244 | 64 | 25 |
| Tum-5 | 54____132 | 79 | 26 |
| T1 | 1_20 | 20 | 27 |
| T2 | 53_72 | 20 | 28 |
| T3 | 69_88 | 20 | 29 |
| T4 | 83_102 | 20 | 30 |
| T5 | 98_116 | 19 | 31 |
| T6 | 113_131 | 19 | 32 |
| Tumstatin-44-131 | 44____131 | 88 | 33 |
| Tum-5-125-C-A | 44____131[1] | 88 | 34 |
| T7 | 73_97 | 25 | 37 |
| T7-mutant | 73_97[2] | 25 | 38 |
| T8 | 68_94[3] | 27 | 39 |
| T8-3 | 68_94[4] | 27 | 40 |
| TP3 | 76_94[5] | 19 | 41 |
| P2 | 68_94[6] | 27 | 42 |

[1] In Tum-5-125-C-A, alanine has been substituted for the cysteine residue at position 125 of the full-length Tumstatin molecule.
[2] In T7-mutant, methionine has been substituted for the leucine residue at position 77 of the full-length Tumstatin molecule, and isoleucine has been substituted for valine at position 81, and asparagine has been substituted for aspartic acid at position 83.
[3] In T8, lysine has been substituted for the leucine residue at position 68 of the full-length Tumstatin molecule.
[4] In T8-3, lysine has been substituted for the leucine residue at position 68 of the full-length Tumstatin molecule, and serine has been substituted for the cysteine residues at positions 79 and 85.
[5] In TP3, lysine has been substituted for the phenylalanine residue at position 76 of the full-length Tumstatin molecule, and cysteine has been substituted for the aspartic acid at position 83.
[6] In P2, lysine has been substituted for the leucine residue at position 68 of the full-length Tumstatin molecule, and aspartic acid has been substituted for the cysteine residues at positions 79 and 85.

Although Tum-4 inhibits melanoma cell proliferation (WM-164 cells) as shown herein, and binds the $\alpha_v\beta_3$ receptor, this region may not be responsible for the anti-angiogenic activity of Tumstatin. In contrast, the Tumstatin deletion mutant Tum-2, which contains the N-terminal half of Tumstatin, exhibited anti-angiogenic properties but no anti-tumor cell activity. It appears, therefore, that under some experimental conditions, these two activities can be separated.

Figure 34A:
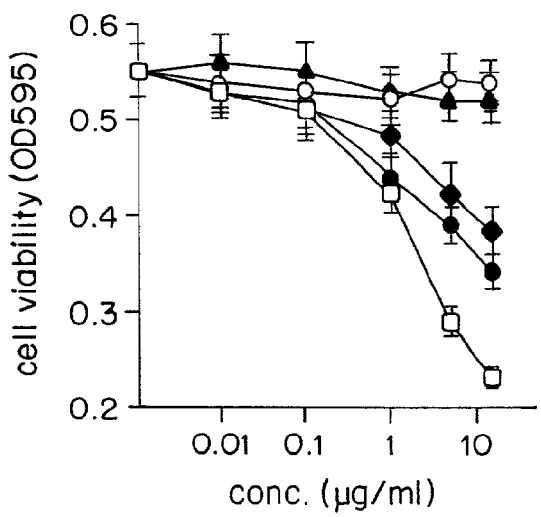
FIGS. 34A and 34B are a pair of graphs showing the effect of increasing concentration (x-axis) of Tumstatin (♦), Tum-1 (□), Tum-2 (●), Tum-3 (◇) and Tum-4 (▲) on the cell viability (y-axis) of C-PAE cells (FIG. 34A) and WM-164 cells (FIG. 34B). Each point represents the mean ±the standard error of the mean for triplicate wells.

As shown in FIGS. 34A and 35A, the fact that full-length Tumstatin and the deletion mutant Tum-1 both exhibit equivalent anti-angiogenic activity shows that the region of residues 1-53 is not necessary for this activity. The increased anti-angiogenic activity of Tum-1 over full-length Tumstatin can reasonably be explained by the increased number of active molecules per microgram for the mutant protein, as opposed to the larger full-length molecule.

The fact that full-length Tumstatin and the deletion mutants Tum-1 and Tum-2 all exhibit anti-angiogenic activity (i.e., inhibiting endothelial cell proliferation and causing their apoptosis), while Tum-3 and Tum-4 do not, suggests that the anti-angiogenic properties of Tumstatin are located primarily in the region of residues 54-132. The activity could also extend some residues beyond residue 132, but it is clear that Tum-3 does not contain enough of the anti-angiogenic region to exhibit anti-angiogenic properties.

Figure 33A:
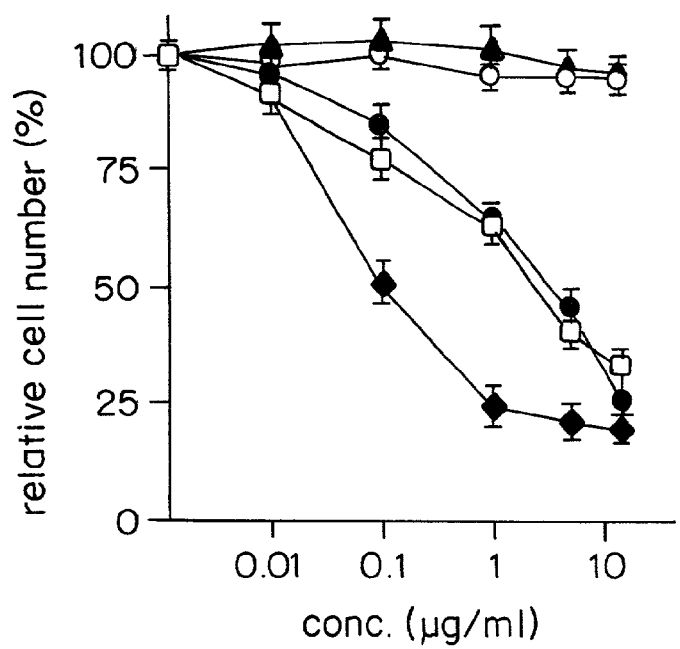
FIGS. 33A and 33B are a pair of graphs showing the effect of increasing concentration (x-axis) of Tumstatin (♦), Tum-1 (□), Tum-2 (●), Tum-3 (◇) and Tum-4 (▲) on the relative number (y-axis) of C-PAE cells (FIG. 33A) and WM-164 cells (FIG. 33B).
Figure 33B:
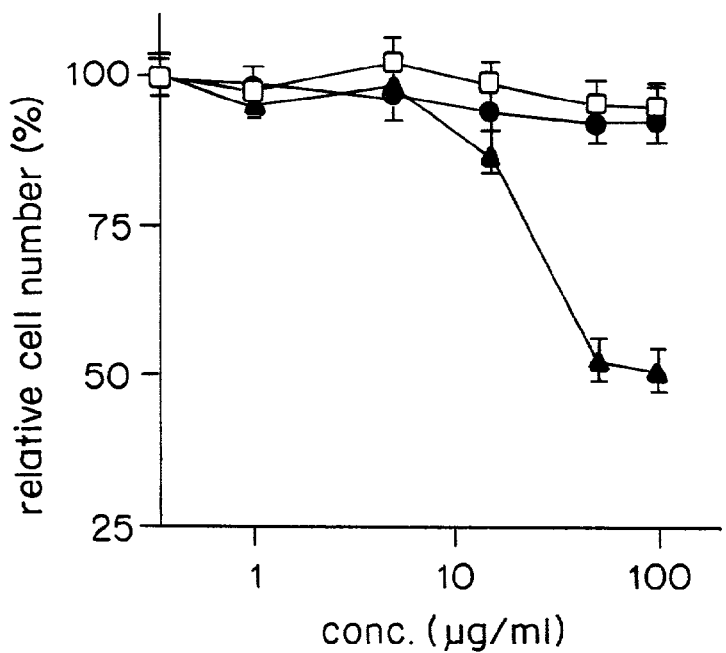

However, Tum-4 inhibited the growth of WM-164 melanoma cells (as shown in FIG. 33B), while Tum-1 and Tum-2 did not, indicating that the anti-tumor cell activity of Tumstatin may reside within residues 181-244. Considering the results of Shahan et al. (1999, Cancer Res. 59:4584-90), it is more likely that the anti-tumor cell activity is located within residues 185-203. The separation of Tumstatin's anti-angiogenic activity and anti-tumor cell activity is surprising, as most research in the field of anti-angiogenesis is directed to inhibiting tumors by restricting their blood supply.

Interestingly, because the anti-angiogenic activity of deletion mutants Tum-1 and Tum-2 are equivalent to those of Tumstatin, it is clear that the anti-angiogenic activity of the residue 54-132 region is also effective when it is contained within a full-length folded Tumstatin molecule. In contrast, Tum-4 had anti-tumor cell activity, whereas Tum-3 (which, like Tum-4, contains residues 185-203) did not. The anti-tumor cell activity of region 185-203 is therefore not available when the region is present as part of a full-length folded Tumstatin, or even within a larger Tumstatin fragment (e.g., within Tum-3). This activity is only realized when this region is exposed either by truncation of the molecule (as in the Examples below) or by synthesis of a representative peptide, as done by Han et al. (1997, J. Biol. Chem. 272:20395-401).

Other fragments and mutants of full-length Tumstatin also possess anti-angiogenic activity. Tumstatin-44-131 specifically inhibits proliferation and caused apoptosis of endothelial cells with no significant effect on non-endothelial cells. It is as active as the full-length molecule of 244 amino acids, even though it represents truncation of 64% from the parent protein. The anti-angiogenic effects of Tumstatin-44-131 were further confirmed in vivo using a Matrigel plug assay. Tumstatin-44-131 at 1 µg/ml was found to inhibit PC-3 tumors, and decrease neovascularization and microvascular density in mouse xenografts. Binding of biotinylated Tumstatin-44-131 onto the endothelial cell surface was confirmed by immunocytochemistry. Immunoprecipitation experiments revealed that Tumstatin-44-131 binds to the $\alpha_v\beta_3$ and the $\beta_1$ integrins on the surface of endothelial cells as determined by the competition proliferation assay.

In addition, alkaline-reduced Tumstatin-44-131 was found to be as effective as unreduced Tumstatin-44-131. Alkaline reduction destroys the disulfide bonds between cysteine residues, which play a role in maintaining the conformational structure of a folded protein molecule. The lack of decreased activity of alkaline-reduced Tumstatin-44-131 relative to the unreduced molecule, indicates that the cysteine bond-mediated conformational nature of Tumstatin-44-131 is not essential to its anti-angiogenic activity. The term "mutant", can therefore also mean all or a portion of the Tumstatin molecule that has been reduced, or in which one or more of the cysteine residues have been mutated to another amino acid or deleted entirely.

A mutant of Tumstatin-44-131 was created, Tum-5-125-C-A, in which the cysteine at residue number 125 (in the full-length molecule) is mutated to alanine. This mutation exhibits enhanced protein expression, and the molecule possesses anti-angiogenic properties equivalent to Tumstatin-44-131, with the exception of inhibition of tumor growth in mouse xenograft studies, where the mutant actually inhibited tumor growth more strongly than Tumstatin-44-131.

These activities are further defined by study of the synthetic peptides, T1, T2, T3, T4, T5, T6, T7, T7-mutant, T8, T8-3, TP3 and P2. Of the synthetic peptides, T3 inhibited in vivo neovascularization. The T1 peptide on the other hand, which contains the 20 N-terminal amino acids of full-length Tumstatin, and therefore the RGD sequence, did not inhibit endothelial cell proliferation. T3 was found to cause $G_1$ arrest of proliferating endothelial cells, and this effect was decreased when the cells were pre-incubated with $\alpha_v\beta_3$ integrin protein before exposure to T3 peptide. T3 peptide inhibited endothelial cell proliferation regardless of whether or not the two cysteines contained within it were connected by a disulfide bond. This shows that like Tumstatin-44-131, the anti-angiogenic activity of the T3 peptide is not dependent on its conformational nature. The activity of the T3 peptide was 2-fold to 5-fold less active on a molar basis as Tumstatin or Tumstatin-44-131. The T4 peptide overlaps with T3, and while T4 did not inhibit proliferation of endothelial cells, it did exhibit weak binding to $\alpha_v\beta_3$ integrin in these cells. The T3 sequence was therefore extended by the first nine residues of the T4 peptide, and the new peptide sequence was called "T7."

The T7 peptide exhibited a level of activity higher than that of T3, and similar to that of Tumstatin and Tumstatin-44-131, at equimolar concentrations. Tumstatin, Tumstatin-44-131 and T7 peptide showed anti-proliferative effects with an $ED_{50}$ of 1 µM, while T3 peptide had an $ED_{50}$ of 2.5 µM. These results indicate that while the first nine amino acids of the T4 peptide do not themselves exhibit anti-angiogenic activity, they nevertheless contribute to the binding of Tumstatin to the $\alpha_v\beta_3$ integrin, possibly facilitating better interaction between these molecules and helping to attain maximal anti-angiogenic activity.

Interestingly, amino acids 8-29 of the T7 sequence also exhibit some homology (50% identity) to the C-terminal region of amino acids 187-207, which is the region that exhibits tumor cell inhibiting activity.

A number of additional peptides and mutants were synthesized, and tested for their activity in in vivo animal models of cancer. These peptides are listed in Table 1, above, and their alignment with the Tumstatin sequence is shown below. Amino acid residues that differ from the Tumstatin sequence are shown in lower case.

```
Tumstatin:
 60      65      70      75      80      85      90      95      100
  QDLGTLGSCLQRFTTMPFLFCNVNDVCNFASRNDYSYWLST

T7
                    TMPFLFCNVNDVCNFASRNDYSYWL

T7-mutant
                    TMPFmFCNiNnVCNFASRNDYSYWL

T8
              kQRFTTMPFLFCNVNDVCNFASRNDYS

T8-3
              kQRFTTMPFLFsNVNDVsNFASRNDYS

TP3
                    kLFCNVNcVCNFASRNDYS

P2
              kQRFTTMPFLFdNVNDVdNFASRNDYS
```

Tumstatin peptide T7 is a fragment of full-length Tumstatin, with no alterations in the sequence. Peptide T7-mutant is based on the T7 sequence, but has methionine, isoleucine and asparagine substituting for leucine, valine and aspartic acid at Tumstatin residues 77, 81 and 83, respectively. Peptide T8 has lysine substituted for leucine at Tumstatin position 68. Peptide T8-3 has two additional substitutions, where a serine has been substituted for each of the cysteine residues at Tumstatin positions 79 and 85. Peptide TP3 has lysine substituted for the phenylalanine residue at position 76, and cysteine has been substituted for the aspartic acid at position 83. Peptide P2 is also similar to the T8-3 peptide, also having a lysine substituted for the leucine at Tumstatin position 68, but with the cysteines at positions 79 and 85 being replaced by an aspartic acid.

In in vivo mouse tumor models, peptide T8 showed no toxicity, and inhibited tumor growth in MDAMB-435 orthotopic human breast tumor xenografts. Inhibition was over 28% at daily dosages of 1 mg/kg body weight, and nearly 49% at 2.5 mg/kg. Interestingly, at a daily dosage of 5 mg/kg, the inhibition was only 31%, but when the same dosage (5 mg/kg) was administered twice a week, the inhibition was over 41%. In the same tumor model, peptide TP3 showed over 30% inhibition when 1 mg/kg was administered daily, and 50% inhibition at 1 mg/kg daily. In another experiment, T8 and T8-3 inhibited tumor growth by 50.5% and 41.9%, respectively, when administered at 5 mg/kg, and T8-3 was ineffective at 1 mg/kg. Peptide P2 inhibited tumor growth in this cancer model by 26.4% at 1 mg/kg, and 15.9% at 5 mg/kg.

In a PC3 human prostate tumor xenograft model, where peptides T7, T8, TP3, and control scrambled peptide SP1 and SP2 were administered daily, T8, T7 and TP3 at mg/kg inhibited PC3 tumor growth by 45%, 66.8% and 53.2%, respectively. SP1 and SP2 inhibited growth by 31.7 and 18.7%. When administered at 5 mg/kg once a week, T8 inhibited tumor growth by 39.5%, but only 8.1% when administered twice a week, thus mirroring the results in the MDAMB-435 model. In another experiment, both the T8 and T8-3 peptides inhibited tumor growth by 35.4% at dosages of 5 mg/kg, showing that the cysteines at positions 80 and 86 do not provide a secondary structure that is required for this biological activity. P2 proved to be more effective at lower doses in the PC3 model as well as the MDAMB-435 model, inhibiting tumor growth by 31.6% and only 15.9% at 1 mg/kg and 5 mg/kg, respectively.

As shown herein, Tumstatin peptide-induced apoptosis is associated with an increase in caspase-3, an enzyme implicated in the regulation of cap-dependent protein translation (Maeshima, Y. et al., 2000, J. Biol. Chem. 275:23745-50; Maeshima, Y. et al., 2001, J. Biol. Chem. 276:31959-68; Maeshima, Y. et al., 2001, J. Biol. Chem. 276:15240-8; Bushell, M. et al., 1999, FEBS Lett. 451: 332-336). Using cells from integrin $\beta_3$-deficient mice, the results herein (see, e.g., Examples 52-55) show that the inhibitory effect of various Tumstatin peptides on protein synthesis is mediated via $\alpha_v\beta_3$ integrin expressed on endothelial cells. Through its interaction with $\alpha_v\beta_3$ integrin, the Tumstatin peptides inhibit activation of FAK, PI-3 kinase, AKT, mTOR and prevents the dissociation of eIF4E/4E-BP 1 complex, resulting in the inhibition of cap-dependent protein translation in endothelial cells, similar to rapamycin; while such effects are not observed with endostatin, another matrix-derived angiogenesis inhibitor. This establishes a novel role for integrins in mediating cell-specific inhibition of cap-dependent protein synthesis. Tumstatin and related peptides are therefore $\alpha_v\beta_3$ integrin-dependent, endothelial cell-specific inhibitors of cap-dependent protein synthesis.

The lack of the activities' dependency on the tertiary structure or conformation of the peptides and proteins should facilitate engineering of these peptides and proteins for pharmaceutical purposes. For instance, because there is no difference in the activities of the folded or unfolded versions of the T3 peptide, or the reduced and alkylated Tumstatin-44-131 versus the unreduced and unalkylated version, one can use whichever version of the protein or peptide has fewer side effects in patients, which is expressed at a higher level in a given expression system, or whichever is more soluble. In addition, the small size of the active sequence allows the addition of flanking sequences for manipulation of expression, solubility, side effects, etc.

Therefore, the proteins and peptides of the invention may also be modified to improve or alter various pharmaceutical characteristics, e.g., additional amino acid sequences can be incorporated into the overall peptide or protein sequence to impart desirable qualities to the molecule, or remove undesired qualities. For instance, the short sequence of the peptides increases their potency on a weight basis, but may also reduce their effective half-life. It may be desirable to increase the biological half-life (e.g., serum half-life) of the peptides or proteins by, for example, modification. Various methods for increasing the half-life of a protein are well known in the art and include, for example, conjugation of the protein to polyethylene glycol moieties, i.e., PEGylation (see, e.g., U.S. Pat. Nos. 4,179,337; 5,166,322; 5,206,344; Nucci et al., 1991, Adv. Drug Delivery Rev. 4:133-51) and conjugation of the protein to dextran (Maksimenko, 1986, Bull. Exp. Biol. Med. (Russian) 52:567-9).

Both the anti-angiogenic and anti-tumor cell activities lie outside the Goodpasture epitope region. A "non-Goodpasture fragment" of α3(IV) NC1 domain means a fragment (e.g., of a protein, peptide or polypeptide) or a portion of the amino acid sequence of the NC1 domain of the α3 chain of mammalian Collagen Type IV, where the fragment does not include the Goodpasture auto-epitope. It was recently reported that the autoantibody reacted solely with the N-terminus of α3(IV) NC1.

Neither the anti-angiogenic nor the anti-tumor cell region contains the classic "RGD" (Arg-Gly-Asp) binding site, therefore both regions bind their ligands via an RGD-independent mechanism. Saying that the ability of a fragment (e.g., of a protein, peptide or polypeptide) to bind an integrin or integrin subunit is "RGD-independent" means that the fragment can bind an integrin or integrin subunit even though the fragment does not contain the peptide sequence "RGD" (Arg-Gly-Asp). Even though neither contains the RGD sequence, both the anti-angiogenic and the anti-tumor cell region still bind $\alpha_v\beta_3$ integrin, and both bind to endothelial cells. Saying that a fragment (e.g., of a protein, peptide or polypeptide) has the "ability to bind $\alpha_v\beta_3$ integrin" means that the fragment can bind this integrin or its subunits (i.e., $\alpha_v$ and/or $\beta_3$) or that pre-treatment with antibodies to this integrin or its subunits results in inhibition of binding of the fragment to this integrin and/or its subunits (e.g., as demonstrated by the methods provided in Examples 12 or 28, below).

In light of these similarities, it is surprising that (1) the anti-angiogenic region inhibits endothelial cell proliferation, while the anti-tumor cell region does not, and (2) the anti-angiogenic region fails to inhibit tumor cells, while the anti-tumor cell region does inhibit such cells.

Saying that a fragment (e.g., of a protein, peptide or polypeptide) has an "inability to inhibit tumor cell proliferation" or that it "lacks the ability to inhibit tumor cell proliferation," means that the fragment does not prevent the proliferation of tumor cells (e.g., cultured melanoma cells, e.g., WM-164 cells). Methods for testing are given in the Examples below, e.g., in Examples 36, 37 and 38. Likewise, saying that a fragment (e.g., of a protein, peptide or polypeptide) has an "ability to inhibit tumor cell proliferation" means that the fragment does prevent the proliferation of tumor cells (e.g., cultured melanoma cells, e.g., WM-164 cells). Methods for testing for such an ability are also given in the Examples below, e.g., in Examples 36, 37 and 38.

Saying that a fragment (e.g., of a protein, peptide or polypeptide) has an "inability to inhibit proliferation of endothelial cells" or that it "lacks the ability to inhibit proliferation of endothelial cells" means that the fragment does not prevent the proliferation of endothelial cells (e.g., cultured C-PAE cells). Methods for testing for such an inability are given in the Examples below, e.g., in Examples 5, 6, 7, 26, 34, 36, 38, and others.

Saying that a fragment (e.g., of a protein, peptide or polypeptide) has an "ability to bind endothelial cells" means that the fragment binds to endothelial cells (e.g., C-PAE cells). Methods for testing for such ability are also given in the Examples below, e.g., in Examples 26, 28, 37.

It would be neither difficult nor burdensome for one to use the methods described in the Examples below to make additional deletion mutants in order to further delineate the exact minimum length required for either the anti-angiogenic activity or the anti-tumor cell activity. Such efforts would be very advantageous because the smallest possible molecule that still exhibits the desired activity would be more powerful on a per weight basis than larger molecules that contain amino acids unnecessary for the desired activity.

The specific inhibition of endothelial cell proliferation by Tumstatin strongly suggests that it may function via a cell surface protein/receptor. Angiogenesis also depends on specific endothelial cell adhesive events mediated by integrin $\alpha_v\beta_3$ (Brooks, P. C. et al., 1994, Cell 79:1157-64). Cell attachment assays revealed that Tumstatin binds to endothelial cells via $\alpha_v\beta_3$ and $\alpha_6\beta_1$ integrins. The anti-proliferative effect of Tumstatin was partially recovered by soluble $\alpha_v\beta_3$ integrin protein. Tumstatin may disrupt the interaction of proliferating endothelial cells to the matrix component, and thus drive endothelial cells to undergo apoptosis (Re, F. et al., 1994, J. Cell. Biol. 127:537-46). Matrix Metalloproteinases (MMP's) have been implicated as key enzymes that regulate the formation of new blood vessels in tumors (Ray, J. M. et al., 1994, Eur. Respir. J 7:2062-72). Recently, it was demonstrated that an inhibitor of MMP-2 (PEX) can suppress tumor growth by inhibiting angiogenesis (Brooks, P. C. et al., Cell 92:391-400). Tumstatin may function through inhibiting the activity of MMPs.

Petitclerc et al. (2000, J. Biol. Chem. 275:8051-61) showed that α3(IV) NC1 binds to endothelial cells via the $\alpha_v\beta_3$ integrin, but speculated that the binding was via the RGD sequence present in the N-terminus of the α3(IV) NC1 domain. This RGD sequence is not part of the NC1 domain, however, but is derived from the triple helical region, and is included in an original clone described by Neilson et al. (1993, J. Biol. Chem. 268:8402-5). Petitclerc et al., used this clone to recombinantly express α3(IV) NC1 in 293 embryonic kidney cells. When this sequence is removed using site-directed mutagenesis, the $\alpha_v\beta_3$ binding site is preserved, indicating an RGD-independent binding mechanism.

Shahan et al (1999, Cancer Res. 59:4584-90) identified residues 185-203 as a ligand for $\alpha_v\beta_3$ integrin, and speculated that this interaction is important for the associated anti-tumor cell property. This peptide domain was further identified to bind to a 3 integrin subunit site distinct from the RGD recognition site in HT-144 melanoma cells (Pasco, S. et al., 2000, J. Biol. Chem. 275:32999-3007). Examples 37 and 38, below, show an additional, distinct, RGD-independent $\alpha_v\beta_3$ (not $\alpha_v\beta_5$ or $\beta_1$) integrin binding site within the 54-132 residue region of Tumstatin. This second site is not necessary for inhibition of tumor cell proliferation, but is required for anti-angiogenic activity. Tum-2 binds both endothelial cells and melanoma cells, but only inhibits proliferation of endothelial cells, and has no effect on tumor cell proliferation. Tum-4, which contains residues 185-203, binds both endothelial and melanoma cells, but only inhibits the proliferation of melanoma cells. For both integrin binding sites, competition assays with soluble $\alpha_v\beta_3$ protein is sufficient to reverse the anti-proliferative activity. This suggests that the two distinct RGD-independent $\alpha_v\beta_3$ binding sites on Tumstatin mediate two separate anti-tumor activities, possibly via distinct $\alpha_v\beta_3$ integrin-mediated mechanisms. The results described herein show that $\alpha_v\beta3$ and $\alpha_6\beta_1$ integrins bind Tumstatin, and that the $\alpha v\beta3$ binding is RGD-independent.

Deletion mutants were used in cell adhesion assays to detect the integrin binding sites. In the N-terminal portion of Tumstatin, there is an RGD sequence (amino acid residues 7-9) derived from the triple-helical non-collagenous portion. RGD is a binding site for the $\alpha_v\beta_3$ receptor. However, Tum-1, which lacks this sequence, still binds to $\alpha_v\beta_3$ integrin. This binding site is therefore RGD independent, as was shown for the 185-203 region. Antibody for this region (e.g., anti-Tum-4 antibody), which was shown to partially bind to the $\alpha_v\beta_3$ binding site, does not prevent Tum-1 from binding to the $\alpha_v\beta_3$ receptor, and the anti-proliferative effect of Tum-1 was also unaffected. Furthermore, Tum-2 (residues 1-132), which does not contain the C-terminal $\alpha_v\beta_3$ binding site (residues 185-203), is shown in Example 38 to bind to $\alpha_v\beta_3$ in a cell adhesion assay and inhibit endothelial cell proliferation. When Tumstatin or Tum-2 is incubated with $\alpha_v\beta_3$ protein to saturate the $\alpha_v\beta_3$ receptor on the endothelial cell membrane, the anti-proliferative effect of Tumstatin was significantly decreased (by 43-74%). This is surprising considering that the affinity of soluble $\alpha_v\beta_3$ receptor for Tumstatin may be much weaker and inefficient relative to membrane-bound $\alpha_v\beta_3$. The results described herein show that the $\alpha_v\beta_3$ binding site is likely located within amino acids 54-132.

That Tumstatin's anti-angiogenic activity is mediated by $\alpha_v\beta_3$ is consistent with the notion that VEGF upregulates the expression of $\alpha_v\beta_3$ on endothelial cells (Senger et al., 1996, Am. J. Pathol. 149:293-305; Suzume et al, 1998, Invest. Opthalmol. Vis. Sci. 39:1028-35). Because angiogenesis depends on specific endothelial cell adhesive events mediated by $\alpha_v\beta_3$ integrin (Brooks et al., 1994, Science 264:569-71; Brooks et al., 1994, Cell 79:1157-83), the anti-angiogenic effect of Tumstatin may be mediated by disrupting the interaction of proliferating endothelial cells to matrix components such as vitronectin and fibronectin, which is considered an important anti-apoptotic signal.

The second RGD-independent site does not show significant homology at the amino acid level to the 185-203 site, although both bind $\alpha_v\beta_3$ integrin on endothelial and melanoma cells. Although $\alpha_v\beta_3$ integrin binds to residues 185-203, no inhibition of endothelial cell proliferation was observed.

Tumstatin inhibits angiogenesis in vitro and in vivo, resulting in the suppression of tumor progression. In order to apply this strategy to patients, its potential toxicity or side effects by systemic administration must also be considered. The fact that Tumstatin's distribution is limited and is mostly absent in dermal basement membrane suggest less possibility of side effects by Tumstatin treatment. Also, existence of Tumstatin in vascular basement membrane of limited organs such as kidney suggests its potential unique advantage in targeting tumors arising in limited organs.

Ultimately it is desirable to develop alternative strategies to express the Tumstatin gene in vivo in tumor vasculature employing gene transfer approaches (Kashihara, N. et al., 1997, Exp. Nephrol. 5:126-31; Maeshima, Y. et al., 1996, J. Am. Soc. Nephrol. 7:2219-29; Maeshima, T. et al., 1998,J. Clin. Invest. 101:2589-97).

The distribution of the α3 (IV) chain is limited to basement membranes of selected organs, and so Tumstatin is likely to be less harmful considering the possible mechanism of this molecule by inhibiting the assembly of α-chains. Furthermore the α3 (IV) chain is observed in the vascular basement membrane of the kidney (Kalluri, R. et al., 1997, J. Clin. Invest. 99:2470-78), and these vessels are thought to be involved in the progression of primary renal tumors such as renal cell carcinoma. Therefore, Tumstatin may be effective in the treatment of such tumors through disrupting the assembly of the α3 (IV) chain with the other α-chains.

As used herein, the term "angiogenesis" means the generation of new blood vessels into a tissue or organ, and involves endothelial cell proliferation. Under normal physiological conditions, humans or animals undergo angiogenesis only in very specific restricted situations. For example, angiogenesis is normally observed in wound healing, fetal and embryonal development, and formation of the corpus luteum, endometrium and placenta. The term "endothelium" means a thin layer of flat epithelial cells that lines serous cavities, lymph vessels, and blood vessels. "Anti-angiogenic activity" therefore refers to the capability of a composition to inhibit the growth of blood vessels. The growth of blood vessels is a complex series of events, and includes localized breakdown of the basement membrane lying under the individual endothelial cells, proliferation of those cells, migration of the cells to the location of the future blood vessel, reorganization of the cells to form a new vessel membrane, cessation of endothelial cell proliferation, and, incorporation of pericytes and other cells that support the new blood vessel wall. "Anti-angiogenic activity" as used herein therefore includes interruption of any or all of these stages, with the end result that formation of new blood vessels is inhibited.

Anti-angiogenic activity may include endothelial inhibiting activity, which refers to the capability of a composition to inhibit angiogenesis in general and, for example, to inhibit the growth or migration of bovine capillary endothelial cells in culture in the presence of fibroblast growth factor, angiogenesis-associated factors, or other known growth factors. A "growth factor" is a composition that stimulates the growth, reproduction, or synthetic activity of cells. An "angiogenesis-associated factor" is a factor which either inhibits or promotes angiogenesis. An example of an angiogenesis-associated factor is an angiogenic growth factor, such as basic fibroblastic growth factor (bFGF), which is an angiogenesis promoter. Another example of an angiogenesis-associated factor is an angiogenesis inhibiting factor such as e.g., angiostatin (see, e.g., U.S. Pat. No. 5,801,012; No. 5,837,682; No. 5,733,876; No. 5,776,704; No. 5,639,725; No. 5,792,845; WO 96/35774; WO 95/29242; WO 96/41194; WO 97/23500) or endostatin (see, e.g., U.S. Pat. No. 5,854,205; No. 6,174,861; WO 97/15666).

"Substantially the same biological activity" or "substantially the same or superior biological activity" means that a composition has anti-angiogenic activity, and behaves similarly as do Arresten, Canstatin and Tumstatin, as determined in standard assays. "Standard assays" include, but are not limited to, those protocols used in the molecular biological arts to assess anti-angiogenic activity, cell cycle arrest, and apoptosis. Such assays include, but are not limited to, assays of endothelial cell proliferation, endothelial cell migration, cell cycle analysis, and endothelial cell tube formation, detection of apoptosis, e.g., by apoptotic cell morphology or Annexin V-FITC assay, chorioallantoic membrane (CAM) assay, and inhibition of renal cancer tumor growth in nude mice. Such assays are provided in the Examples below.

"Arresten," also referred to herein as "Arrestin," is intended to include fragments, mutants, homologs, analogs, and allelic variants of the amino acid sequence of the Arresten sequence, as well as Arresten from other mammals, and fragments, mutants, homologs, analogs and allelic variants of the Arresten amino acid sequence.

"Canstatin," as used herein, is intended to include fragments, mutants, homologs, analogs, and allelic variants of the amino acid sequence of the Canstatin sequence, as well as Canstatin from other mammals, and fragments, mutants, homologs, analogs and allelic variants of the Canstatin amino acid sequence.

"Tumstatin," as used herein, is intended to include fragments, mutants, homologs, analogs, and allelic variants of the amino acid sequence of the Tumstatin sequence, as well as Tumstatin from other mammals, and fragments, mutants, homologs, analogs and allelic variants of the Tumstatin amino acid sequence.

It is to be understood that the present invention is contemplated to include any derivatives of Arresten, Canstatin or Tumstatin that have endothelial inhibitory activity (e.g., the capability of a composition to inhibit angiogenesis in general and, for example, to inhibit the growth or migration of bovine capillary endothelial cells in culture in the presence of fibroblast growth factor, angiogenesis-associated factors, or other known growth factors). The present invention includes the entire Arresten, Canstatin or Tumstatin protein, derivatives of these proteins and biologically-active fragments of these proteins. These include proteins with Arresten, Canstatin or Tumstatin activity that have amino acid substitutions or have sugars or other molecules attached to amino acid functional groups.

The invention also describes fragments, mutants, homologs and analogs of Arresten, Canstatin and Tumstatin. A "fragment" of Arresten, Canstatin or Tumstatin is any amino acid sequence shorter that the Arresten, Canstatin or Tumstatin molecule, comprising at least 25 consecutive amino acids of the Arresten, Canstatin or Tumstatin polypeptide. Such molecules may or may not also comprise additional amino acids derived from the process of cloning, e.g., amino acid residues or amino acid sequences corresponding to full or partial linker sequences. To be encompassed by the present invention, such mutants, with or without such additional amino acid residues, must have substantially the same biological activity as the natural or full-length version of the reference polypeptide.

A "fragment" of a protein is any amino acid sequence shorter than that protein, comprising 12 or more consecutive amino acids of the full-length polypeptide. Such a fragment may alternatively comprise 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 consecutive amino acids of the full polypeptide. The fragment may comprise 51, 52, 53, 54, 55, 56, 57, 58, 59, 60, 61, 62, 63, 64, 65, 66, 67, 68, 69, 70, 71, 72, 73, 74 or 75 consecutive amino acids of the full polypeptide. Such molecules may or may not also comprise additional amino acids derived from the process of cloning, e.g., amino acid residues or amino acid sequences corresponding to full or partial linker sequences.

Such a fragment can also be based on the following formula for producing a generic active peptide based on the Tumstatin sequence. The Tumstatin sequence from amino acid 60 through 100 is provided below, aligned with active Tumstatin peptides. Residues in common across the sequences are shown in capital letters.

```
Tumstatin:
 60    65    70    75    80    85    90    95    100
  qdlgtlgsclqrfttmpfLFcNVNdVcNFasrndysywlst T3
            lqrfttmpfLFcNVNdVcNF T7
                 tmpfLFcNVNdVcNFasrndysywl T8
              kqrfttmpfLFcNVNdVcNFasrndys T8-3
              kqrfttmpfLFsNVNdVsNFasrndys Tp3
                  kLFcNVNcVcNFasrndys P2
              kqrfttmpfLFdNVNdVdNFasrndys Generic
                    xLFxNVNxVxNF
                    f   c   d  c
                    k   s   c  s
                        d      d
```

One can therefore create peptides based on this formula and test them for anti-angiogenic properties as described herein. For instance, one can make a peptide with the sequence of amino acid F or K, followed by LF, followed by C or S or D, followed by NVN, followed by D or C, then V, then C or S or D, and ending in NF. A total of only 36 different peptides can be produced with this formula, a number easily tested by the assays described herein.

Other fragments can also be made. One fragment of Tumstatin, designated "Tumstatin N-53," was found to have anti-angiogenic activity equivalent to that of full-length Tumstatin, as determined by standard assays. Tumstatin N-53 comprises a Tumstatin molecule wherein the N-terminal 53 amino acids have been deleted. Other mutant fragments described herein have been found to have very high levels of anti-angiogenic activity, as shown by the assays described herein. These fragments, "Tumstatin 333," "Tumstatin 334," "12 kDa Arresten fragment," "8 kDa Arresten fragment," and "10 kDa Canstatin fragment" have $ED_{50}$ values of 75 ng/ml, 20 ng/ml, 50 ng/ml, 50 ng/ml, and 80 ng/ml, respectively. By contrast, full-length Arresten, Canstatin and Tumstatin were found to have $ED_{50}$ values of 400 ng/ml, 400 ng/ml and 550 ng/ml, respectively. Tumstatin 333 comprises amino acids 1 to 124 of SEQ ID NO:10, and Tumstatin 334 comprises amino acids 125 to 244 of SEQ ID NO:10.

A "mutant" of Arresten, Canstatin or Tumstatin means a polypeptide that includes any change in the amino acid sequence relative to the amino acid sequence of the equivalent reference Arresten, Canstatin or Tumstatin polypeptide. Such changes can arise either spontaneously or by manipulations by man, by chemical energy (e.g., X-ray), or by other forms of chemical mutagenesis, or by genetic engineering, or as a result of mating or other forms of exchange of genetic information. Mutations include, e.g., base changes, deletions, insertions, inversions, translocations, or duplications.

Mutant forms of Arresten, Canstatin or Tumstatin may display either increased or decreased anti-angiogenic activity relative to the equivalent reference Arresten, Canstatin or Tumstatin polynucleotide, and such mutants may or may not also comprise additional amino acids derived from the process of cloning, e.g., amino acid residues or amino acid sequences corresponding to full or partial linker sequences.

Mutants/fragments of the anti-angiogenic proteins of the present invention can be generated by PCR cloning. The fragments designated "Tumstatin 333" and "Tumstatin 334" were generated in this way, and have anti-angiogenic activity superior to that of full-length Tumstatin, as is described in Example 23, below, and shown in FIGS. 30 and 31. To make such fragments, PCR primers are designed from known sequence in such a way that each set of primers will amplify known subsequence from the overall protein. These subsequences are then cloned into an appropriate expression vector, such as the pET22b vector, and the expressed protein tested for its anti-angiogenic activity as described in the assays below.

Mutants/fragments of the anti-angiogenic proteins of the present invention can also be generated by *Pseudomonas* elastase digestion, as described by Mariyama, M. et al. (1992, J. Biol. Chem. 267:1253-8), and in Example 33, below. This method was used to produce the 12 kDa and 8 kDa Arresten mutants, and the 10 kDa Canstatin mutant, all three of which have higher levels of anti-angiogenic activity than the original full-length proteins.

An "analog" of Arresten, Canstatin or Tumstatin means a non-natural molecule substantially similar to either the entire Arresten, Canstatin or Tumstatin molecule or a fragment or allelic variant thereof, and having substantially the same or superior biological activity. Such analogs are intended to include derivatives (e.g., chemical derivatives, as defined above) of the biologically active Arresten, Canstatin or Tumstatin, as well as its fragments, mutants, homologs, and allelic variants, which derivatives exhibit a qualitatively similar agonist or antagonist effect to that of the unmodified Arresten, Canstatin or Tumstatin polypeptide, fragment, mutant, homolog, or allelic variant.

An "allele" of Arresten, Canstatin or Tumstatin means a polypeptide sequence containing a naturally-occurring sequence variation relative to the polypeptide sequence of the reference Arresten, Canstatin or Tumstatin polypeptide. An "allele" of a polynucleotide encoding the Arresten, Canstatin or Tumstatin polypeptide means a polynucleotide containing a sequence variation relative to the reference polynucleotide sequence encoding the reference Arresten, Canstatin and Tumstatin polypeptide, where the allele of the polynucleotide encoding the Arresten, Canstatin or Tumstatin polypeptide encodes an allelic form of the Arresten, Canstatin or Tumstatin polypeptide.

It is possible that a given polypeptide may be either a fragment, a mutant, an analog, or allelic variant of Arresten, Canstatin or Tumstatin, or it may be two or more of those things, e.g., a polypeptide may be both an analog and a mutant of the Arresten, Canstatin or Tumstatin polypeptide. For example, a shortened version of the Arresten, Canstatin or Tumstatin molecule (e.g., a fragment of Arresten, Canstatin or Tumstatin) may be created in the laboratory. If that fragment is then mutated through means known in the art, a molecule is created that is both a fragment and a mutant of Arresten, Canstatin or Tumstatin. In another example, a mutant may be created, which is later discovered to exist as an allelic form of Arresten, Canstatin or Tumstatin in some mammalian individuals. Such a mutant Arresten, Canstatin or Tumstatin molecule would therefore be both a mutant and an allelic variant. Such combinations of fragments, mutants, allelic variants, and analogs are intended to be encompassed in the present invention.

For example, the Tumstatin made by the *E. Coli* expression cloning method described in Example 23, below, is a monomer. It is also a fusion or chimeric protein because the *E. Coli* expression cloning method adds polylinker sequence and a histidine tag to the expressed protein that do not exist in the native protein. The Tumstatin fragment "Tumstatin N-53," also described in Example 23, is a fragment and a deletion mutant of the full-length Tumstatin protein, and when made by the same *E. Coli* expression cloning method, also has additional sequences added to it, and is therefore a fusion or chimeric mutant fragment of the full-length Tumstatin protein. Subunits of this Tumstatin N-53, when combined together, e.g., into a dimer, trimer, etc., would produce a multimeric fusion of chimeric mutant fragment of the Tumstatin protein.

Encompassed by the present invention are proteins that have substantially the same amino acid sequence as Arresten, Canstatin or Tumstatin, or polynucleotides that have substantially the same nucleic acid sequence as the polynucleotides encoding Arresten, Canstatin or Tumstatin. "Substantially the same sequence" means a nucleic acid or polypeptide that exhibits at least about 70% sequence identity with a reference sequence, e.g., another nucleic acid or polypeptide, typically at least about 80% sequence identity with the reference sequence, preferably at least about 90% sequence identity, more preferably at least about 95% identity, and most preferably at least about 97% sequence identity with the reference sequence. The length of comparison for sequences will generally be at least 36 nucleotide bases or 12 amino acids, more preferably at least 75 nucleotide bases or at least 25 amino acids, still more preferably at least 150 nucleotide bases or 50 amino acids, and most preferably 243-264 nucleotide bases or 81-88 amino acids. "Polypeptide" as used herein indicates a molecular chain of amino acids and does not refer to a specific length of the product. Thus, peptides, oligopeptides and proteins are included within the definition of polypeptide. This term is also intended to include polypeptide that have been subjected to post-expression modifications such as, for example, glycosylations, acetylations, phosphorylations and the like.

"Sequence identity," as used herein, refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length) of the positions in two peptide or compound sequences are identical, then the two sequences are 50% identical; if 90% of the positions, e.g., 9 of 10 are matched, the two sequences share 90% sequence identity. By way of example, the amino acid sequences $R_2R_5R_7R_{10}R_6R_3$ and $R_9R_8R_1R_{10}R_6R_3$ have 3 of 6 positions in common, and therefore share 50% sequence identity, while the sequences $R_2R_5R_7R_{10}R_6R_3$ and $R_8R_1R_{10}R_6R_3$ have 3 of 5 positions in common, and therefore share 60% sequence identity. The identity between two sequences is a direct function of the number of matching or identical positions. Thus, if a portion of the reference sequence is deleted in a particular peptide, that deleted section is not counted for purposes of calculating sequence identity, e.g., $R_2R_5R_7R_{10}R_6R_3$ and $R_2R_5R_7R_{10}R_3$ have 5 out of 6 positions in common, and therefore share 83.3% sequence identity.

Identity is often measured using sequence analysis software e.g., BLASTN or BLASTP available on-line through the NIH. The default parameters for comparing two sequences (e.g., "Blast"-ing two sequences against each other) by BLASTN (for nucleotide sequences) are reward for match=1, penalty for mismatch=2, open gap=5, and extension gap=2. When using BLASTP for protein sequences, the default parameters are reward for match=0, penalty for mismatch=0, open gap=11, and extension gap=1.

When two sequences share "sequence homology," it is meant that the two sequences differ from each other only by conservative substitutions, and are "conserved variants" of each other. For polypeptide sequences, such conservative substitutions consist of substitution of one amino acid at a given position in the sequence for another amino acid of the same class (e.g., amino acids that share characteristics of hydrophobicity, charge, pK or other conformational or chemical properties, e.g., valine for leucine, arginine for lysine), or by one or more non-conservative amino acid substitutions, deletions, or insertions, located at positions of the sequence that do not alter the conformation or folding of the polypeptide to the extent that the biological activity of the polypeptide is destroyed. Examples of "conservative substitutions" include substitution of one non-polar (hydrophobic) residue such as isoleucine, valine, leucine or methionine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue, such as aspartic acid or glutamic acid for another; or the use of a chemically derivatized residue in place of a non-derivatized residue; provided that the polypeptide displays the requisite biological activity. Two sequences which share sequence homology may be called "sequence homologs."

The invention contemplates mutants of the proteins and peptides disclosed herein, where the mutation(s) do not substantially alter the activity of the protein or peptide, that is the mutations are effectively "silent" mutations. One such mutant, Tum-5-125-C-A, is presented herein, in which the cysteine at the 125th residue of the full-length Tumstatin molecule has been mutated from cysteine to alanine. This mutation prevents a disulfide bond from being formed at that residue, yet Tum-5-125-C-A retains the full activity of its parent molecule Tumstatin 44-131.

Homology, for polypeptides, is typically measured using sequence analysis software (e.g., Sequence Analysis Software Package of the Genetics Computer Group, Univ. Wisconsin Biotechnology Cntr, 1710 Univ. Ave., Madison, Wis. 53705). Protein analysis software matches similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Also encompassed by the present invention are chemical derivatives of Arresten, Canstatin and Tumstatin. "Chemical derivative" refers to a subject polypeptide having one or more residues chemically derivatized by reaction of a functional side group. Such derivatized residues include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For example: 4-hydroxyproline may be substituted for proline; 5-hydroxylysine may be substitute for lysine; 3-methylhistidine may be substituted for histidine; homoserine may be substituted for serine; and ornithine may be substituted for lysine.

The present invention also includes fusion proteins and chimeric proteins comprising the anti-angiogenic proteins, their fragments, mutants, homologs, analogs, and allelic variants, e.g., Tumstatin and Canstatin, or T1 and T4, etc. A fusion or chimeric protein can be produced as a result of recombinant expression and the cloning process, e.g., the protein may be produced comprising additional amino acids or amino acid sequences corresponding to full or partial linker sequences, e.g., the Arresten of the present invention, when produced in E. Coli (see Example 2, below), comprises additional vector sequence added to the protein, including a histidine tag. As used herein, the term "fusion" or "chimeric protein" is intended to encompass changes of this type to the original protein sequence. Similar changes were made to the Canstatin and Tumstatin proteins (Examples 14 and 23, respectively). A fusion or chimeric protein can consist of a multimer of a single protein, e.g., repeats of the anti-angiogenic proteins, or the fusion and chimeric proteins can be made up of several proteins, e.g., several of the anti-angiogenic proteins. The fusion or chimeric protein can comprise a combination of two or more known anti-angiogenic proteins (e.g., angiostatin and endostatin, or biologically active fragments of angiostatin and endostatin), or an anti-angiogenic protein in combination with a targeting agent (e.g., endostatin with epidermal growth factor (EGF) or RGD peptides), or an anti-angiogenic protein in combination with an immunoglobulin molecule (e.g., endostatin and IgG, specifically with the Fc portion removed). The fusion and chimeric proteins can also include the anti-angiogenic proteins, their fragments, mutants, homologs, analogs, and allelic variants, and other anti-angiogenic proteins, e.g., endostatin, or angiostatin. Other anti-angiogenic proteins can include restin and apomigren; (WO 99/29856, the teachings of which are herein incorporated by reference) and fragments of endostatin (WO 99/29855, the teachings of which are herein incorporated by reference). The term "fusion protein" or "chimeric protein" as used herein can also encompass additional components for e.g., delivering a chemotherapeutic agent, wherein a polynucleotide encoding the chemotherapeutic agent is linked to the polynucleotide encoding the anti-angiogenic protein. Fusion or chimeric proteins can also encompass multimers of an anti-angiogenic protein, e.g., a dimer or trimer. Such fusion or chimeric proteins can be linked together via post-translational modification (e.g., chemically linked), or the entire fusion protein may be made recombinantly.

Multimeric proteins comprising Arresten, Canstatin, Tumstatin, their fragments, mutants, homologs, analogs and allelic variants are also intended to be encompassed by the present invention. A "multimer" means a protein comprising two or more copies of a subunit protein. The subunit protein may be one of the proteins of the present invention, e.g., Arresten repeated two or more times, or a fragment, mutant, homolog, analog or allelic variant, e.g., a Tumstatin mutant or fragment, e.g., Tumstatin 333, repeated two or more times. Such a multimer may also be a fusion or chimeric protein, e.g., a repeated Tumstatin mutant may be combined with polylinker sequence, and/or one or more anti-angiogenic peptides, which may be present in a single copy, or may also be tandemly repeated, e.g., a protein may comprise two or more multimers within the overall protein.

The invention also encompasses a composition comprising one or more isolated polynucleotide(s) encoding Arresten, Canstatin or Tumstatin, as well as vectors and host cells containing such a polynucleotide, and processes for producing Arresten, Canstatin and Tumstatin, and their fragments, mutants, homologs, analogs and allelic variants. The term "vector" as used herein means a carrier into which pieces of nucleic acid may be inserted or cloned, which carrier functions to transfer the pieces of nucleic acid into a host cell. Such a vector may also bring about the replication and/or expression of the transferred nucleic acid pieces. Examples of vectors include nucleic acid molecules derived, e.g., from a plasmid, bacteriophage, or mammalian, plant or insect virus, or non-viral vectors such as ligand-nucleic acid conjugates, liposomes, or lipid-nucleic acid complexes. It may be desirable that the transferred nucleic molecule is operatively linked to an expression control sequence to form an expression vector capable of expressing the transferred nucleic acid. Such transfer of nucleic acids is generally called "transformation," and refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome. "Operably linked" refers to a situation wherein the components described are in a relationship permitting them to function in their intended manner, e.g., a control sequence "operably linked" to a coding sequence is ligated in such a manner that expression of the coding sequence is achieved under conditions compatible with the control sequence. A "coding sequence" is a polynucleotide sequence which is transcribed into mRNA and translated into a polypeptide when placed under the control of (e.g., operably linked to) appropriate regulatory sequences. The boundaries of the coding sequence are determined by a translation start codon at the 5'-terminus and a translation stop codon at the 3'-terminus. Such boundaries can be naturally-occurring, or can be introduced into or added to the polynucleotide sequence by methods known in the art. A coding sequence can include, but is not limited to, mRNA, cDNA, and recombinant polynucleotide sequences.

The vector into which the cloned polynucleotide is cloned may be chosen because it functions in a prokaryotic organism, or alternatively, it is chosen because it functions in a eukaryotic organism. Two examples of vectors which allow for both the cloning of a polynucleotide encoding the Arresten, Canstatin and Tumstatin protein, and the expression of those proteins from the polynucleotides, are the pET22b and pET28(a) vectors (Novagen, Madison, Wis., USA) and a modified pPICZαA vector (InVitrogen, San Diego, Calif., USA), which allow expression of the protein in bacteria and yeast, respectively. See for example, WO 99/29878 and U.S. Ser. No. 09/589,483, the entire teachings which are hereby incorporated by reference.

Once a polynucleotide has been cloned into a suitable vector, it can be transformed into an appropriate host cell. A "host cell" means a cell which has been or can be used as the recipient of transferred nucleic acid by means of a vector. Host cells can prokaryotic or eukaryotic, mammalian, plant, or insect, and can exist as single cells, or as a collection, e.g., as a culture, or in a tissue culture, or in a tissue or an organism. Host cells can also be derived from normal or diseased tissue from a multicellular organism, e.g., a mammal. Host cell, as used herein, is intended to include not only the original cell which was transformed with a nucleic acid, but also descendants of such a cell, which still contain the nucleic acid.

In one embodiment, the isolated polynucleotide encoding the anti-angiogenic protein additionally comprises a polynucleotide linker encoding a peptide. Such linkers are known to those of skill in the art and, for example the linker can comprise at least one additional codon encoding at least one additional amino acid. Typically the linker comprises one to about twenty or thirty amino acids. The polynucleotide linker is translated, as is the polynucleotide encoding the anti-angiogenic protein, resulting in the expression of an anti-angiogenic protein with at least one additional amino acid residue at the amino or carboxyl terminus of the anti-angiogenic protein. Importantly, the additional amino acid, or amino acids, do not compromise the activity of the anti-angiogenic protein.

After inserting the selected polynucleotide into the vector, the vector is transformed into an appropriate prokaryotic strain and the strain is cultured (e.g., maintained) under suitable culture conditions for the production of the biologically active anti-angiogenic protein, thereby producing a biologically active anti-angiogenic protein, or mutant, derivative, fragment or fusion protein thereof. In one embodiment, the invention comprises cloning of a polynucleotide encoding an anti-angiogenic protein into the vectors pET22b, pET17b or pET28a, which are then transformed into bacteria. The bacterial host strain then expresses the anti-angiogenic protein. Typically the anti-angiogenic proteins are produced in quantities of about 10-20 milligrams, or more, per liter of culture fluid.

In another embodiment of the present invention, the eukaryotic vector comprises a modified yeast vector. One method is to use a pPICzα plasmid wherein the plasmid contains a multiple cloning site. The multiple cloning site has inserted into the multiple cloning site a His.Tag motif. Additionally the vector can be modified to add a NdeI site, or other suitable restriction sites. Such sites are well known to those of skill in the art. Anti-angiogenic proteins produced by this embodiment comprise a histidine tag motif (His.tag) comprising one, or more histidines, typically about 5-20 histidines. The tag must not interfere with the anti-angiogenic properties of the protein.

One method of producing Arresten, Canstatin or Tumstatin, for example, is to amplify the polynucleotide of SEQ ID NO:1, SEQ ID NO:5, or SEQ ID NO:9, respectively, and clone it into an expression vector, e.g., pET22b, pET28(a), pPICZαA, or some other expression vector, transform the vector containing the polynucleotide into a host cell capable of expressing the polypeptide encoded by the polynucleotide, culturing the transformed host cell under culture conditions suitable for expressing the protein, and then extracting and purifying the protein from the culture. Exemplary methods of producing anti-angiogenic proteins in general, and Arresten, Canstatin and Tumstatin in particular, are provided in the Examples below. The Arresten, Canstatin or Tumstatin protein may also be expressed as a product of transgenic animals, e.g., as a component of the milk of transgenic cows, goats, sheep or pigs, or as a product of a transgenic plant, e.g., combined or linked with starch molecules in maize. These methods can also be used with subsequences of SEQ ID NO:1, SEQ ID NO:5 or SEQ ID NO:9 to produce portions of the proteins of SEQ ID NO:2, SEQ ID NO:6 or SEQ ID NO:10. These methods were used to produce, for instance, the fragments Tumstatin-333, Tumstatin-334, Tumstatin-N53, Tum-2, Tum-3, Tum-4, Tumstatin-44-131, and peptides T1, T2, T3, T4, T5 and T6.

Arresten, Canstatin or Tumstatin may also be produced by conventional, known methods of chemical synthesis. Methods for constructing the proteins of the present invention by synthetic means are known to those skilled in the art. The synthetically-constructed Arresten, Canstatin or Tumstatin protein sequences, by virtue of sharing primary, secondary or tertiary structural and/or conformational characteristics with e.g., recombinantly-produced Arresten, Canstatin or Tumstatin, may possess biological properties in common therewith, including biological activity. Thus, the synthetically-constructed Arresten, Canstatin or Tumstatin protein sequences may be employed as biologically active or immunological substitutes for e.g., recombinantly-produced, purified Arresten, Canstatin or Tumstatin protein in screening of therapeutic compounds and in immunological processes for the development of antibodies.

The Arresten, Canstatin and Tumstatin proteins are useful in inhibiting angiogenesis, as determined in standard assays, and provided in the Examples below. Arresten, Canstatin or Tumstatin do not inhibit the growth of other cell types, e.g., non-endothelial cells.

Polynucleotides encoding Arresten, Canstatin or Tumstatin can be cloned out of isolated DNA or a cDNA library. Nucleic acids and polypeptides, referred to herein as "isolated" are nucleic acids or polypeptides substantially free (i.e., separated away from) the material of the biological source from which they were obtained (e.g., as exists in a mixture of nucleic acids or in cells), which may have undergone further processing.

"Isolated" nucleic acids or polypeptides include nucleic acids or polypeptides obtained by methods described herein, similar methods, or other suitable methods, including essentially pure nucleic acids or polypeptides, nucleic acids or polypeptides produced by chemical synthesis, by combinations of chemical or biological methods, and recombinantly produced nucleic acids or polypeptides which are isolated. An isolated polypeptide therefore means one which is relatively free of other proteins, carbohydrates, lipids, and other cellular components with which it is normally associated. An isolated nucleic acid is not immediately contiguous with (i.e., covalently linked to) both of the nucleic acids with which it is immediately contiguous in the naturally-occurring genome of the organism from which the nucleic acid is derived. The term, therefore, includes, for example, a nucleic acid which is incorporated into a vector (e.g., an autonomously replicating virus or plasmid), or a nucleic acid which exists as a separate molecule independent of other nucleic acids such as a nucleic acid fragment produced by chemical means or restriction endonuclease treatment.

The polynucleotides and proteins of the present invention can also be used to design probes to isolate other antiangiogenic proteins. Exceptional methods are provided in U.S. Pat. No. 5,837,490, by Jacobs et al., the entire teachings of which are herein incorporated by reference in their entirety. The design of the oligonucleotide probe should preferably follow these parameters: (a) it should be designed to an area of the sequence which has the fewest ambiguous bases ("N's"), if any, and (b) it should be designed to have a $T_m$ of about 80° C. (assuming 2° C. for each A or T and 4° C. for each G or C).

The oligonucleotide should preferably be labeled with G-$^{32}$P-ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately $4 \times 10^6$ dpm/pmole. The bacterial culture containing the pool of full-length clones should preferably be thawed and 100 µl of the stock used to inoculate a sterile culture flask containing 25 ml of sterile L-broth containing ampicillin at 100 µg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 µg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them. Highly stringent condition are those that are at least as stringent as, for example, 1×SSC at 65° C., or 1×SSC and 50% formamide at 42° C. Moderate stringency conditions are those that are at least as stringent as 4×SSC at 65° C., or 4×SSC and 50% formamide at 42° C. Reduced stringency conditions are those that are at least as stringent as 4×SSC at 50° C., or 6×SSC and 50% formamide at 40° C.

The filter is then preferably incubated at 65° C. for 1 hour with gentle agitation in 6×SSC (20× stock is 175.3 g NaCl/liter, 88.2 g Na citrate/liter, adjusted to pH 7.0 with NaOH) containing 0.5% SDS, 100 µg/ml of yeast RNA, and 10 mM EDTA (approximately 10 mL per 150 mm filter). Preferably, the probe is then added to the hybridization mix at a concentration greater than or equal to 1×10 dpm/mL. The filter is then preferably incubated at 65° C. with gentle agitation overnight. The filter is then preferably washed in 500 mL of 2×SSC/0.5% SDS at room temperature without agitation, preferably followed by 500 mL of 2×SSC/0.1% SDS at room temperature with gentle shaking for 15 minutes. A third wash with 0.1×SSC/0.5% SDS at 65° C. for 30 minutes to 1 hour is optional. The filter is then preferably dried and subjected to autoradiography for sufficient time to visualize the positives on the X-ray film. Other known hybridization methods can also be employed. The positive colonies are then picked, grown in culture, and plasmid DNA isolated using standard procedures. The clones can then be verified by restriction analysis, hybridization analysis, or DNA sequencing.

Stringency conditions for hybridization refers to conditions of temperature and buffer composition which permit hybridization of a first nucleic acid sequence to a second nucleic acid sequence, wherein the conditions determine the degree of identity between those sequences which hybridize to each other. Therefore, "high stringency conditions" are those conditions wherein only nucleic acid sequences which are very similar to each other will hybridize. The sequences may be less similar to each other if they hybridize under moderate stringency conditions. Still less similarity is needed for two sequences to hybridize under low stringency conditions. By varying the hybridization conditions from a stringency level at which no hybridization occurs, to a level at which hybridization is first observed, conditions can be determined at which a given sequence will hybridize to those sequences that are most similar to it. The precise conditions determining the stringency of a particular hybridization include not only the ionic strength, temperature, and the concentration of destabilizing agents such as formamide, but also on factors such as the length of the nucleic acid sequences, their base composition, the percent of mismatched base pairs between the two sequences, and the frequency of occurrence of subsets of the sequences (e.g., small stretches of repeats) within other non-identical sequences. Washing is the step in which conditions are set so as to determine a minimum level of similarity between the sequences hybridizing with each other. Generally, from the lowest temperature at which only homologous hybridization occurs, a 1% mismatch between two sequences results in a 1° C. decrease in the melting temperature ($T_m$) for any chosen SSC concentration. Generally, a doubling of the concentration of SSC results in an increase in the $T_m$ of about 17° C. Using these guidelines, the washing temperature can be determined empirically, depending on the level of mismatch sought. Hybridization and wash conditions are explained in CURRENT PROTOCOLS IN MOLECULAR BIOLOGY (Ausubel, F. M. et al., eds., John Wiley & Sons, Inc., 1995, with supplemental updates) on pages 2.10.1 to 2.10.16, and 6.3.1 to 6.3.6.

High stringency conditions can employ hybridization at either (1) 1×SSC (10×SSC=3 M NaCl, 0.3 M Na$_3$-citrate.2H$_2$O (88 g/liter), pH to 7.0 with 1 M HCl), 1% SDS (sodium dodecyl sulfate), 0.1-2 mg/ml denatured salmon sperm DNA at 65° C., (2) 1×SSC, 50% formamide, 1% SDS, 0.1-2 mg/ml denatured salmon sperm DNA at 42° C., (3) 1% bovine serum albumen (fraction V), 1 mM Na$_2$ EDTA, 0.5 M NaHPO$_4$ (pH 7.2) (1 M NaHPO$_4$=134 g Na$_2$HPO$_4$.7H$_2$O, 4 ml 85% H$_3$PO$_4$ per liter), 7% SDS, 0.1-2 mg/ml denatured salmon sperm DNA at 65° C., (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured salmon sperm DNA at 42° C., (5) 5×SSC, 5×Denhardt's solution, 1% SDS, 100 µg/ml denatured salmon sperm DNA at 65° C., or (6) 5×SSC, 5×Denhardt's solution, 50% formamide, 1% SDS, 100 µg/ml denatured salmon sperm DNA at 42° C., with high stringency washes of either (1) 0.3-0.1×SSC, 0.1% SDS at 65° C., or (2) 1 mM Na$_2$EDTA, 40 mM NaHPO$_4$ (pH 7.2), 1% SDS at 65° C. The above conditions are intended to be used for DNA-DNA hybrids of 50 base pairs or longer. Where the hybrid is believed to be less than 18 base pairs in length, the hybridization and wash temperatures should be 5-10° C. below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6 (log$_{10}$M+0.41 (% G+C)−0.61 (% formamide)−500/L), where "M" is the molarity of monovalent cations (e.g., Na$^+$), and "L" is the length of the hybrid in base pairs.

Moderate stringency conditions can employ hybridization at either (1) 4×SSC, (10×SSC=3 M NaCl, 0.3 M Na$_3$-citrate.2H$_2$O (88 g/liter), pH to 7.0 with 1 M HCl), 1% SDS (sodium dodecyl sulfate), 0.1-2 mg/ml denatured salmon sperm DNA at 65° C., (2) 4×SSC, 50% formamide, 1% SDS, 0.1-2 mg/ml denatured salmon sperm DNA at 42° C., (3) 1% bovine serum albumen (fraction V), 1 mM Na$_2$EDTA, 0.5 M NaHPO$_4$ (pH 7.2) (1 M NaHPO$_4$=134 g Na$_2$HPO$_4$7H$_2$O, 4 ml 85% H$_3$PO$_4$ per liter), 7% SDS, 0.1-2 mg/ml denatured salmon sperm DNA at 65° C., (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured salmon sperm DNA at 42° C., (5) 5×SSC, 5×Denhardt's solution, 1% SDS, 100 µg/ml denatured salmon sperm DNA at 65° C., or (6) 5×SSC, 5×Denhardt's solution, 50% formamide, 1% SDS, 100 µg/ml denatured salmon sperm DNA at 42° C., with moderate stringency washes of 1×SSC, 0.1% SDS at 65° C. The above conditions are intended to be used for DNA-DNA hybrids of 50 base pairs or longer. Where the hybrid is believed to be less than 18 base pairs in length, the hybridization and wash temperatures should be 5-10° C. below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6(log$_{10}$M)+0.4-1(% G+C)−0.61 (% formamide)−500/L), where "M" is the molarity of monovalent cations (e.g., Na$^+$), and "L" is the length of the hybrid in base pairs.

Low stringency conditions can employ hybridization at either (1) 4×SSC, (10×SSC=3 M NaCl, 0.3 M Na$_3$-citrate.2H$_2$O (88 g/liter), pH to 7.0 with 1 M HCl), 1% SDS (sodium dodecyl sulfate), 0.1-2 mg/ml denatured salmon sperm DNA at 50° C., (2) 6×SSC, 50% formamide, 1% SDS, 0.1-2 mg/ml denatured salmon sperm DNA at 40° C., (3) 1% bovine serum albumen (fraction V), 1 mM Na$_2$EDTA, 0.5 M NaHPO$_4$ (pH 7.2) (1 M NaHPO$_4$=134 g Na$_2$HPO$_4$7H$_2$O, 4 ml 85% H$_3$PO$_4$ per liter), 7% SDS, 0.1-2 mg/ml denatured salmon sperm DNA at 50° C., (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured salmon sperm DNA at 40° C., (5) 5×SSC, 5×Denhardt's solution, 1% SDS, 100 µg/ml denatured salmon sperm DNA at 50° C., or (6) 5×SSC, 5×Denhardt's solution, 50% formamide, 1% SDS, 100 µg/ml denatured salmon sperm DNA at 40° C., with low stringency washes of either 2×SSC, 0.1% SDS at 50° C., or (2) 0.5% bovine serum albumin (fraction V), 1 mM Na$_2$EDTA, 40 mM NaHPO$_4$ (pH 7.2), 5% SDS. The above conditions are intended to be used for DNA-DNA hybrids of 50 base pairs or longer. Where the hybrid is believed to be less than 18 base pairs in length, the hybridization and wash temperatures should be 5-10° C. below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6 (log$_{10}$M)+0.41(% G+C)−0.61 (% formamide)−500/L), where "M" is the molarity of monovalent cations (e.g., Na$^+$), and "L" is the length of the hybrid in base pairs.

The present invention includes methods of inhibiting angiogenesis in mammalian tissue using Arresten, Canstatin, Tumstatin or their biologically-active fragments, analogs, homologs, derivatives or mutants. In particular, the present invention includes methods of treating an angiogenesis-mediated disease with an effective amount of one or more of the anti-angiogenic proteins, or one or more biologically active fragment thereof, or combinations of fragments that possess anti-angiogenic activity, or agonists and antagonists. An effective amount of anti-angiogenic protein is an amount sufficient to inhibit the angiogenesis which results in the disease or condition, thus completely, or partially, alleviating the disease or condition. Alleviation of the angiogenesis-mediated disease can be determined by observing an alleviation of symptoms of the disease, e.g., a reduction in the size of a tumor, or arrested tumor growth. As used herein, the term "effective amount" also means the total amount of each active component of the composition or method that is sufficient to show a meaningful patient benefit, i.e., treatment, healing, prevention or amelioration of the relevant medical condition, or an increase in rate of treatment, healing, prevention or amelioration of such conditions. When applied to a combination, the term refers to combined amounts of the active ingredients that result in the therapeutic effect, whether administered in combination, serially or simultaneously. Angiogenesis-mediated diseases include, but are not limited to, cancers, solid tumors, blood-born tumors (e.g., leukemias), tumor metastasis, benign tumors (e.g., hemangiomas, acoustic neuromas, neurofibromas, organ fibrosis, trachomas, and pyogenic granulomas), rheumatoid arthritis, psoriasis, ocular angiogenic diseases (e.g., diabetic retinopathy, retinopathy of prematurity, macular degeneration, corneal graft rejection, neovascular glaucoma, retrolental fibroplasia, rubeosis), Osler-Webber Syndrome, myocardial angiogenesis, plaque neovascularization, telangiectasia, hemophiliac joints, angiofibroma, and wound granulation. The anti-angiogenic proteins are useful in the treatment of diseases of excessive or abnormal stimulation of endothelial cells. These diseases include, but are not limited to, intestinal adhesions, Crohn's disease, atherosclerosis, scleroderma, fibrosis and hypertrophic scars (i.e., keloids). The anti-angiogenic proteins can be used as a birth control agent by preventing vascularization required for embryo implantation. The anti-angiogenic proteins are useful in the treatment of diseases that have angiogenesis as a pathologic consequence such as cat scratch disease (*Rochele minalia quintosa*) and ulcers (*Heliobacter pylori*). The anti-angiogenic proteins can also be used to prevent dialysis graft vascular access stenosis, and obesity, e.g., by inhibiting capillary formation in adipose tissue, thereby preventing its expansion. The anti-angiogenic proteins can also be used to treat localized (e.g., nonmetastisized) diseases. "Cancer" means neoplastic growth, hyperplastic or proliferative growth or a pathological state of abnormal cellular development and includes solid tumors, non-solid tumors, and any abnormal cellular proliferation, such as that seen in leukemia. As used herein, "cancer" also means angiogenesis-dependent cancers and tumors, i.e., tumors that require for their growth (expansion in volume and/or mass) an increase in the number and density of the blood vessels supplying them with blood. "Regression" refers to the reduction of tumor mass and size as determined using methods well-known to those of skill in the art.

Alternatively, where an increase in angiogenesis is desired, e.g., in wound healing, or in post-infarct heart tissue, antibodies or antisera to the anti-angiogenic proteins can be used to block localized, native anti-angiogenic proteins and processes, and thereby increase formation of new blood vessels so as to inhibit atrophy of tissue.

The anti-angiogenic proteins may be used in combination with themselves, or other compositions and procedures for the treatment of diseases, e.g., Arresten and Canstatin can be combined in a pharmaceutical composition, Tum-4 and T7 can be combined in a composition, or a tumor may be treated conventionally with surgery, radiation, chemotherapy, or immunotherapy, combined with the anti-angiogenic proteins and then the anti-angiogenic proteins may be subsequently administered to the patient to extend the dormancy of micrometastases and to stabilize and inhibit the growth of any residual primary tumor. The anti-angiogenic proteins, or fragments, antisera, receptor agonists, or receptor antagonists thereof, or combinations thereof can also be combined with other anti-angiogenic compounds, or proteins, fragments, antisera, receptor agonists, receptor antagonists of other anti-angiogenic proteins (e.g., angiostatin, endostatin). Additionally, the anti-angiogenic proteins, or their fragments, antisera, receptor agonists, receptor antagonists, or combinations thereof, are combined with pharmaceutically acceptable excipients, and optionally sustained-release matrix, such as biodegradable polymers, to form therapeutic compositions. The compositions of the present invention may also contain other anti-angiogenic proteins or chemical compounds, such as endostatin or angiostatin, and mutants, fragments, and analogs thereof. The compositions may further contain other agents which either enhance the activity of the protein or compliment its activity or use in treatment, such as chemotherapeutic or radioactive agents. Such additional factors and/or agents may be included in the composition to produce a synergistic effect with protein of the invention, or to minimize side effects. Additionally, administration of the composition of the present invention may be administered concurrently with other therapies, e.g., administered in conjunction with a chemotherapy or radiation therapy regimen.

The invention includes methods for inhibiting angiogenesis in mammalian (e.g., human) tissues by contacting the tissue with a composition comprising the proteins of the invention. "Contacting" means not only topical application, but also those modes of delivery that introduce the composition into the tissues, or into the cells of the tissues.

Use of timed release or sustained release delivery systems are also included in the invention. Such systems are highly desirable in situations where surgery is difficult or impossible, e.g., patients debilitated by age or the disease course itself, or where the risk-benefit analysis dictates control over cure.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The angiogenesis-modulating composition of the present invention may be a solid, liquid or aerosol and may be administered by any known route of administration. Examples of solid compositions include pills, creams, and implantable dosage units. The pills may be administered orally, the therapeutic creams may be administered topically. The implantable dosage unit may be administered locally, for example at a tumor site, or which may be implanted for systemic release of the angiogenesis-modulating composition, for example subcutaneously. Examples of liquid composition include formulations adapted for injection subcutaneously, intravenously, intraarterially, and formulations for topical and intraocular administration. Examples of aerosol formulation include inhaler formulation for administration to the lungs.

The proteins and protein fragments with the anti-angiogenic activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the anti-angiogenic proteins may be incorporated into biodegradable polymers allowing for sustained release of the compound, the polymers being implanted in the vicinity of where drug delivery is desired, for example, at the site of a tumor or implanted so that the anti-angiogenic proteins are slowly released systemically. Osmotic minipumps may also be used to provide controlled delivery of high concentrations of the anti-angiogenic proteins through cannulae to the site of interest, such as directly into a metastatic growth or into the vascular supply to that tumor. The biodegradable polymers and their use are described, for example, in detail in Brem et al. (1991, J. Neurosurg. 74:441-46), which is hereby incorporated by reference in its entirety.

The compositions containing a polypeptide of this invention can be administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

Modes of administration of the compositions of the present inventions include intravenous, intramuscular, intraperitoneal, intrasternal, subcutaneous and intraarticular injection and infusion. Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyois (e.g., glycerol, propylene glycol, polyethylene glycol and the like), carboxymethylcellulose and suitable mixtures thereof, vegetable oils (e.g., olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular pohner employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

The therapeutic compositions of the present invention can include pharmaceutically acceptable salts of the components therein, e.g., which may be derived from inorganic or organic acids. "Pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in J. Pharmaceutical Sciences (1977) 66:1 et seq., which is incorporated herein by reference. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. The salts may be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

As used herein, the terms "pharmaceutically acceptable," "physiologically tolerable" and grammatical variations thereof as they refer to compositions, carriers, diluents and reagents, are used interchangeably and represent that the materials are capable of administration to or upon a mammal with a minimum of undesirable physiological effects such as nausea, dizziness, gastric upset and the like. The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The anti-angiogenic proteins of the present invention can also be included in a composition comprising a prodrug. As used herein, the term "prodrug" refers to compounds which are rapidly transformed in vivo to yield the parent compound, for example, by enzymatic hydrolysis in blood. A thorough discussion is provided in T. Higuchi & V. Stella, Prodrugs as Novel Delivery Systems, Vol. 14 of the ACS Symposium Series, and in BIOREVERSIBLE CARRIERS IN DRUG DESIGN, (Edward B. Roche, ed., American Pharmaceutical Assoc. and Permagon Press, 1987), both of which are incorporated herein by reference. As used herein, the term "pharmaceutically acceptable prodrug" refers to (1) those prodrugs of the compounds of the present invention which are, within the scope of sound medical judgement, suitable for use in contact with the tissues of humans and animals without undue toxicity, irritation, allergic response and the like, commensurate with a suitable benefit-to-risk ratio and effective for their intended use and (2) zwitterionic forms, where possible, of the parent compound.

The dosage of the anti-angiogenic proteins of the present invention will depend on the disease state or condition being treated and other clinical factors such as weight and condition of the human or animal and the route of administration of the compound. For treating humans or animals, about 10 mg/kg of body weight to about 20 mg/kg of body weight of the protein can be administered. In combination therapies, e.g., the proteins of the invention in combination with radiotherapy, chemotherapy, or immunotherapy, it may be possible to reduce the dosage, e.g., to about 0.1 mg/kg of body weight to about 0.2 mg/kg of body weight. Depending upon the half-life of the anti-angiogenic proteins in the particular animal or human, the anti-angiogenic proteins can be administered between several times per day to once a week. It is to be understood that the present invention has application for both human and veterinary use. The methods of the present invention contemplate single as well as multiple administrations, given either simultaneously or over an extended period of time. In addition, the anti-angiogenic proteins can be administered in conjunction with other forms of therapy, e.g., chemotherapy, radiotherapy, or immunotherapy.

The anti-angiogenic protein formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The anti-angiogenic protein formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

When an effective amount of protein of the present invention is administered orally, the anti-angiogenic proteins of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5% to 95% protein of the present invention, and preferably from about 25% to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5% to 90% by weight of protein of the present invention, and preferably from about 1% to 50% protein of the present invention.

When an effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Preferred unit dosage formulations are those containing a daily dose or unit, daily sub-dose, or an appropriate fraction thereof, of the administered ingredient. It should be understood that in addition to the ingredients, particularly mentioned above, the formulations of the present invention may include other agents conventional in the art having regard to the type of formulation in question. Optionally, cytotoxic agents may be incorporated or otherwise combined with the anti-angiogenic proteins, or biologically functional protein fragments thereof, to provide dual therapy to the patient.

The therapeutic compositions are also presently valuable for veterinary applications. Particularly domestic animals and thoroughbred horses, in addition to humans, are desired patients for such treatment with proteins of the present invention.

Cytotoxic agents such as ricin, can be linked to the anti-angiogenic proteins, and fragments thereof, thereby providing a tool for destruction of cells that bind the anti-angiogenic proteins. These cells may be found in many locations, including but not limited to, micrometastases and primary tumors. Proteins linked to cytotoxic agents are infused in a manner designed to maximize delivery to the desired location. For example, ricin-linked high affinity fragments are delivered through a cannula into vessels supplying the target site or directly into the target. Such agents are also delivered in a controlled manner through osmotic pumps coupled to infusion cannulae. A combination of antagonists to the anti-angiogenic proteins may be co-applied with stimulators of angiogenesis to increase vascularization of tissue. This therapeutic regimen provides an effective means of destroying metastatic cancer.

Additional treatment methods include administration of the anti-angiogenic proteins, fragments, analogs, antisera, or receptor agonists and antagonists thereof, linked to cytotoxic agents. It is to be understood that the anti-angiogenic proteins can be human or animal in origin. The anti-angiogenic proteins can also be produced synthetically by chemical reaction or by recombinant techniques in conjunction with expression systems. The anti-angiogenic proteins can also be produced by enzymatically cleaving isolated Type IV collagen to generate proteins having anti-angiogenic activity. For instance, one can obtain the proteins and peptides of the invention by subjecting vascular basement membrane, e.g., Type IV collagen, to proteolysis by proteases, e.g., MMP-2, MMP-3, MMP-9, elastase. The anti-angiogenic proteins may also be produced by compounds that mimic the action of endogenous enzymes that cleave Type IV collagen to the anti-angiogenic proteins. Production of the anti-angiogenic proteins may also be modulated by compounds that affect the activity of cleavage enzymes.

The present invention also encompasses gene therapy whereby a polynucleotide encoding the anti-angiogenic proteins, integrins, integrin subunits, or a mutant, fragment, or fusion protein thereof, is introduced and regulated in a patient. Various methods of transferring or delivering DNA to cells for expression of the gene product protein, otherwise referred to as gene therapy, are disclosed in Gene Transfer into Mammalian Somatic Cells in vivo, N. Yang (1992) Crit. Rev. Biotechn. 12(4):335-56, which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen. As an example of a prophylactic strategy, a gene such as that encoding one or more of the anti-angiogenic proteins may be placed in a patient and thus prevent occurrence of angiogenesis; or a gene that makes tumor cells more susceptible to radiation could be inserted and then radiation of the tumor would cause increased killing of the tumor cells.

Many protocols for transfer of the DNA or regulatory sequences of the anti-angiogenic proteins are envisioned in this invention. Transfection of promoter sequences, other than one normally found specifically associated with the anti-angiogenic proteins, or other sequences which would increase production of the anti-angiogenic proteins are also envisioned as methods of gene therapy. An example of this technology is found in Transkaryotic Therapies, Inc., of Cambridge, Mass., using homologous recombination to insert a "genetic switch" that turns on an erythropoietin gene in cells. See Genetic Engineering News, Apr. 15, 1994. Such "genetic switches" could be used to activate the anti-angiogenic proteins (or their receptors) in cells not normally expressing those proteins (or receptors).

Gene transfer methods for gene therapy fall into three broad categories: physical (e.g., electroporation, direct gene transfer and particle bombardment), chemical (e.g., lipid-based carriers, or other non-viral vectors) and biological (e.g., virus-derived vector and receptor uptake). For example, non-viral vectors may be used which include liposomes coated with DNA. Such liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene maybe directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, then the transfected cells are selected and expanded for either implantation into a patient or for other uses.

In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed. Additionally, the other methods described herein, such as use of a "gene gun," may be used for in vitro insertion of the DNA or regulatory sequences controlling production of the anti-angiogenic proteins.

Chemical methods of gene therapy may involve a lipid based compound, not necessarily a liposome, to transfer the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct the tissue-specific expression of foreign genes, cis-acting regulatory elements or promoters that are known to be tissue-specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed at by the 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome.

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product proteins at high levels. Adenoviral vectors have high efficiencies of infectivity, even with low titers of virus. Additionally, the virus is fully infective as a cell-free virion, so injection of producer cell lines is not necessary. Another potential advantage to adenoviral vectors is the ability to achieve long term expression of heterologous genes in vivo.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs. Another method, ligand-mediated gene therapy, involves complexing the DNA with specific ligands to form ligand-DNA conjugates, to direct the DNA to a specific cell or tissue.

It has been found that injecting plasmid DNA into muscle cells yields high percentage of the cells which are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Electroporation for gene transfer uses an electrical current to make cells or tissues susceptible to electroporation-mediated mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex can be conveniently introduced into body fluids or the bloodstream and then site-specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialo-glycoprotein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

Gene regulation of the anti-angiogenic proteins may be accomplished by administering compounds that bind to the gene encoding one of the anti-angiogenic proteins, or control regions associated with the gene, or its corresponding RNA transcript to modify the rate of transcription or translation. Additionally, cells transfected with a DNA sequence encoding the anti-angiogenic proteins may be administered to a patient to provide an in vivo source of those proteins. For example, cells may be transfected with a vector containing a nucleic acid sequence encoding the anti-angiogenic proteins. The transfected cells may be cells derived from the patient's normal tissue, the patient's diseased tissue, or may be non-patient cells.

For example, tumor cells removed from a patient can be transfected with a vector capable of expressing the proteins of the present invention, and re-introduced into the patient. The transfected tumor cells produce levels of the protein in the patient that inhibit the growth of the tumor. Patients may be human or non-human animals. Cells may also be transfected by non-vector, or physical or chemical methods known in the art such as electroporation, ionoporation, or via a "gene gun." Additionally, the DNA may be directly injected, without the aid of a carrier, into a patient. In particular, the DNA may be injected into skin, muscle or blood.

The gene therapy protocol for transfecting the anti-angiogenic proteins into a patient may either be through integration of the anti-angiogenic protein DNA into the genome of the cells, into minichromosomes or as a separate replicating or non-replicating DNA construct in the cytoplasm or nucleoplasm of the cell. Expression of the anti-angiogenic proteins may continue for a long-period of time or may be reinjected periodically to maintain a desired level of the protein(s) in the cell, the tissue or organ or a determined blood level.

In addition, the invention encompasses antibodies and antisera, which can be used for testing of novel anti-angiogenic proteins, and can also be used in diagnosis, prognosis, or treatment of diseases and conditions characterized by, or associated with, angiogenic activity or lack thereof. Such antibodies and antisera can also be used to up-regulate angiogenesis where desired, e.g., in post-infarct heart tissue, antibodies or antisera to the proteins of the invention can be used to block localized, native anti-angiogenic proteins and processes, and increase formation of new blood vessels and inhibit atrophy of heart tissue.

Such antibodies and antisera can be combined with pharmaceutically-acceptable compositions and carriers to form diagnostic, prognostic or therapeutic compositions. The term "antibody" or "antibody molecule" refers to a population of immunoglobulin molecules and/or immunologically active portions of immunoglobulin molecules, i.e., molecules that contain an antibody combining site or paratope.

Passive antibody therapy using antibodies that specifically bind the anti-angiogenic proteins can be employed to modulate angiogenic-dependent processes such as reproduction, development, and wound healing and tissue repair. In addition, antisera directed to the Fab regions of antibodies of the anti-angiogenic proteins can be administered to block the ability of endogenous antisera to the proteins to bind the proteins.

The anti-angiogenic proteins of the present invention also can be used to generate antibodies that are specific for the inhibitor(s) and receptor(s). The antibodies can be either polyclonal antibodies or monoclonal antibodies. These antibodies that specifically bind to the anti-angiogenic proteins or their receptors can be used in diagnostic methods and kits that are well known to those of ordinary skill in the art to detect or quantify the anti-angiogenic proteins or their receptors in a body fluid or tissue. Results from these tests can be used to diagnose or predict the occurrence or recurrence of a cancer and other angiogenic mediated diseases.

The invention also includes use of the anti-angiogenic proteins, antibodies to those proteins, and compositions comprising those proteins and/or their antibodies in diagnosis or prognosis of diseases characterized by angiogenic activity. As used herein, the term "prognostic method" means a method that enables a prediction regarding the progression of a disease of a human or animal diagnosed with the disease, in particular, an angiogenesis dependent disease. The term "diagnostic method" as used herein means a method that enables a determination of the presence or type of angiogenesis-dependent disease in or on a human or animal.

The anti-angiogenic proteins can be used in a diagnostic method and kit to detect and quantify antibodies capable of binding the proteins. These kits would permit detection of circulating antibodies to the anti-angiogenic proteins which indicates the spread of micrometastases in the presence of the anti-angiogenic proteins secreted by primary tumors in situ. Patients that have such circulating anti-protein antibodies may be more likely to develop multiple tumors and cancers, and may be more likely to have recurrences of cancer after treatments or periods of remission. The Fab fragments of these anti-protein antibodies may be used as antigens to generate anti-protein Fab-fragment antisera which can be used to neutralize anti-protein antibodies. Such a method would reduce the removal of circulating protein by anti-protein antibodies, thereby effectively elevating circulating levels of the anti-angiogenic proteins.

The present invention also includes isolation of receptors specific for the anti-angiogenic proteins. Protein fragments that possess high affinity binding to tissues can be used to isolate the receptor of the anti-angiogenic proteins on affinity columns. Isolation and purification of the receptor(s) is a fundamental step towards elucidating the mechanism of action of the anti-angiogenic proteins. Isolation of a receptor and identification of agonists and antagonists will facilitate development of drugs to modulate the activity of the receptor, the final pathway to biological activity. Isolation of the receptor enables the construction of nucleotide probes to monitor the location and synthesis of the receptor, using in situ and solution hybridization technology. Further, the gene for the receptor can be isolated, incorporated into an expression vector and transfected into cells, such as patient tumor cells to increase the ability of a cell type, tissue or tumor to bind the anti-angiogenic proteins and inhibit local angiogenesis.

The anti-angiogenic proteins are employed to develop affinity columns for isolation of the receptor(s) for the anti-angiogenic proteins from cultured tumor cells. Isolation and purification of the receptor is followed by amino acid sequencing. Using this information the gene or genes coding for the receptor can be identified and isolated. Next, cloned nucleic acid sequences are developed for insertion into vectors capable of expressing the receptor. These techniques are well known to those skilled in the art. Transfection of the nucleic acid sequence(s) coding for the receptor into tumor cells, and expression of the receptor by the transfected tumor cells enhances the responsiveness of these cells to endogenous or exogenous anti-angiogenic proteins and thereby decreasing the rate of metastatic growth.

Angiogenesis-inhibiting proteins of the present invention can be synthesized in a standard microchemical facility and purity checked with HPLC and mass spectrophotometry. Methods of protein synthesis, HPLC purification and mass spectrophotometry are commonly known to those skilled in these arts. The anti-angiogenic proteins and their receptors proteins are also produced in recombinant E. Coli or yeast expression systems, and purified with column chromatography.

Different protein fragments of the intact the anti-angiogenic proteins can be synthesized for use in several applications including, but not limited to the following; as antigens for the development of specific antisera, as agonists and antagonists active at binding sites of the anti-angiogenic proteins, as proteins to be linked to, or used in combination with, cytotoxic agents for targeted killing of cells that bind the anti-angiogenic proteins.

The synthetic protein fragments of the anti-angiogenic proteins have a variety of uses. The protein that binds to the receptor(s) of the anti-angiogenic proteins with high specificity and avidity is radiolabeled and employed for visualization and quantitation of binding sites using autoradiographic and membrane binding techniques. This application provides important diagnostic and research tools. Knowledge of the binding properties of the receptor(s) facilitates investigation of the transduction mechanisms linked to the receptor(s).

The anti-angiogenic proteins and proteins derived from them can be coupled to other molecules using standard methods. The amino and carboxyl termini of the anti-angiogenic proteins both contain tyrosine and lysine residues and are isotopically and nonisotopically labeled with many techniques, for example radiolabeling using conventional techniques (tyrosine residues-chloramine T, iodogen, lactoperoxidase; lysine residues-Bolton-Hunter reagent). These coupling techniques are well known to those skilled in the art. Alternatively, tyrosine or lysine is added to fragments that do not have these residues to facilitate labeling of reactive amino and hydroxyl groups on the protein. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

The anti-angiogenic proteins are chemically coupled to isotopes, enzymes, carrier proteins, cytotoxic agents, fluorescent molecules, chemiluminescent, bioluminescent and other compounds for a variety of applications. The efficiency of the coupling reaction is determined using different techniques appropriate for the specific reaction. For example, radiolabeling of a protein of the present invention with $^{125}I$ is accomplished using chloramine T and $Na^{125}I$ of high specific activity. The reaction is terminated with sodium metabisulfite and the mixture is desalted on disposable columns. The labeled protein is eluted from the column and fractions are collected. Aliquots are removed from each fraction and radioactivity measured in a gamma counter. In this manner, the unreacted $Na^{125}I$ is separated from the labeled protein. The protein fractions with the highest specific radioactivity are stored for subsequent use such as analysis of the ability to bind to antisera of the anti-angiogenic proteins.

In addition, labeling the anti-angiogenic proteins with short lived isotopes enables visualization of receptor binding sites in vivo using positron emission tomography or other modern radiographic techniques to locate tumors with the proteins' binding sites.

Systematic substitution of amino acids within these synthesized proteins yields high affinity protein agonists and antagonists to the receptor(s) of the anti-angiogenic proteins that enhance or diminish binding to the receptor(s). Such agonists are used to suppress the growth of micrometastases, thereby limiting the spread of cancer. Antagonists to the anti-angiogenic proteins are applied in situations of inadequate vascularization, to block the inhibitory effects of the anti-angiogenic proteins and promote angiogenesis. For example, this treatment may have therapeutic effects to promote wound healing in diabetics.

The invention is further illustrated by the following examples, which are not meant to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Isolation of Native Arresten

Arresten can be generated in milligram quantities from human placenta and amnion tissue. The protocol for isolating this and similar proteins has been described by others (e.g., Langeveld, J. P. et al., 1988, J. Biol. Chem. 263:10481-8; Saus, J. et al., 1988, J. Biol. Chem. 263:13374-80; Gunwar, S. et al., 1990, J. Biol. Chem. 265:5466-9; Gunwar S. et al., 1991, J. Biol. Chem. 266:15318-24; Kahsai, T. Z. et al., 1997, J. Biol. Chem. 272:17023-32). Production of the recombinant form of Arresten is described in Neilson et al. (1993, J. Biol. Chem. 268:8402-6). The protein can also be expressed in 293 kidney cells (e.g., by the method described in Hohenester, E. et al., 1998, EMBO J. 17:1656-64). Arresten can also be isolated according to the method of Pihlajaniemi, T. et al. (1985, J. Biol. Chem. 260:7681-7).

The nucleotide (SEQ ID NO:1) and amino acid (SEQ ID NO:2) sequence of the α1 chain of the NC1 domain of Type IV collagen are shown in FIG. 1, and correspond to GenBank Accession No. M11315 (Brinker, J. M. et al., 1994). Arresten generally comprises the NC1 domain of the α1 chain of Type IV collagen, and possibly also the junction region, which are the 12 amino acids immediately before the NC1 domain.

Native Arresten was isolated from human placenta using bacterial collagenase, anion-exchange chromatography, gel filtration chromatography, HPLC, and affinity chromatography (Gunwar, S. et al., 1991, J. Biol. Chem. 266:15318-24; Weber, S. et al., 1984, Eur. J. Biochem. 139:401-10). Type IV collagen monomers isolated from human placenta were HPLC-purified using a C-18 hydrophobic column (Pharmacia, Piscataway, N.J., USA). The constituent proteins were resolved with an acetonitrile gradient (32%-39%). A major peak was visible, and a small double peak. SDS-PAGE analysis revealed two bands within the first peak, and no detectable proteins in the second peak. Immunoblotting, also found no immunodetectable protein in the second peak, and the major peak was identified as Arresten.

Example 2

Recombinant Production of Arresten in E. Coli

The sequence encoding Arresten was amplified by PCR from the al NC1(IV)/pDS vector (Neilson, E. G. et al., 1993, J. Bio. Chem. 268:8402-5) using the forward primer 5'-CGG GAT CCT TCT GTT GAT CAC GGC TTC-3' (SEQ ID NO:3) and the reverse primer 5'-CCC AAG CTT TGT TCT TCT CAT ACA GAC-3' (SEQ ID NO:4). The resulting cDNA fragment was digested with BamHI and HindIII and ligated into predigested pET22b(+) (Novagen, Madison, Wis., USA). This construct is shown in FIG. 2. This placed Arresten downstream of and in frame with The pelB leader sequence, allowing for periplasmic localization and expression of soluble protein. Additional vector sequence was added to the protein encoding amino acids MDIGINSD (SEQ ID NO:13). The 3' end of the sequence was ligated in frame with the polyhistidine tag sequence. Additional vector sequence between the 3' end of the cDNA and the his-tag encoded the amino acids KLAAALE (SEQ ID NO:14). Positive clones were sequenced on both strands.

Plasmid constructs encoding Arresten were first transformed into E. Coli HMS174 (Novagen, Madison, Wis., USA) and then transformed into BL21 (Novagen, Madison, Wis., USA) for expression. An overnight bacterial culture was used to inoculate a 500 ml culture of LB medium. This culture was grown for approximately four hours until the cells reached an $OD_{600}$ of 0.6. Protein expression was then induced by addition of IPTG to a final concentration of 1-2 mM. After a two-hour induction, cells were harvested by centrifugation at 5000×g and lysed by resuspension in 6 M guanidine, 0.1 M $NaH_2PO_4$, 0.01M Tris-HCl (pH 8.0). Resuspended cells were sonicated briefly, and centrifuged at 12,000×g for 30 minutes. The supernatant fraction was passed over a 5 ml Ni-NTA agarose column (Qiagen, Hilden, Germany) four to six times at a speed of 2 ml per minute. Non-specifically bound protein was removed by washing with both 10 mM and 25 mM imidazole in 8 M urea, 0.1 M $NaH_2PO_4$, 0.01 M Tris-HCl (pH 8.0). Arresten protein was eluted from the column with increasing concentrations of imidazole (50 mM, 125 mM and 250 mM) in 8 M urea, 0.1 M $NaH_2PO_4$, 0.01 M Tris-HCl (pH 8.0). The eluted protein was dialyzed twice against PBS at 4.degree. C. A minor portion of the total protein precipitated during dialysis. Dialyzed protein was collected and centrifuged at approximately 3500×g and separated into pellet and supernatant fractions. Protein concentration in each fraction was determined by the BCA assay (Pierce Chemical Co., Rockford, Ill., USA) and quantitative SDS-PAGE analysis. The fraction of total protein in the pellet was approximately 22%, with the remaining 78% recovered as a soluble protein. The total yield of protein was approximately 10 mg/liter.

The E. Coli-expressed protein was isolated predominantly as a soluble protein, and SDS-PAGE revealed a monomeric band at 29 kDa. The additional 3 kDa arises from polylinker and histidine tag sequences and was immunodetected by both Arresten and 6-Histidine tag antibodies.

Example 3

Expression of Arresten in 293 Embryonic Kidney Cells

The pDS plasmid containing α1(IV) NC1 was used to amplify Arresten in a way that it would add a leader signal sequence in-frame into the pcDNA 3.1 eukaryotic expression vector (InVitrogen, San Diego, Calif., USA). The leader sequence from the 5' end of the full length α1(IV) chain was cloned 5' to the NC1 domain to enable protein secretion into the culture medium. The Arresten-containing recombinant vectors were sequenced using flanking primers. Error-free cDNA clones were further purified and used for in vitro translation studies to confirm protein expression. The Arresten-containing plasmid and control plasmid were used to transfect 293 cells using the calcium chloride method. Transfected clones were selected by geneticin antibiotic treatment (Life Technologies/Gibco BRL, Gaithersburg, Md., USA). The cells were passed for three weeks in the presence of the antibiotic until no cell death was evident. Clones were then expanded into T-225 flasks and grown until confluent. The supernatant was then collected and concentrated using an amicon concentrator (Amicon, Inc., Beverly, Mass., USA).

The concentrated supernatant was analyzed by SDS-PAGE, immunoblotting and ELISA for Arresten expression. Strong binding in the supernatant was detected by ELISA. SDS-PAGE analysis revealed a single major band at about 30 kDa. Arresten-containing supernatant was subjected to affinity chromatography using Arresten-specific antibodies (Gunwar, S. et al., 1991, J. Biol. Chem. 266:15318-24). A major peak was identified, containing a monomer of about 30 kDa that was immunoreactive with Arresten antibodies. Approximately 1-2 mg of recombinant Arresten was produced per liter of culture fluid.

Example 4

Arresten Inhibits Endothelial Cell Proliferation

Figure 3A:
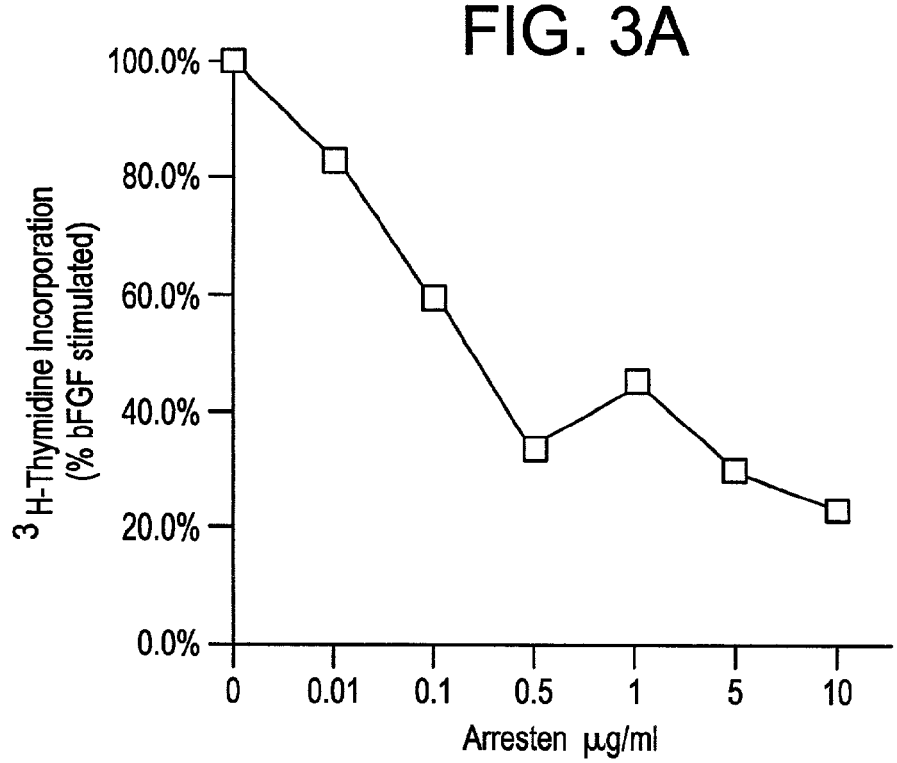
FIGS. 3A and 3B are a pair of line graphs showing the effects of Arresten (FIG. 3A, 0 μg/ml to 10 μg/ml, x-axis) and endostatin (FIG. 3B, 0 μg/ml to 10 μg/ml, x-axis) on $^3$H-thymidine incorporation (y-axis) as an indicator of endothelial cell (C-PAE) proliferation.
Figure 3B:
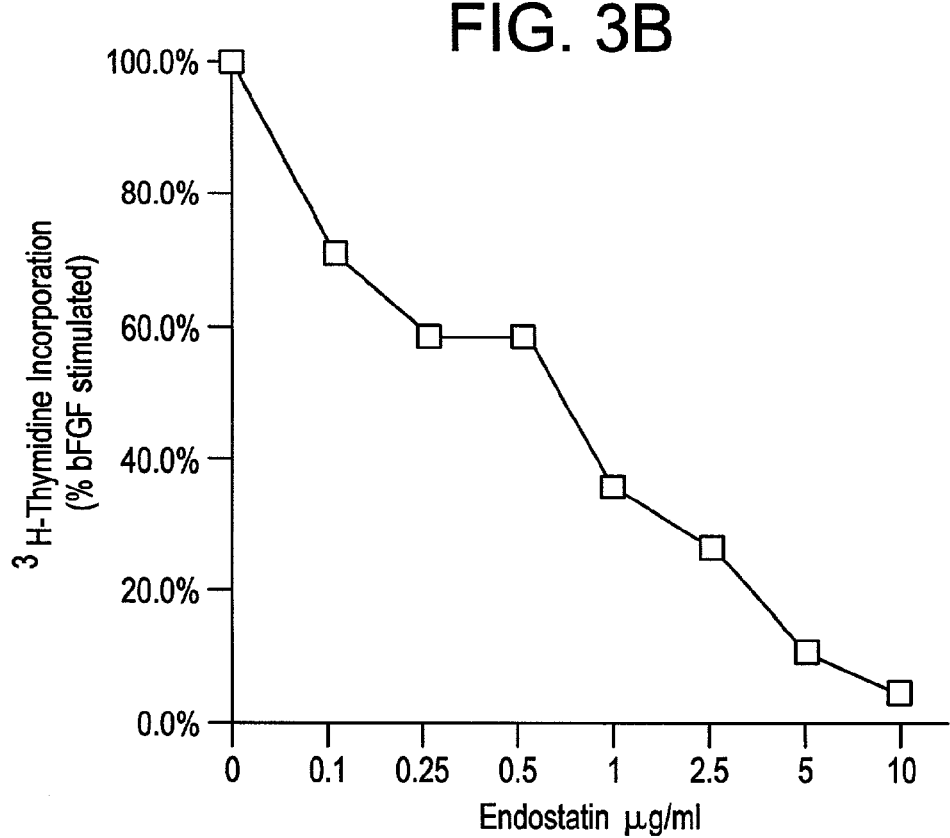
Figure 4A:
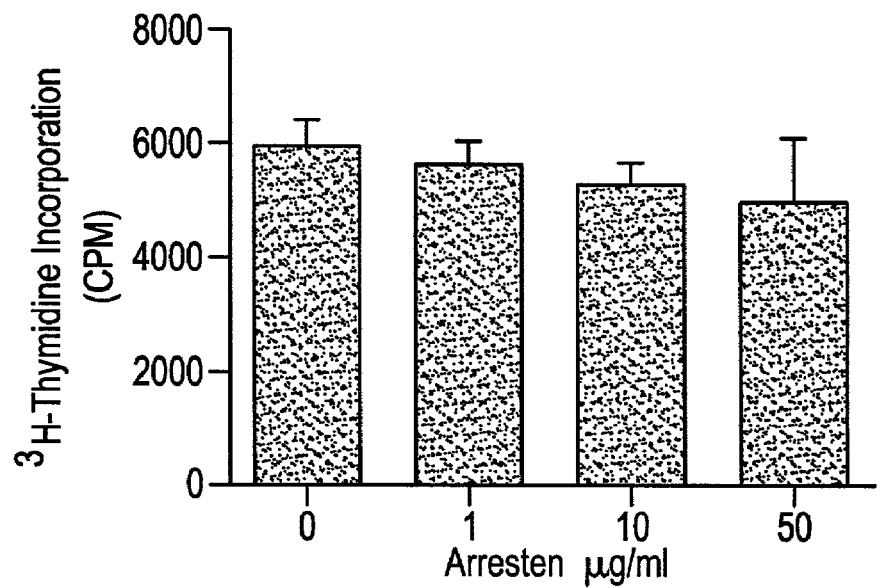
FIGS. 4A, 4B, 4C and 4D are a set of four bar charts showing the effect of Arresten and endostatin on $^3$H-thymidine incorporation (y-axis) as an indicator of endothelial cell proliferation.
Figure 4B:
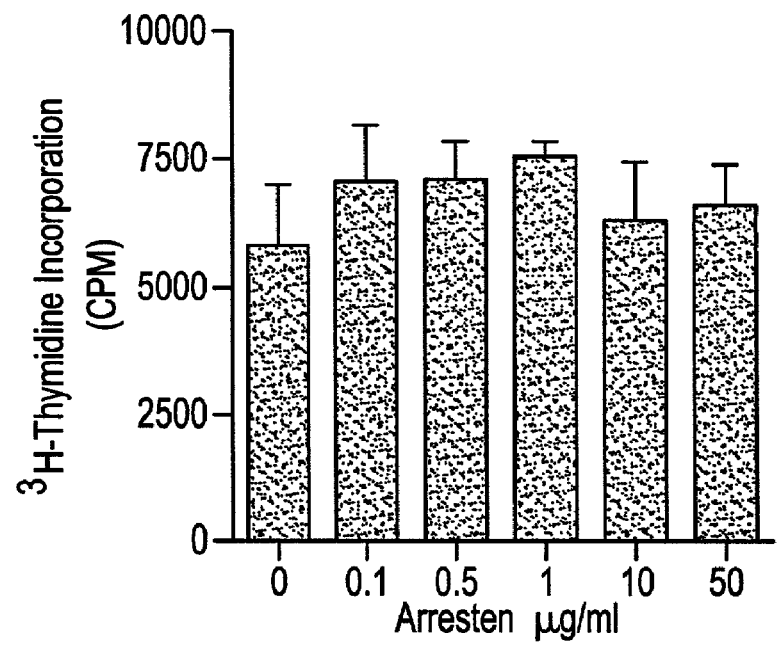
Figure 4C:
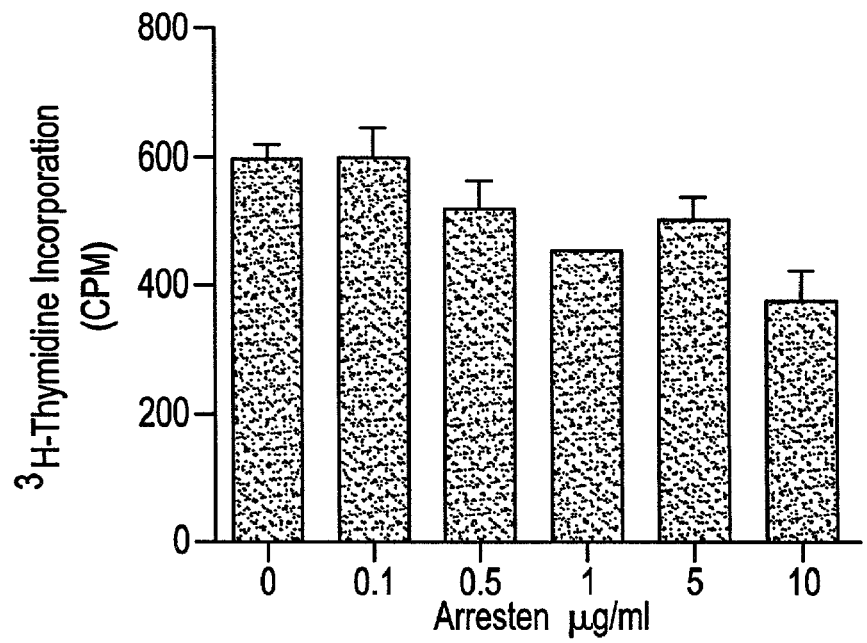
Figure 4D:
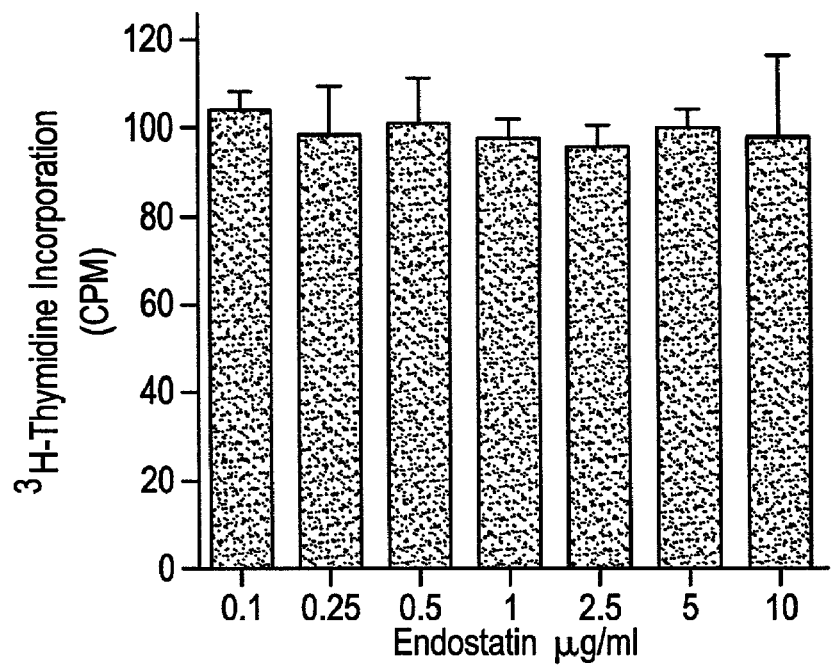

C-PAE cells were grown to confluence in DMEM with 10% fetal calf serum (FCS) and kept contact inhibited for 48 hours. Control cells were 786-O (renal carcinoma) cells, PC-3 cells, HPEC cells, and A-498 (renal carcinoma) cells. Cells were harvested with trypsinization (Life Technologies/Gibco BRL, Gaithersburg, Md., USA) at 37° C. for five minutes. A suspension of 12,500 cells in DMEM with 1% FCS was added to each well of a 24-well plate coated with 10 μg/ml fibronectin. The cells were incubated for 24 hours at 37° C. with 5% $CO_2$ and 95% humidity. Medium was removed and replaced with DMEM containing 0.5% FCS and 3 ng/ml bFGF (R&D Systems, Minneapolis, Minn., USA). Unstimulated controls received no bFGF. Cells were treated with concentrations of Arresten or endostatin ranging from 0.01 to 50 μg/ml. All wells received 1 μCurie of $^3$H-thymidine at the time of treatment. After 24 hours, medium was removed and the wells were washed with PBS. Cells were extracted with 1N NaOH and added to a scintillation vial containing 4 ml of ScintiVerse II (Fisher Scientific, Pittsburgh, Pa., USA) solution. Thymidine incorporation was measured using a scintillation counter. The results are shown in FIGS. 3A and 3B, which are a pair of graphs showing incorporation of $^3$H-thymidine into C-PAE cells treated with varying amounts of Arresten (FIG. 3A) or endostatin (FIG. 3B). Arresten appeared to inhibit thymidine incorporation in C-PAE as well as did endostatin. Behavior of control cells treated with Arresten and endostatin is also shown in FIG. 4A, 4B, 4C, and 4D, with Arresten having little effect on 786-O cells (FIG. 4A), PC-3 cells (FIG. 4B), or HPEC cells (FIG. 4C). Endostatin had little effect on A-498 cells (FIG. 4D). All groups in FIGS. 3 and 4 represent triplicate samples.

Example 5

Arresten Induces Apoptosis in Endothelial Cells

Fifty thousand C-PAE cells were added to each well of a 6-well tissue culture plate in DMEM supplemented with 10% FBS for 12 hours. Fresh medium together and either 5 μg/ml Arresten or 40 ng/ml TNFα (positive control) was added at 2, 4 and 6 hour time points. Control wells received an equal of volume of PBS. Detached cells and adherent cells were pooled together and centrifuged at 1500 rpm. Cells were washed with binding buffer (Clontech, Palo Alto, Calif., USA), and phosphatidyl-serine (PS) externalization, an indicator of apoptosis, was measured by labeling with FITC-labeled annexin V (Clontech) according to manufacturer's instructions. Annexin-FITC labeled cells were counted using a FACStar Plus flow cytometer (Becton-Dickinson, Waltham, Mass., USA). For each treatment, 10,000 cells were counted and stored. This data was then analyzed using standard Cell Quest software (Becton-Dickinson). Relative to controls, the percentage of annexin-V-stained (apoptotic) cells increased to about 27% at 2 hours, and near 20% at 4 and 6 hours for the positive control, TNFα. For Arresten-treated cells, the percentage of apoptotic cells was about 18% at 2 hours, and about 23% at 4 and 6 hours. The endothelial cell morphology changes were also observed during the experiment, with control cells showing no significant change, while Arresten-treated and non-adherent cells showed changes in cell morphology indicative of apoptosis.

Example 6

Arresten Inhibits Endothelial Cell Migration

Figure 5A:
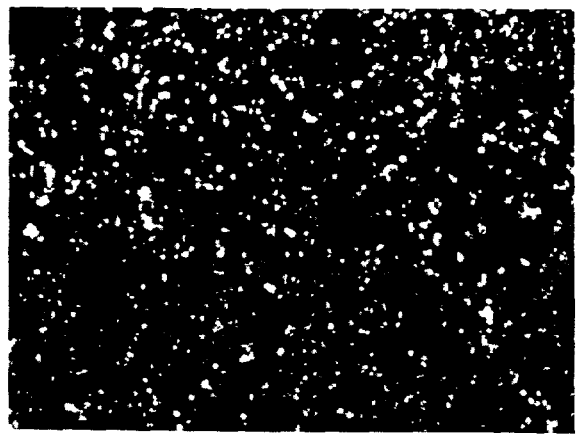
FIGS. 5A, 5B and 5C are a set of four photomicrographs showing the effects of Arresten (2 μg/ml, FIG. 5B) and endostatin (20 μg/ml, FIG. 5C) on endothelial cell migration via FBS-induced chemotaxis in human umbilical endothelial (ECV-304) cells.
Figure 5B:
Figure 5C:
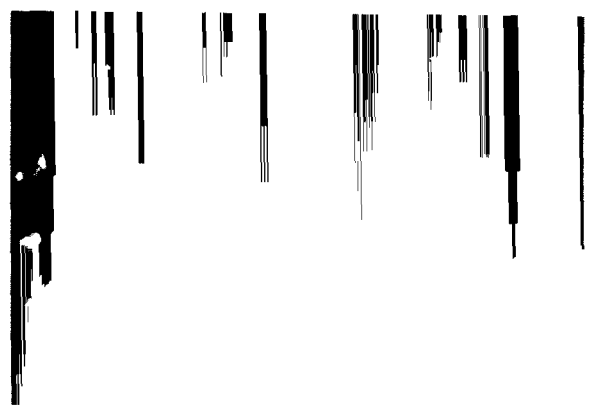
Figure 6:
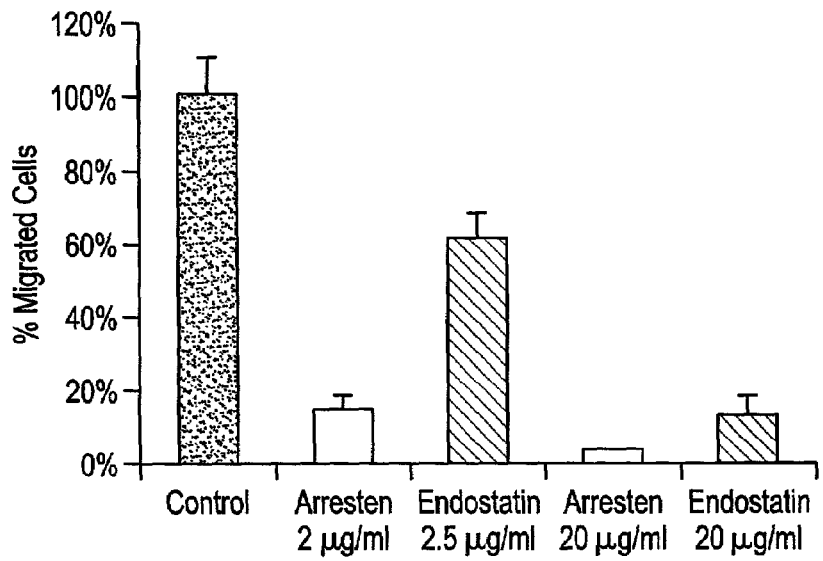
FIG. 6 is a bar chart showing in graphic form the results of FIG. 5.

The inhibitory effect of Arresten and endostatin on FBS-induced chemotaxis was tested on human umbilical endothelial cells (ECV-304 cells, ATCC 1998-CRL, ATCC (American Type Culture Collection, 10801 University Boulevard, Manassas, Va., 20110-2209, USA)) using a Boyden chamber assay (Neuro-Probe, Inc., Cabin John, Md., USA). ECV-304 cells were grown in M199 medium containing 10% FBS and 5 ng/mlDilC18(3) living fluorescent stain (Molecular Probes, Inc., Eugene, Oreg., USA) overnight. After trypsinization, washing and diluting cells in M199 containing 0.5% FBS, 60,000 cells were seeded on the upper chamber wells, together with or without Arresten or endostatin (2-40 μg/ml). M199 medium containing 2% FBS was placed in the lower chamber as a chemotactant. The cell-containing compartments were separated from the chemotactant with polycarbonate filters (Poretics Corp., Livermore, Calif., USA) of 8 μm pore size. The chamber was incubated at 37° C. with 5% $CO_2$ and 95% humidity for 4.5 hours. After discarding the non-migrated cells and washing the upper wells with PBS, the filters were scraped with a plastic blade, fixed in 4% formaldehyde in PBS, and placed on a glass slide. Using a fluorescent high power field, several independent homogenous images were recorded by a digital SenSys™ camera operated with image processing software PMIS (Roper Scientific/Photometrics, Tucson, Ariz., USA). Representative pictures are shown in FIGS. 5A, 5B and 5C, which show Arresten at 2 μg/ml as effective as endostatin at 20 μg/ml. Cells were counted using the OPTIMAS 6.0 software (Media Cybernetics, Rochester, N.Y.), and the results are shown in FIG. 6, which shows in graphic form the results seen in the photomicrographs.

Example 7

Arresten Inhibits Endothelial Tube Formation

Figure 7:
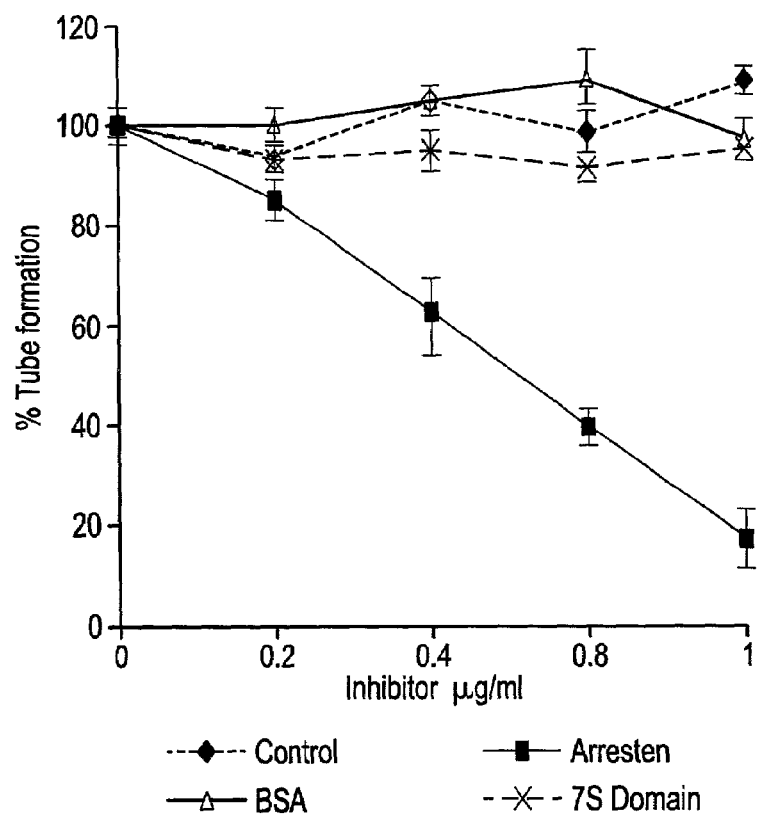
FIG. 7 is a line graph showing the effect of Arresten on the endothelial tube formation. Percent tube formation is shown on the y-axis, and concentration of inhibitor on the x-axis. The treatments were: none (control, ♦), BSA (control, Δ), 7S domain (control, X) and Arresten (■).
Figure 8A:
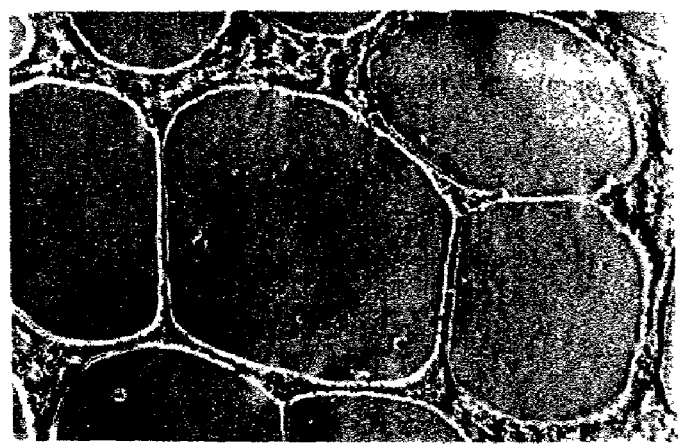
FIGS. 8A and 8B are a pair of photomicrographs showing the effect of Arresten (0.8 μg/ml, FIG. 8B) on endothelial tube formation relative to control (FIG. 8A).
Figure 8B:
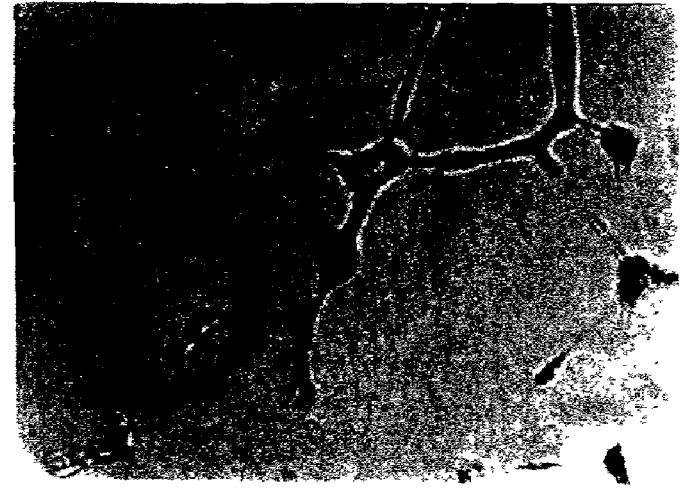

To measure inhibition of endothelial tube formation, 320 μl of Matrigel (Collaborative Biomedical Products, Bedford, Mass., USA) was added to each well of a 24-well plate and allowed to polymerize (Grant, D. S. et al., 1994, Pathol. Res. Pract. 190:854-63). A suspension of 25,000 mouse aortic endothelial cells (MAE) in EGM-2 medium (Clonetics Corp., San Diego, Calif., USA) without antibiotic was passed into each well coated with Matrigel. The cells were treated with increasing concentrations of either Arresten, BSA, sterile PBS or the 7S domain. All assays were performed in triplicate. Cells were incubated for 24-48 hours at 37° C. and viewed using a CK2 Olympus microscope (3.3 ocular, 10× objective). The cells were then photographed using 400 DK coated TMAX film (Kodak). Cells were stained with diff-quik fixative (Sigma Chemical Company, St. Louis, Mo., USA) and photographed again. Ten fields were viewed, and the tubes counted and averaged. The results are shown in FIG. 7, which shows that Arresten (■) inhibits tube formation relative to controls (sterile PBS, +; BSA, Δ; 7S domain, —X—). Representative well-formed tubes can be observed in FIG. 8A, which shows the cells treated with the 7S domain (100× magnification). FIG. 8B, on the other hand, shows poor or no tube formation in MAE cells treated with 0.8 μg/ml Arresten (100× magnification).

The matrigel assay was also conducted in vivo in C57/BL6 mice. Matrigel was thawed overnight at 4° C. It was then mixed with 20 U/ml of heparin (Pierce Chemical Co., Rockford, Ill., USA), 150 ng/ml of bFGF (R&D Systems, Minneapolis, Minn., USA), and either 1 μg/ml of Arresten or 10 μg/ml of endostatin. The matrigel mixture was injected subcutaneously using a 21 g needle. Control groups received the same mixture, but with no angiogenic inhibitor. After 14 days, mice were sacrificed and the matrigel plugs removed. The matrigel plugs were fixed in 4% paraformaldehyde in PBS for 4 hours at room temperature, then switched to PBS for 24 hours. The plugs were embedded in paraffin, sectioned, and H&E stained. Sections were examined by light microscopy and the number of blood vessels from 10 high-power fields were counted and averaged.

When Matrigel was placed in the presence of bFGF, with or without increasing concentrations of Arresten, a 50% reduction in the number of blood vessels was observed at 1 μg/ml Arresten and 10 μg/ml of endostatin. These results show that Arresten affects the formation of new blood vessels by inhibiting various steps in the angiogenic process. The results also show that Arresten at 1 μg/ml is as effective as 10 μg/ml endostatin in inhibiting new vessel formation in vivo.

Example 8

Arresten Inhibits Tumor Metastases In Vivo

C57/BL6 mice were intravenously injected with 1 million MC38/MUC 1 (Gong, J. et al., 1997, Nat. Med. 3:558-61). Every other day for 26 days, five control mice were injected with 10 mM of sterile PBS, while six experimental mice received 4 mg/ml Arresten. After 26 days of treatment, pulmonary tumor nodules were counted for each mouse, and averaged for the two groups. Two deaths were recorded in each group. Arresten significantly reduced the average number of primary nodules from 300 in control mice, to 200.

Example 9

Arresten Inhibits Tumor Growth In Vivo

Figure 9A:
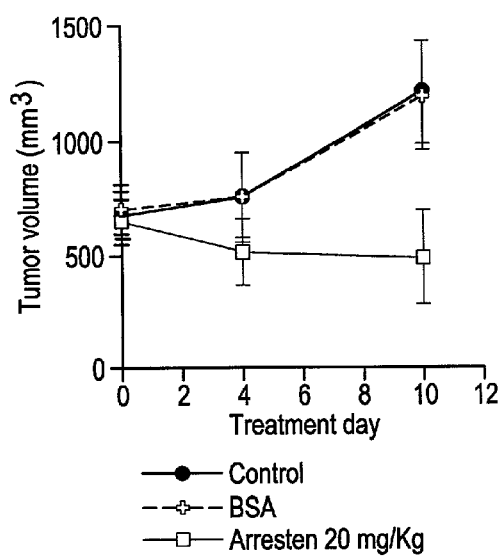
FIGS. 9A, 9B, 9C and 9D are a set of four line graphs showing the effect of Arresten and endostatin on tumor growth in vivo.
Figure 9B:
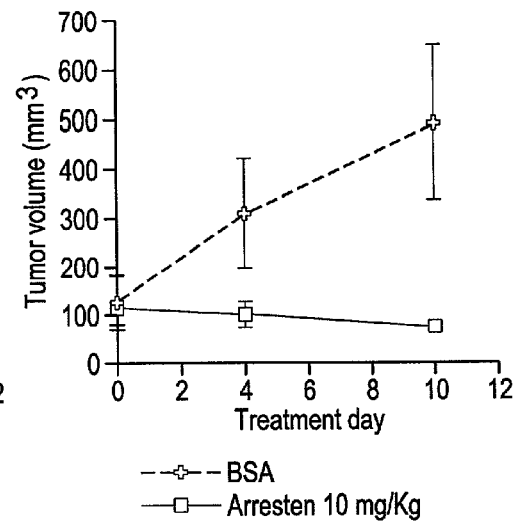

Two million 786-O cells were injected subcutaneously into 7- to 9-week-old male athymic nude mice. In the first group of six mice, the tumors were allowed to grow to about 700 mm$^3$. In a second group of six mice, the tumors were allowed to group to 100 mm$^3$. Arresten in sterile PBS was injected I.P. daily for 10 days, at a concentration of 20 mg/kg for the mice with tumors of 700 mm$^3$, and 10 mg/kg for the mice with tumors of 100 mm$^3$. Control mice received either BSA or the PBS vehicle. The results are shown in FIGS. 9A and 9B. FIG. 9A is a plot showing the increase in tumor volume from 700 mm$^3$ for 10 mg/kg Arresten-treated (□), BSA-treated (+), and control mice (●). Tumors in the Arresten-treated mice shrank from 700 to 500 mm$^3$, while tumors in BSA-treated and control mice grew to about 1200 mm$^3$ in 10 days. FIG. 9B shows that in mice with tumors of 100 mm$^3$, Arresten (□) also resulted in tumor shrinkage, to about 80 mm$^{-3}$, while BSA-treated tumors (+) increased in size to nearly 500 mm$^3$ in 10 days.

Figure 9C:
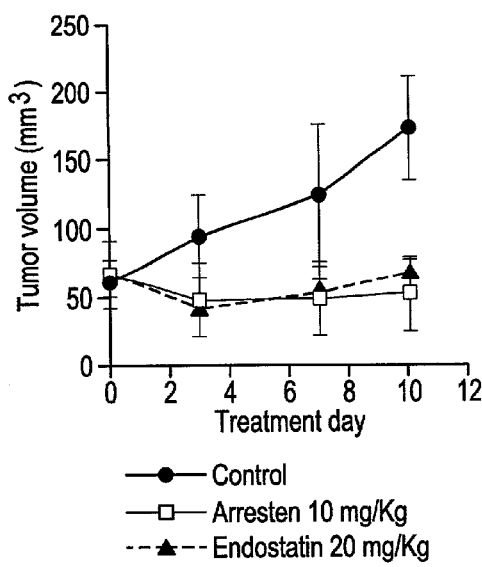
Figure 9D:
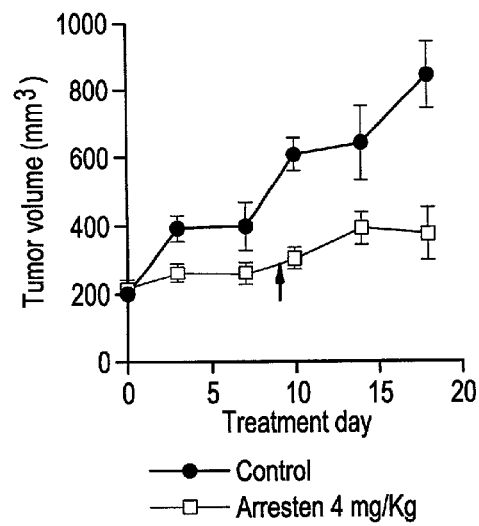

About 5 million PC-3 cells (human prostate adenocarcinoma cells) were harvested and injected subcutaneously into 7- to 9-week-old male athymic nude mice. The tumors grew for 10 days, and were then measured with Vernier calipers. The tumor volume was calculated using the standard formula (width$^2$×length×0.52 (O'Reilly, M. S. et al., 1997, Cell 88:277-85; O'Reilly, M. S. et al., 1994, Cell 79:315-28). Animals were divided into groups of 5-6 mice. Experimental groups were injected I.P. daily with Arresten (10 mg/kg/day) or endostatin (10 mg/kg/day). The control group received PBS each day. The results are shown in FIG. 9C, which shows that Arresten (□) inhibited the growth of tumors as well, or slightly better, than did endostatin (▲) or controls (●). The experiment was repeated, but with an Arresten dosage of 4 mg/kg/day. The results are shown in FIG. 9D (Arresten, □; control, ●). The treatment was stopped after eight days (arrow), but significant inhibition continued for twelve more days without additional Arresten treatments. After twelve days of no treatment, the tumors began to escape the inhibitory affects of Arresten.

Example 10

Immunohistochemistry of Arresten

Mice from the tumor studies were sacrificed after 10-20 days of treatment. Tumours were excised and fixed in 4% paraformaldehyde. Tissues were paraffin embedded and 3 μm sections were cut and mounted on glass slides. Sections were deparaffinized, rehydrated and treated with 300 mg/ml protease XXIV (SIGMA Chemical Co., St. Louis, Mo., USA) at 37° C. for 5 minutes. Digestion was stopped with 100% ethanol and sections were air dried and blocked with 10% rabbit serum. Slides were then incubated at 4° C. overnight with 1:50 dilution of rat anti-mouse CD-31 monoclonal antibody (PharMingen, San Diego, Calif., USA), followed by two successive 30-minute incubations at 37° C. in 1:50 dilutions of rabbit anti-rat immunoglobulin (DAKO) and rat APAAP (DAKO). The color reaction was performed with new fuchsin, and sections were counterstained with hematoxylin. The CD-31 staining pattern showed a decrease in the vasculature of treated vs. control mice.

For PCNA staining, tissue sections were incubated for 60 minutes at room temperature with a 1:200 dilutions of anti-PCNA antibody (Signet Laboratories, Dedham, Mass., USA). Detection was carried out per the manufacturer's recommendations using the USA Horeseradish peroxidase system (Signet Laboratories). The slides were counterstained with hematoxylin. Staining for fibronectin and type IV collagen was perform using polyclonal anti-fibronectin (SIGMA Chemical Co., St. Louis, Mo., USA) at a dilution of 1:500 and anti-type IV collagen (ICN Pharmaceuticals, Costa Mesa, Calif., USA) at a dilution of 1:100. The Vectastain Elite ABC kit (Vector Laboratories. Inc., Burlingame, Calif., USA) was used for detection per manufacturer's recommendations. The PCNA, fibronectin and collagen Type IV staining of the extracellular matrix showed no differences in tumor cell proliferation or in the content or architecture of the Type IV collagen and the fibronectin surrounding the tumor cells.

Example 11

Circulating Half-Life of Arresten

Native Arresten isolated from human placenta was injected intravenously into rate 200 g in size. Each rat received 5 mg of human Arresten. Serum was analyzed by direct ELISA at different time points for the presence of circulating Arresten by use of anti-Arresten antibodies. As a control, serum albumin was also evaluated at each time point to ensure that identical amounts of serum were used for the analysis. Arresten was found to circulate in the serum with a half-life of about 36 hours.

Another group of rats were injected with 200 μg of human Arresten I.P. and/or subcutaneously, and evaluated for signs of disease pathogenesis in the lung, kidney, liver, pancreas, spleen, brain, testis, ovary, etc. Direct ELISA was performed and Arresten antibodies were detected in the serum of these rats and some endogenous IgG deposition was noticed on the kidney glomerular basement membrane, as was observed previously (Kalluri, R. et al., 1994, Proc. Natl. Acad. Sci. USA 91:6201-5). The antibody deposition in the kidney was not accompanied by any signs of inflammation or deterioration of renal function. These experiments suggest that Arresten is non-pathogenic.

Example 12

Effect of Arresten on Cell Adhesion 96-well plates were coated with either human Arresten or human type IV collagen (Collaborative Biomedical Products, Bedford, Mass., USA) at a concentration of 10 μg/ml overnight at 37° C. The remaining protein binding sites were blocked with 10% BSA (SIGMA Chemical Co., St. Louis, Mo., USA) in PBS for 2 hours at 37° C. HUVEC cells were grown to subconfluence (70-80%) in EGM-2 MV medium (Clonetics Corporation, San Diego, Calif., USA). The cells were gently trypsinized and resuspended in serum-free medium ($5 \times 10^4$ cells per ml). The cells were then mixed with 10 µg/ml of antibody and incubated for 15 minutes with gentle agitation at room temperature. 100 µl of the cell suspension were then added to each well and the plate incubated for 45 minutes at 37° C. with 5% $CO_2$. Unattached cells were removed by washing with serum free medium and attached cells were counted. Control mouse IgG and mouse monoclonal antibody to the human β1 integrin subunit (clone P4C1O) were purchased from Life Technologies (Gibco/BRL, Gaithersburg, Md., USA). Monoclonal antibody $\alpha_1$ integrin subunit and $\alpha_v\beta_3$ (clones CD49a and LM609 respectively) were purchased from CHEMICON International (Temecula, Calif., USA).

The results are shown in FIGS. 10A and 10B, which are two histograms showing the percentage of adherent HUVEC cells (y-axis) on coated plates, where the cells were mixed with mouse IgG (c, control), or antibodies to the $\alpha_1$ or $\beta_1$ integrin subunits, or antibodies to $\alpha_v\beta_3$ integrin. FIGS. 10A and 10B show the percentage of adherent cells on Arresten-coated and collagen Type IV-coated plates, respectively. An inhibition of 60% was observed in the cell adhesion for the $\alpha_1$ subunit and a 70% inhibition for $\beta_1$ subunit for Arresten-coated plates (FIG. 10A), while the collagen Type IV-coated plates (FIG. 10B) showed a more moderate inhibition of 30% with $\alpha_1$, 40% with $\beta_1$ and 15% with $\alpha_v\beta_3$ neutralizing antibodies.

Example 13

Binding and Inhibition of Matrix Metalloproteinases by Arresten

MMP-2, MMP-9, and antibodies to these enzymes were purchased from Oncogene, Inc. Direct ELISA was performed using native Arresten isolated from human placenta as described previously (Kalluri, R. et al., 1994, Proc. Natl. Acad. Sci. USA 91:6201-5). Both MMP-2 and MMP-9 specifically bound Arresten. They did not bind the 7S domain. This binding is independent of TIMP-2 and TIMP-1 binding, respectively.

To assess Arresten's ability to degrade basement membranes, Matrigel was incubated with MMP-2 and MMP-9 for six hours at 37° C. with gentle shaking. The supernatant was analyzed by SDS-PAGE, and immunoblot with antibody to the α2 chain of Type IV collagen. At the beginning of the degradation assay, Arresten was added at increasing concentrations, and inhibition of MMP-2 activity was observed. The NC1 domains resolved in SDS-PAGE gels as monomers of 26 kDa and dimers of 56 kDa, and could be visualized by Western blot using Type IV collagen antibodies. Increasing concentrations of Arresten inhibited the degradation of basement membrane by MMP-2, showing that Arresten can bind MMP-2 and prevent it from degrading basement membrane collagen. Similar results were obtained for MMP-9.

Example 14

Recombinant Production of Canstatin in E. Coli

Human Canstatin was produced in E. Coli as a fusion protein with a C-terminal six-histidine tag, using pET22b, a bacterial expression plasmid.

Figure 12:
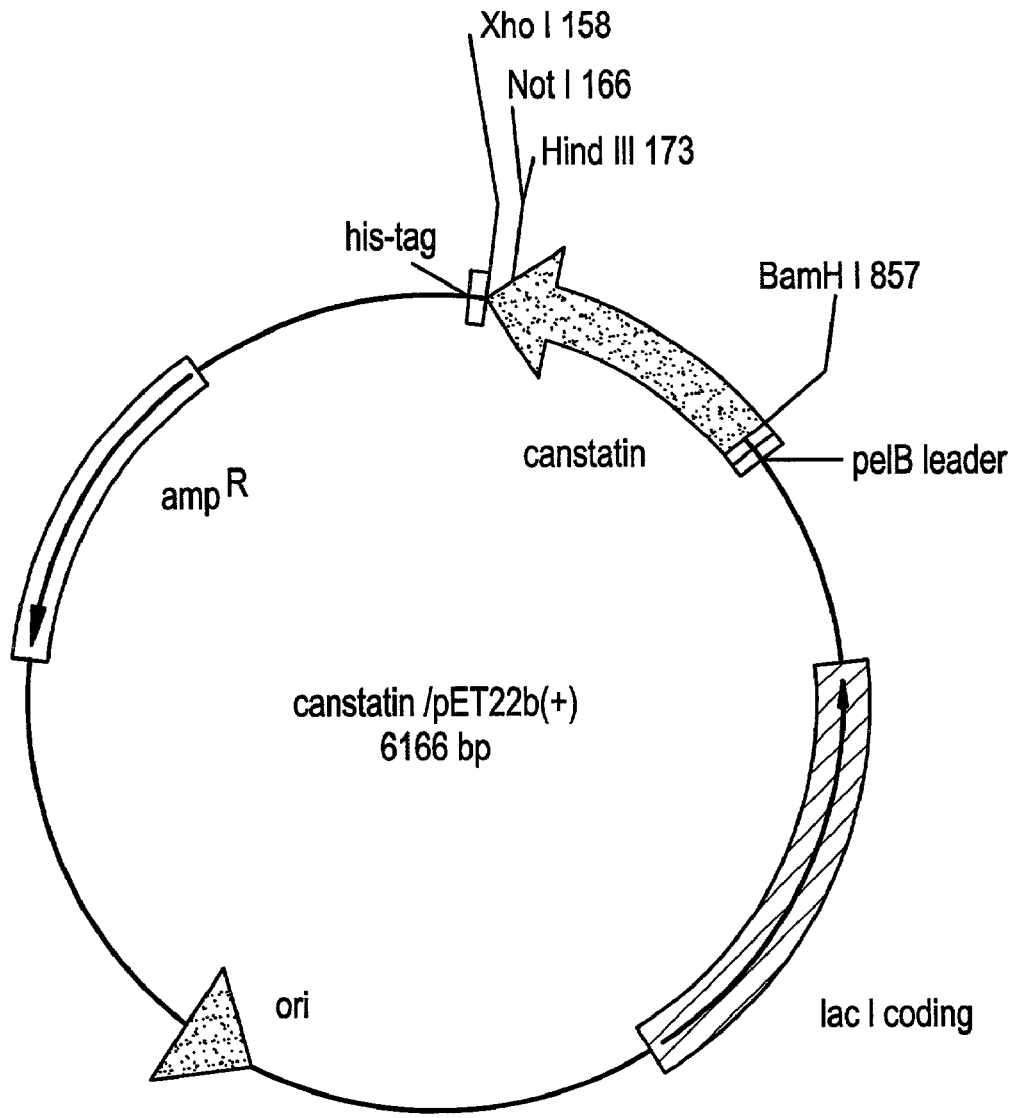
FIG. 12 is a schematic diagram representing the Canstatin cloning vector pET22b(+). Forward (SEQ ID NO:7) and reverse (SEQ ID NO:8) primers and site into which Canstatin was cloned are indicated.

The nucleotide (SEQ ID NO:5) and amino acid (SEQ ID NO:6) sequence for the α2 NC1 domain of Type IV collagen are shown in FIGS. 11A and 11B, respectively. The sequence encoding Canstatin was amplified by PCR from the α2 NC1 (IV)/pDS vector (Neilson, E. G. et al., 1993, J. Biol. Chem. 268:8402-05; GenBank Accession No. M24766 (Killen, P. D. et al., 1994)) using forward primer 5'-CGG GAT CCT GTC AGC ATC GGC TAC CTC-3' (SEQ ID NO:7) and reverse primer 5'-CCC AAG CTT CAG GTT CTT CAT GCA CAC-3' (SEQ ID NO:8). The resulting cDNA fragment was digested with BamHI and HindIII and ligated into predigested pET22b(+) (Novagen, Madison, Wis., USA). The construct is shown in FIG. 12. This ligation placed Canstatin downstream of, and in-frame with, the pelB leader sequence, allowing for periplasmic localization and expression of soluble protein. Additional vector sequence was added to the protein encoding amino acids MDIGINSD (SEQ ID NO:13). The 3' end of the sequence was ligated in-frame with the poly-histidine-tag sequence. Additional vector sequence between the 3' end of the cDNA and the his-tag encoded the amino acids KLAAALE (SEQ ID NO: 14). Positive clones were sequenced on both strands.

Plasmid constructs encoding Canstatin were first transformed into E. Coli HMS174 (Novagen, Madison, Wis., USA) and then transformed into BL21 for expression (Novagen). An overnight bacterial culture was used to inoculate a 500 ml culture in LB medium. This culture was grown for approximately 4 hours until the cells reached an $OD_{600}$ of 0.6. Protein expression was then induced by addition of IPTG to a final concentration of 0.5 mM. After a 2-hour induction, cells were harvested by centrifugation at 5,000.times.g and lysed by resuspension in 6 M guanidine, 0.1 M $NaH_2PO_4$, 0.01 M Tris-HCl, pH 8.0. Resuspended cells were sonicated briefly, and centrifuged at 12,000× for 30 minutes. The supernatant fraction was passed over a 5 ml Ni-NTA agarose column (Qiagen, Hilden, Germany) 4-6 times at a speed of 2 ml/min. Non-specifically bound protein was removed by washing with 15 ml each of 10 mM, 25 mM and 50 mM imidazole in 8 M urea, 0.1 M $NaH_2PO_4$, 0.01 M Tris-HCl, pH 8.0. Canstatin protein was eluted from the column with two concentrations of imidazole (125 mM and 250 mM) in 8 M urea, 0.1 M $NaH_2PO_4$, 0.01 M Tris-HCl, pH 8.0. The eluted protein was dialyzed twice against PBS at 4° C. A portion of the total protein precipitated during dialysis. Dialyzed protein was collected and centrifuged at approximately 3,500.times.g and separated into pellet and supernatant fractions. Protein concentration in each fraction was determined by the BCA assay (Pierce Chemical Co., Rockford, Ill., USA) and quantitative SDS-PAGE analysis. The SDS-PAGE analysis revealed a monomeric band at about 26-32 kDa, most likely 27 kDa, of which 3 kDa would arise from polylinker and histidine tag sequences. The elutions containing Canstatin were combined and dialyzed against PBS for use in subsequent assays. Canstatin protein analyzed by SDS-PAGE and Western blotting was detected by poly-histidine tag antibodies. Canstatin antibodies also detected bacterially-expressed recombinant constatin protein.

The E. Coli expressed protein was isolated predominantly as a soluble protein. The fraction of total protein in the pellet was approximately 40%, with the remaining 60% recovered as a soluble protein. The total yield of protein was approximately 15 mg/liter.

Example 15

Expression of Canstatin in 293 Embryonic Kidney Cells

Human Canstatin was also produced as a secreted soluble protein in 293 embryonic kidney cells using the pcDNA 3.1 eukaryotic vector, and was isolated (without any purification or detection tags) using affinity chromatography.

The pDS plasmid containing α2(IV) NC1 (Neilson, E. G. et al., 1993, J. Biol. Chem. 268:8402-05) was used to PCR amplify Canstatin in such a way that a leader signal sequence would be added in-frame into the pcDNA 3.1 eukaryotic expression vector (InVitrogen, San Diego, Calif., USA). The leader sequence from the 5' end of full length α2(IV) chain was cloned 5' to the NC1 domain to enable protein secretion into the culture medium. The Canstatin-containing recombinant vectors were sequenced using flanking primers. Error free cDNA clones were further purified and used for in vitro translation studies to confirm protein expression. The Canstatin-containing plasmid and control plasmid were used to transfect 293 cells using the calcium chloride method. Kingston, R. E., 1996, Calcium Phosphate Transfection, pp. 9.1.4-9.1.7, in: CURENT PROTOCOLS IN MOLECULAR BIOLOGY (Ausubel, F. M., et al., eds., Wiley & Sons, Inc., New York, N.Y., USA). Transfected clones were selected by geneticin (Life Technologies/Gibco BRL, Gaithersberg, Md., USA) antibiotic treatment. The cells were passed for three weeks in the presence of the antibiotic until no cell death was evident. Clones were expanded into T-225 flasks and grown until confluent. Then, the supernatant was collected and concentrated using an amicon concentrator (Amicon, Inc., Beverly, Mass., USA). The concentrated supernatant was analyzed by SDS-PAGE, immunoblotting and ELISA for Canstatin expression. Strong binding in the supernatant was detected by ELISA. Canstatin-containing supernatant was subjected to affinity chromatography using Canstatin specific antibodies. Gunwar, S. et al., 1991, J. Biol. Chem. 266:15318-24. A major peak was identified, containing a pure monomer of about 24 kDa that was immunoreactive with Canstatin antibodies (anti-α2 NC1 antibody, 1:200 dilution).

Example 16

Canstatin Inhibits Endothelial Cell Proliferation

Bovine calf aortic endothelial (C-PAE) cells were grown to confluence in DMEM with 10% fetal calf serum (FCS) and kept contact inhibited for 48 hours. Cells were harvested by trypsinization (Life Technologies/Gibco BRL, Gaithersberg, Md., USA) at 37° C. for 5 minutes. A suspension of 12,500 cells in DMEM with 0.5% FCS was added to each well of a 24-well plate coated with 10 µg/ml fibronectin. The cells were incubated for 24 hours at 37° C. C. with 5% $CO_2$ and 95% humidity. Medium was removed, and replaced with DMEM containing 0.5% FCS (unstimulated) or 10% FCS (stimulated and treated cells). 786-O, PC-3 and HEK 293 cells served as controls and were also grown to confluency, trypsinized and plated in the same manner. Cells were treated with concentrations of Canstatin or endostatin ranging from 0.025 to 40 mg/ml in triplicate. In thymidine incorporation experiments, all wells received 1 mCurie of $^3$H-thymidine at the time of treatment. After 24 hours, medium was removed and the wells were washed 3 times with PBS. Radioactivity was extracted with 1N NaOH and added to a scintillation vial containing 4 ml of ScintiVerse II (Fisher Scientific, Pittsburgh, Pa., USA) solution. Thymidine incorporation was measured using a scintillation counter.

Figure 13A:
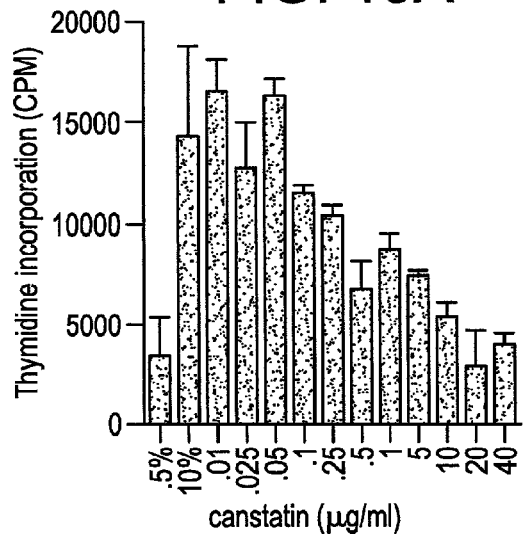
FIGS. 13A, 13B, 13C and 13D are histograms showing the effect of varying concentrations of Canstatin (x-axis) on proliferation of endothelial (C-PAE) cells (FIGS. 13A and 13C) and non-endothelial (786-O, PC-3 and HEK 293) cells (FIGS. 13B and 13D). Proliferation was measured as a function of $^3$H-thymidine incorporation (FIGS. 13A and 13B) and methylene blue staining (FIGS. 13C and 13D).
Figure 13B:
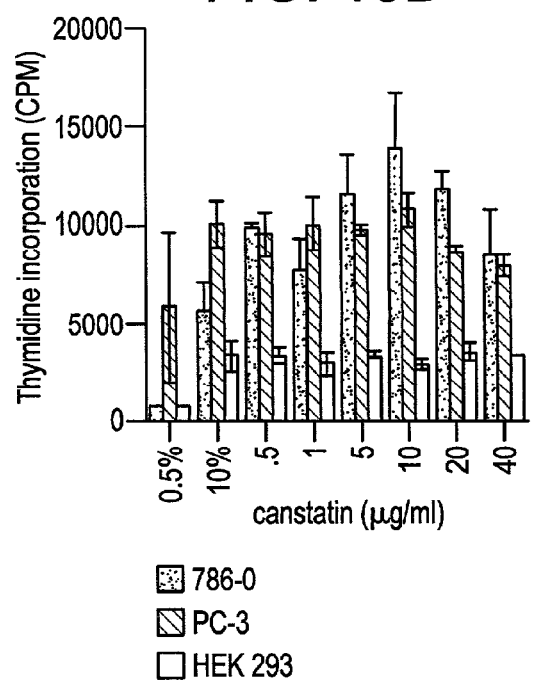

The results are shown in FIGS. 13A and 13B. FIG. 13A is a histogram showing the effect of varying amounts of Canstatin on the proliferation of C-PAE cells. Thymidine incorporation in counts per minute is on the y-axis. "0.5%" on the x-axis is the 0.5% FCS (unstimulated) control, and "10%" is the 10% FCS (stimulated) control. Treatment with increasing concentrations of Canstatin steadily reduced thymidine incorporation. FIG. 13B is a histogram showing the effect of increasing amounts of Canstatin on thymidine incorporation in the nonendothelial cells 786-O (speckled bars), PC-3 (cross-hatched bars) and HEK 293 (white bars). Thymidine incorporation in counts per minute is show in the y-axis, and the x-axis shows, for each of the three cell lines, the 0.5% FCS (unstimulated) and the 10% FCS (stimulated) control, followed by increasing concentrations of Canstatin. All groups represent triplicate samples, and the bars represent mean counts per minute ±the standard error of the mean.

A methylene blue staining test was also done. 3,100 cells were added to each well and treated as above, and cells were then counted using the method of Oliver et al. (Oliver, M. H. et al., 1989, J. Cell. Science 92:513-18). All wells were washed one time with 100 ml of 1×PBS and the cells were fixed by adding 100 ml of 10% formalin in neutral-buffered saline (Sigma Chemical Co., St. Louis, Mo., USA) for 30 minutes at room temperature. After formalin removal cells were stained with a solution of 1% methylene blue (Sigma Chemical Co.) in 0.01 M borate buffer (pH 8.5) for 30 minutes at room temperature. After removal of staining solution, the wells were washed 5 times with 100 ml of 0.01 M borate buffer (pH 8.5). Methylene blue was extracted from the cells with 100 ml of 0.1N HCi/ethanol (1:1 mixture) for 1 hour at room temperature. The amount of methylene blue staining was measured on a microplate reader (BioRad, Hercules, Calif., USA) using light absorbance at 655 nm wavelength.

Figure 13C:
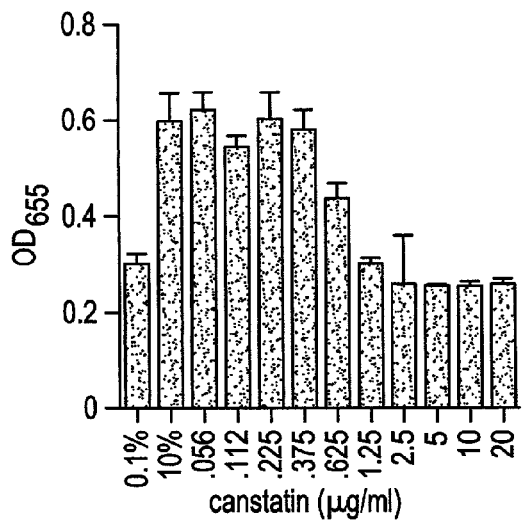
Figure 13D:
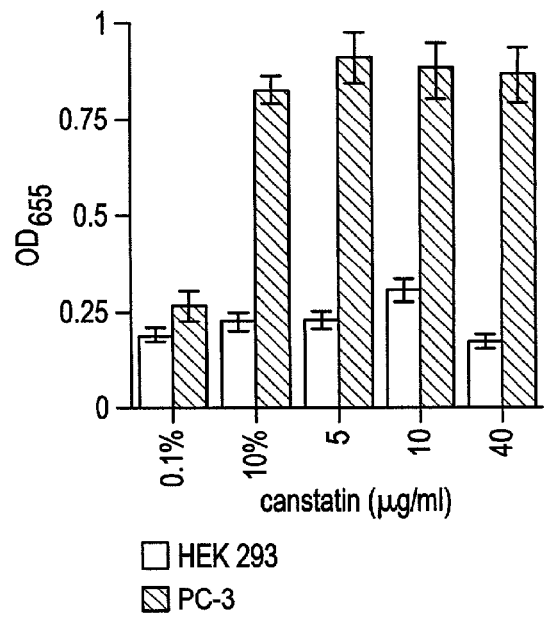

The results are shown in FIGS. 13C and 13D. FIG. 13C is a histogram showing the effect of increasing amounts of Canstatin on the uptake of dye by C-PAE cells. Absorbance at $OD_{655}$ is shown on the y-axis. "0.1%" represents the 0.1% FCS-treated (unstimulated) control, and "10%" is the 10% FCS-treated (stimulated) control. The remaining bars represent treatments with increasing concentrations of Canstatin. In C-PAE cells, dye uptake dropped off to the level seen in unstimulated cells at a Canstatin treatment level of about 0.625-1.25 µg/ml. FIG. 13D is a histogram showing the effect of varying concentrations of Canstatin on non-endothelial cells HEK 293 (white bars) and PC-3 (cross-hatched bars). Absorbance at $OD_{655}$ is on the y-axis. "0.1%" represents the 0.1% FCS-treated (unstimulated) control, and "10%" is the 10% FCS-treated (stimulated) control. Bars represent mean of the relative absorbance units at 655 nm ±the standard error for 8 wells per treatment concentration.

A dose-dependent inhibition of 10% serum-stimulated endothelial cells was detected with an $ED_{50}$ value of approximately 0.5 µg/ml (FIGS. 13A and 13C). No significant effect was observed on the proliferation of renal carcinoma cells (786-O), prostate cancer cells (PC-3) or human embryonic kidney cells (HEK293), at Canstatin doses up to 40 mg/ml (FIGS. 13B and 13D). This endothelial cell specificity indicates that Canstatin is likely a particularly effective anti-angiogenic agent.

Example 17

Canstatin Inhibits Endothelial Cell Migration

In the process of angiogenesis, endothelial cells not only proliferate but also migrate. Therefore, the effect of Canstatin on endothelial cell migration was assessed. The inhibitory effect of Canstatin and endostatin on FBS-induced chemotaxis was tested on human umbilical endothelial cells (HUVECs) using the Boyden chamber assay (Neuro-Probe, Inc., Cabin John, Md., USA). HUVECs cells were grown in M199 (Life Technologies/Gibco BRL, Gaithersburg, Md., USA) containing 10% FBS and 5 ng/ml DiC 18(3) living fluorescent stain (Molecular Probes, Inc., Eugene, Oreg., USA) overnight. After trypsinizing, washing and diluting cells in M199 containing 0.5% FBS, 60,000 cells were seeded in the upper chamber wells, together with or without Canstatin (0.01 or 1.00 mg/ml). M199 medium containing 2% FBS was placed in the lower chamber as a chemotactant. The cell-containing compartments were separated from the chemotactant with polycarbonate filters (Poretics Corp., Livermore, Calif., USA) of 8 μm pore size. The chamber was incubated at 37° C. with 5% $CO_2$ and 95% humidity for 4.5 hours. After discarding the non-migrated cells and washing the upper wells with PBS, the filters were scraped with a plastic blade, fixed in 4% formaldehyde in PBS and placed on a glass slide. Using a fluorescent high power field, several independent homogenous images were recorded by a digital SenSys™ camera operated with Image Processing Software PMIS (Roper Scientific/Photometrics, Tucson, Ariz., USA). Cells were counted by employing the OPTI-MIZE 6.0 software-program (Media Cybernetics, Rochester, N.Y.) (Klemke, R. L. et al., 1994, J. Cell. Biol. 127:859-66).

Figure 14:
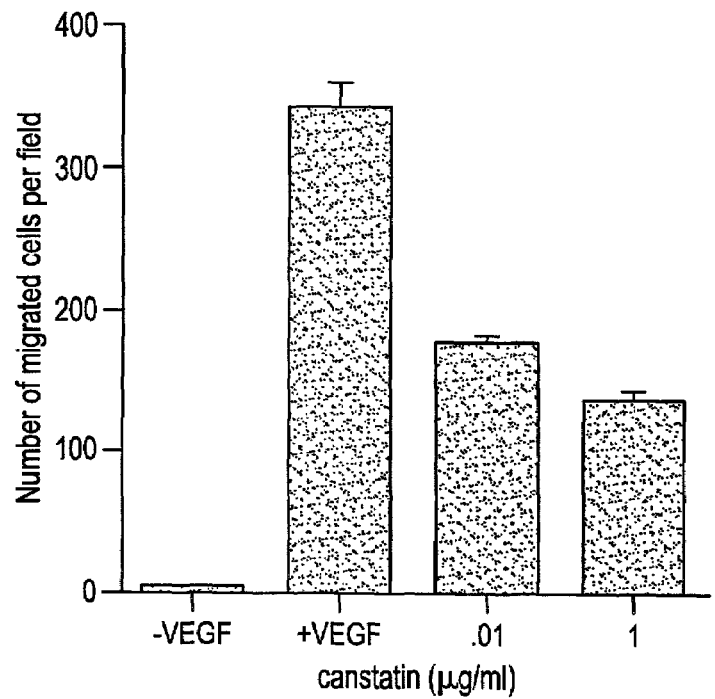
FIG. 14 is a bar chart showing the number of migrated endothelial cells per field (y-axis) for treatments of no VEGF (no VEGF or serum), and VEGF (1% FCS and 10 ng/ml VEGF) cells, and for treatments of 0.01 Canstatin (1% FCS and 10 ng/ml VEGF and 0.01 µg/ml Canstatin) and 1.0 µg/ml Canstatin (1% FCS and 10 ng/ml VEGF and 1 µg/ml Canstatin).

The results are shown in FIG. 14, which is a bar chart showing the number of migrated endothelial cells per field (y-axis) for treatments of no VEGF (no VEGF or serum), and VEGF (1% FCS and 10 ng/ml VEGF) cells, and for treatments of 0.01 Canstatin (1% FCS and 10 ng/ml VEGF and 0.01 μg/ml Canstatin) and 1.0 μg/ml Canstatin (1% FCS and 10 ng/ml VEGF and 1 μg/ml Canstatin).

Canstatin inhibited the migration of HUVECs with a significant effect observed at 10 ng/ml. The ability of Canstatin to inhibit both proliferation and migration of endothelial cells suggests that it works at more than one step in the process of angiogenesis. Alternatively, Canstatin may act as an apoptotic signal for stimulated endothelial cells which would be able to affect both proliferation and migration. Apoptotic induction has been reported for angiostatin, another anti-angiogenic molecule (O'Reilly, M. S. et al, 1994, Cell 79:315-28; Lucas, R. et al., 1998, Blood 92:4730-41).

Example 18

Canstatin Inhibits Endothelial Tube Formation

As a first test of Canstatin's anti-angiogenic capacity, it was assessed for its ability to disrupt tube formation by endothelial cells in Matrigel, a solid gel of mouse basement membrane proteins derived from sarcoma tumors. When mouse aortic endothelial cells are cultured on Matrigel, they rapidly align and form hollow tube-like structures (Grant, D. S. et al., 1994, Pathol. Res. Pract. 190:854-63).

Matrigel (Collaborative Biomedical Products, Bedford, Mass., USA) was added (320 ml) to each well of a 24 well plate and allowed to polymerize (Grant, D. S. et al., supra). A suspension of 25,000 mouse aortic endothelial cells (MAE) in EGM-2 (Clonetics Corporation, San Diego, Calif., USA) medium without antibiotic was passed into each well coated with Matrigel. The cells were treated with either Canstatin, BSA, sterile PBS or α5-NC1 domain in increasing concentrations. All assays were performed in triplicate. Cells were incubated for 24-48 hours at 37° C. and viewed using a CK2 Olympus microscope (3.3 ocular, 10× objective). The cells were then photographed using 400 DK coated TMAX film (Kodak). Cells were stained with diff-quik fixative (Sigma Chemical Co., St. Louis, Mo., USA) and photographed again (Grant, D. S. et al., 1994, Pathol. Res. Pract. 190:854-63). Ten fields were viewed, tubes counted and averaged.

Figure 15:
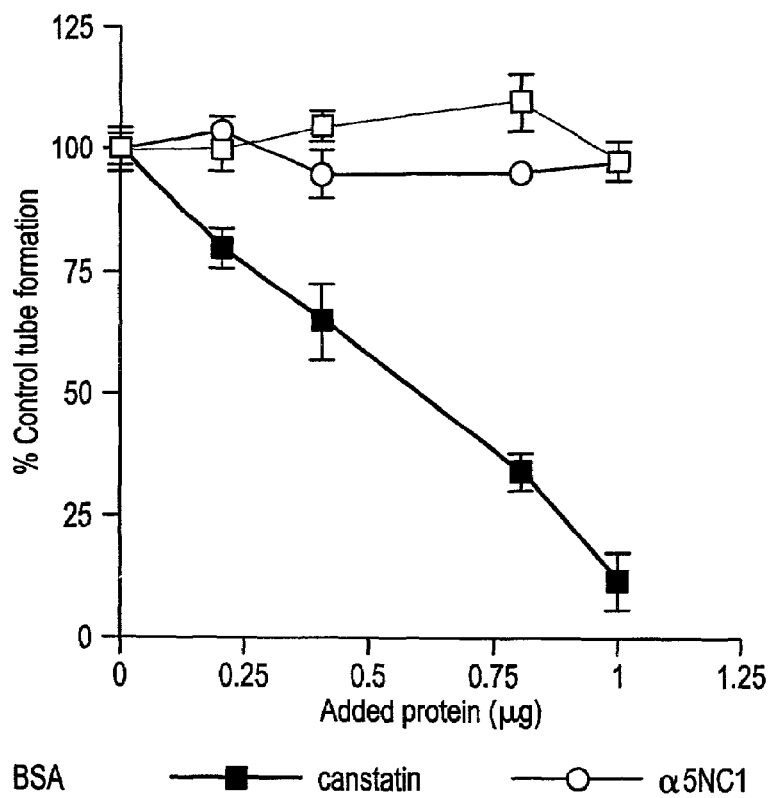
FIG. 15 is a line graph showing the amount of endothelial tube formation as a percent of control (PBS-treated wells) tube formation (y-axis) under varying treatments of BSA (□), Canstatin (■), and α5NC1 (○). Vertical bars represent the standard error of the mean.

The results are shown in FIG. 15, which is a graph showing the amount of tube formation as a percent of control (PBS-treated wells) tube formation (y-axis) under varying treatments of BSA (□), Canstatin (■), and α5NC1 (○). Vertical bars represent the standard error of the mean. The results show that Canstatin greatly reduces endothelial tube formation relative to controls.

Canstatin produced in 293 cells selectively inhibited endothelial tube formation in a dose dependent manner, with a near complete inhibition of tube formation seen with the addition of 1 mg of Canstatin protein (FIG. 15). Neither a control protein, bovine serum albumin (BSA), nor the NC1 domain of type IV collagen α5 chain, had an effect on endothelial tube formation, demonstrating that Canstatin's inhibitory effect in this assay is specific to Canstatin and not due to the added protein content. These results indicated that Canstatin is an anti-angiogenic agent.

Example 19

Effect of Canstatin on ERK Activation

In order to further understand the molecular mechanisms involved in Canstatin's anti-proliferative and anti-migratory activities, the effect of Canstatin on ERK (Extracellular signal-Regulated Kinase) activation induced by 20% fetal bovine serum and endothelial mitogens was assessed. HUVEC cells were cultured overnight in McCoy's medium supplemented with 20% FBS, 1% penicillin/streptomycin, 100 μg/ml heparin and 50 μg/ml endothelial mitogen (Biomedical Technologies, Inc., Cambridge, Mass., USA). The following day, cells were washed and grown for 4 hours in low serum medium (McCoy's medium supplemented with 1% penicillin/streptomycin, 100 μg/ml heparin and 5% FBS). After 4 hours, the medium was replaced with fresh low serum medium with or without 20 μg/ml Canstatin. One hour later the serum concentration was adjusted to 20% and endothelial mitogen was added to a final concentration of 50 μg/ml. At 0, 5, 10, 25, and 40 minutes, the cells were washed with PBS and lysed with passive lysis mix (Promega, Madison, Wis., USA) plus leupeptin, PMSF, NaF, $Na_3VO_4$, β-glycerophosphate, and sodium pyrophosphate. Lysates were quantified for protein concentration and separated on 12% SDS-PAGE gels. Western blots of phospho-ERK were made for serum-treated and serum+Canstatin-treated HUVECs using anti-phospho-ERK antibodies (New England Biolabs, Beverly, Mass., USA). ERK phosphorylation in HUVECs was evident within 5 minutes after growth factor stimulation. Treatment with 20 μg/ml of Canstatin did not alter early activation of ERK. A decrease in ERK phosphorylation was observed at later time points, a profile which is consistent with responses observed with several mitogens (Gupta, K. et al., 1999, Exp. Cell. Res. 247:495-504; Pedram, A. et al., 1998, J. Biol. Chem. 273:

26722-28). These observations indicate that Canstatin does not primarily work by inhibiting proximal events activated by VEGF or bFGF receptors.

Example 20

Canstatin Induces Apoptosis in Endothelial Cells

Annexin V-FITC Labeling. In order to establish apoptosis as the potential mode of action for Canstatin, Annexin V-FITC was used to label externalized phosphatidylserine (PS), to assess apoptotic cells. $0.5 \times 10^6$ C-PAE cells, PC-3, 786-O and HEK 293 cells were added to each well of a 6 well tissue culture plate in 10% FBS supplemented DMEM (BioWhittaker, Walkersville, Md., USA) overnight. The next day, fresh medium was added to all wells together with 40 ng/ml TNF-α (positive control) or 15 µg/ml Canstatin. Control cells received an equal volume of PBS. After 24 hours of treatment, medium containing detached cells was collected and attached cells were trypsinized and combined with detached cells and centrifuged at 3,000×g. Cells were then washed and phosphatidyl-serine externalization (an early apoptotic indicator) was measured by labeling with FITC-labeled annexin V (Clontech, Palo Alto, Calif., USA) according to the manufacturer's instructions. Annexin V-FITC-labeled cells were counted using a FAC Star Plus flow cytometer (Becton-Dickenson, Waltham, Mass., USA). For each treatment 15,000 cells were counted and stored in listmode. This data was then analyzed using standard Cell Quest software (Becton-Dickenson).

Canstatin was found to specifically induce apoptosis of endothelial cells with no significant effect observed on PC-3, 786-O or HEK 293 cell lines. FLIP Protein Levels. HUVEC cells were treated as for the ERK assay, supra, and harvested at 0, 1, 3, 6, and 24 hours. FLIP protein levels in serum treated HUVEC cells and serum+Canstatin-treated HUVEC cells were quantified using anti-FLIP antibody (Sata, M. et al., 1998, J. Biol. Chem. 273:33103-6) and normalized for protein loading using levels of vinculin and plotted as a percentage of the 0 hour time points.

Figure 16:
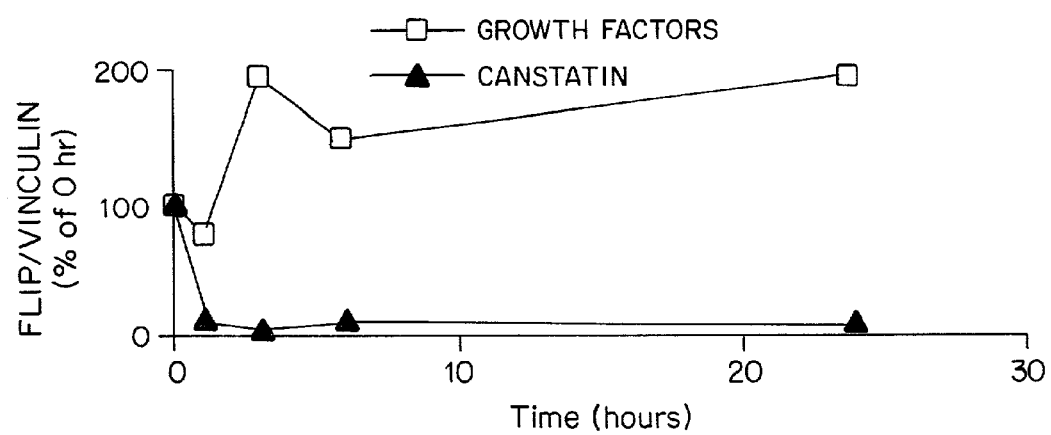
FIG. 16 is a graph of the FLIP (FLICE-Inhibitory Protein, or FADD-Like Interleukin-1β-Converting Enzyme-Inhibitory Protein) levels as a function of the level of vinculin as a percentage of the protein present at t=0 (y-axis), over time (x-axis).

The results are shown in FIG. 16, which is a graph of the FLIP protein levels as a function of the level of vinculin as a percentage of the protein present at t=0 (y-axis), over time (x-axis). There was a decrease in FLIP protein levels one hour after treatment with Canstatin, persisting up to 24 hours post serum stimulation, indicating that the apoptotic action of Canstatin is likely mediated by the Fas activated apoptosis inhibitor, FLIP. Since endothelial cells express both Fas and FasL constitutively (Sata, M. et al., supra), it is likely that this decrease in FLIP triggers caspase activation and delivers a terminal apoptotic signal.

Example 21

Canstatin Inhibits Tumor Growth In Vivo

Figure 17A:
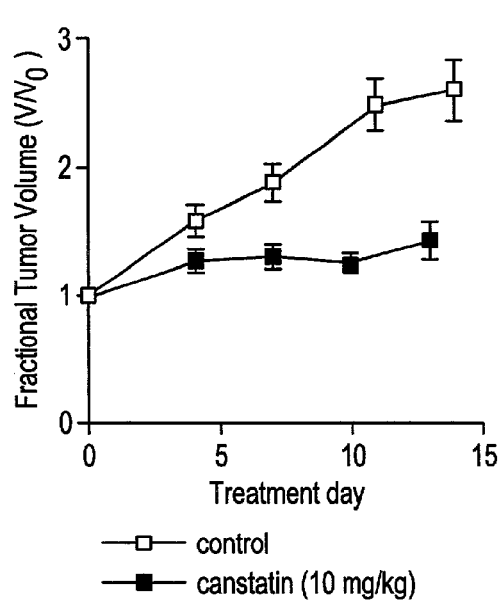
FIGS. 17A, 17B, 17C and 17D are line graphs depicting the effect on PC-3 cells (FIGS. 17A and 17B) and 786-O cells (FIGS. 17C and 17D) of Canstatin (■), endostatin (○) and controls (□) on fractional tumor volume (y-axis, FIGS. 17A and 17B) or tumor volume in mm$^3$ (y-axis, FIGS. 17C and 17D), plotted over the days of treatment x-axis).

Human prostate adenocarcinoma cells (PC-3 cells) were harvested from culture and 2 million cells in sterile PBS were injected subcutaneously into 7- to 9-week-old male SCID mice. The tumors grew for approximately 4 weeks after which animals were divided into groups of 4 mice. Experimental groups were injected daily I.P. with Canstatin at a dosage of 10 mg/kg in a total volume of 0.1 ml of PBS. The control group received equal volumes of PBS each day. At the start of treatment (day 0), the tumors ranged in volume from 88 mm$^3$ to 135 mm$^3$ for the control mice, and 108 mm$^3$ to 149 mm$^3$ for the Canstatin-treated mice. Each group contained five mice. The calculated tumor volume on a given day was divided by the volume on treatment day 0 to produce a fractional tumor volume (V/V$_0$). The results are shown in FIG. 17A, which is a graph depicting the fractional tumor volume (y-axis) ±the standard error, plotted over the treatment day (x-axis). Canstatin-treated (■) tumors increased only marginally in size relative to controls (□).

Figure 17B:
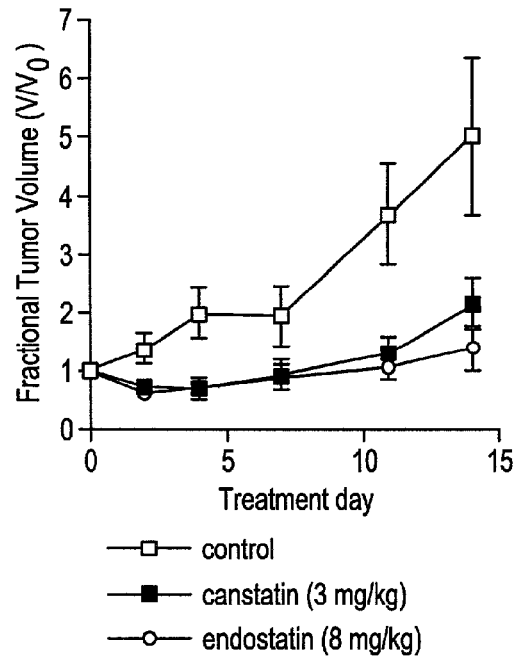

In a second PC-3 experiment, PC-3 cells were harvested from culture and 3 million cells were injected into 6- to 7-week-old athymic nude mice, and tumors were allowed to grow subcutaneously for approximately 2 weeks after which the animals were divided into groups of four mice. Experimental groups (4 mice) were injected daily I.P. with Canstatin at a dosage of 3 mg/kg in a total volume of 0.2 ml of PBS or endostatin at a dosage of 8 mg/kg in the same volume of PBS. The control group (4 mice) received equal volumes of PBS each day. Tumor length and width were measured using a Vernier caliper and the tumor volume was calculated using the standard formula: length×width$^2$×0.52. Tumor volumes ranged from 26 mm$^3$ to 73 mm$^3$, and the calculated tumor volume on a given day was divided by the volume on treatment day 0 to produce a fractional tumor volume (V/V$_0$), as described above. The results are shown in FIG. 17B, which is a graph depicting the fractional tumor volume (y-axis) ±the standard error, plotted over the treatment day (x-axis). Relative to controls (□), Canstatin-treated (■) tumors increased only marginally in size, and the results compared favorably with those achieved with endostatin (○).

Figure 17C:
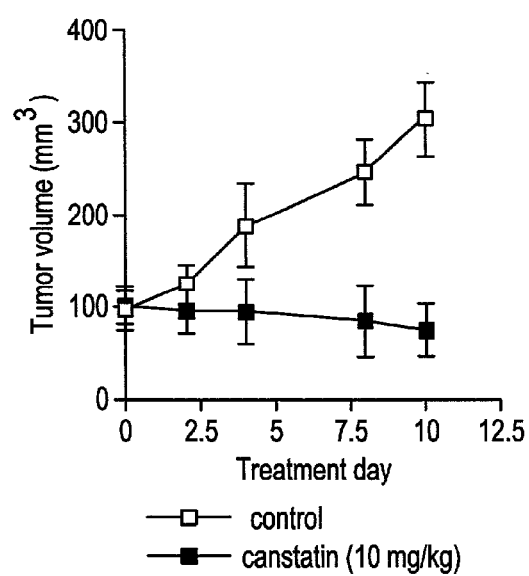

For the renal cell carcinoma cell model, 2 million 786-O cells were injected subcutaneously into 7- to 9-week-old male athymic nude mice. The tumors were allowed to grow to either about 100 mm$^3$ or about 700$^3$. Each group contained 6 mice. Canstatin in sterile PBS was injected I.P. daily at a concentration of 10 mg/kg for 10 days. The control group received the same volume of PBS. The results are shown in FIGS. 17C (100 mm$^3$ tumors) and 15D (700 mm$^3$ tumors). In both groups, the Canstatin-treated (.box-solid.) tumors actually shrank relative to the controls (□).

Figure 17D:
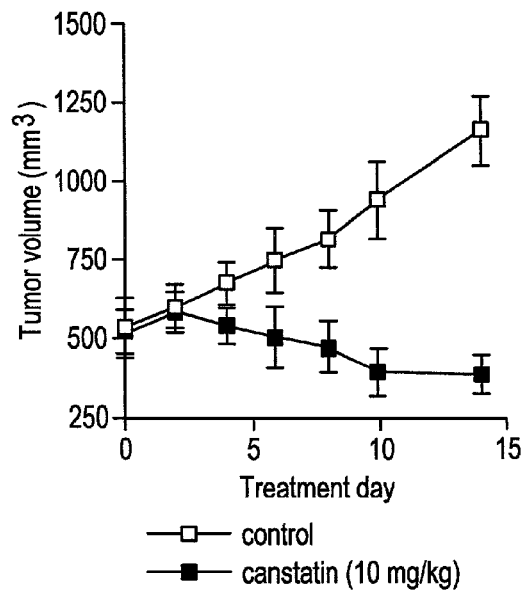

Canstatin produced in *E. Coli* inhibited the growth of small (100 mm, FIG. 17C) and large (700 mm$^3$, FIG. 17D) renal cell carcinoma (786-O) tumors by 4-fold and 3-fold, respectively, compared to placebo-treated mice. For established human prostate (PC-3) tumors in severe combined immunodeficient (SCID) mice, Canstatin at 10 mg/kg held the fractional tumor volume to 55% of (1.8-fold less than) the vehicle only-injected mice. In athymic (nu/nu) mice, the treated tumors were 2.4-fold less than placebo-treated mice. The decrease in tumor size was consistent with a decrease in CD-31-positive vasculature (see Example 29, infra). In athymic mice, lower doses of both Canstatin and endostatin were used, and 3 mg/kg of Canstatin had the same suppressive effect as 8 mg/kg of endostatin, and a 5 mg/kg dose of endostatin was not able to suppress tumor growth. In all in vivo studies, mice appeared healthy with no signs of wasting and none of the mice died during treatment.

Example 22

CD31 Immunohistochemistry on Canstatin-Treated Mice

The decreased size of the tumors in vivo suggested a suppressive effect on the formation of blood vessels in these tumors. At the end of the xenograft tumor studies, the mice were sacrificed and the tumors excised. To detect tumor blood vessels, anti-CD31 antibody alkaline phosphatase-conjugated immunocytochemistry was performed on paraffin-embedded tumor sections. The removed tumors were dissected with a scalpel into several pieces approximately 3 mm-4 mm thick then fixed in 4% paraformaldehyde for 24 hours. Tissues were then switched to PBS for 24 hours before dehydration and parffin embedding. After embedding in paraffin, 3 mm tissue sections were cut and mounted. Sections were deparaffinized, rehydrated, and pretreated with 300 mg/ml protease XXIV (Sigma Chemical Co., St. Louis, Mo., USA) at 37° C. for 5 minutes. Digestion was stopped in 100% ethanol. Sections were air dried, rehydrated and blocked with 10% rabbit serum. Slides were then incubated at 4° C. overnight with a 1:50 dilution of rat anti-mouse CD31 monoclonal antibody (PharMingen, San Diego, Calif., USA), followed by two successive incubations at 37° C. for 30 minutes each with 1:50 dilutions of rabbit anti-rat immunoglobulin (DAKO) and rat APAAP (DAKO). The color reaction was performed with new fuchsin. Sections were counterstained with hematoxylin.

A decrease in tumor size in Canstatin-treated tumors was found to be consistent with a decrease in CD31-positive vasculature.

Example 23

Recombinant Production of Tumstatin and Tumstatin Mutants in *E. Coli*

Figure 19:
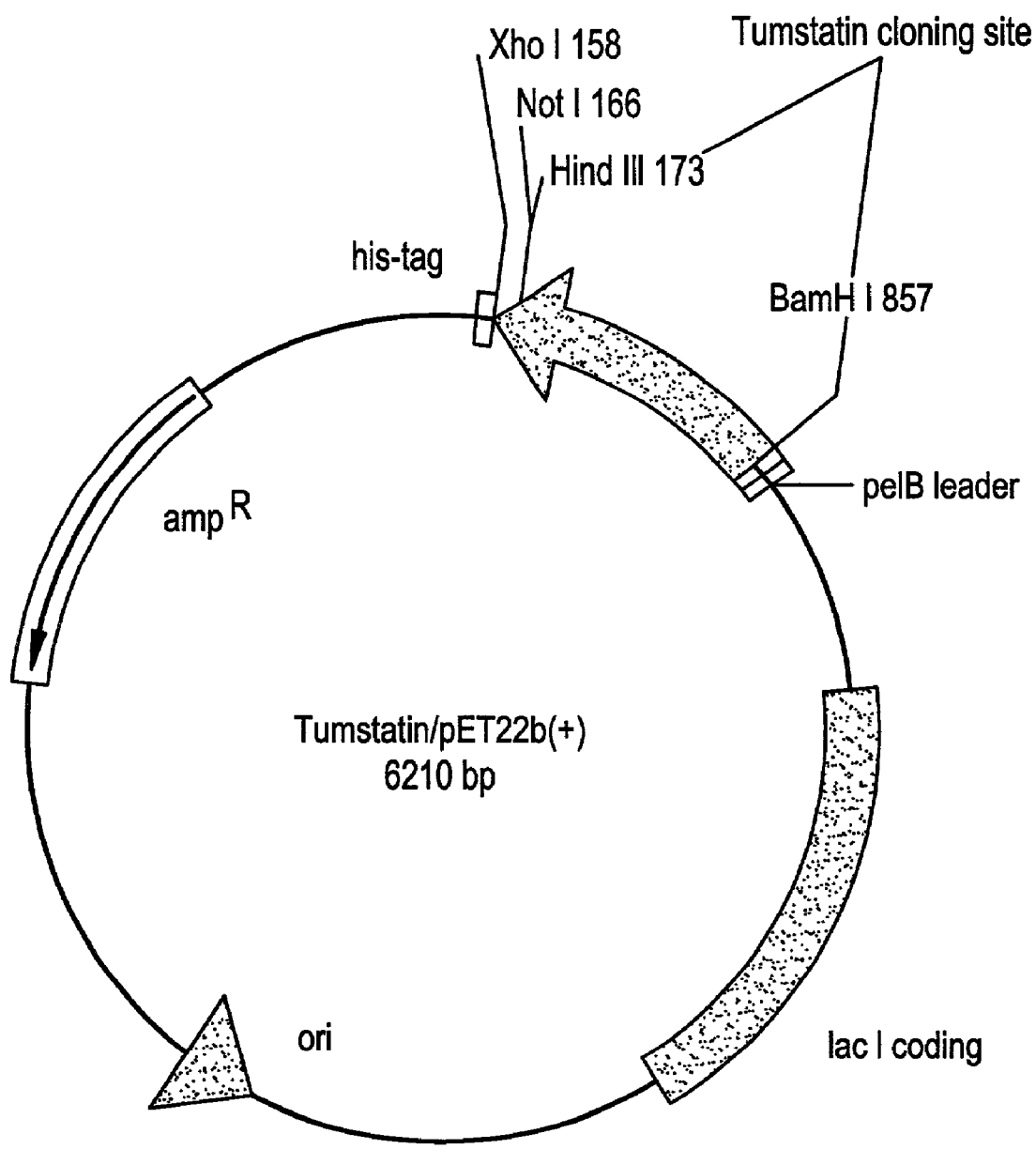
FIG. 19 is a schematic diagram representing the Tumstatin cloning vector pET22b(+). Forward (SEQ ID NO:11) and reverse (SEQ ID NO:12) primers and site into which Tumstatin was cloned are indicated.

The nucleotide (SEQ ID NO:9) and amino acid (SEQ ID NO:10) sequences for the α3 chain of the NC1 domain of Type IV collagen are shown in FIGS. 18A and 18B, respectively. The sequence encoding Tumstatin was amplified by PCR from the α3 NCI (IV)/pDS vector (Neilson, E. G. et al., 1993, J. Biol. Chem. 268:8402-5; GenBank Accession Nos. M92993 (Quinones, S. et al., 1994), M81379 (Turner, N. et al., 1994), and X80031 (Leionin, A. K., & Mariyama, M. et al., 1998)) using the forward primer 5'-CGG GAT CCA GGT TTG AAA GGA AAA CGT-3' (SEQ ID NO:11) and the reverse primer 5'-CCC AAG CTT TCA GTG TCT TTT CTT CAT-3' (SEQ ID NO:12). The resulting cDNA fragment was digested with BamHI and HindIII and ligated into predigested pET22b(+) (Novagen, Madison, Wis., USA). The construct is shown in FIG. 19. The ligation placed Tumstatin downstream of and in-frame with the pelB leader sequence, allowing for periplasmic localization and expression of soluble protein. Additional vector sequence was added to the protein encoding amino acids MDIGINSD (SEQ ID NO:13). The 3' end of the sequence was ligated in-frame with the polyhistidine tag sequence. Additional vector sequence between the 3' end of the cDNA and the his-tag encoded the amino acids KLAAALE (SEQ ID NO:14). Positive clones were sequenced on both strands. Plasmid constructs encoding Tumstatin were first transformed into *E. Coli* HMS 174 (Novagen) and then transformed into BL21 for expression (Novagen). Overnight bacterial culture was used to inoculate a 500 ml culture in LB medium (Fisher Scientific, Pittsburgh, Pa., USA). This culture was grown for approximately 4 hours until the cells reached an $OD_{600}$ of 0.6. Protein expression was then induced by addition of IPTG to a final concentration of 1 mM. After a 2-hour induction, cells were harvested by centrifugation at 5,000×g and lysed by resuspension in 6 M guanidine, 0.1 M $NaH_2PO_4$, 0.01 M Tris-HCl, pH 8.0. Resuspended cells were sonicated briefly, and centrifuged at 12,000×g for 30 minutes. The supernatant fraction was passed over a 5 ml Ni-NTA agarose column (Qiagen, Hilden, Germany) 4-6 times at a speed of 2 ml per minute. Non-specifically bound protein was removed by washing with both 10 mM and 25 mM imidazole in 8 M urea, 0.1 M $NaH_2PO_4$, 0.01 M Tris-HCl, pH 8.0. Tumstatin protein was eluted from the column with increasing concentrations of imidazole (50 mM, 125 mM, and 250 mM) in 8 M urea, 0.1 M $NaH_2PO_4$, 0.01 M Tris-HCl, pH 8.0. The eluted protein was dialyzed twice against PBS at 4° C. A portion of the total protein precipitated during dialysis. Dialyzed protein was collected and centrifuged at approximately 3,500×g and separated into insoluble (pellet) and soluble (supernatant) fractions.

*E. Coli*-expressed Tumstatin was isolated predominantly as a soluble protein and SDS-PAGE analysis revealed a monomeric band at 31 kDa. The additional 3 kDa arises from polylinker and histidine tag sequences. The eluted fractions containing this band were used in following experiments. Protein concentration in each fraction was determined by the BCA assay (Pierce Chemical Co., Rockford, Ill., USA) and quantitative SDS-PAGE analysis using scanning densitometry. Under reducing conditions, a band observed around 60 kDa representing a dimer of Tumstatin in non-reduced condition resolved as a single band of 31 kDa. The total yield of protein was approximately 5 mg per liter.

Figure 20:
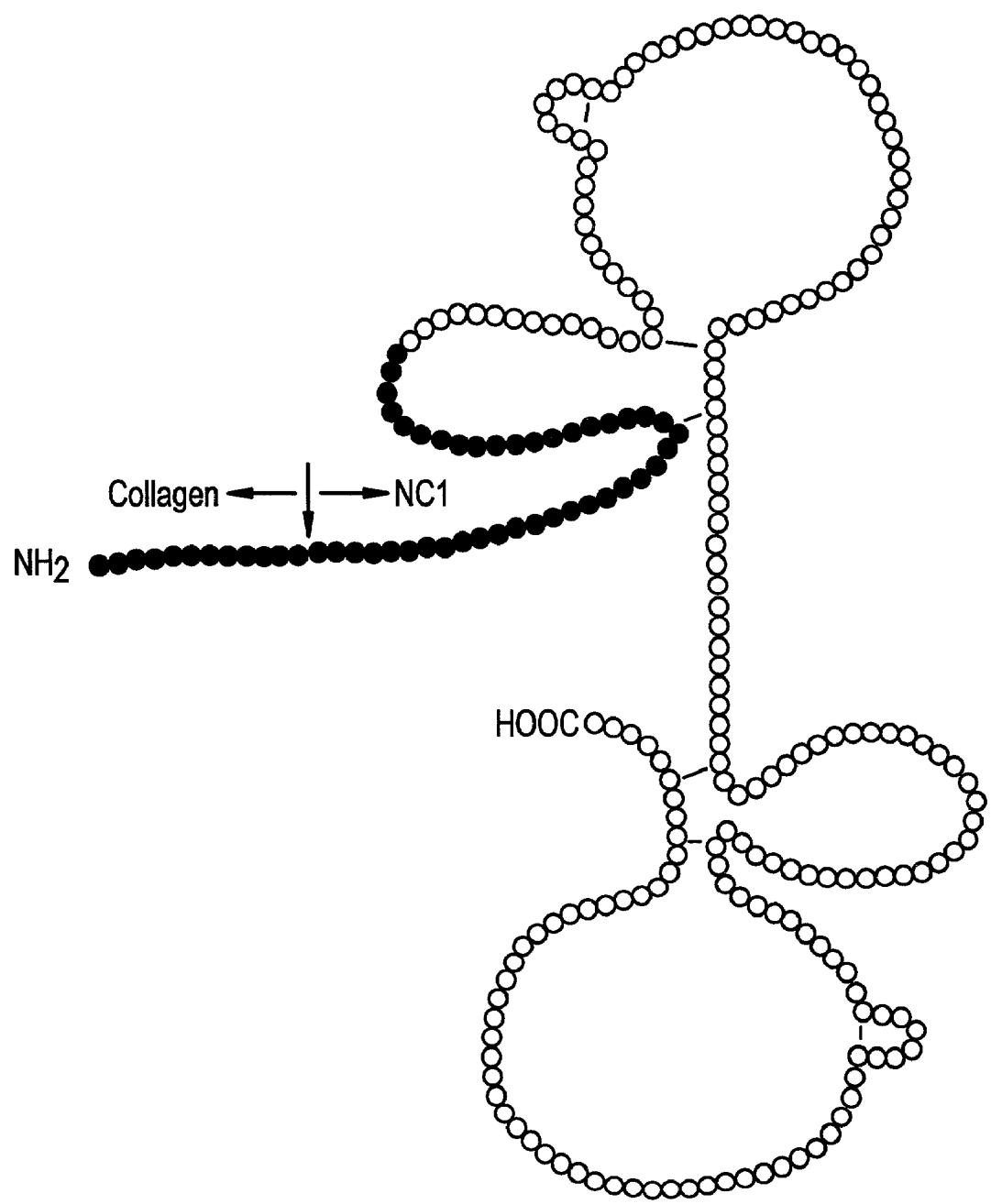
FIG. 20 is a schematic diagram showing the location of truncated amino acids within the α3(IV) NC1 monomer in the Tumstatin mutant Tumsatin N-53 (Tum-1). The filled circles correspond to the N-terminal 53 amino acid residues deleted from Tumstatin to generate this mutant. The disulfide bonds, marked by short bars, are arranged as they occur in α1(IV) NC1 and α2(IV) NC1.

Recombinant truncated Tumstatin (Tumstatin-N53) lacking the 53 N-terminal amino acids was produced in *E. Coli* and purified as previously described for another mutant (Kalluri, R. et al., 1996, J. Biol. Chem. 271:9062-8). This mutant is depicted in FIG. 20, which is a composite diagram showing the location of truncated amino acids within the α3(IV) NC1 monomer. The filled circles correspond to the N-terminal 53 amino acid residues deleted from Tumstatin to generate 'Tumstatin-N53' (Kalluri, R. et al., 1996, J. Biol. Chem. 271:9062-8). The disulfide bonds, marked by short bars, are arranged as they occur in α1(IV) NC1 and a2(IV) NC1 (Siebold, B. et al., 1988, Eur. J. Biochem. 176:617-24). For clarity, only one of two possible disulfide configurations is indicated.

Rabbit antibodies raised against human α3 (IV) NC1 were prepared as previously described (Kalluri, R. et al., 1997, J. Clin. Invest. 99:2470-8). Monoclonal rat anti-mouse CD31 (platelet endothelial cell adhesion molecule, PECAM-1) antibody was purchased from (PharMingen, San Diego, Calif., USA). FITC-conjugated goat anti-rat IgG antibody, FITC-conjugated goat anti-rabbit IgG antibody, and goat anti rabbit IgG antibody conjugated with horseradish peroxidase were purchased from Sigma Chemical Co. (St. Louis, Mo., USA).

The concentrated supernatant obtained above was analyzed by SDS-PAGE and immunoblotting for the Tumstatin expression as previously described (Kalluri, R. et al., 1996, J. Biol. Chem. 271:9062-8). SDS-PAGE in one dimension was carried out with 12% resolving gels and the discontinuous buffer system. The separated proteins were transferred to nitrocellulose membrane and blocked with 2% BSA for 30 minutes at room temperature. After blocking the remaining binding sites, the membrane was washed thoroughly with wash buffer and incubated with a primary antibody at a dilution of 1:1000 in PBS containing 1% BSA. Incubation was carried out at room temperature overnight on a shaker. The blot was then washed thoroughly with washing buffer and incubated with a secondary antibody conjugated to horseradish peroxidase for 3 hours at room temperature on a shaker. The blot was again washed thoroughly and substrate (diaminobenzidine in 0.05 M phosphate buffer containing 0.01% cobalt chloride and nickel ammonium) was added and incubated for 10 minutes at room temperature. The substrate solution was then poured out, and substrate buffer containing hydrogen peroxide was added. After development of bands, the reaction was stopped with distilled water and the blot was dried. A single band of 31 kDa was seen.

Example 24

Expression of Tumstatin in 293 Embryonic Kidney Cells

Human Tumstatin was also produced as a secreted soluble protein in 293 embryonic kidney cells using the pcDNA 3.1 eukaryotic vector. This recombinant protein (without any purification or detection tags) was isolated using affinity chromatography and a pure monomeric form was detected in the major peak by SDS-PAGE and immunoblot analyses.

The pDS plasmid containing α3(IV) NC1 (Neilson, E. G. et al., 1993, J. Biol. Chem. 268:8402-5) was used to PCR amplify Tumstatin in a way that it would add a leader signal sequence in-frame into the pcDNA 3.1 eukaryotic expression vector (InVitrogen, San Diego, Calif., USA). The leader sequence from the 5' end of full length α3(IV) chain was cloned 5' to the NC1 domain to enable protein secretion into the culture medium. The Tumstatin-containing recombinant vectors were sequenced on both strands using flanking primers. Error-free cDNA clones were further purified and used for in vitro translation studies to confirm protein expression. The Tumstatin-containing plasmid and control plasmid were used to transfect 293 cells using the calcium chloride method (Sambrook, J. et al., 1989, MOLECULAR CLONING: A LABORATORY MANUAL, Cold Spring Harbor Lab., Cold Spring Harbor, N.Y., USA, pps. 16.32-16.40). Transfected clones were selected by geneticin (Life Technologies/Gibco BRL, Gaithersburg, Md., USA) antibiotic treatment. The cells were passed for three weeks in the presence of the antibiotic until no cell death was evident. Clones were expanded into T-225 flasks and grown until confluent. The supernatant was then collected and concentrated using an amicon concentrator (Amicon, Inc., Beverly, Mass., USA). The concentrated supernatant was analyzed by SDS-PAGE, immunoblotting and ELISA for the Tumstatin expression. Strong binding in the supernatant was detected by ELISA.

Tumstatin-containing supernatant was subjected to affinity chromatography and immunodetected with both anti-Tumstatin and anti-6-Histidine tag antibodies (Gunwar, S. et al., 1991, J. Biol. Chem. 266:15318-24). A major peak was identified, containing a monomer of about 31 kDa that was immunoreactive with Tumstatin antibodies.

Example 25

Tumstatin Inhibits Endothelial Cell Proliferation

The anti-proliferative effect of Tumstatin on C-PAE cells was examined by $^3$H-thymidine incorporation assay using *E. Coli* produced soluble protein. Cell lines and culture. 786-O (renal clear cell carcinoma line), PC-3 (human prostate adenocarcinoma cell line), C-PAE (bovine pulmonary arterial endothelial cell line), HPE (human primary prostate endothelial cells), HUVEC (human umbilical vein endothelial cells), MAE (mouse aortic endothelial cell line) were all obtained from American Type Culture Collection. The 786-O and C-PAE cell lines were maintained in DMEM (Life Technologies/Gibco BRL, Gaithersburg, Md., USA) supplemented with 10% fetal calf serum (FC S) supplemented with 10% fetal calf serum (FCS), 100 units/ml of penicillin, and 100 mg/ml of streptomycin, the HPE cells in Keratinocyte-SFM supplemented with bovine pituitary extract and recombinant human EGF (Life Technologies/Gibco BRL), and the HUVEC and MAE cells in EGM-2 (Clonetics Corp., San Diego, Calif., USA). Proliferation assay. C-PAE cells were grown to confluence in DMEM with 10% FCS and kept contact-inhibited for 48 hours. C-PAE cells were used between the second and fourth passages. 786-O and PC-3 cells were used as non-endothelial controls in this experiment. Cells were harvested by trypsinization (Life Technologies/Gibco BRL) at 37° C. for 5 minutes. A suspension of 12,500 cells in DMEM with 0.1% FCS was added to each well of a 24-well plate coated with 10 μg/ml fibronectin. The cells were incubated for 24 hours at 37° C. with 5% $CO_2$ and 95% humidity. Medium was removed and replaced with DMEM containing 20% FCS. Unstimulated control cells were incubated with 0.1% FCS. Cells were treated with various concentrations of Tumstatin ranging from 0.01 to 10 mg/ml. All wells received 1 mCurie of $^3$H-thymidine 12 hours after the beginning of treatment. After 24 hours, medium was removed and the wells were washed with PBS three times. Cells were extracted with 1N NaOH and added to a scintillation vial containing 4 ml of ScintiVerse II (Fisher Scientific, Pittsburgh, Pa., USA) solution. Thymidine incorporation was measured using a scintillation counter.

In the methylene-blue staining method, 7000 cells were plated into each well of a 96-well plate, and treated as described above. Cells were then counted using the method of Oliver et al. (1989, J. Cell. Sci. 92:513-8). After 48 hours of treatment, all wells were washed with 100 μl of PBS, and the cells fixed with 10% formalin in neutral-buffered saline (Sigma Chemical Co., St. Louis, Mo., USA). The cells were then stained with 1% methylene blue (Sigma) in 0.01M borate buffer, pH 8.5. Wells were washed with 0.01M borate buffer, and the methylene blue extracted from the cells with 0.1N HCl/ethanol, and the absorbance measured in a microplate reader (Bio-Rad, Hercules, Calif., USA) at 655 nm. Polymyxin B (Sigma) at a final concentration of 5 μg/ml was used to inactivate endotoxin (Liu, S. et al., 1997, Clin. Biochem. 30:455-63).

The results are shown in FIGS. 21A, 21B and 21C, which are histograms showing $^3$H-thymidine incorporation (y-axis) for C-PAE cells (FIG. 21A), PC-3 cells (FIG. 21B) and 786-O cells (FIG. 21C) when treated with varying concentrations of Tumstatin (x-axis). All groups represent triplicate samples. Tumstatin significantly inhibited 20% FCS stimulated $^3$H-thymidine incorporation in a dose dependent manner with an $ED_{50}$ of approximately 0.01 mg/ml (FIG. 21A). Also, no significant anti-proliferative effect was observed with prostate cancer cells (PC-3) or renal carcinoma cells (786-O), even at Tumstatin doses of up to 20 mg/ml (FIGS. 21B and 21C). The difference between the mean value of $^3$H-thymidine incorporation in Tumstatin treated (0.1-10 mg/ml) and control was significant (P<0.05). When PC-3 cells or 786-O cells were treated with Tumstatin, no inhibitory effect was observed (FIGS. 21B, 21C). Each column represents the mean ±SEM of triplicate wells. This experiment was repeated for three times. Bars marked with an asterisk are significant, with P<0.05 by one tailed Student's t-test.

Example 26

Competition Proliferation Assay

C-PAE cells were plated into 96-well plates as described above for the endothelial cell proliferation assay. Tumstatin at a final concentration of 0.1 μg/ml was incubated with varying concentrations (0, 0.008, 0.08, 0.8, 1.6 and 2.4 μg/ml) of human $\alpha_v\beta_3$ protein (CHEMICON Int'l, Temecula, Calif., USA) for 30 minutes at room temperature. This mixture was then added into the wells, and incubated for 48 hours. The proliferation assay was then performed using the methylene blue staining method, as described above for the endothelial cell proliferation assay.

The results are shown in FIG. 22, which is a histogram showing on the x-axis the effect of 0.1 μg/ml Tumstatin combined with increasing amounts of $\alpha_v\beta_3$ on the uptake of dye by C-PAE cells. Absorbance at $OD_{655}$ is shown on the y-axis. "0.1% FCS" represents the 0.1% FCS-treated (unstimulated) control, and "20% FCS" is the 20% FCS-treated (stimulated) control. The remaining bars represent a control of $\alpha_v\beta_3$ alone, and treatments with Tumstatin plus increasing concentrations of $\alpha_v\beta_3$. Each bar represents the mean ±the standard error of the mean for triplicate well. The experiments were repeated three times. An asterisk indicates that P<0.05 by the one-tailed Student's t-test.

As described above, Tumstatin normally inhibits cell proliferation in a dose-dependent manner. With the addition of $\alpha_v\beta_3$ integrin protein, however, Tumstatin's anti-proliferative effect was reversed in a dose-dependent manner with increasing concentration of $\alpha_v\beta_3$ protein, indicating that the αvβ3 integrin protein was effectively "saturating" the Tumstatin available to inhibit endothelial cell proliferation. $\alpha_v\beta_3$ at 2.4 μg/ml (a 3-fold molar excess) significantly reversed the Tumstatin-induced anti-proliferative effect by 43.1%. Treatment with $\alpha_v\beta_3$ alone failed to inhibit endothelial cell proliferation.

Example 27

Tumstatin Induces Apoptosis in Endothelial Cells

Annexin V-FITC assay. In the early stage of apoptosis, translocation of the membrane phospholipid PS from the inner surface of plasma membrane to outside is observed (van Engeland, M. et al., 1998, Cytometry 31:1-9; Zhang, G. et al, 1997, Biotechniques 23:525-31; Koopman, G. et al. 1994, Blood 84:1415-20). Externalized PS can be detected by staining with a FITC conjugate of Annexin V that has a naturally high binding affinity to PS (van Engeland, supra). Apoptosis of endothelial cells upon treatment with Tumstatin was therefore evaluated using annexin V-FITC labeling.

C-PAE cells ($0.5 \times 10^6$ per well) were seeded onto a 6-well plate in 10% FCS supplemented DMEM. The next day, fresh medium containing 10% FCS was added with either 80 ng/ml of TNF-α (positive control) or Tumstatin ranging from 0.02 to 20 μg/ml. Control cells received an equal volume of PBS. After 18 hours of treatment, medium containing floating cells was collected, and attached cells were trypsinized and centrifuged together with floating cells at 3,000×g. The cells were then washed in PBS and resuspended in binding buffer (10 mM HEPES/NaOH, pH 7.4, 140 mM NaCl, 2.5 mM $CaCl_2$). Annexin V-FITC (Clontech, Palo Alto, Calif., USA) was added to a final concentration of 150 ng/ml, and the cells were incubated in the darkness for 10 minutes. The cells were washed again in PBS and resuspended in binding buffer. Annexin V-FITC labeled cells were counted using a FACStar Plus flow cytometer (Becton-Dickinson, Waltham, Mass., USA). For each treatment, 15,000 cells were counted and stored in listmode. This data was then analyzed using Cell Quest software (Becton-Dickinson).

Tumstatin at 20 μg/ml showed a distinct shift of annexin fluorescence peak after 18 hours. The shift in fluorescence intensity was similar for Tumstatin at 20 μg/ml and the positive control TNF-α (80 ng/ml). Tumstatin at 2 μg/ml also showed a mild shift in annexin fluorescence intensity, but concentrations below 0.2 μg/ml did not demonstrate any annexin V positivity. This shift of peak intensity was not observed when nonendothelial cells (PC-3) were used.

Tumstatin also altered cell morphology of C-PAE cells as monitored by phase contrast microscopy. After treating cells with 20 μg/ml of Tumstatin in the presence of 10% FCS for 24 hours on fibronectin-coated plates, the typical morphological features of apoptotic cells, membrane blebbing, cytoplasmic shrinkage, and chromatin condensation could be observed. In control wells, cells exhibited intact morphology. Caspase-3 assay: Caspase-3 (CPP32) is an intracellular protease activated at the early stage of apoptosis, and initiates cellular breakdown by degrading structural and DNA repair proteins (Casciola-Rosen, L. et al., 1996, J. Exp. Med. 183:1957-64; Salvesen, G. S. et al., 1997, Cell 91:443-46). The protease activity of Caspase-3 was measured spectrophotometrically by detection of the chromophore (p-nitroanilide) cleaved from the labeled substrate (DEVD-pNA). C-PAE cells or PC-3 cells ($0.5 \times 10^6$ per well) were plated onto a 6-well plate precoated with fibronectin (10 μg/ml) in DMEM supplemented with 10% FCS, and incubated overnight. The next day, the medium was replaced with DMEM containing 2% FCS and then incubated overnight at 37° C. Then cells were then stimulated with bFGF (3 ng/ml) in DMEM supplemented with 2% FCS, and also containing either TNF-α (80 ng/ml, positive control) or Tumstatin (10 μg/ml), and incubated for 24 hours. Controls received PBS buffer. After 24 hours, the supernatant cells were collected, and attached cells were trypsinized and combined with the supernatant cells. Cells were counted and resuspended in cell lysis buffer (Clontech) at a concentration of $4 \times 10^7$ cells/ml. The rest of the protocol followed the manufacturer's instructions (Clontech). A specific inhibitor of Caspase-3, DEVD-fmk (Asp-Glu-Val-Asp-fluoromethyl ketone) was used to confirm the specificity of the assay. The absorbance was measured in a microplate reader (Bio-Rad, Hercules, Calif., USA) at 405 nm. The assay was repeated three times for each cell type.

Figure 23A:
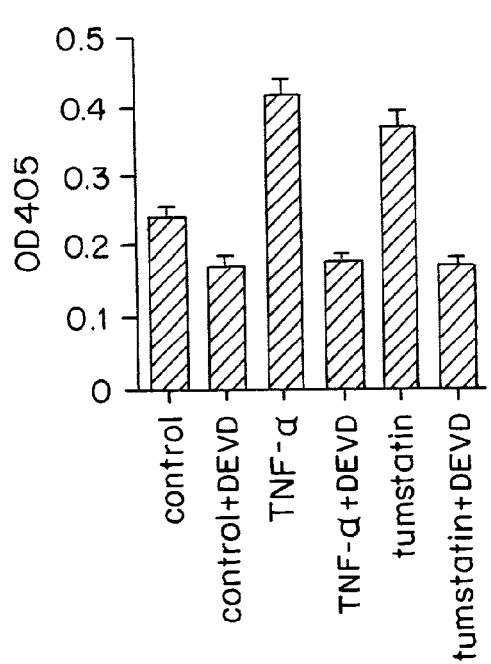
FIGS. 23A and 23B are a pair of histograms showing the amount of Caspase-3 activity as a function of absorbance at $OD_{405}$ (y-axis) for C-PAE cells (FIG. 23A) and PC-3 cells (FIG. 23B) under various treatments (x-axis). Each column represents the mean the standard error of the mean of triplicate well.
Figure 23B:
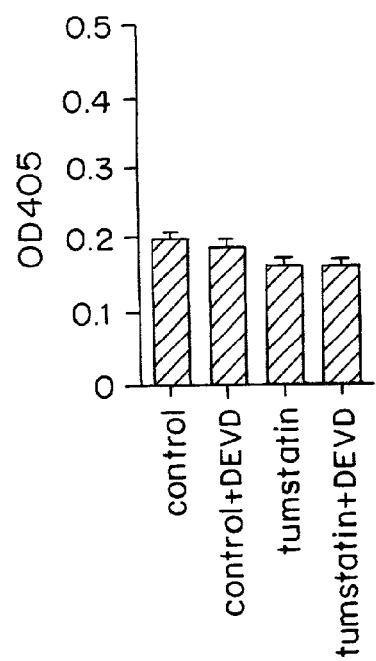
Figure 24A:
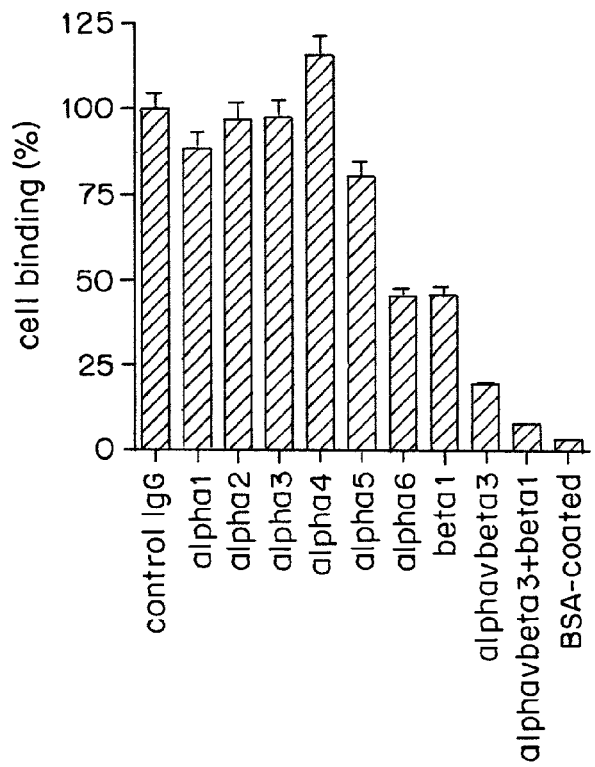
FIGS. 24A, 24B, 24C and 24D are a set of four histograms showing binding of HUVEC cells to plates coated with Tumstatin (FIG. 24A), or controls of type IV collagen (FIG. 24B), vitronectin (FIG. 24C) or laminin-1 (FIG. 24A) in the presence of integrin subunits α1 through $\alpha_6$, $\beta_1$, or $\alpha_v\beta_3$ integrin blocking antibody. The plate coating is listed at the top of each graph, and the antibodies used for incubation are on the x-axis of each graph. BSA-coated plates were used as negative controls.
Figure 24B:
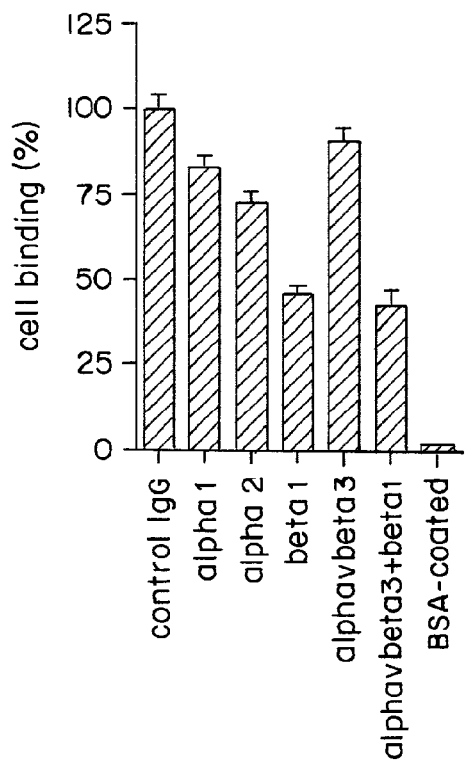
Figure 24C:
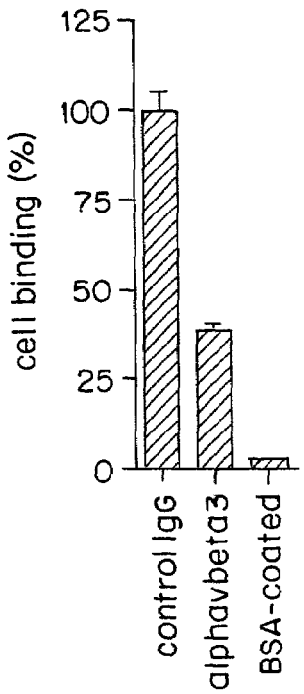
Figure 24D:
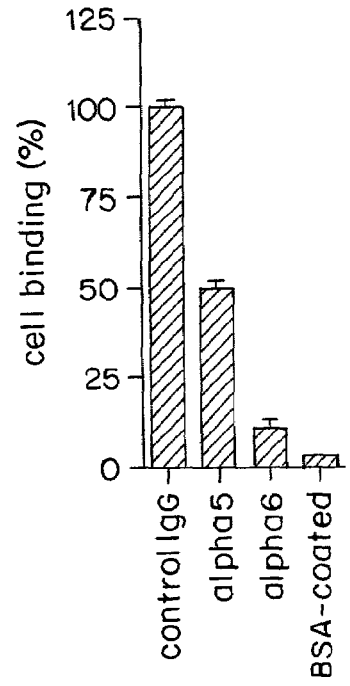

The results are shown in FIGS. 23A and 23B, which are a pair of histograms showing the amount of Caspase-3 activity as a function of absorbance at $OD_{405}$ (y-axis) for C-PAE cells (FIG. 23A) and PC-3 cells (FIG. 23B) under various treatments (x-axis). Each column represents the mean ±the standard error of the mean of triplicate well.

C-PAE cells treated with 20 μg/ml Tumstatin exhibited a 1.6-fold increase in Caspase-3 activity, whereas the positive control TNF-α gave a comparable (1.7-fold) increase compared with control. A specific inhibitor of Caspase-3, DEVD-fmk, decreased the protease activity to baseline indicating that the increase in the measured activity was specific for Caspase-3. In nonendothelial PC-3 cells, there was no difference in Caspase-3 activity between control and Tumstatin-treated cells.

Example 28

Cell Adhesion Assay

The attachment of HUVECs to Tumstatin-coated plates in the presence of integrin subunits $\alpha_1$ through $\alpha_6$, $\beta_1$, and $\alpha_v\beta_3$ integrin blocking antibody was examined. This assay was performed according to the method of Senger et al. (Senger, D. R. et al, 1997, Proc. Natl. Acad. Sci. USA 94:13612-7), with minor modification. 96-well plates were coated with either human Tumstatin, mouse laminin-1, or human Type IV collagen (Collaborative Biomedical Prods., Bedford, Mass., USA) at a concentration of 10 µg/ml overnight at 37° C. Vitronectin (Collaborative Biomed. Prods.) at a concentration of 0.5 µg/ml was then used to coat the plates. The remaining protein binding sites were blocked with 100 mg/ml of BSA (Sigma Chemical Co., St. Louis, Mo., USA) in PBS for 2 hours. HUVEC cells were grown to subconfluence (70-80%) in EGM-2 medium, gently trypsinized and resuspended in serum-free medium ($1.5 \times 10^5$ cells/ml). The cells were mixed with 10 µg/ml of either mouse IgG, (control) (Life Technologies/Gibco BRL, Gaithersberg, Md., USA) or antibody (mouse monoclonal antibody to the human $\beta_1$ integrin (clone P4C10) (Life Technologies/Gibco BRL); monoclonal antibody to human integrins $\alpha_1$ through $\alpha_6$ (CHEMICON Int'l, Temecula, Calif., USA); $\alpha_v\beta_3$ integrin (clone LM609) (CHEMICON Int'l) and incubated for 15 minutes at room temperature, with gentle agitation. One hundred microliters of the cell suspension was then added to each well and incubated for 45 minutes at 37° C. Unattached cells were removed by washing, and the number of attached cells were counted after staining with methylene blue. C-PAE cells were used in separate experiments, following the above procedure.

Figure 25:
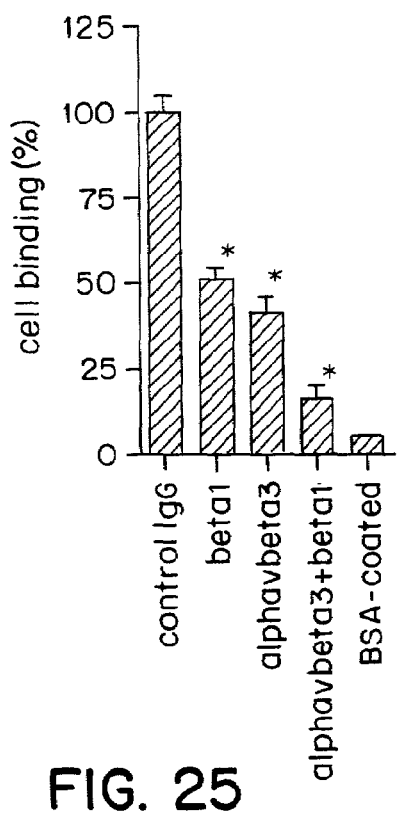
FIG. 25 is a histogram showing binding of C-PAE cells to Tumstatin-coated plates. BSA-coated plates were used as negative controls.

The results are shown in FIGS. 24A through 24D, and FIG. 25. FIGS. 24A, 24B, 24C and 24D are a set of four histograms showing binding of HUVEC cells to plates coated with Tumstatin (FIG. 24A), or controls of type IV collagen (FIG. 24B), vitronectin (FIG. 24C) or laminin-1 (FIG. 24D) in the presence of integrin subunits $\alpha1$ through $\alpha_6$, $\beta_1$, or $\alpha_v\beta_3$ integrin blocking antibody. FIG. 25 is a histogram showing binding of C-PAE cells to Tumstatin-coated plates. The plate coating is listed at the top of each graph, and the antibodies used for incubation are on the x-axis of each graph. BSA-coated plates were used as negative controls.

HUVEC cell attachment to Tumstatin-coated plates was significantly blocked by anti-$\alpha_6$, anti-$\beta_1$ or anti-$\alpha\beta_3$ antibody, compared to IgG-coated control plates. Cell attachment was further inhibited when anti-$\beta_1$ and anti-$\alpha_v\beta_3$ antibody were used together. The $\alpha_v\beta_3$ antibody inhibited the attachment of cells by 80%, and $\alpha_6$ or $\beta_1$ antibody blocked by 54% as compared to control IgG treatment. Although $\alpha_5$ antibody exhibited minor inhibition (20%), antibody to subunits $\alpha_1$ through $\alpha_4$ did not block cell attachment. When $\alpha_v\beta_3$ antibody and $\beta_1$ antibody were used together, cell binding was blocked by 91%.

Comparable inhibition was also observed using C-PAE cells on Tumstatin-coated plates instead of HUVEC cells. Plates coated with Type IV collagen, vitronectin and laminin-1 also served as controls. The $a_1\beta_1$ and $\alpha_2\beta_1$ integrins bind collagens (Elices, M. J. et al., 1989, Proc. Natl. Acad. Sci. USA 86:9906-10; Ignatius, M. J. et al., 1990, J. Cell. Biol. 111:709-20). Cell binding onto type IV collagen-coated plates was partially inhibited by antibodies to $\alpha_1$ (20%), $\alpha_2$ (27%), and $\beta_1$ (53%), as compared to cells incubated with control IgG. $\alpha_v\beta_3$ integrin is a receptor for vitronectin (Hynes, R. O. et al., 1992, Cell 69:11-25). Cell binding onto vitronectin-coated plates was inhibited by $\alpha_v\beta_3$ antibody by 61%. The $\alpha_5\beta_1$, and $\alpha_6\beta_1$ integrins bind laminin (Wayner, E. A. et al., 1988, J. Cell. Biol. 107:1881-91; Sonnenberg, A. et al., 1988, Nature 336:487-9). Anti-$\alpha_5$ or anti-$\alpha_6$ antibody blocked the binding of endothelial cells onto laminin-1 coated plates by 50% and 89% respectively. Cell attachment onto Tumstatin-coated plates (FIG. 25) was significantly inhibited by anti-$\beta_1$ or anti-$\alpha_v\beta_3$ antibody, compared to IgG-treated controls. When anti-$\beta_1$ or anti-$\alpha_v\beta_3$ antibody were used together, cell attachment was further inhibited.

Example 29

Tumstatin Inhibits Endothelial Tube Formation

Matrigel (Collaborative Biomedical Prods., Bedford, Mass., USA) was added (320 ml) to each well of a 24-well plate and allowed to polymerize (Grant, D. S. et al., 1994, Pathol. Res. Pract. 190:854-63). A suspension of 25,000 MAE cells in EGM-2 medium (Clonetics Corporation, San Diego, Calif., USA) without antibiotic was passed into each well coated with Matrigel (Grant, D. S. et al., 1994, Pathol. Res. Pract. 190:854-63). The cells were treated with either Tumstatin, BSA or 7S domain in increasing concentrations. Control cells were incubated with sterile PBS. All assays were performed in triplicate. Cells were incubated for 24-48 hours at 37° C. and viewed using a CK2 Olympus microscope (magnification of 3.3× ocular, 10× objective). The cells were then photographed using 400 DK coated TMAX film (Kodak). Cells were stained with diff-quik fixative (Sigma Chemical Co.) and photographed again (Grant, D. S. et al., 1994, Pathol. Res. Pract. 190:854-63). Ten fields were viewed, and the number of tubes were counted by two investigators unaware of the experimental protocols, and averaged.

Figure 26:
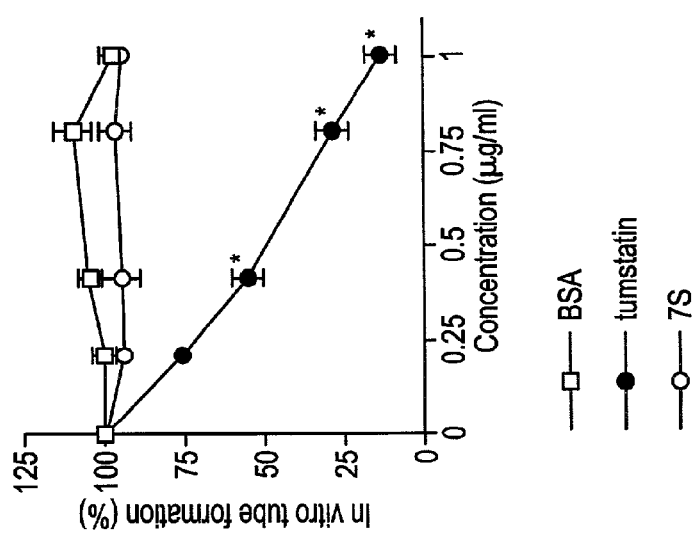
FIG. 26 is a line graph showing the effect on endothelial tube formation (y-axis) of varying amounts (x-axis) of Tumstatin (●), BSA (control, □) and 7S domain (control, ○).

The results are shown in FIG. 26. When mouse aortic endothelial cells are cultured on Matrigel, a solid gel of mouse basement membrane proteins, they rapidly align and form hollow tube-like structures (Haralabopoulos, G. C. et al., 1994, Lab. Invest. 71:575-82). Tumstatin, produced in 293 cells, significantly inhibited endothelial tube formation in MAE cells in a dose dependent manner as compared to BSA controls (FIG. 26). Percentage of tube formation after treatment with 1 mg/ml of protein was, BSA 98.0±4.0, Tumstatin 14.0±4.0. Similar results were also obtained using E. Coli produced Tumstatin. The 7S domain of type IV collagen (N-terminal non-collagenous domain) had no effect on endothelial tube formation. Maximum inhibition with Tumstatin was attained between 800-1000 ng/ml. The difference between the mean percentage value of Tumstatin-treated (●, 0.1-10 mg/ml) and control (BSA (□), 7S domain (○) was significant (P<0.05). Each point represents the mean ±SE of triplicate wells. This experiment was repeated three times. Data points marked by an asterisk were significant, with P<0.05 by one tailed Student's t test. Well-formed tubes were observed in the 7S domain treatments. MAE cells treated with 0.8 mg/ml Tumstatin exhibiting decreased tube formation.

To evaluate the in vivo effect of Tumstatin on the formation of new capillaries, a Matrigel plug assay was performed (Passaniti, A. et al., 1992, Lab. Invest. 67:519-29). Five- to six-week-old male C57/BL6 mice (Jackson Laboratories, Bar Harbor, Me., USA) were obtained. Matrigel (Collaborative Biomedical Prods.) was thawed overnight at 4° C. Before injection into C57/BL6 mice, it was mixed with 20 U/ml of heparin (Pierce Chemical Co., Rockford, Ill., USA), 150 ng/ml of bFGF (R&D Sys., Minneapolis, Minn., USA), and 1 mg/ml of Tumstatin. Control groups received no angiogenic inhibitor. The Matrigel mixture was injected sub-cutaneously using a 21 gauge needle. After 14 days, mice were sacrificed and the Matrigel plugs were removed. Matrigel plugs were fixed in 4% para-formaldehyde (in PBS) for 4 hours at room temperature, then switched to PBS for 24 hours. The plugs were embedded in paraffin, sectioned, and H & E stained. Sections were examined by light microscopy and the number of blood vessels from 10 high power fields were counted and averaged. All sections were coded and observed by a pathologist who was unaware of the study protocols.

When Matrigel was placed in the presence of bFGF and heparin, with or without *E. Coli*-produced Tumstatin, a 67% reduction in the number of blood vessels was observed with treatment of 1 mg/ml Tumstatin. The number of vessels per high power field was, Tumstatin, 2.25±1.32 and control, 7.50±2.17. Each column represents the mean ±SE of 5-6 mice per group. Tumstatin (1 mg/ml) significantly inhibited in vivo neo-vascularization as compared to controls treated with PBS. The difference between the mean percentage value of Tumstatin-treated animals and control animals was significant (P<0.05). The Tumstatin treatment was significant, with P<0.05 by one tailed Student's t-test.

Example 30

Tumstatin and Tumstatin Mutant Inhibit Tumor Growth In Vivo

Figure 27B:
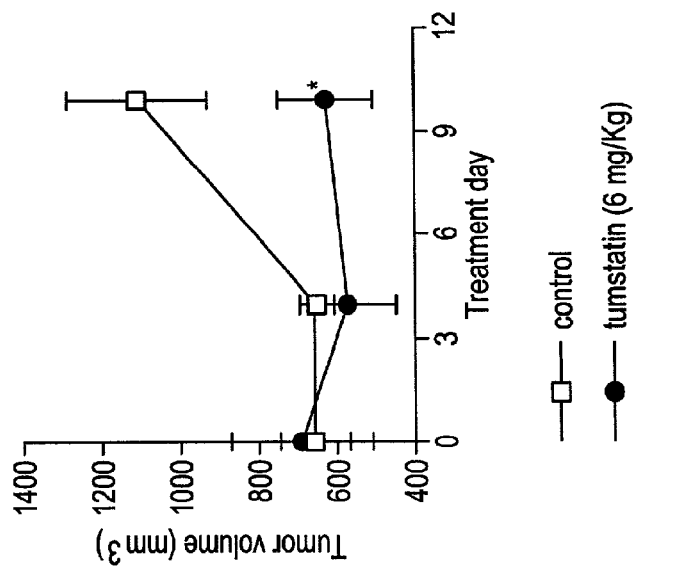
FIGS. 27A and 27B are a pair of line graphs showing the effects on tumor volume (mm$^3$, y-axis) against days of treatment (x-axis) of Tumstatin (●) and endostatin (○) versus controls (□). Data points marked with an asterisk are significant, with P<0.05 by one-tailed Student's test.
Figure 27A:
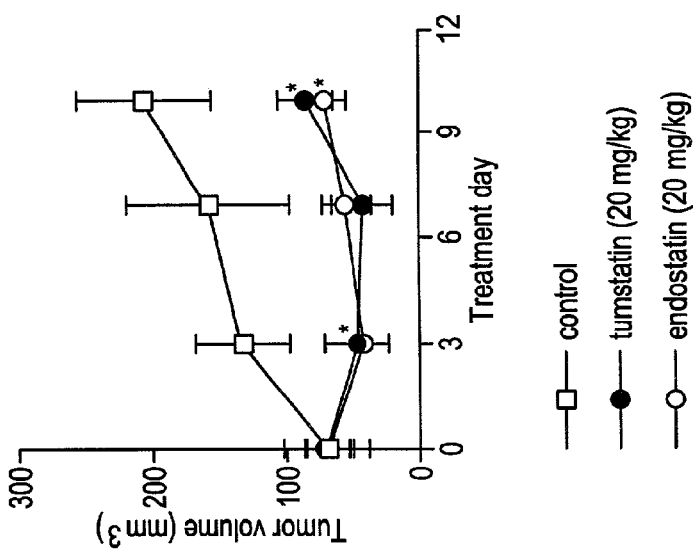

Five million PC-3 cells were harvested and injected subcutaneously on the back of 7- to 9-week-old male athymic nude mice. The tumors were measured using Vernier calipers and the volume was calculated using the standard formula width$^2$×length×0.52. The tumors were allowed to grow to about 100 mm$^3$, and animals were then divided into groups of 5 or 6 mice. Tumstatin or mouse endostatin was intraperitoneally injected daily (20 mg/kg) for 10 days in sterile PBS to their respective experimental group. The control group received vehicle injection (either BSA or PBS). Tumor volume was calculated every 2 or 3 days over 10 days. The results are shown in FIG. 27A, which is a graph showing tumor volume in mm$^3$ (y-axis) against days of treatment (x-axis) for the PBS control (□), 20 mg/kg Tumstatin (0) and 20 mg/kg endostatin (o). Tumstatin, produced in *E. Coli*, significantly inhibited the growth of PC-3 human prostate tumors (FIG. 27A). Tumstatin at 20 mg/Kg inhibited tumor growth similar to endostatin at 20 mg/kg (FIG. 27A). Significant inhibitory effect on tumor growth was observed on day 10 (control 202.8±50.0 mm$^3$, Tumstatin 82.9±25.2 mm$^3$, endostatin 68.9±16.7 mm$^3$). Daily intraperitoneal injection of Tumstatin or endostatin inhibited the growth of human prostate adenocarcinoma cell (PC-3) tumor as compared to the control. This experiment was started when the tumor volumes were less than 100 mm$^3$.

Tumstatin's effect on another established primary tumors in mice was also studied. Two million 786-O renal cell carcinoma cells were injected subcutaneously on the back of 7- to 9-week-old male athymic nude mice. The tumors were allowed to grow to about 600 to about 700 mm$^3$ and animals were then divided into groups of 6. Tumstatin was intraperitoneally injected daily (6 mg/kg) for 10 days in sterile PBS. The control group received BSA injections. The results are shown in FIG. 27B, which is a graph showing tumor volume in mm$^3$ (y-axis) against days of treatment (x-axis) for the PBS control (□) and for 6 mg/kg Tumstatin (●). *E. Coli*-produced Tumstatin at 6 mg/kg inhibited the tumor growth of 786-O human renal cell carcinoma as compared to the BSA control (FIG. 27B). Significant inhibitory effect on tumor growth was observed on day 10 (control 1096±179.7 mm$^3$, Tumstatin 619±120.7 mm$^3$) Daily intraperitoneal injection of Tumstatin inhibited the tumor growth of human renal cell carcinoma (786-O) as compared to the control. This experiment was started when the tumor volumes were 600-700 mm$^3$. Each point represents the mean i SE of 5-6 mice per group. Data points marker with an asterisk were significant, with P<0.05 by one tailed Student's t test.

A portion of the NC1 domain of the α3 chain of type IV collagen (α3 (IV) NC1) is the pathogenic epitope of Goodpasture syndrome (Butkowski, R. J. et al., 1987, J. Biol. Chem. 262:7874-77; Saus, J. et al., 1988, J. Biol. Chem. 263:13374-80; Kalluri, R. et al., 1991, J. Biol. Chem. 266:24018-24). Goodpasture syndrome is an autoimmune disease characterized by pulmonary hemorrhage and/or rapidly progressing glomerulonephritis (Wilson, C. & F. Dixon, 1986, The Kidney, W. B. Sanders Co., Philadelphia, Pa., USA, pps. 800-89; Hudson, B. G. et al., 1993, J. Biol. Chem. 268:16033-6). These symptoms are caused by the disruption of glomerular and alveolar basement membrane through binding of auto-antibody against α3 (IV) NC1 (Wilson, 1986, supra; Hudson, 1993, supra). Several groups have attempted to map or predict the location of the Goodpasture autoantigen on α3 (IV) (Kalluri, R. et al., 1995, J. Am. Soc. Nephrol. 6:1178-85; Kalluri, R. et al., 1996, J. Biol. Chem. 271:9062-68; Levy, J. B. et al., 1997, J. Am. Soc. Nephrol. 8:1698-1705; Kefalides, N. A. et al., 1993, Kidney Int. 43:94-100; Quinones, S. et al., 1992, J. Biol. Chem. 267:19780-84 (erratum in J. Biol. Chem. 269:17358); Netzer, K. O. et al., 1999, J. Biol. Chem. 274:11267-74), residues in the N-terminus, C-terminus, and mid-portion have been reported to be the epitope position. Recently, the most probable disease-related pathogenic epitope was identified in the first 40 amino acids of the N-terminal portion (Hellmark, T. et al., 1999, Kidney Int. 55:936-44) and was further confined to be the N-terminal 40 amino acids. A truncated Tumstatin was designed lacking N-terminal 53 amino acids (Tumstatin-N53) corresponding to the pathogenic Goodpasture auto-epitopes. This mutant protein was used in the following experiments.

Figure 28:
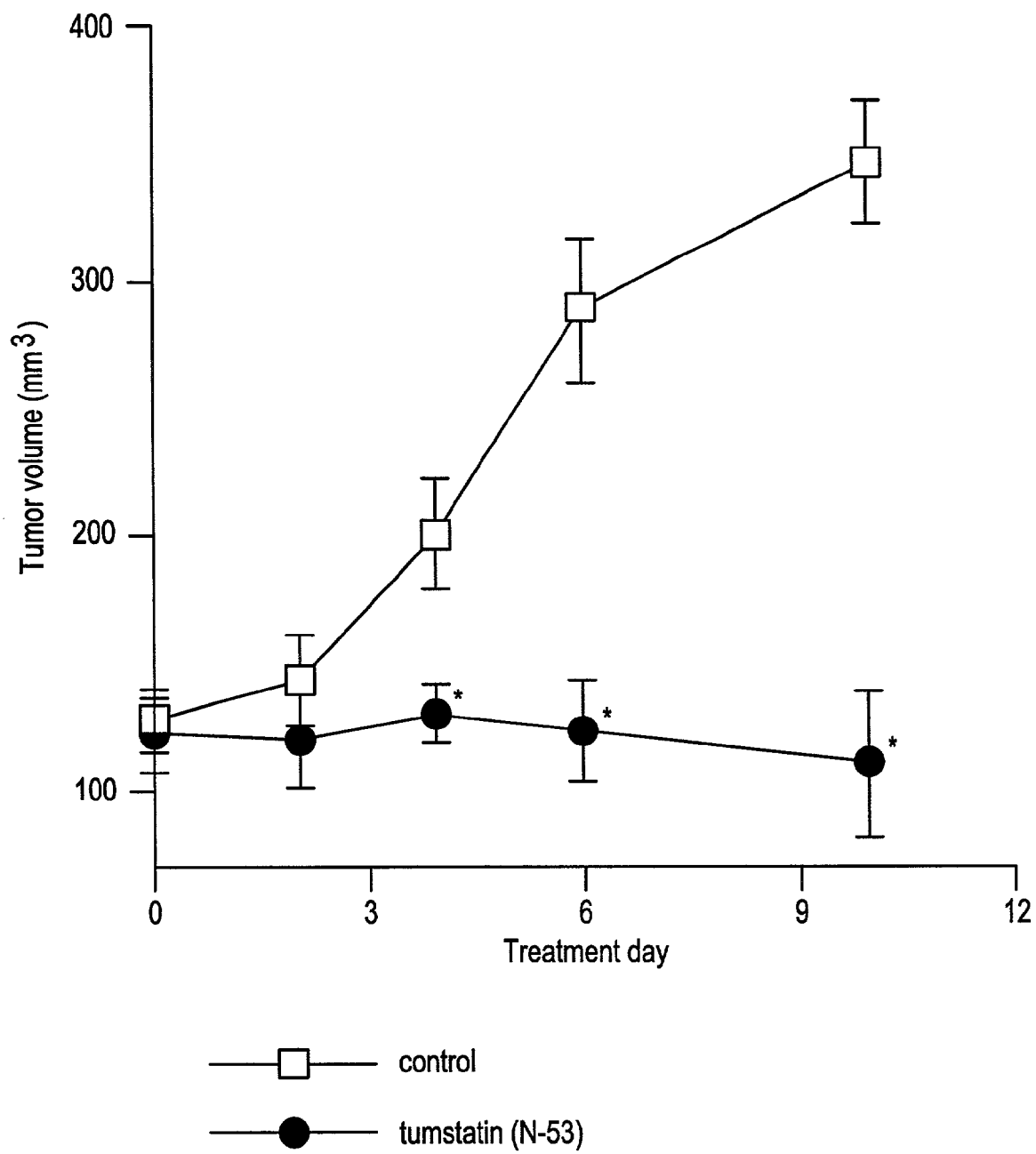
FIG. 28 is a graph showing increase in tumor volume (y-axis) against day of treatment (x-axis) for control mice (□) and mice treated with the Tumstatin mutant N-53 (●). Data points marked with an asterisk are significant, with P<0.05 by one-tailed Student's test.

Two million 786-O renal cell carcinoma cells were injected subcutaneously on the back of 7- to 9-week-old male athymic nude mice. The tumors were allowed to grow to a size of about 100-150 mm$^3$. The mice were then divided into groups of 5, and were injected daily intraperitoneally with 20 mg/kg of the *E. Coli*-expressed truncated Tumstatin lacking the 53 N-terminal amino acids (Kalluri, R. et al., 1996, J. Biol. Chem. 271:9062-68) for 10 days. Control mice received PBS injection. The results are shown in FIG. 28, which is a graph showing increase in tumor volume (y-axis) against day of treatment (x-axis) for control mice (□) and mice treated with the Tumstatin mutant N53 (●). *E. Coli*-produced Tumstatin-N53 at 6 mg/kg inhibited the growth of 786-O human renal tumors significantly from day 4 to day 10 as compared to control (day 10: Tumstatin-N53 110.0±29.0 mm$^3$, control 345.0±24.0 mm$^3$) (FIG. 28). Each point represents the mean ±SE of 5-6 mice/group. Data points marked with an asterisk were significant, with P<0.05 by one-tailed Student's t test.

Example 31

Immunohistochemical Staining for α3 (IV) NC1 and CD31

Kidney and skin tissue from a 7-week-old male C57/BL6 mouse was processed for evaluation by immunofluorescence microscopy. The tissue samples were frozen in liquid nitrogen, and sections 4 mm thick were used. Tissue was processed by indirect immunofluorescence technique as previously described (Kalluri, R. et al., 1996, J. Biol. Chem. 271:9062-68). Frozen sections were stained with the primary antibodies, polyclonal anti-CD31 antibody (1:100 dilution) or polyclonal anti-α3 (IV) NC1 antibody (1:50 dilution), followed by the secondary antibody, FITC-conjugated anti-rat IgG antibody or FITC-conjugated anti-human IgG antibody. Immunofluorescence was examined under an Olympus fluorescent microscope (Tokyo, Japan). Negative controls were performed by substituting the primary antibody with an irrelevant pre-immune serum.

In mouse kidney, expression of α3 (IV) NC1 was observed in GBM and in vascular basement membrane. The expression of CD31, PECAM-1, was observed in glomerular endothelium and vascular endothelium. In mouse skin, α3 (IV) NC1 was absent in epidermal basement membrane and vascular basement membranes. The expression of CD31 was observed in vascular endothelium of the skin. CD31 expression was observed in the endothelium of glomeruli and small vessels in mouse kidney α3 (IV) NC1 expression was observed in glomerular basement membrane and in extra-glomerular vascular basement membranes. Expression of CD31 was observed in the endothelium of dermal small vessels in mouse skin. α3 (IV) NC1 expression was absent in the epidermal basement membrane and almost not observed in the basement membrane of dermal small vessels. These results show an example of restricted distribution of Tumstatin.

Example 32

Tumstatin N-53 Causes Apoptosis in Endothelial Cells

The pro-apoptotic activity of Tumstatin N-53 was examined in C-PAE cells. Cell viability was assessed by MTT (3-(4,5-dimethylthiazol-2-yl)-2-,5-diphenyl tetrasolium bromide) assay (Sugiyama, H. et al., 1998, Kidney Int. 54:1188-96). This assay is a quantitative calorimetric analysis for cell survival based on the ability of living cells to cleave the tetrasolium ring in active mitochondria. C-PAE cells (7,000 cells perwell) were plated to a 96-well plate in 10% FCS containing DMEM. The next day, either TNF-α (positive control, 80 ng/ml), or varying concentrations of Tumstatin or Tumstatin N-53 was added to the wells and incubated for 24 hours. MTT solution (5 mg/ml; CHEMICON International, Temecula, Calif., USA) was then added to the wells at a rate of 10 μl/well and incubated at 37° C. for 4 hours. Acid-isopropanol was added and mixed thoroughly. The absorbance was measured in a microplate reader (Bio-Rad, Hercules, Calif., USA) at 590 nm.

Figure 29:
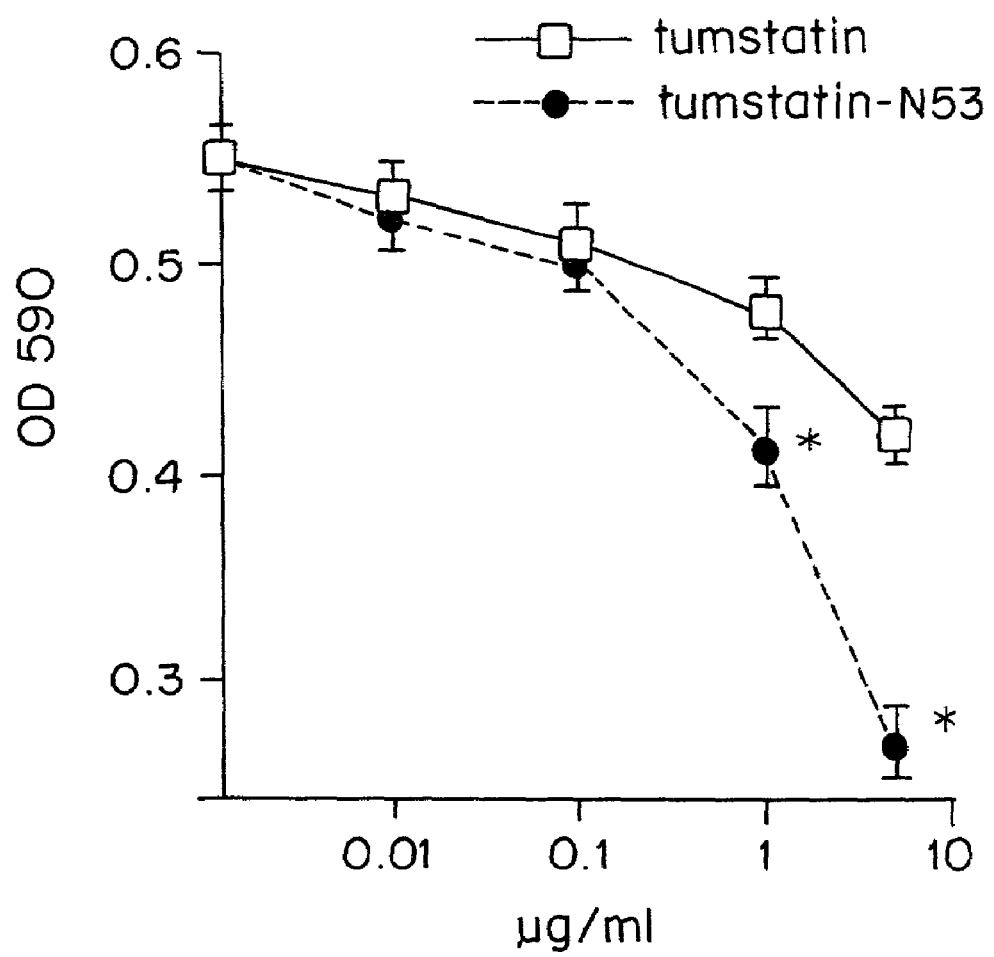
FIG. 29 is a graph showing cell viability (as a function of $OD_{590}$, y-axis) at increasing concentrations of Tumstatin and Numstatin N-53 (x-axis). Each point represents the mean ±the standard error of the mean for triplicate well. An asterisk indicates P<0.05 by the one-tailed Student's t test.

The results are shown in FIG. 29, which is a graph showing cell viability (as a function of $OD_{590}$, y-axis) at increasing concentrations of Tumstatin and Numstatin N-53 (x-axis). Each point represents the mean the standard error of the mean for triplicate well. An asterisk indicates P<0.05 by the one-tailed Student's t test.

Tumstatin N-53 decrease cell viability in a dose-dependent manner. At 5 μg/ml, Tumstatin N-53 decreased the cell viability by 49.4% compared to controls, and this effect was comparable to 80 ng/ml TNF-α, which was used as a positive control. In other experiments, full-length Tumstatin decreased cell viability by only 22.5% at 5 μg/ml and by 60% at 10 μg/ml, as compared to 49.4% for 5 μg/ml Tumstatin N-53. Surprisingly, Tumstatin N-53 at 5 μg/ml or 1 μg/ml induces more apoptosis of endothelial cells then even full-length Tumstatin.

Example 33

Mutants and Fragments of the Anti-Angiogenic Proteins

Fragments and mutants of Arresten and Canstatin were also made according to the *Pseudomonas* elastase digestions of Mariyama et al. (1992, J. Biol. Chem. 267:1253-58). The digest was resolved by gel filtration HPLC and the resultant fragments were analyzed by SDS-PAGE and evaluated in the endothelial tube assay described above. These fragments included a 12 kDa fragment of Arresten, an 8 kDa fragment of Arresten, and a 10 kDa fragment of Canstatin. In addition, two fragments of Tumstatin ('333' and '334') were generated by PCR cloning.

Figure 30:
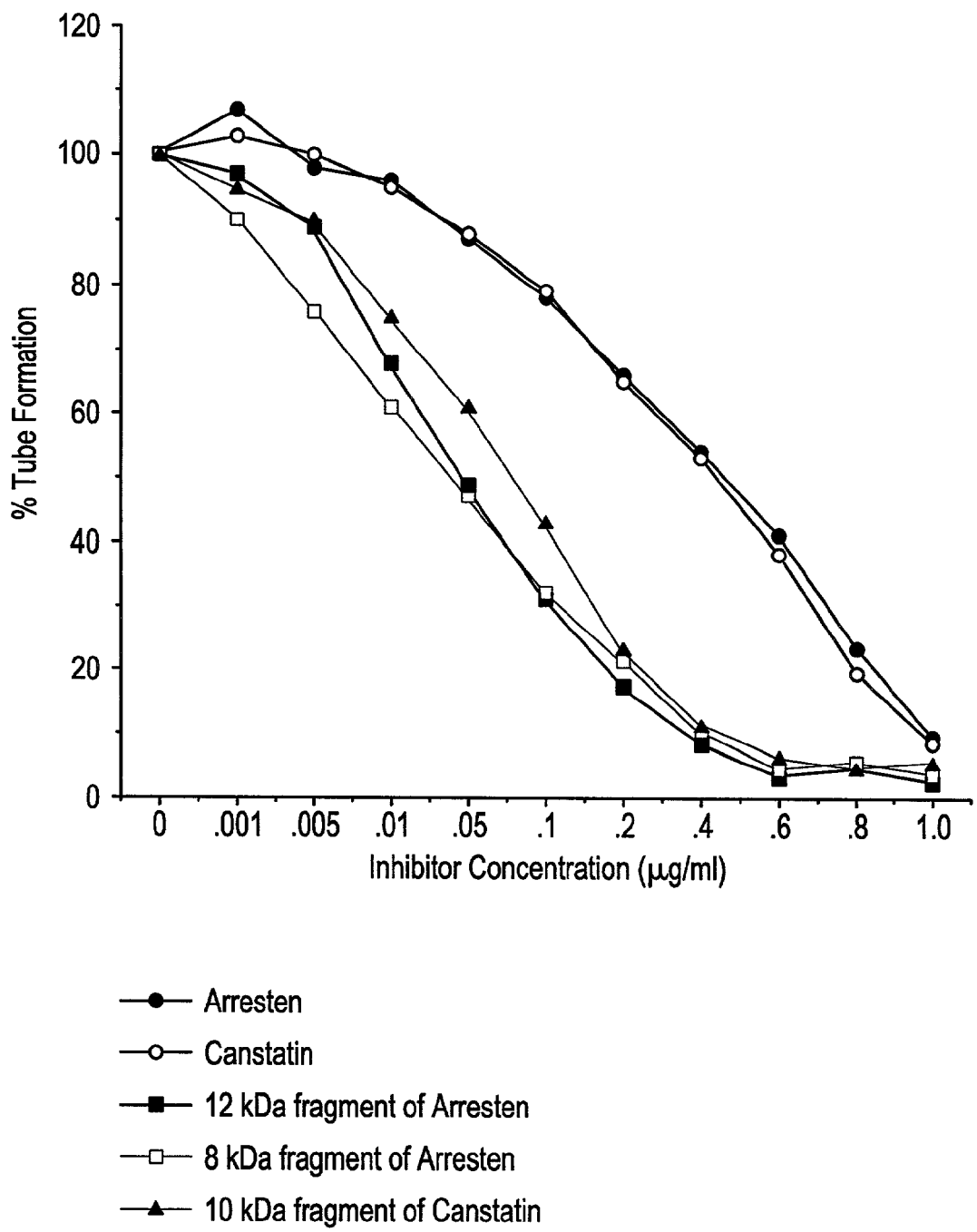
FIG. 30 is a line graph showing the inhibition of endothelial tube formation (y-axis) by varying concentrations (x-axis) of Arresten (●), Canstatin (○), the 12 kDa Arresten fragment (■), the 8 kDa Arresten fragment (□), and the 10 kDa Canstatin fragment (▲).
Figure 31:
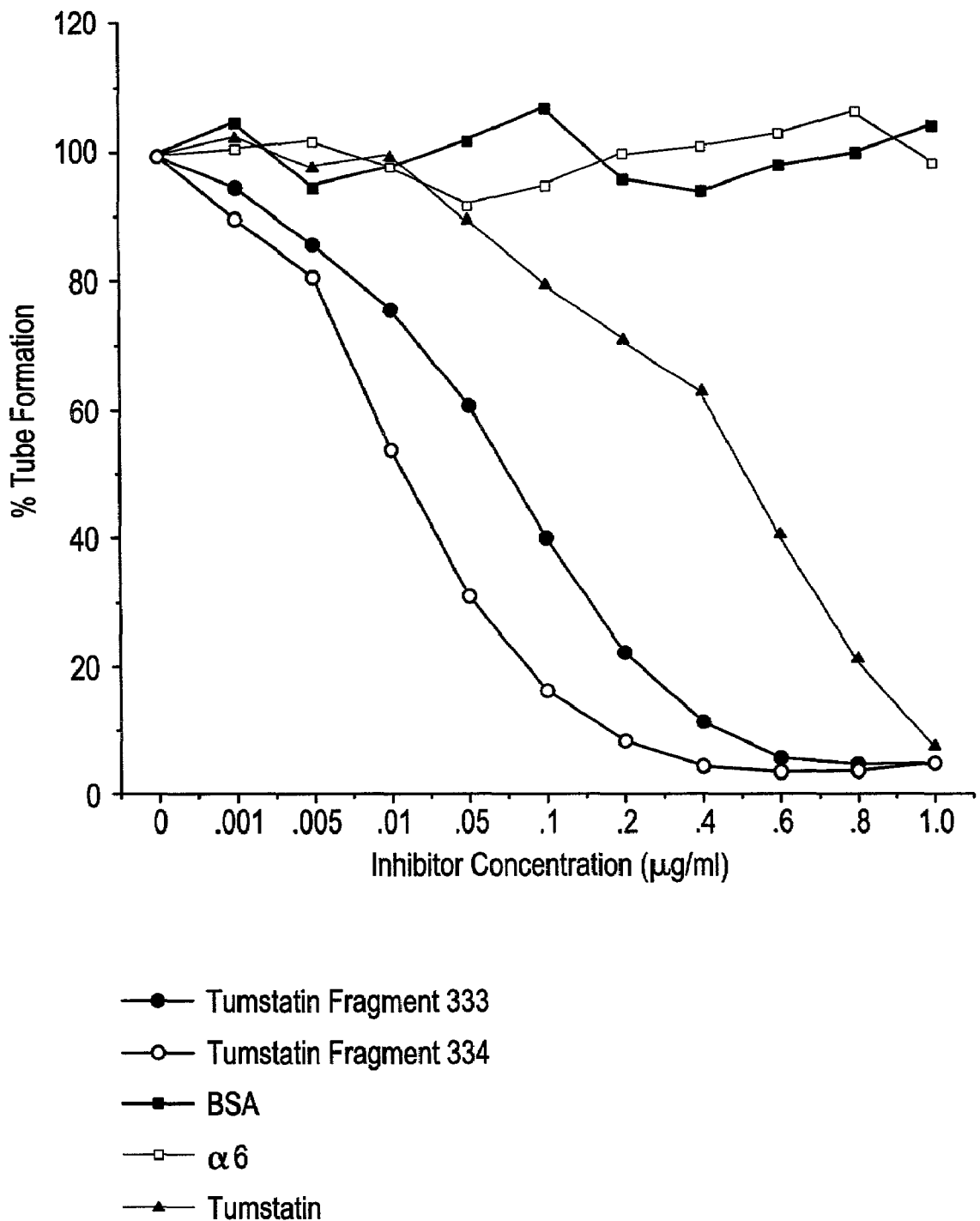
FIG. 31 is a line graph showing the inhibition of endothelial tube formation (y-axis) by varying concentrations (x-axis) of Tumstatin fragment 333 (●), Tumstatin fragment 334 (○), BSA (control, ■), α6 (control, □), and Tumstatin (▲).

As shown in FIG. 30, the endothelial tube assay, performed as described above, the two Arresten fragments (12 kDa (■) and 8 kDa (□)) and the Canstatin fragment (19 kDa (▲)) inhibited the formation of endothelial tubes to an even greater extent than did Arresten (●) or Canstatin (○). FIG. 31 shows that the Tumstatin fragments, "333" (●) and "334" (○) likewise outperformed Tumstatin (▲), with BSA (■) and the α6 chain (□) serving as controls.

Example 34

Effect of Tumstatin on Proliferation of Endothelial and WM-164 Cells

Endothelial cell proliferation was performed by $^3$H-thymidine incorporation or methylene blue staining as described above in Example 25. C-PAE cells (passages 2-4) were grown to confluence and kept contact inhibited for 48 hours. 786-O, PC-3 and WM-164 cells were used as non-endothelial controls, and were cultured as described in Example 25, above. HPE (human primary prostate epithelial cells) were cultured in keratinocyte-SFM supplemented with bovine pituitary and recombinant human EGF (Life Technologies/Gibco BRL, Gaithersburg, Md., USA). The melanoma cell line WM-164 was obtained from Dr. Meenhard Herlyn at the Wistar Institute (Philadelphia, Pa., USA), and was cultivated in 78% MCDB-153 medium, 10% L-15 medium, 10% tryptose phosphate broth, 2% FBS, and 50 units/ml insulin, as described by Herlyn et al. (1990, Adv. Cancer Res. 54:213-34).

Figure 32A:
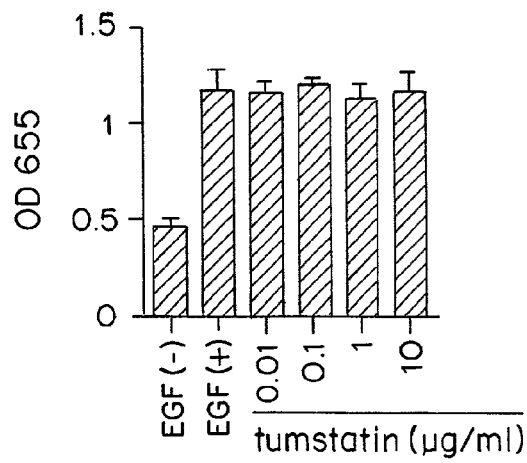
FIGS. 32A, 32B and 32C are the set of three histograms showing the effect of increasing concentrations of Tumstatin (x-axis) on proliferation (y-axis) of HPE (FIG. 32A), C-PAE (FIG. 32B) and WM-164 (FIG. 32C) cells.
Figure 32B:
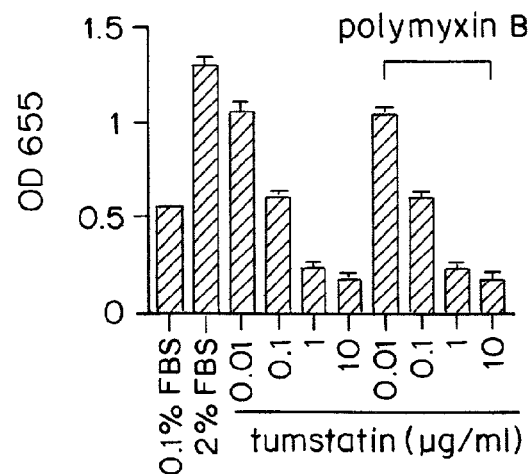
Figure 32C:
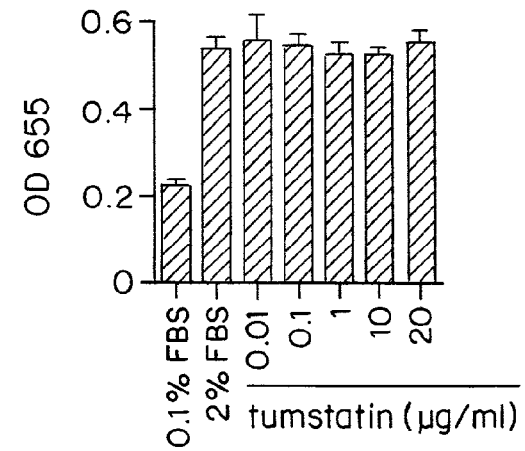

The results of the $^3$H-thymidine incorporation in C-PAE, PC-3 and 786-O cells were shown in FIGS. 21A-C, and described in Example 25, above. Methylene blue staining of HPE, C-PAE and WM-164 cells is shown in FIGS. 32A, 32B and 32C, which are a set of three histograms showing the effect of increasing concentrations of Tumstatin (x-axis) on proliferation (y-axis) of HPE (FIG. 32A), C-PAE (FIG. 32B) and WM-164 (FIG. 32C) cells. The results show that Tumstatin inhibits FCS-stimulated proliferation of C-PAE cells in a dose-dependent manner (FIG. 21A). The difference between the mean value of $^3$H-thymidine incorporation in Tumstatin-treated (0.1-10 μg/ml) and control cells was significant (P<0.05). PC-3 (FIG. 21B), 786-O (FIG. 21C), HPE (FIG. 32A) and WM-164 cells (FIG. 32C) showed no inhibitory effects by Tumstatin. When polymyxin B (5 μg/ml) was added to activate endotoxin, Tumstatin's inhibitory effects were not changed (FIG. 32B).

Interestingly, full-length Tumstatin had no effect on the proliferation of WM-164 cells, even though others (Han et al., 1997, J. Biol. Chem. 272:20395-401) have reported inhibition of these cells by amino acids 185-203 of α3(IV)

NC1 domain. This suggests that the anti-tumor cell activity of region 185-203 is not available when present as part of a full-length folded Tumstatin.

Example 35

Recombinant Production of Tumstatin Mutants Tum-1, Tum-2, Tum-3 and Tum-4

The α3(IV) NC1 domain has been shown to bind and inhibit the proliferation of melanoma, and other epithelial tumor cell lines, in vitro (Han et al., 1997, J. Biol. Chem. 272:20395-401). Han et al. localized the binding site for melanoma cells to amino acids 185-203 of α3(IV) NC1 domain. Monoclonal and polyclonal antibodies raised against this site were able to block melanoma cell adhesion and inhibition of proliferation (Han et al., supra). Han et al. also found that the specific sequence "SNS", located within amino acids 189-191, was required for both the melanoma cell adhesion and inhibition of proliferation. (Han et al., supra). In these studies, the 185-203 α3(IV) NC1 synthetic peptide was not tested on other cell types, including endothelial cells. In addition, Han et al. did not use isolated human α3(IV) NC1 domain.

Four recombinant deletion mutants were produced and purified as described above in Example 23 and in Kalluri, R. et al., 1996 J. Biol. Chem. 271:9062-8. Tum-1, also known as Tumstatin N53, consists of the C-terminal 191 amino acids of SEQ ID NO:10, and is lacking the N-terminal 53 amino acids. Tum-1 is also described in Example 23, above. Tumstatin 333 consists of the N-terminal amino acids 1 through 124 of Tumstatin (SEQ ID NO:10). Tum-3 consists of the C-terminal 112 amino acids. Tum-4 is the C-terminal 64 amino acids, which includes amino acids 185-203 (Han et al., supra). These deletion mutants were expressed in E. Coli using pET22b or pET28a(+) expression system (Novagen, Madison, Wis., USA) as described in Example 23, above. These mutants are illustrated in Table 1, above.

Example 36

Effect of Tumstatin Mutants on Endothelial and WM-164 Cell Proliferation and Apoptosis Proliferation of endothelial cells (C-PAE cells) and WM-164 melanoma cells was assayed by methylene blue staining, as described above in Examples 25 and 34. The results are shown in FIGS. 33A and 33B, which are a pair of graphs showing the effect of increasing concentration (x-axis) of Tumstatin, Tum-1, Tum-2, Tum-3 and Tum-4 on the relative number (y-axis) of C-PAE cells (FIG. 33A) and WM-164 cells (FIG. 33B). FIG. 33A shows that Tumstatin, Tum-1 and Tum-2 inhibited C-PAE cell proliferation in a dose-dependent manner. FIG. 33B shows that WM-164, a melanoma cell line, was not affected by either Tum-1 or Tum-2. Tum-4, however, did have anti-proliferative activity in this cell line. As shown in Table 2, below, Tumstatin at 15 µg/ml inhibited the proliferation of C-PAE cells by 78.5%. Tum-1 and Tum-2 inhibited C-PAE cells by 65.6 and 73.3%, respectively. In contrast, Tum-3 and Tum-4 did not inhibit C-PAE cells. Only Tum-4 inhibited WM-164 melanoma cells. 50 µg/ml of Tum-4 inhibited these cells 46.1%, but failed to inhibited C-PAE cells.

TABLE 2

Recombinant Tumstatin and deletion mutants of Tumstatin.

| Protein | Residues | | | Size | Relative Cell No. (%) C-PAE | WM-164 |
|---|---|---|---|---|---|---|
| Tumstatin | 1————244 | | | 244 | 100.0 ± 3.2 | 100.0 ± 2.9 |
| Tum-1 (Tumstatin N53) | | 54————244 | | 191 | 20.5 ± 3.4* | 100.7 ± 2.7 |
| Tum-2 | 1———132 | | | 132 | 34.3 ± 3.9* | 96.2 ± 3.7 |
| Tum-3 | | 133——244 | | 112 | 94.9 ± 3.1 | N.D. |
| Tum-4 | | | 181—244 | 64 | 95.7 ± 3.6 | 52.4 ± 3.4* |

Recombinant Tumstatin and deletion mutants were expressed in E. coli using pET22b or pET28a(+) expression system (Novagen, Madison, Wisconsin, USA). 7,000 cells per well were plated onto 96-well plates, and stimulated with 20% FCS (C-PAE cells) or 3% FCS (WM-164 cells) in the presence or absence of 15 µg/ml (for C-PAE cells) or 50 µg/ml (for WM-164 cells) of recombinant protein. Relative cell number was determined by methylene blue staining as described above. Data represents the mean ± standard error of the mean for triplicate wells. N.D. = not determined. *= $P < 0.05$ as compared to no protein ("None").

Figure 34B:
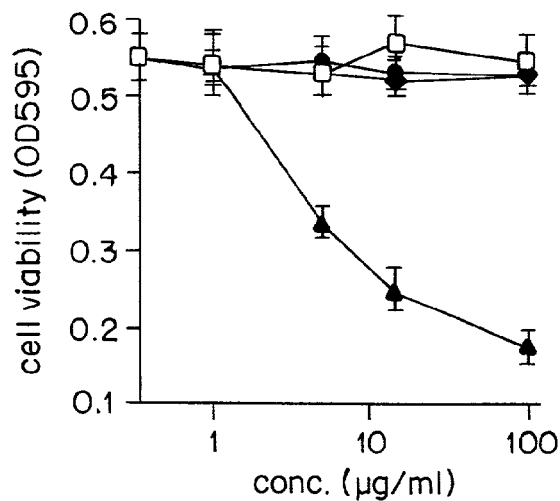

The MTT assay was used to evaluate cell viability in C-PAE endothelial cells and WM-164 melanoma cells after treatment with Tumstatin, Tum-1, Tum-2, Tum-3 and Tum-4. The results are shown in FIGS. 34A and 34B, which are a pair of graphs showing the effect of increasing concentration (x-axis) of Tumstatin, Tum-1, Tum-2, Tum-3 and Tum-4 on the cell viability (y-axis) of C-PAE cells (FIG. 34A) and WM-164 cells (FIG. 34B). Each point represents the mean ±the standard error of the mean for triplicate wells. FIG. 34A shows that Tum-1 decreases cell viability in a dose-dependent manner. At dosages of 1 and 5 µg/ml, Tum-I was significantly more effective than Tumstatin at decreasing cell survival. Tum-4 was the only deletion mutant that decreased the viability of the WM-164 melanoma cells (FIG. 34B).

Figure 35:
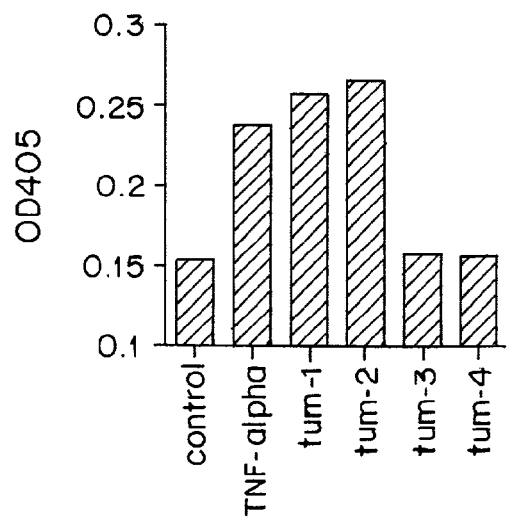
FIG. 35 is a histogram showing Caspase-3 activity as a measure of absorbance at $OD_{405}$ (y-axis) of C-PAE cells treated (x-axis) with 5 μg/ml Tum-1, Tum-2, Tum-3 or Tum-4, or 80 ng/ml TNF-α or PBS buffer (control).

Apoptosis was also evaluated by measuring Caspase-3 activity as described in Example 27, above. The results are shown in FIG. 35, which is a histogram showing Caspase-3 activity as a measure of absorbance at $OD_{405}$ (y-axis) of C-PAE cells treated (x-axis) with 5 µg/ml Tum-1, Tum-2, Tum-3 or Tum-4, or 80 ng/ml TNF-α or PBS buffer (control). Tum-1 and Tum-2 increased the activity of Caspase-3 in C-PAE cells, while Tum-3 and Tum-4 did not.

Example 37

Binding of Tumstatin Mutants to αvβ3 Integrin on Endothelial Cells

Figure 36A:
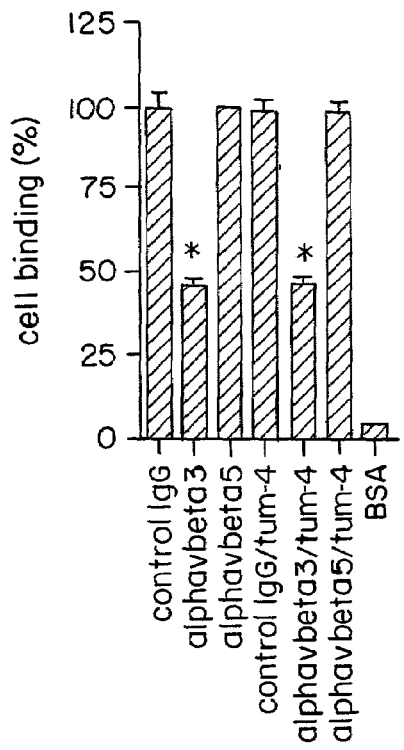
FIGS. 36A, 36B and 36C are a set of three histograms.
Figure 36B:
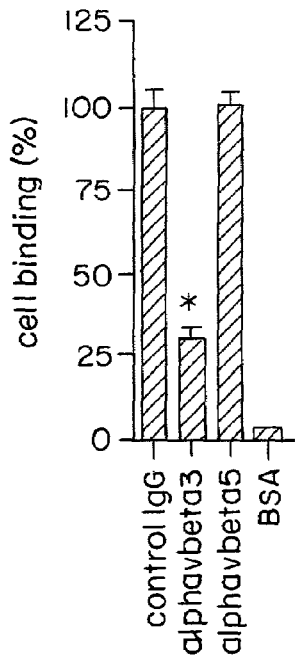
Figure 36C:
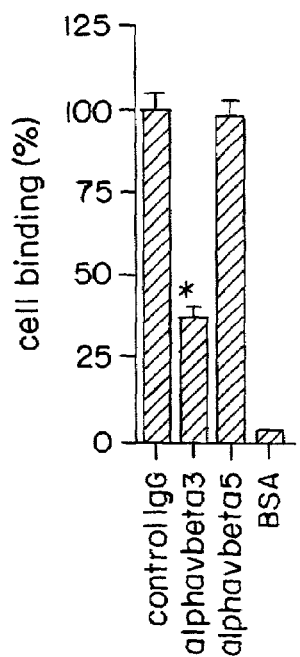

To determine the attachment of C-PAE cells to plates coated with the Tumstatin deletion mutants, the cell attachment assay was performed as described above (see, e.g., Example 28). Rabbit antibody raised against Tum-4 was prepared as previously described (Kalluri et al., 1997, J. Clin. Invest. 99:2470-8). Goat anti-rabbit IgG antibody conjugated with horseradish peroxidase was purchased from Sigma Chemical Company (St. Louis, Mo., USA). The results are shown in FIGS. 36A, 36B and 36C, which are a set of three histograms showing the percent binding of C-PAE cells (y-axis) to plates coated with Tum-1 (FIG. 36A), Tum-2 (FIG. 36B) and Tum-4 (FIG. 36C) in the presence of control IgG, $\alpha_v\beta_3$, $\alpha_v\beta_5$ and BSA. Plates coated with Tum-1 (FIG. 36A) were also treated with anti-Tum-4 antibody (1:200 dilution) to block the previously reported (Shahan et al, 1999, Cancer Res. 59:4584-90) $\alpha_v\beta_3$ binding site, as well as the $\alpha_v\beta_5$ binding site.

The $\alpha_v\beta_3$ antibody inhibited the attachment of C-PAE cells to Turn-1, Tum-2 or Tum-4 by 55.9%, 69.8, and 62.6%, respectively. Binding of C-PAE cells to plates coated with Turn-1, Tum-2 or Tum-4 was not inhibited by $\alpha_v\beta_5$ antibody. Even when anti-Tum-4 antibody (which binds to amino acids 209-244) was added, $\alpha_v\beta_3$ antibody still inhibited the attachment of C-PAE cells to Tum-1 (FIG. 36A).

Figure 37:
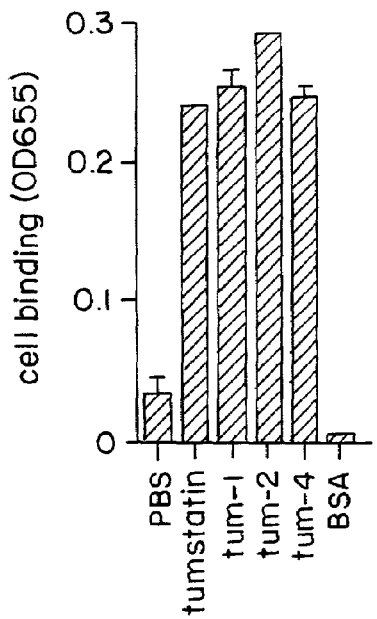
FIG. 37 is a histogram showing the level of methylene blue staining by absorbance at $OD_{655}$ (y-axis) for WM-164 cells that attached to plates coated with PBS, Tumstatin, Tum-1, Tum-2, Tum-4 or BSA (x-axis).

Tumstatin, Turn-1, Tum-2 and Tum-4 also bind to WM-164 cells, as shown in FIG. 37, which is a histogram showing the level of methylene blue staining by absorbance at $OD_{655}$ (y-axis) for WM-164 cells that attached to plates coated with PBS, Tumstatin, Turn-1, Tum-2, Tum-4 or BSA (x-axis). Tumstatin and all three of the deletion mutants enhanced attachment of WM-164 melanoma cells to the plates.

Example 38

Reversal of Activities of Tumstatin Deletion Mutants

To determine if Turn-1's inhibition of endothelial cell proliferation could be nullified by anti-Tum-4 antibody, a competitive proliferation assay was performed as described in Example 26, above. Tum-1 was preincubated with anti-Tum-4 antibody for the purpose of at least partially blocking the $\alpha_v\beta_3$ integrin binding site. It was then used in endothelial cell proliferation assays.

Figure 38A:
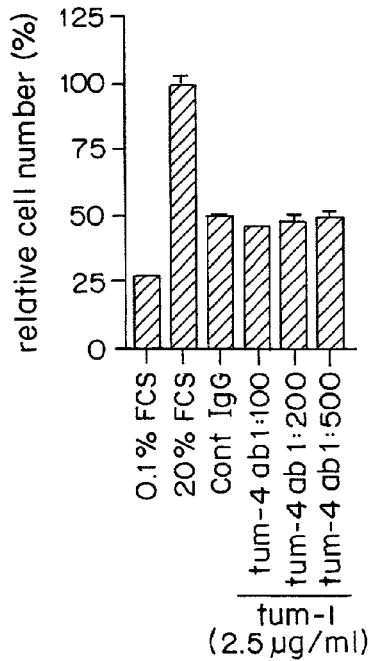
FIGS. 38A, 38B, 38C, 38D and 38E are a set of five histograms showing proliferation of C-PAE cells (y-axis) treated with 1.5 μg/ml Tum-1 (FIG. 38A) or Tum-2 (FIG. 38B) that had been preincubated with anti-Tum-4 antibody (1:100, 1:200, 1:500 dilution) (x-axis), or $\alpha_v\beta_3$ protein (FIG. 38C), or WM-164 cells treated with Tumstatin (FIG. 38D) or Tum-4 (FIG. 38E).
Figure 38B:
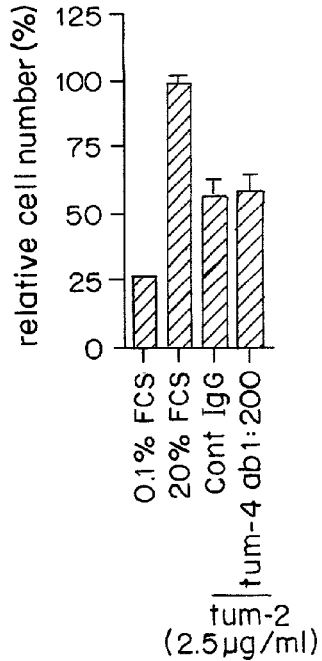

The results are shown in FIGS. 38A and 38B, which are histograms showing proliferation of C-PAE cells (y-axis) treated with 1.5 µg/ml Tum-1 (FIG. 38A) or Tum-2 (FIG. 38B) that had been preincubated with anti-Tum-4 antibody (1:100, 1:200, 1:500 dilution) (x-axis). Each column represents the mean ±the standard error of the mean for triplicate wells. The experiments were repeated three times. Asterisks indicate P<0.05 by one-tailed Student's t-test.

The anti-proliferative effect of Tum-1 was not altered even when it was pre-incubated with anti-Tum-4 antibody or control rabbit IgG (FIG. 38A). Similarly, the anti-proliferative affect of Tum-2 was not affected by the pre-incubation of anti-Tum-4 antibody or control rabbit IgG (FIG. 38B).

Figure 38C:
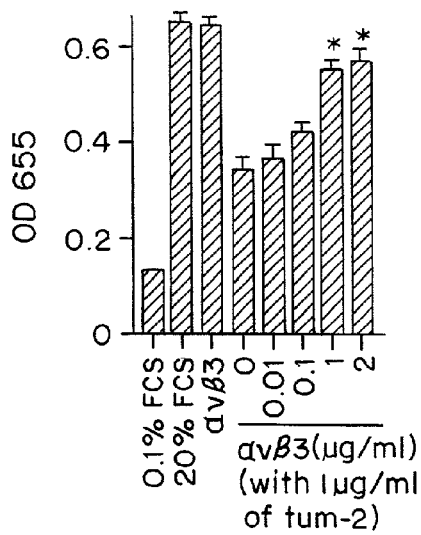

The integrin $\alpha_v\beta_3$ was then investigated for its ability to reverse the anti-proliferative effects of Tumstatin and Tum-2. Tumstatin and Tum-2 were incubated with $\alpha_v\beta_3$ protein for 30 minutes, and added to C-PAE cells which were plated in 96-well plates and incubated overnight with growth media. After incubation for 48 hours, the cell number was determined by methylene blue staining. As shown in FIG. 22 and described in Example 26, the anti-proliferative effect of Tumstatin was reversed dose-dependently with increasing doses of $\alpha_v\beta_3$ soluble protein, and at 2.4 µg/ml (3-fold molar excess relative to Tumstatin), $\alpha_v\beta_3$ significantly recovered Tumstatin's anti-proliferative effect (by 43.1%). Treatment with $\alpha_v\beta_3$ protein alone did not inhibit endothelial cell proliferation. As shown in FIG. 38C, Tum-2's anti-proliferative effect was reversed dose-dependently by increasing doses of $\alpha_v\beta_3$ soluble protein, and Tum-2's anti-proliferative effect was significantly recovered by 74.1% with 2 g/ml $\alpha_v\beta_3$ protein.

Figure 38D:
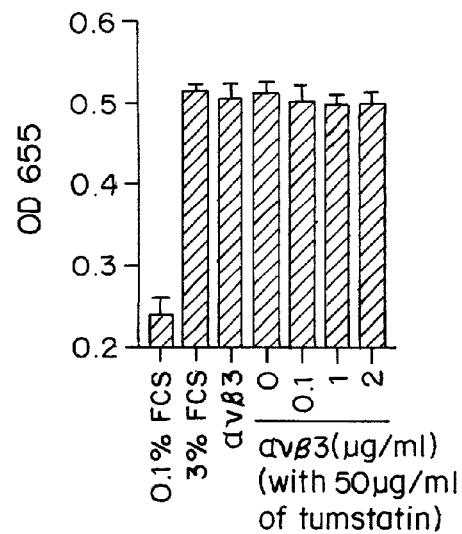
Figure 38E:
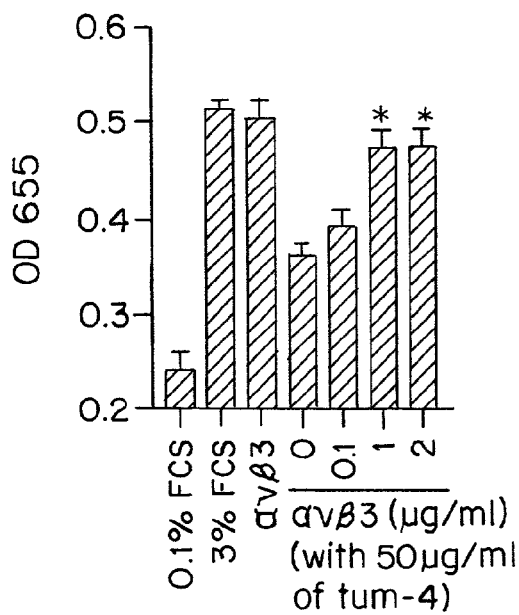

$\alpha_v\beta_3$ was then tested for its ability to negate the anti-proliferative effect of Tum-4 on melanoma cells. Tumstatin and Tum-4 were pre-incubated for 30 minutes at room temperature with $\alpha_v\beta_3$ integrin protein, then added to WM-164 cells grown in 96-well plates. After 48 hours of incubation, the increase in cell number was determined by methylene blue staining. The results are shown in FIGS. 38D and 38E. Tumstatin had no effect on WM-164 cells. The anti-proliferative effect of Tum-4 was reversed dose-dependently with increasing doses of $\alpha_v\beta_3$ soluble protein. $\alpha_v\beta_3$ protein at 2 µg/ml significantly recovered the Tum-4-induced anti-proliferative effect by 76.7%. Treatment with $\alpha_v\beta_3$ protein alone did not inhibit melanoma cell proliferation.

Figure 39:
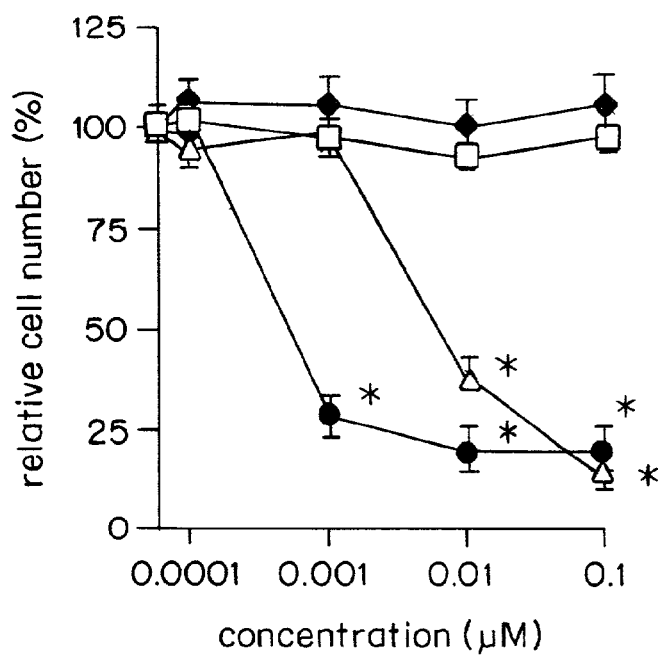
FIG. 39 is a graph showing concentration of Tumstatin (●), endostatin (▲), anti-$\alpha_v\beta_3$ (□) antibody and IgG (♦) (control) on the x-axis, versus relative cell number on the y-axis. Each point represents the mean ±the standard error of the mean for triplicate wells. The experiments were repeated three times. Asterisks indicate P<0.05 by one-tailed Student's t-test.

Tumstatin's proliferative effect was compared to that of endostatin and anti-$\alpha_v\beta_3$ antibodies. Equimolar amounts of Tumstatin and anti-$\alpha_v\beta_3$ integrin antibody were added to C-PAE cells. The results are shown in FIG. 39, which is a graph showing concentration of Tumstatin, endostatin, anti-$\alpha_v\beta_3$ antibody and IgG (control) on the x-axis, versus relative cell number on the y-axis. Each point represents the mean ±the standard error of the mean for triplicate wells. The experiments were repeated three times. Asterisks indicate P<0.05 by one-tailed Student's t-test. Increasing amounts of anti-$\alpha_v\beta_3$ antibody did not inhibit endothelial cell proliferation, whereas Tumstatin and endostatin exhibited dose-dependent inhibition of endothelial cell proliferation.

Example 39

Deletion Mutants of Canstatin

Deletion mutants of Canstatin were constructed as described above in Examples 23 and 35. Can-1 consists of the N-terminal 114 amino acids of full-length Canstatin (SEQ ID NO:6), and Can-2 consists of the C-terminal 113 amino acids. These two mutants were cloned into pET22b and pET28a, respectively, and shuttled into BL21 cells (Novagen, Madison, Wis., USA) for expression of the proteins. The proteins were readily produced from the expression clones, were purified over a Ni-TA column, using a polyhistidine tag incorporated into the vectors. The protein was eluted from the column with increasing concentrations of imidazole, and then dialyzed against PBS. Any protein that fell out of solution during dialysis was termed insoluble, and that which stayed in solution was termed the soluble fraction. The soluble fraction was concentrated, sterile filtered, and stored at −20° C. The insoluble protein was resuspended in PBS and stored at −20° C.

Figure 40:
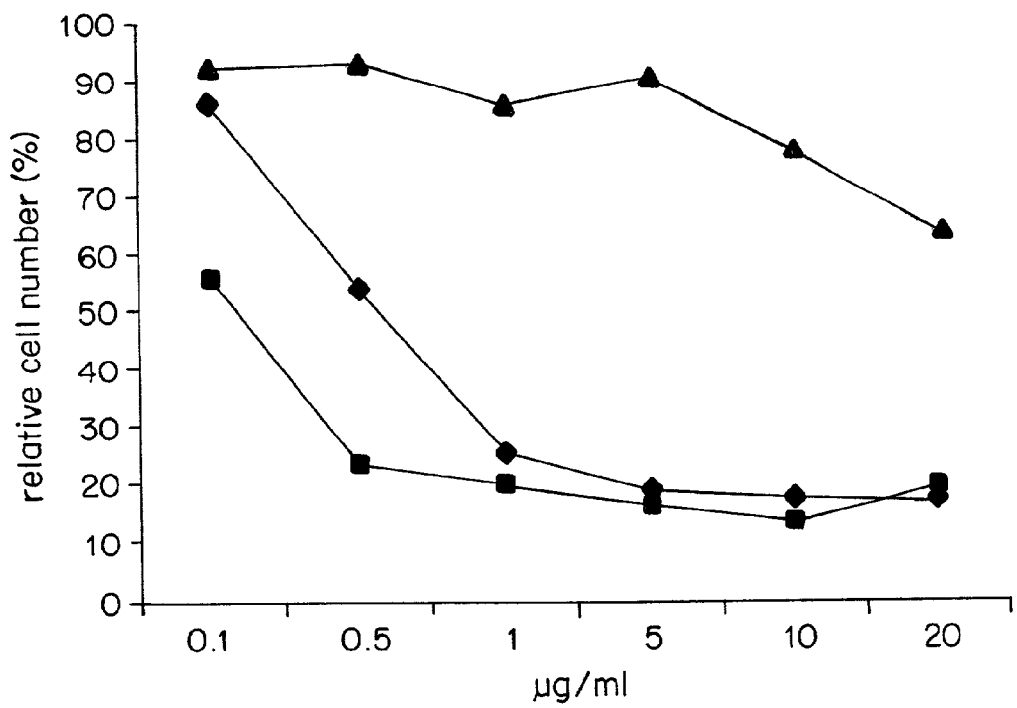
FIG. 40 is a graph showing the effect of increasing concentrations of Canstatin (♦), Can-1 (■) and Can-2 (▲) (x-axis) on the relative cell number (y-axis) of C-PAE cells. Each concentration of each protein was tested in quadruplicate.

For the proliferation assay, Canstatin, Can-1 and Can-2 soluble proteins (0.1-20.0 µg/ml) were added to the growth medium of proliferating C-PAE cells, which were stimulated with 10% FBS in DMEM, in addition to 5 ng/ml bFGF and 3 ng/ml VEGF. The results are shown in FIG. 40, which is a graph showing the effect of increasing concentrations of Canstatin (♦), Can-1 (■) and Can-2 (▲) (x-axis) on the relative cell number (y-axis) of C-PAE cells. Each concentration of each protein was tested in quadruplicate. Bovine serum albumin (BSA) was used as a control treatment.

Polymyxin B was used to control for endotoxin interference, and no differences were found between assays run with and without polymyxin B added to the medium. Cells were allowed to proliferate for 48 hours, and were then fixed, stained and the density read with a Bio-Rad plate reader (Bio-Rad, Hercules, Calif., USA). Canstatin and Can-1 both caused dose-dependent decreases in the percent cell number, and both reduced the number of cells by 80% at concentrations of 5 μg/ml and higher. Can-2 exhibited a slight decrease in percent cell number at concentrations higher than 10 μg/ml, and at the highest concentration (20 μg/ml), Can-2 inhibited proliferation by 33%.

Apoptosis was measured by Annexin V-FITC assay, using the ApoAlert kit (Clontech, Palo Alto, Calif., USA). Propidium iodide was used to stain the nuclei of cells that had died by ways other than apoptosis. Canstatin, Can-1 and Can-2 all induced apoptosis of endothelial cells at concentrations above 1 μg/ml. At 5 concentrations of less than 1 μg/ml, Can-I was the most potent in inducing apoptosis.

Anti-angiogenic activity was measured by the in vivo Matrigel plug assay, in which 0.5 ml of Matrigel containing either 2 μg/ml or 20 μg/ml insoluble protein, 50 ng/ml VEGF, and 20 U/ml heparin was injected simultaneously into both flanks of C57/1BL6 mice. The plugs remained in the mice for 14 days, when the mice were sacrificed and the plugs resected and fixed. The plugs were embedded, sectioned and H&E stained. Samples were blinded and the blood vessels quantitated. No difference in the number of blood vessels was found between the two concentrations of protein, so all six counts were averaged and plotted.

Figure 41:
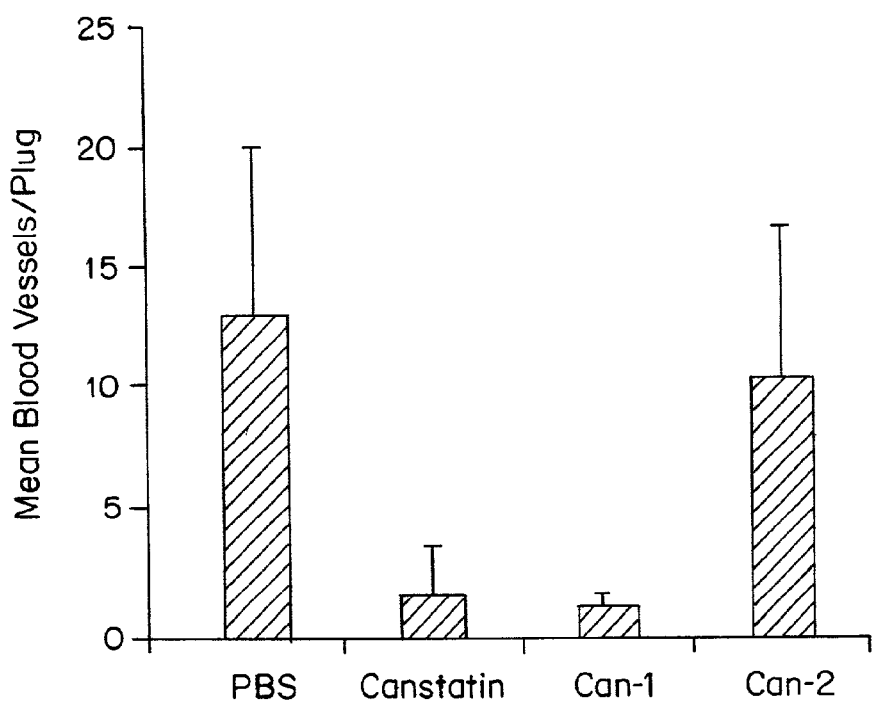
FIG. 41 is a histogram showing the mean number of vessels per plug (y-axis) for treatments with PBS (control), Canstatin, Can-1 and Can-2.

The results are shown in FIG. 41, which is a histogram showing the mean number of vessels per plug (y-axis) for treatments with PBS (control), Canstatin, Can-1 and Can-2. Plugs treated with Canstatin or Can-1 exhibited significantly fewer blood vessels as compared to plugs treated with PBS or Can-2.

Example 40

Activities of Synthetic Fragments of Tumstatin

Peptide fragments of Tumstatin: The region of amino acids 54-132 of Tumstatin was designated Tum-5. Peptides T1, T2, T3, T4, T5 and T6 were synthesized. T2, T3, T4, T5 and T6 are partially overlapping, and are located within Tum-5. The location of these peptides in Tumstatin is shown in FIG. 42, and in Table 3, below.

TABLE 3

| | | Tumstatin deletion mutants | |
|---|---|---|---|
| Peptide | Length | Location w/in Tumstatin | Sequence |
| T1 | 20 | 1-20 | GLKGKRGDSGSPATWTTRGF |
| T2 | 20 | 53-72 | NQRAHGQDLGTLGSCLQRFT |
| T3 | 20 | 68-87 | LQRFTTMPFLFCNVNDVCNF |
| T4 | 20 | 83-102 | DVCNFASRNDYSYWLSTPAL |
| T5 | 19 | 98-116 | STPALMPMNMAPITGRALE |
| T6 | 19 | 113-131 | RALEPYISRCTVCEGPAIA |

Figure 43A:
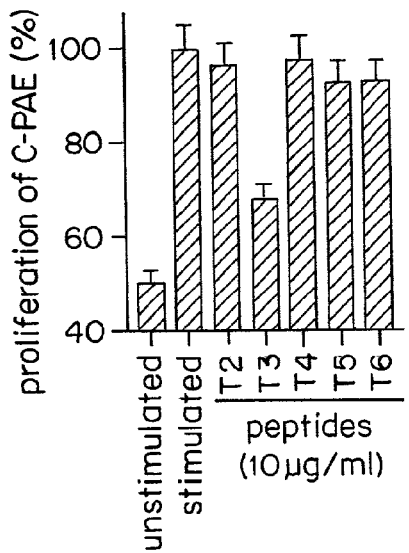
FIGS. 43A, 43B, 43C and 43D are four histograms showing inhibition of endothelial cell proliferation (FIGS. 43A, 43B and 43C) and induction of endothelial cell apoptosis (FIG. 43D) by the T3 peptide.
Figure 43B:
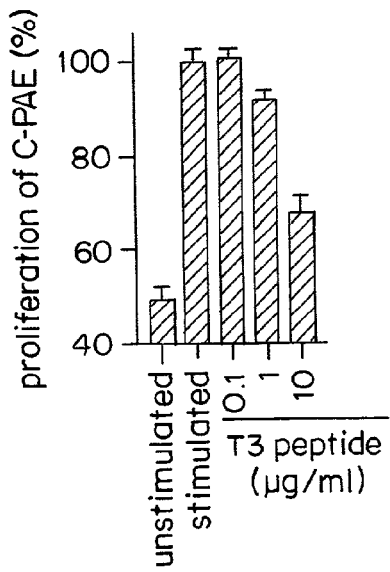

Anti-Proliferative Activity: The anti-proliferative activity of peptides T2, T3, T4, T5 and T6 on endothelial cells (C-PAE cells) was examined. The results are shown in FIG. 43A, which is a histogram showing the inhibition of endothelial cell proliferation (y-axis) by 10 μg/ml T2, T3, T4, T5 and T6 (x-axis). Controls are unstimulated cells and cells stimulated with 20% FCS. Peptide T3 was found to significantly ($p<0.05$) inhibit the proliferation of the endothelial cells, and the inhibition was dose-dependent, as is shown in FIG. 43B. FIG. 43B is a histogram showing inhibition of proliferation of C-PAE cells (y-axis) when treated with 0.1, 1.0 and 10.0 μg/ml of peptide T3 (x-axis). This inhibition was not seen with the other peptides, nor was it seen when WM-164 cells were substituted for C-PAE cells.

Figure 43C:
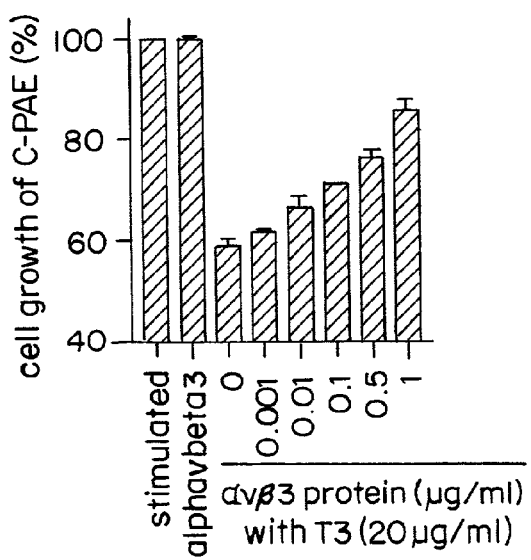

Integrin $\alpha_v\beta_3$ was investigate for its ability to reverse the anti-proliferative affects of peptide T3. T3 peptide was incubated with 0, 0.001, 0.01, 0.1, 0.5, or 1.0 μg/ml $\alpha_v\beta_3$ integrin protein (CHEMICON Int'l, Temecula, Calif., USA) for 30 minutes at room temperature, and was then added, at 20 μg/ml final concentration, to C-PAE cells that had been grown in 96-well plates in growth media. After 48 hours of additional incubation, cell number was determined by the methylene blue assay. The results are shown in FIG. 43C, which is a histogram showing the growth of C-PAE cells (y-axis) when treated with T3 peptide that had been pre-incubated with varying concentrations (x-axis) of $\alpha_v\beta_3$ integrin. The anti-proliferative effect of peptide T3 was significantly decreased by pre-incubation with $\alpha_v\beta_3$ integrin protein. $\alpha_v\beta_3$ integrin itself did not inhibit proliferation (control).

Figure 43D:
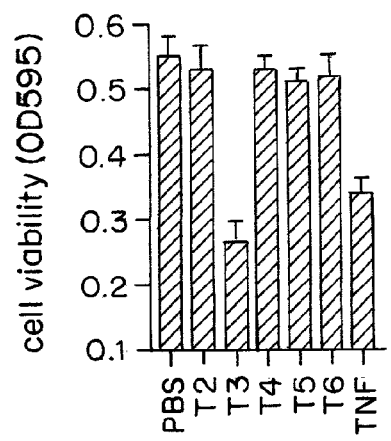

To further evaluate the mechanism of T3 peptide on endothelial cell proliferation, the effect of T3 peptide on cell cycle progression was analyzed. In the growth arrested and contact inhibited cells (0 hour), 4.1% of cells were in S phase. When the cells were stimulated with bFGF for 24 hours, there was a 5.4-fold increase in the percentage of cells in S phase, to 22.1%. Treatment with T3 peptide, at a maximal dosage of 50 μg/ml, decreased the percentage of cells in S phase to 13.8%. In contrast, T1 or T6 peptide treatment exhibited no significant decrease in cells in S phase, with 22.3% and 21.2% of the cells in S phase for treatment with T1 and T6, respectively. This was true even at a maximal dosage of 100 μg/ml. The effect of the T3 peptide was dose-dependent, however, with the percentage of cells in S phase at 21.4% at 10 μg/ml, and 20.5% at 25 μg/ml. The percentage of cells in G0/G1 phase was 88.3% at 0 hour, 53.4% for the bFGF control, and 57.6%, 57.6% and 71.0% for treatments with T1, T6 and T3 peptide, respectively. The percentage of cells in G0/G1 phase was lowest in the bFGF control group, and was elevated with T3 treatment, indicating that treatment of endothelial cells with T3 causes G1 arrest of proliferating endothelial cells. Apoptotic Activity: Peptides T2, T3, T4, T5 and T6 (10 μg/ml concentration) were tested for their effect of viability of C-PAE cells using the MTT assay, as described in Examples 32 and 36 above. The results are shown in FIG. 43D, which is a histogram showing cell viability as measured at $OD_{595}$ (y-axis), and treatments with the synthetic peptides (x-axis). Peptide T3 was found to significantly decrease cell viability relative to the other peptides derived from Tum-5. TNF-α (100 ng/ml) was used to serve as a positive control in inducing endothelial cell apoptosis.

Figure 44A:
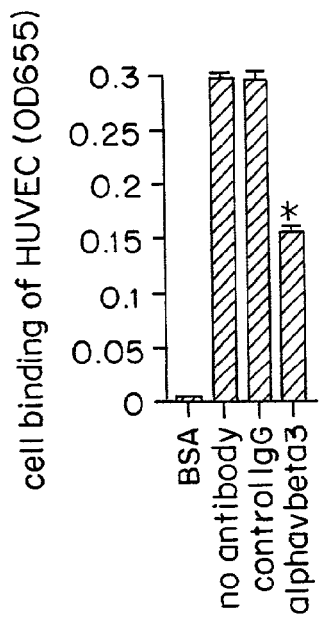
FIGS. 44A, 44B, 44C, 44D, 44E, 44F and 44G are a set of seven histograms showing attachment of C-PAE cells when treated with anti-human integrin antibodies, mouse IgG (control), or peptides T2, T3, T4, T5 or T6.
Figure 44B:
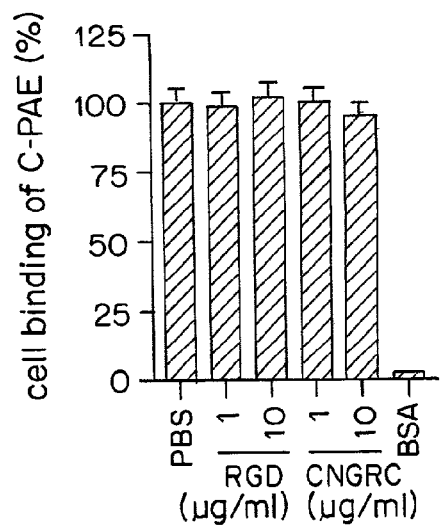

Cell Attachment Activity: Cell attachment using endothelial cells was performed as described above. HUVEC or C-PAE cells were incubated with monoclonal anti-human integrin antibodies, control mouse IgG (10 μg/ml), or synthetic peptide, plated onto pre-coated 96-well plates, and the number of cells attaching to the plates was determined using measurement of methylene blue staining at $OD_{655}$. FIG. 44A shows binding of HUVEC cells to plates coated with Tum-5 peptide (10 μg/ml), in the presence of BSA (control), no antibody (control), mouse IgG (control) and $\alpha v\beta_3$ integrin antibody. Cell attachment was significantly inhibited by anti-$\alpha v\beta_3$ integrin antibody. Control mouse IgG showed no inhibition of cell attachment. FIG. 44B is a histogram showing attachment of C-PAE cells to 96-well plates that were coated with 10 μg/ml recombinant Tum-5 peptide. Attachment of C-PAE cells to these plates was not inhibited by incubation with RGD peptide, showing that binding of these endothelial cells to Tum-5 is RGD-independent. CNGRC peptide was used as a control.

Figure 44C:
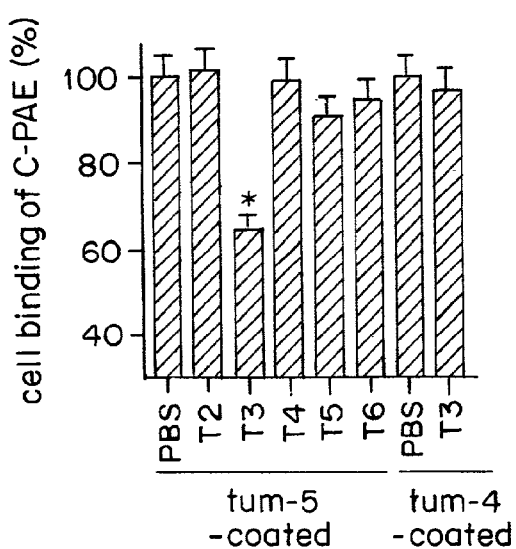

The effect of synthetic peptides T2, T3, T4, T5 and T6 on the attachment of C-PAE cells to Tum-5-coated plates was then tested. The results are shown in FIG. 44C, which is a histogram showing binding of C-PAE cells (y-axis) to 96-well plates coated (x-axis) with Tum-5 and treated with peptides 2.5 µg/ml T2, T3, T4, T5 or T6, or Tum-4-coated plates and treated with T3. PBS treatment served as control.

and associated, activity. Special efforts were made to ensure the removal of contaminating endotoxins from the protein preparations. Full-length Tumstatin, Tumstatin-N53 and two additional deletion mutants (Tum-2C and Tum-KE) were made and tested. The deletion mutants were tested for endothelial cell proliferation, cell cycle progression, apoptosis, and endothelial tube formation. The effect of the active Tumstatin fragments on non-endothelial cells was also analyzed to demonstrate the endothelial cell specificity of the molecules. These activities are summarized in Table 4, below.

TABLE 4

Activities of Additional Tumstatin Deletion Mutants

| Construct | | | MW (kDa) | pI | G1 | Apo | Tube | Cells tested | EU/mg |
|---|---|---|---|---|---|---|---|---|---|
| Tumstatin (full-length) | 1 | 12 | 27 | 8.5 | 10 µg | 10 µg | active | C-PAE | 200 |
| Tumstatin-N53 | 2 | 12 | 21.3 | 8.1 | 5 µg | 5 µg | active | C-PAE | 33 |
| Tum-2C | 7 | 12 | 14 | 8.5 | not | not | | C-PAE | <25 |
| Tum-KE | 9 | 12 | 18 | 9.4 | not | not | not | C-PAE | 4.5 |
| Tumstatin-45-132 | 2 | 6 | 12 | 8.8 | <5 µg | active | active | C-PAE | <14 |

1-12 in "Construct" column refers to the twelve cysteine residues located within full-length Tumstatin, at amino acid positions 35, 68, 80, 86, 123, 126, 145, 179, 191, 197, 237, 240.
Disulfide bond pairs occur at Cysteine 1 and 6; Cysteine 2 and 5; Cysteine 3 and 4; Custeine 7 and 12; Cysteine 8 and 11; and Cysteine 9 and 10.
G1: cell cycle arrest assay.
Apo: Annexin V-FITC assay.
Tube: Endothelial tube formation assay.
EU: Endotoxin levels as measured by BioWhitaker reagent.

Figure 44D:
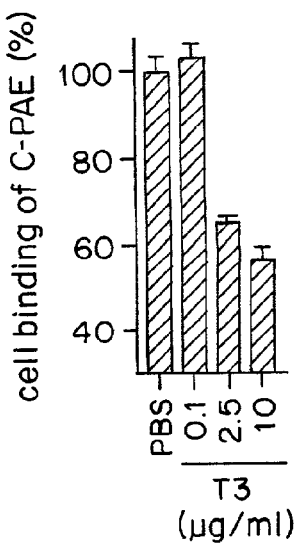

Cell attachment onto Tum-5-coated plates was significantly inhibited by T3 peptide, indicating that T3 is responsible in the interaction of endothelial cells with Tum-5. The other synthetic peptides did not show this effect, and T3 failed to inhibit the attachment of endothelial cells to plates coated with Tum-4 peptide. FIG. 44D, a histogram, shows the effect on binding of C-PAE cells (y-axis) to Tum-5-coated plates of varying concentrations of T3 peptide (x-axis). PBS treatment served as a control. T3 peptide was found to inhibit attachment of endothelial cells to Tum-5-coated plates in a dose-dependent manner.

Figure 44E:
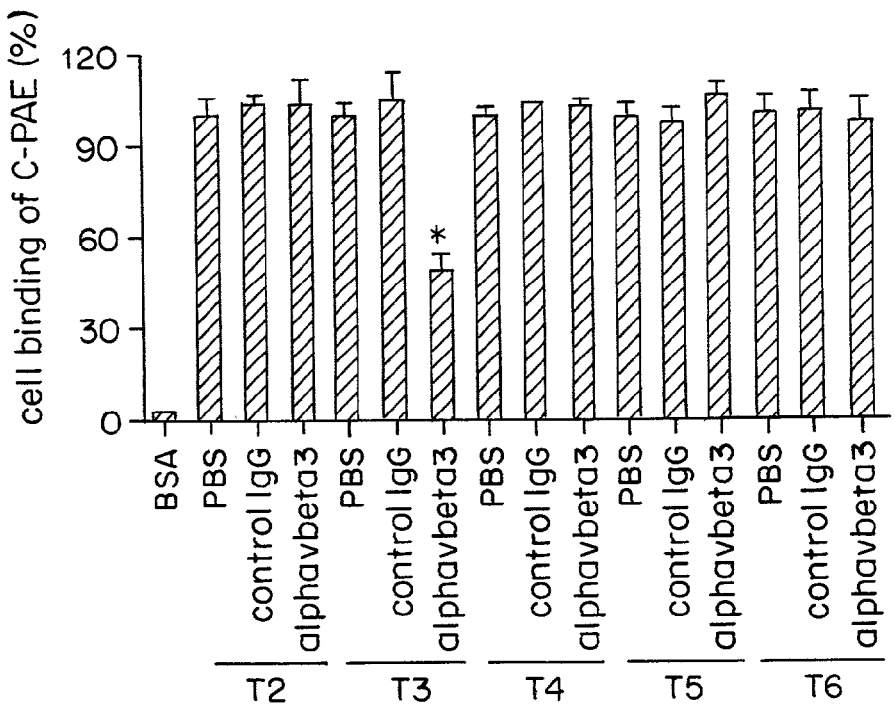
Figure 44F:
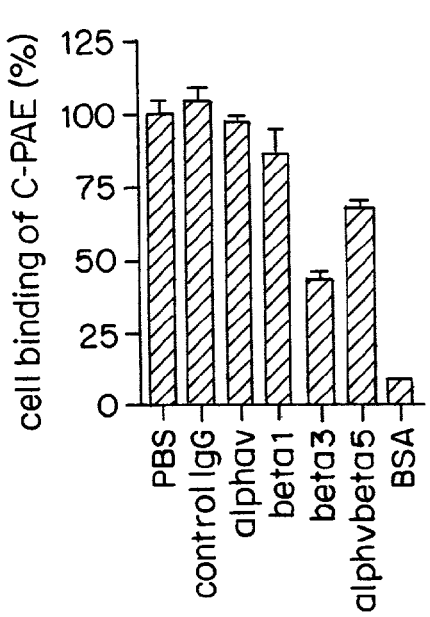

Attachment of endothelial cells to peptide-coated plates was only inhibited by $\alpha v \beta_3$s integrin for the T3 peptide, as is shown in FIG. 44E, indicating that the interaction of endothelial cells and peptide T3 is mediated by $\alpha_v \beta_3$ integrin. FIG. 44F shows that attachment of C-PAE cells to T3 peptide-coated plates was inhibited by a preincubation with anti-$\beta_3$ integrin antibody. Anti-$\alpha_v$ or anti-$\beta_1$ integrin antibody, however, did not inhibit cell attachment to T3-coated plates, suggesting that $\beta_1$ integrin potentially does not play a major role in both the binding of T3 to endothelial cells and T3-mediated anti-angiogenic activity. The $\beta_1$ integrin binding site may reside in other, non-anti-angiogenic peptides.

Figure 44G:
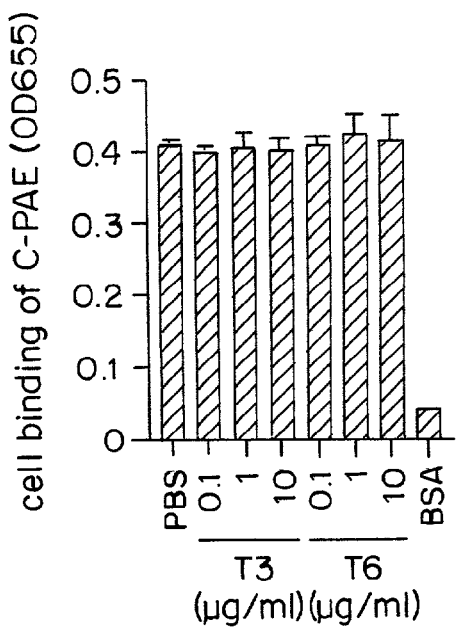

FIG. 44G shows that binding of C-PAE cells to plates coated with 2.5 µg/ml vitronectin was not inhibited by incubation with T3 peptide, indicating that T3 binds to a distinct domain on the $\alpha v \beta_3$ integrin which is not used for vitronectin binding. Incubation of the cells with T6 peptide also did not inhibit attachment.

Example 41

Activity of Deletion Mutants of Tumstatin

Deletion fragments of tumstatin were cloned into bacterial expression vectors, expressed, purified using nickel chromoatography, and then analyzed for in vitro anti-angiogenic, Tumstatin-N53 was found to be the most active in these assays. In vitro, Tumstatin-N53 induced endothelial cell apoptosis, and inhibited cell cycle progression in endothelial cells in the presence of 10% fetal bovine serum (FBS). The $IC_{50}$ was about 5 µg/ml for both activities, while Endostatin showed no activity in these same assays at concentrations exceeding 20 µg/ml.

Figure 45:
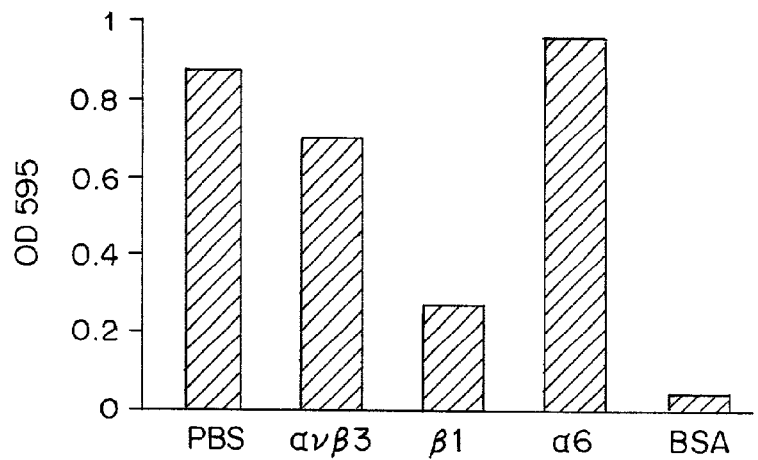
FIG. 45 is a histogram showing adhesion of HUVEC cells to Tumstatin-N53-coated (20 μg/ml) plates, in the presence of PBS (control), $\alpha_v\beta_3$ integrin antibodies, $\beta_1$ integrin antibodies, $\alpha_6$ integrin antibodies, or BSA (control).

Tumstatin-N53 was also used in a cell adhesion assay. Tumstatin-N53 (10 µg/ml) supported human umbilical vein endothelial cell (HUVEC) adhesion when coated on a 96-well plate. Antibodies to $\alpha_v \beta_3$ integrin and $\beta_1$ integrin inhibited this adhesion when preincubated with the HUVECs, as is shown in FIG. 45, while antibodies to α6 did not. Tumstatin-N53 may therefore exert its anti-angiogenic effects via $\alpha_v \beta_3$ integrin and $\beta_1$ integrin. This is consistent with results seen with full-length Tumstatin, as described in Example 28, above.

Figure 46:
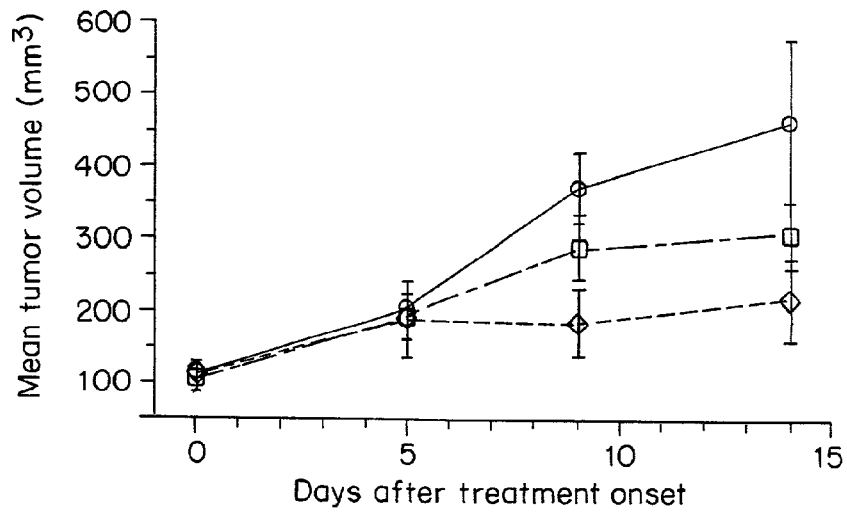
FIG. 46 is a graph showing mean tumor volume in mm³ (y-axis) for PC3 prostate tumors (PC3 prostate xenograft model) over 15 days (x-axis) for tumors treated with vehicle (control, °), Tumstatin-N53 at 5 mg per kilogram per day (□), or Tumstatin-N53 at 20 mg per kilogram per day (◇).
Figure 47:
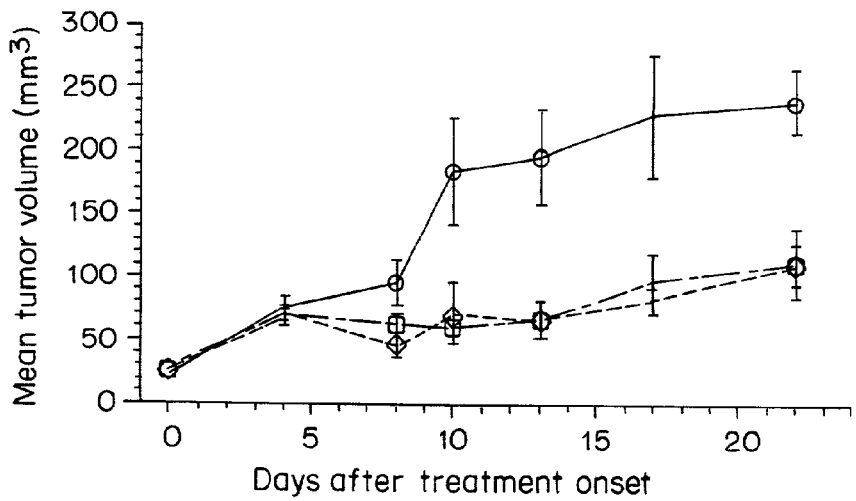
FIG. 47 is a graph showing the mean tumor volume in mm³ (y-axis) for MDA-MB435 breast cancer carcinoma tumors over 22 days (x-axis) for tumors treated with vehicle (control, °), Tumstatin-N53 at 20 mg per kilogram per day (□), or Tumstatin-N53 at 5 mg per kilogram per day (◇).

Tumstatin-N53 also inhibits angiogenesis in the Matrigel plug assay for neovascularization. Tumstatin-N53 also shows substantial anti-tumor activity in both the PC3 prostate xenograft model and the MDA-MB435 breast cancer carcinoma orthotopic model. Tumstatin-N53 (5 mg or 20 mg per kilogram) was administered twice daily. The results of these last two assays are shown in FIGS. 46 and 47. FIG. 46 is a graph showing the mean tumor volume in mm$^3$ (y-axis) for the PC3 prostate tumors over 15 days (x-axis) for tumors treated with vehicle (control, 0), Tumstatin-N53 at 5 mg per kilogram per day (□), or Tumstatin-N53 at 20 mg per kilogram per day (◊). FIG. 47 is a graph showing the mean tumor volume in mm$^3$ (y-axis) for the MDA-MB435 breast cancer carcinoma tumors over 22 days (x-axis) for tumors treated with vehicle (control, °), Tumstatin-N53 at 20 mg per kilogram per day (□), or Tumstatin-N53 at 5 mg per kilogram per day (◊). Because the doses of 5 and 20 mg per kilogram per day showed comparable anti-tumor activity, lower doses can be used while still achieving significant anti-tumor activity.

Figure 48:
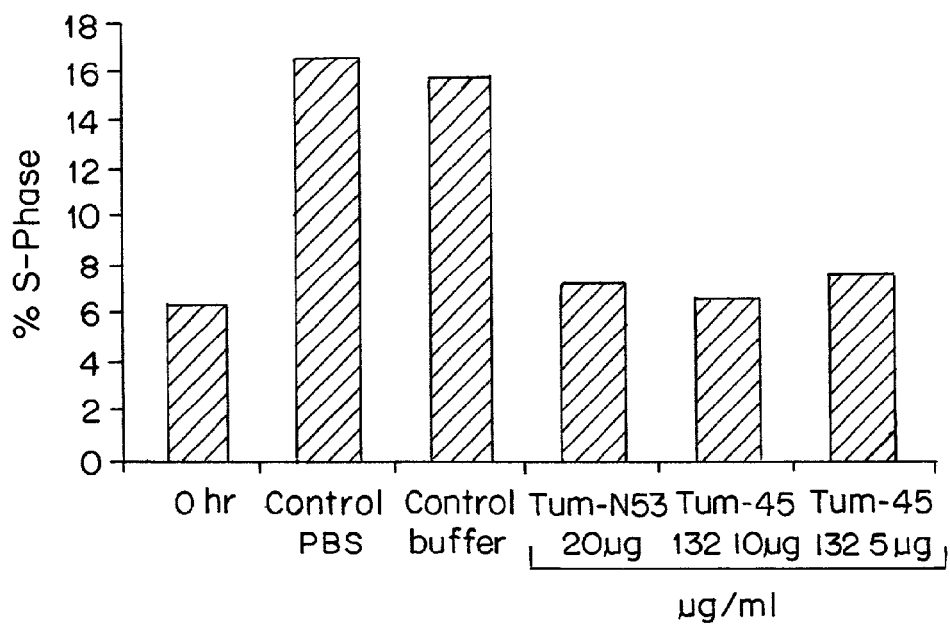
FIG. 48 is a histogram showing the percent of C-PAE cells in S-phase (y-axis) when treated with PBS (control), buffer (control), 20 μg/ml Tumstatin-N53, 10 μg/ml Tumstatin-44-131, and 5 μg/ml Tumstatin-44-131 (x-axis). The cell cycle assay was performed in the presence of 10% FBS.
Figure 49:
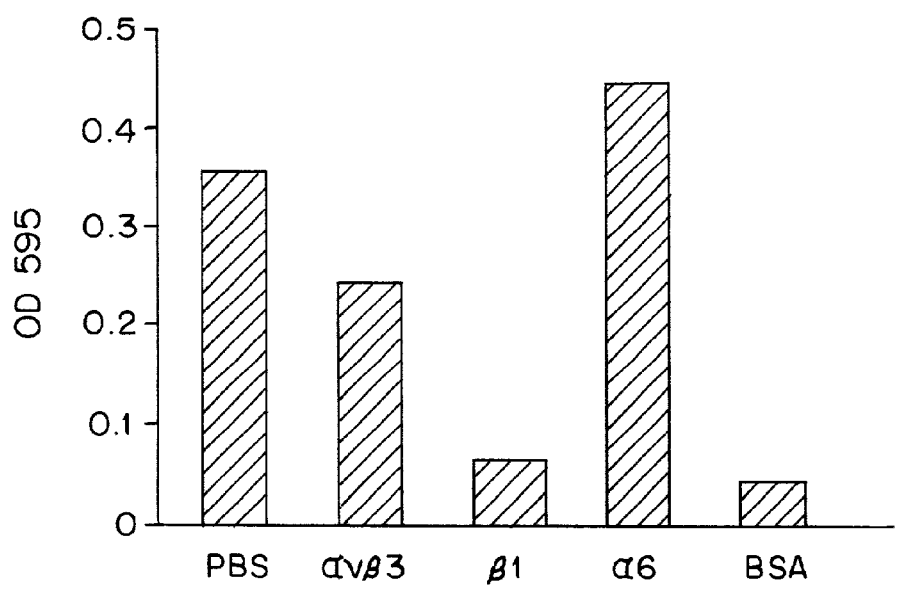
FIG. 49 is a histogram showing adhesion (in $OD_{595}$, y-axis) of HUVEC cells (y-axis) to Tumstatin-44-131-coated (20 μg/ml) plates, in the presence of PBS (control), $\alpha_v\beta_3$ integrin antibodies, $\beta_1$ integrin antibodies, $\alpha_6$ integrin antibodies, or BSA (control).

A second Goodpasture epitope, GPB, was recently mapped to a region within of Tumstatin-N53 (within amino acids 140-153 of full-length Tumstatin). Additional deletion mutants were therefore made, removing this region. The mutant Tumstatin-44-131 was made, consisting of amino acids 44 to 131 of full-length Tumstatin, which includes the N-terminal nine amino acids in addition to the anti-angiogenic domain of residues 54-132. Tumstatin-44-131 shows high levels of expression, and inhibits cell cycle progression at doses lower than that of Tumstatin-N53. This is shown in FIG. 48, which is a histogram showing the percent of C-PAE cells in S-phase (y-axis) when treated with PBS (control), buffer (control), 20 µg/ml Tumstatin-N53, 10 µg/ml Tumstatin-44-131, and 5 µg/ml Tumstatin-44-131 (x-axis). Tumstatin-44-131 also supports HUVEC cell adhesion, and is inhibited by antibodies to $\alpha_v\beta_3$ and $\beta_1$ integrins. This is shown in FIG. 49, which is a histogram showing adhesion (in $OD_{595}$, y-axis) of HUVEC cells (y-axis) to Tumstatin-44-131-coated (20 µg/ml) plates, in the presence of PBS (control), $\alpha_v\beta_3$ integrin antibodies, $\beta_1$ integrin antibodies, $\alpha6$ integrin antibodies, and BSA (control). The anti-angiogenic activity of Tumstatin is therefore likely within the regions of amino acids 44 to 131. Further deletion mutants of these fragments can also be made according to these methods, for example, fragments of Tumstatin-44-131 where the sixth cysteine residue (of full-length Tumstatin) has been deleted.

Example 42

Expression and Purification of Tumstatin-44-131 and Tum-5-125-C-A

Tumstatin-44-131, consisting of amino acids 44-131 of full-length Tumstatin, was expressed in *E. Coli* using the expression plasmid pET28a, as a fusion protein with a C-terminal six-histidine tag. The *E. Coli*-expressed protein was isolated predominantly as a 12 kDa soluble protein after refolding and SDS-PAGE analysis. Tumstatin-44-131 was immunodetectable by anti-polyhistidine tag antibodies. The additional nine amino acids (full-length Tumstatin residues 45-53) over Tum-5 were added to enhance the efficiency of protein expression and solubility. Only soluble protein with a low (less than 50 EU/mg) endotoxin level was used in further experiments.

Recombinant Tumstatin-44-131 was also expressed in the yeast *Pichia pastoris* as described above. The vector pPICZαA was used to subclone Tumstatin-44-131 so that the protein would be fused to a C-terminal 6-histidine tag.

Tum-5-125-C-A (SEQ ID NO:34) was made by site-directed mutagenesis of residue 125 (of full-length Tumstatin) from cysteine to alanine, to enhance secretion of Tumstatin-44-131. It was expressed in *E. Coli*, and was detected at the same molecular weight size with western blotting using anti-polyhistidine tag antibody.

Goodpasture syndrome is an autoimmune disease characterized by pulmonary hemorrhage and/or rapidly progressing glomerulonephritis, which are caused by the disruption of glomerular and alveolar basement membranes through immune injury associated with autoantibody activity against α3(IV) NC1. Recently, the most probable disease-related pathogenic epitope was identified in the N-terminal portion (Kalluri, R. et al., 1996, J. Biol. Chem. 271:9062-8; Hellmark, T. et al., 1999, Kidney Int. 55:938-44), and was then further confined within the N-terminal 40 amino acids (Hellmark, T. et al., 1999, J. Biol. Chem. 274:25862-8; Netzer, K. O. et al., 1999, J. Biol. Chem. 274:11267-74). The N-terminal Tumstatin-44-131 consists of residues 44-131 of Tumstatin, which is outside of the Goodpasture autoepitope. To further confirm that Tumstatin-44-131 would not be detected by Goodpasture autoantibody, antisera from patients with Goodpasture was used for western blotting. This antisera detected 293 cell-expressed full-length Tumstatin with high sensitivity, but failed to detect either *E. Coli*-expressed Tumstatin-44-131 and *Pichia*-expressed Tum-5-125-C-A. This shows that Tumstatin-44-131 and Tum-5-125-C-A do not contain the Goodpasture autoepitope, and excludes the possibility that these recombinant proteins induce this autoimmune disorder upon administration in humans.

Example 43

Activities of Tumstatin-44-131 and Tum-5-125-C-A

Tumstatin-44-131 was examined for its effects on proliferation of endothelial cells, cell cycle ($G_{1/S}$) arrest, and cell viability.

The anti-proliferative affect of Tumstatin-44-131 on C-PAE cells was examined via BrdU incorporation assay. This assay uses bromodeoxyuridine (BrdU) instead of $^3$H-thymidine as a thymidine analog. BrdU is incorporated into newly synthesized DNA strands in actively proliferating cells. The BrdU incorporated into the cells can then be detected immunochemically. The assay was conducted using the BrdU proliferation assay kit (CalbioChem, San Diego, Calif., USA) according to the manufacturer's instructions, with some modifications. C-PAE cells were seeded onto 96-well plates in DMEM containing 10% FCS. The next day, the medium was replaced with DMEM containing 2% FCS with or without *E. Coli*-expressed Tumstatin-44-131, or full-length Tumstatin expressed in 293 cells. The plates were then incubated for 46 hours, and the cells were then pulsed for two hours with 10 nM BrdU. The cells and DNA were then fixed to the wells, reacted with anti-BrdU primary and secondary antibodies, and then developed with a calorimetric reaction supplied with the kit. The plates were then read at $OD_{450}$ on a plate reader (Molecular Dynamics, Sunnyvale, Calif., USA).

The effect of Tumstatin-44-131 and Tum-5-125-C-A on the cell cycle were assayed similarly to Example 4 above. Briefly, C-PAE cells were growth arrested by contact inhibition for 48 hours. The cells, at $10^5$ cells per well, were then harvested and plated into a 12-well plate coated with fibronectin in 5% FCS and either recombinant Tumstatin-44-131 or Tum-5-125-C-A. After 21 hours, the cells were harvested and fixed in 70% ice-cold ethanol. The fixed cells were rehydrated a room temperature for 30 minutes in PBS containing 2% FCS and 0.1% Tween-20, centrifuged and resuspended in 0.5 ml of the same buffer. RNase (5 µg/ml) digestion was done at 37° C. for one hour, followed by staining with propidium iodide (5 µg/ml). The cells were then counted using an EPICS XL-MCL flow cytometer (Beckman-Coulter Instruments, Fullerton, Calif., USA).

Cell viability was measured by MTT assay, as described above.

For some experiments, full-length Tumstatin and Tumstatin-44-131 were also reduced and alkylated. Briefly, 2.5 mg/ml of Tumstatin or Tumstatin-44-131 in 6M guanidine-HCl and 10 mM Tris-HCl (pH 7.5) were incubated for one hour at 50° C. in 10 mM DTT. The reaction mixture was then brought to room temperature, and iodoacetamide was added to a final concentration of 25 mM. The solution was incubated to one hour at room temperature, and dialyzed against 5 mM HCl (with two changes at 5 hours each), and then 1 mM HCl. The absence of free thiol groups in the final product was confirmed by using Ellman reagent. Non-reduced Tumstatin-44-131 can exist as a monomer, dimer, and other oligomers, but reduced and alkylated Tumstatin-44-131 migrates as a single band corresponding to a monomeric protein with a molecular weight of 12 kD.

Figure 50:
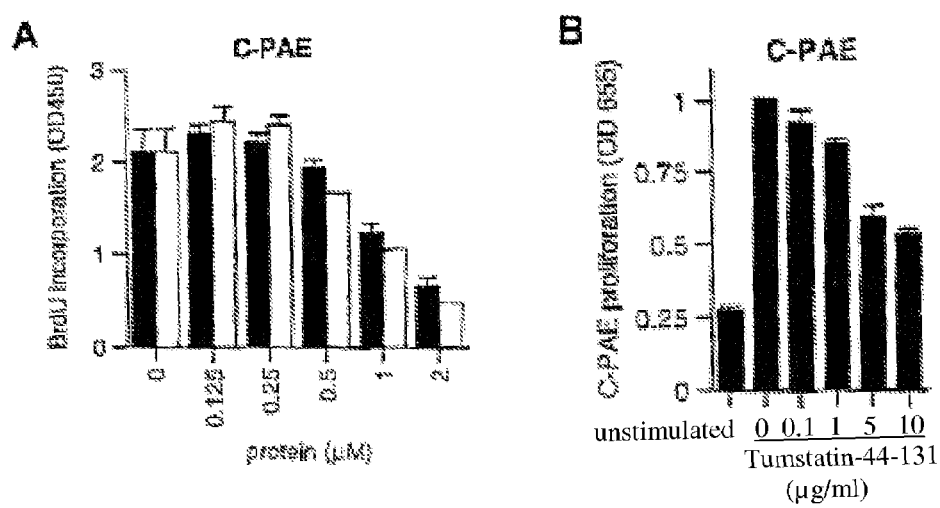
FIGS. 50A and 50B are a set of two histograms showing the effect of Tumstatin-44-131 on cell proliferation.
Figure 51:
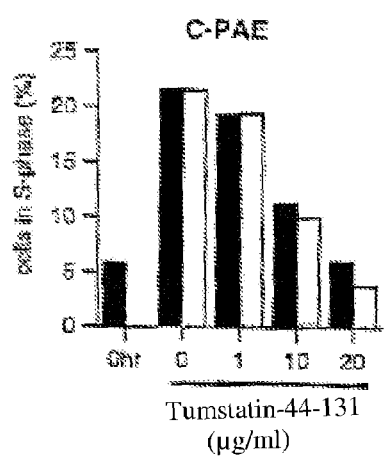
FIG. 51 is a histogram showing the effect of E. Coli-expressed Tumstatin-44-131 and Tum-5-125-C-A on progression of the cell cycle. The percentage of C-PAE cells in S phase (y-axis) is shown at hour 0 (control), and after treatment by 0, 1, 10 and 20 μg/ml (x-axis) Tumstatin-44-131 (black bars) or Tum-5-125-C-A (white bars). The experiments were repeated three times.
Figure 52:
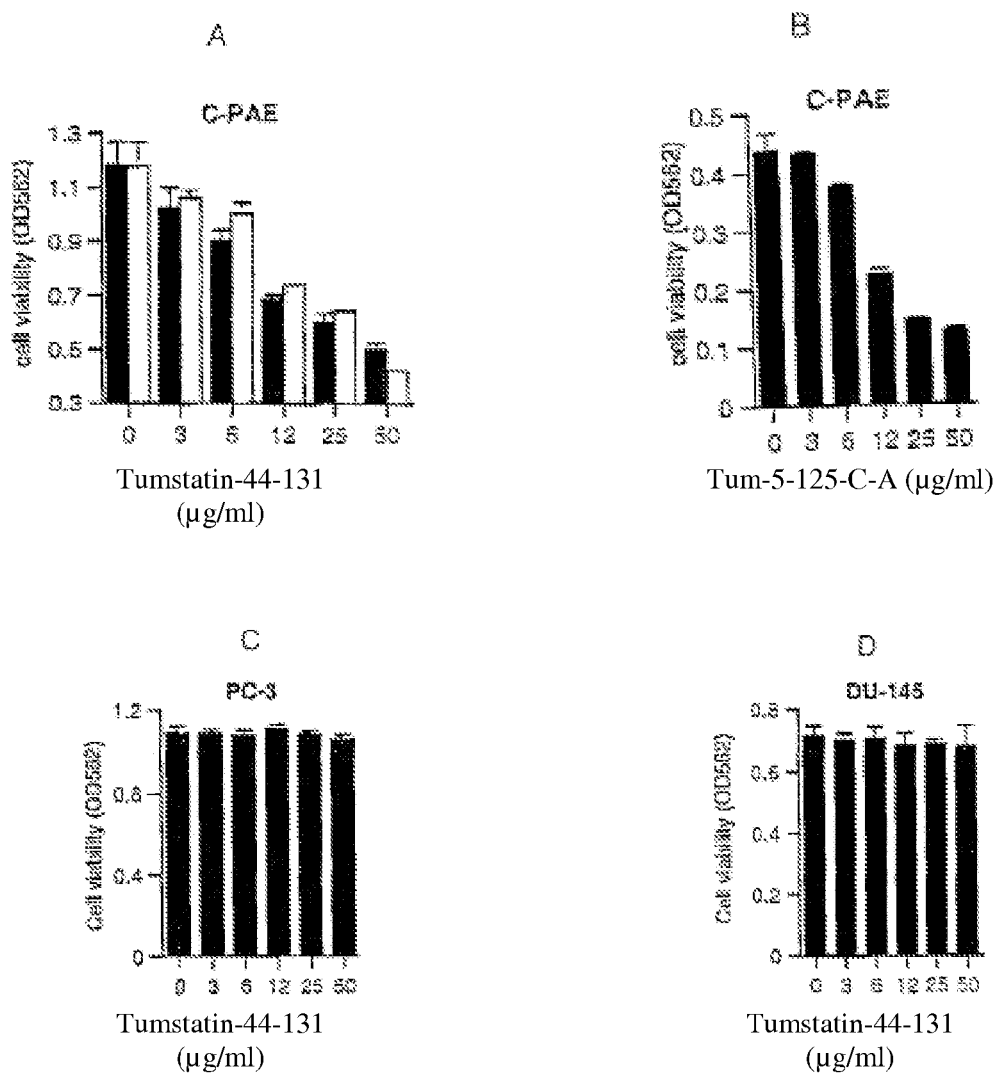
FIGS. 52A, 52B, 52C and 52D are a set of four histograms showing the effects of Tumstatin-44-131 and Tum-5-125-C-A on cell viability.

As is shown in FIGS. 50-52, Tumstatin-44-131 specifically inhibits proliferation of endothelial cells (FIGS. 50A and 50B), induces cell cycle arrest (FIG. 51), and decreases cell viability (FIGS. 52A, 52B, 52C and 52D).

FIG. 50A is a histogram showing cell proliferation as measured at $OD_{450}$ (y-axis) by BrdU assay, with C-PAE cells treated with *E. Coli*-expressed Tumstatin-44-131 (black bars), or 293 cell-expressed full-length Tumstatin (white bars), at concentrations of 0, 0.125, 0.25, 0.5, 1.0 or 2.0 μM (x-axis). Both Tumstatin-44-131 and full-length Tumstatin decreased incorporation of BrdU in C-PAE cells in a dose-dependent manner. FIG. 50B is a histogram showing cell proliferation as measured at $OD_{655}$ (y-axis) by methylene blue staining, with C-PAE cells treated with *Pichia*-expressed Tumstatin-44-131 at concentrations of 0, 0.1, 1.0, 5.0 and 10.0 μg/ml (x-axis). Unstimulated C-PAE cells served as the control. Tumstatin-44-131 inhibited, in a dose-dependent manner, C-PAE cells that had been stimulated with 20% FCS, and the $ED_{50}$ was 5 μg/ml. The difference between the control (0 μg/ml) and the Tumstatin-44-131 (5 and 10 μg/ml) treatment was significant ($P<0.05$ in one-tailed Student's t-test). When control human melanoma cells (WM-164 cells) were used, the anti-proliferative effect of Tumstatin 44-131 was not observed.

FIG. 51 is a histogram showing $G_1$ arrest of proliferating endothelial cells. In the growth-arrested, contact-inhibited cells, 5.8% of the cells were in S phase at 0 hour. When the cells were stimulated with 5% FCS for 21 hours, there was a 3.7-fold increase in the percentage of cells in S phase, to 21.5%. Treatment with Tumstatin-44-131 decreased the percentage of cells in S phase to 6.0%. This effect was dose-dependent, with the percentage of cells in S phase being 19.3% at 1 μg/ml Tumstatin-44-131, and 11.3% at 10 μg/ml Tumstatin-44-131. In another experiment, the percentage of cells in $G_0/G_1$ phase was lowest in the 5% FCS-treated control group, and was elevated with treatment with Tumstatin-44-131. These results show that treatment with Tumstatin-44-131 causes cell cycle arrest in proliferating endothelial cells. Treatment with Tum-5-125-C-A showed results equivalent to treatment with Tumstatin-44-131.

FIGS. 52A, 52B, 52C and 52D are a set of four histograms showing the effects of Tumstatin-44-131 and Tum-5-125-C-A on cell viability. FIG. 52A shows cell viability as measured at $OD_{562}$ (y-axis) in an MTT assay, for C-PAE cells treated with 0, 3, 6, 12, 25 and 50 μg/ml (x-axis) Tumstatin-44-131 (black bars) and Tumstatin-44-131 that was alkylated and reduced (white bars). Tumstatin-44-131 significantly decreased cell viability in a dose-dependent manner with an $ED_{50}$ of 12 μg/ml. Reduced and alkylated Tumstatin and Tumstatin-44-131 exhibited effects similar to that of non-treated Tumstatin and Tumstatin-44-131 in decreasing cell viability of C-PAE cells. The anti-angiogenic effects of Tumstatin and Tumstatin-44-131 are therefore not dependent on their conformation as derived from disulfide bonds between cysteine residues.

Tum-5-125-C-A exhibited effects in cell viability similar to those of Tumstatin-44-131, as shown in FIG. 52B. FIG. 52B shows cell viability as measured at $OD_{562}$ (y-axis) in an MTT assay, for C-PAE cells treated with 0, 3, 6, 12, 25 and 50 μg/ml (x-axis) Tum-5-125-C-A.

The effects of Tumstatin-44-131 and Tum-5-125-C-A on cell viability of C-PAE cells were not seen in control PC-3 and DU-145 cells, as shown in FIGS. 52C and 52D. FIG. 52C shows cell viability as measured at $OD_{562}$ (y-axis) in an MTT assay, for PC-3 cells treated with 0, 3, 6, 12, 25 and 50 μg/ml (x-axis) Tumstatin-44-131. FIG. 52D shows cell viability as measured at $OD_{562}$ (y-axis) in an MTT assay, for DU-145 cells treated with 0, 3, 6, 12, 25 and 50 μg/ml (x-axis) Tumstatin-44-131. The activity of Tumstatin-44-131 is therefore specific to endothelial cells.

Example 44

Effects of Tumstatin-44-131 on Endothelial Cells

Tumstatin-44-131 was found to induce endothelial cell apoptosis and inhibit endothelial tube formation, as shown by the following assays.

Tumstatin-44-131 was found to induce endothelial cell apoptosis, as shown by Annexin V-FITC assay. The assay was performed as described above, by treating C-PAE cells with Tumstatin-44-131 for 18 hours. Control cells received PBS. Tumstatin-44-131 at 5 μg/ml induced a distinct shift of the fluorescence intensity peak as compared with the control TNF-α.

Caspase-3 activity was also assayed as described above. DEVD-fmk, a specific caspase-3 inhibitor, was used as an internal control to show specificity of Tumstatin-44-131. TNF-α (80 ng/ml) was used as a positive control. The experiments were repeated three times.

Figure 53:
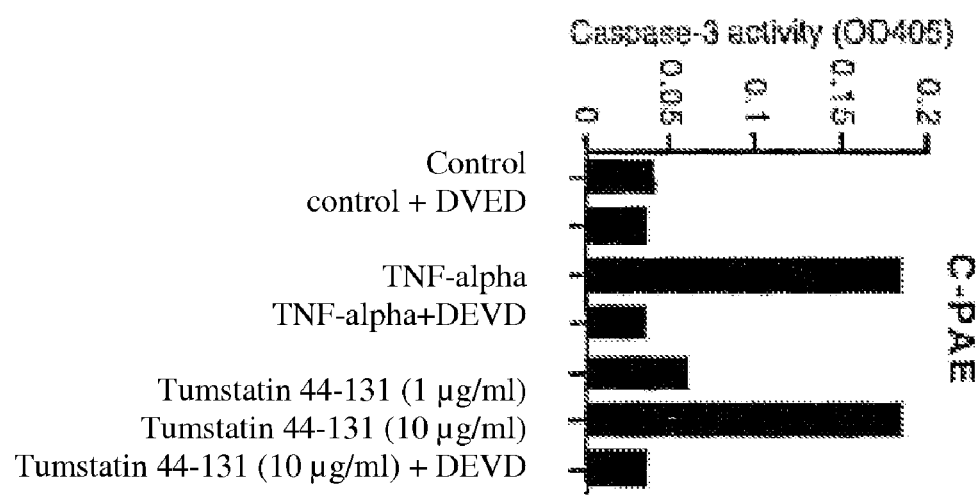
FIG. 53 is a histogram showing caspase-3 activity (as measured at $OD_{405}$, y-axis) of (x-axis) the control, control+ DEVD-fmk, TNF-α, TNF-α+DEVD-fmk, Tumstatin-44-131 (1 µg/ml and 10 µg/ml), and Tumstatin-44-131 (10 µg/ml)+DEVD-fmk.

The results are shown in FIG. 53, which is a histogram showing caspase-3 activity (as measured at $OD_{405}$, y-axis) of (x-axis) the control, control+DEVD-fmk, TNF-α, TNF-α+DEVD-fmk, Tumstatin-44-131 (1 μg/ml and 10 μg/ml), and Tumstatin-44-131 (10 μg/ml)+DEVD-fmk. A 4.5-fold increase in caspase-3 activity was observed by treating C-PAE cells with 10 μg/ml of *E. Coli*-expressed Tumstatin-44-131. The positive control TNF-α also produced a 4.5-fold increase. The specific inhibitor of caspase-3, DEVD-fmk, decreased the protease activity of baseline levels, indicating that the increase in measured activity is specific for caspase-3. This increased activity was not observed by treating PC-3 cells with Tumstatin-44-131.

Tumstatin-44-131 was also found to inhibit endothelial tube formation, as shown by Matrigel assay. The Matrigel assay was performed as described in the examples above. Briefly, HUVECS were allowed to form tubes on Matrigel-coated plates incubated with or without 5 μg/ml *E. Coli*-expressed Tumstatin-44-131. BSA-treated cells and yeast-expressed human endostatin (5 and 20 μg/ml) was used as controls. Tumstatin-44-131 significantly inhibited endothelial tube formation in a dose-dependent manner, relative to controls. The average percentage tube branch formation after treatment was 22.7±3.1 for the BSA treatment, 2.1±2.0 for Tumstatin-44-131 treatment, while the 5 μg/ml and 20 μg/ml endostatin produced an average of 19.4±3.0 and 7.5±6.0, respectively. Tumstatin-44-131, at 5 μg/ml, significantly decreased endothelial tube formation, as compared to controls. Human endostatin, even at 20 μg/ml exhibited less of an inhibitory effect than Tumstatin-44-131 at 5 μg/ml.

Example 45

Binding Activity of Tumstatin-44-131

A cell attachment assay was conducted, which showed that Tumstatin-44-131 binds to the $\alpha_v\beta_3$ and $\beta_1$ integrins on endothelial cells, and that the binding is independent of the "RGD" peptide sequence.

The cell attachment assay was performed as described above. Briefly, 96-well plates were coated overnight with 10 µg/ml of either Tumstatin-44-131 or 0.5-2.5 µg/ml vitronectin (Collaborative Biomed. Prods.) The plates were blocked with BSA, and HUVEC or C-PAE cells were incubated with either 10 µg/ml antibody or synthetic peptide (synthetic peptide CDCRGDCFC (SEQ ID NO:35) or synthetic control peptide CNGRC (SEQ ID NO:36) for 15 minutes. The cells were added to the plates and incubated at 37° C. for 45 minutes. The plates were then washed, and the number of attached cells determined by methylene blue staining.

The attachment of HUVEC cells on plates coated with *E. Coli*-expressed Tumstatin-44-131 was significantly inhibited by antibodies to $\alpha_v\beta_3$ and $\beta_1$ integrin. The $\alpha_v\beta_3$ integrin antibody $\beta_1$ integrin antibody inhibited cell attachment by 47.1% and 47.5%, respectively, relative to mouse IgG, which was used as a control. C-PAE cells exhibited comparable inhibition.

The synthetic peptide CDCRGDCFC, at 5 µg/ml, inhibited attachment of endothelial cells onto vitronectin-coated plates. The control peptide CNGRC did not show such inhibition. However, when cells were incubated with 1.0 or 10.0 µg/ml CDCRGDCFC peptide, attachment of C-PAE cells to plates coated with *E. Coli*-expressed Tumstatin-44-131 was not inhibited, suggesting that Tumstatin-44-131 binds to a distinct site on the $\alpha v\beta 3$ integrin receptor on endothelial cells, a site that is different from the RGD binding site previously described (Arap, W. et al., 1998, Science 279:377-80). The CNGRC control peptide also did not inhibit cell attachment to Tumstatin-44-131 coated plates.

Soluble $\alpha_v\beta_3$ integrin protein reversed the anti-proliferative effects of Tumstatin-44-131. This was shown by a competition proliferation assay as described above in Example 26. The vitronectin-coated plates were incubated with $\alpha_v\beta_3$ soluble protein and the cell attachment assay was then performed. Soluble $\alpha_v\beta_3$ protein at 1 and 2 µg/ml significantly inhibited attachment of C-PAE cells on the coated plates. *E. Coli*-expressed Tumstatin-44-131 was then incubated with $\alpha_v\beta_3$ integrin protein for 30 minutes, and then added to C-PAE cells with 20% FCS. After 48 hours, cell proliferation was determined by methylene blue staining. The anti-proliferative affect of Tumstatin-44-131 was reversed dose-dependently with increasing concentrations of $\alpha_v\beta_3$ soluble protein. At 1 µg/ml, $\alpha_v\beta_3$ protein significantly reversed the Tumstatin-44-131-induced anti-proliferative effect by 65.9%. Treatment with $\alpha_v\beta_3$ protein itself, without Tumstatin-44-131, did not inhibit endothelial cell proliferation, further indicating that the anti-angiogenic activity of Tumstatin-44-131 is mediated by binding to the $\alpha_v\beta_3$ integrin on the surface of endothelial cells.

To further demonstrate the binding of Tumstatin-44-131 to the surface of endothelial cells, biotinylated Tumstatin-44-131 was used for cell surface labeling. Recombinant *E. Coli*-expressed Tumstatin-44-131 was biotinylated using Sulfo-NHS-LC-Biotin (Pierce Chem. Co). Tumstatin-44-131, in a buffer containing 10% DMSO and 5% D-mannitol, was incubated with 12 M excess of Sulfo-NHS-LC-Biotin overnight at 4° C. The biotinylated Tumstatin-44-131 precipitated out of solution during this incubation. The precipitate was washed twice with distilled water, resuspended in DMSO, and then mixed 1:1 with distilled water to obtain a final concentration of approximately 4 mg/ml. The biotinylated Tumstatin-44-131 was stored at 4° C.

For cell surface labeling, subconfluent HUVEC cells were removed from the flask using EDTA with light trypsinization, and then washed twice with DMEM containing 2% BSA. Cells were then resuspended in DMEM/BSA and incubated for 1 hour at 4° C. with either biotin-labeled Tumstatin-44-131 or the product of a mock biotin reaction run without Tumstatin-44-131. Cells were then washed twice with DMEM/BSA and then incubated with streptavidin-FITC ("Neutravidin-FITC", Pierce Chem. Co) for thirty minutes at 4° C. Samples were then viewed on a Nikon Eclipse E600 fluorescent microscope and analyzed by flow cytometry.

FITC that was indirectly bound with Tumstatin-44-131 was detected on the surface of HUVEC cells in suspension, and the fluorescence was widely distributed in a smaller punctate pattern on the cell surface after attachment. When the cells were incubated with free biotin instead of biotinylated Tumstatin-44-131, no significant fluorescence was detected on the cell surface. The number of FITC-positive, i.e., Tumstatin-44-131-bound cells, increased dose-dependently with increasing concentrations of biotinylated Tumstatin-44-131, showing that Tumstatin-44-131 binds the surface of endothelial cells.

Example 46

Effect of Tumstatin-44-131 on Angiogenesis and Tumor Growth

To evaluate the in vivo effect of Tumstatin-44-131 of the formation of new capillaries, a Matrigel plug assay was performed. After 6 days of treatment, the number of new blood formed was reduced 91% upon treatment with 5 µg/ml *E. Coli*-expressed Tumstatin-44-131, relative to the PBS-treated control. Tum-1, which lacks the N-terminal 53 amino acids of full-length Tumstatin, was also tested, and reduced neovascularization by 95%. The average (over 3-4 Matrigel plugs) number of vessels was 0.47.+−.0.16 for Tum-1-treated plugs, 0.80.+−.0.16 for Tumstatin-44-131-treated plugs, and 8.81.+−.0.35 for PBS-treated controls.

Tumstatin-44-131 was also tested for its ability to suppress tumor growth. Male athymic nude NCRNU mice, of 5-6 weeks of age and about 25 g, were implanted with 6 approximately $2\times10^6$ PC-3 (prostate cancer carcinoma) cells into the dorsal subcutis. The tumors were measured using Vernier calipers and the volume of the tumors calculated using the standard formula (width$^2$×length×0.52). The tumors were allowed to grow to about 50 mm$^3$, and animals were then pair-matched into groups of 6 mice. Initial doses of protein or vehicle (PBS, control) were given on the day of pair-matching (Day 1). Tumstatin-44-131, Tum-5-125-C-A, or human endostatin in sterile PBS was intraperitoneally injected daily b.i.d. at doses ranging from 1 to 20 mg/kg for 20 days. Control animals received injection of PBS vehicle. In one treatment, continuous subcutaneous delivery of Tumstatin-44-131 was done using surgically implanted Alzet mini-pumps. The mice were weighed twice weekly, and tumor measurements were taken, starting on Day 1. Estimated mean tumor volumes were calculated, and at Day 21, the mice were weighed, sacrificed, and their tumors excised and examined by light microscopy and CD31 immunostaining. The mean treated tumor weight was divided by the mean control tumor weight was subtracted from one, and expressed as a percentage to give the tumor growth inhibition for each group.

Figure 54:
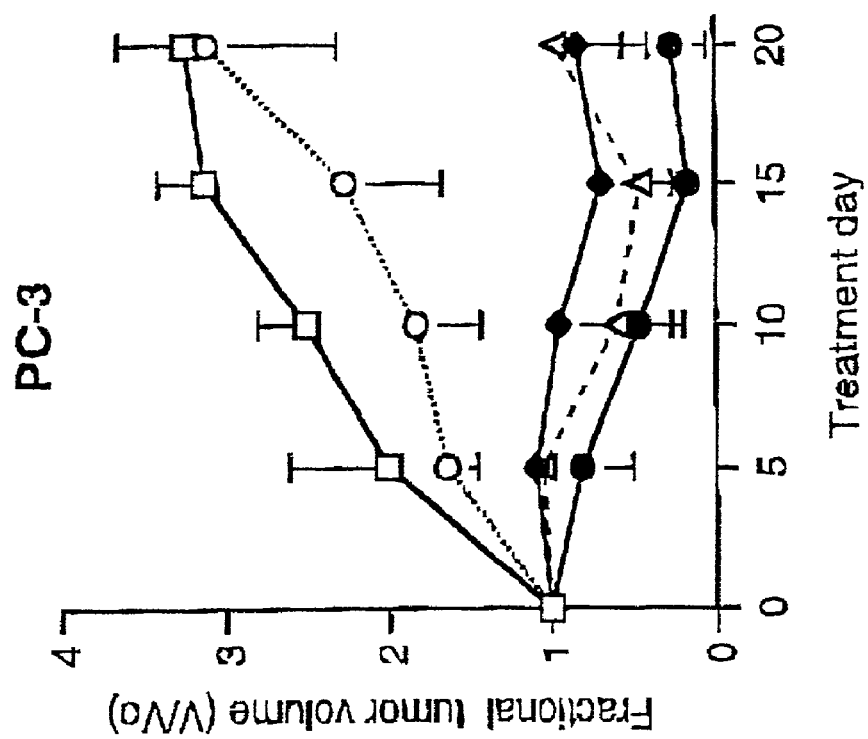
FIG. 54 is a line graph showing the fractional tumor volume (y-axis) in terms of $V/V_0$ (mean tumor volume/ initial tumor volume) at 0, 5, 10, 15 and 20 days (x-axis) of treatment with vehicle (control, □), 1 mg/kg Tumstatin-44-131 (♦), 1 mg/kg Tum-5-125-C-A (●), 20 mg/kg endostatin (°) and mini-pump administered Tumstatin-44-131 (1 mg/kg, Δ).

The results are shown in FIG. 54, which is a line graph showing the fractional tumor volume (y-axis) in terms of $V/V_0$ (mean tumor volume/initial tumor volume) at 0, 5, 10, 15 and 20 days (x-axis) of treatment with vehicle (control, □), 1 mg/kg Tumstatin-44-131 (♦), 1 mg/kg Tum-5-125-C-A (●), 20 mg/kg endostatin (°) and mini-pump administered Tumstatin-44-131 (1 mg/kg, Δ). No toxicity from the protein treatments was seen, as judged by weight change. Both Tumstatin-44-131 and Tum-5-125-C-A significantly inhibited the growth of PC-3 cells. Human Tumstatin-44-131 at 1 mg/kg had a tumor growth inhibition of 74.1% (p=0.02) and Tum-5-125-C-A had a tumor growth inhibition of 92.0% (p=0.001), as compared to the vehicle-injected control group. Continuous delivery of Tumstatin-44-131 (1 mg/kg over 24 hours) via an Alzet mini-pump also showed significant tumor growth inhibition of 70.1% (p=0.03). Endostatin delivered at a dose of 20 mg/kg (b.i.d., bolus injection) showed no significant tumor growth inhibition compared to the vehicle-treated control group.

CD31 immunostaining was used to determine the intratumoral microvessel density (MVD) in frozen histological sections of the PC-3 tumor xenografts, using a rat anti-mouse VD31 monoclonal antibody (PharMingen, San Diego, Calif., USA) with a standard streptavidin-biotin-peroxidase detection system (Vectastain ABC Elite Kit, Vector Labs, Burlingame, Calif., USA). Endogenous peroxidase activity was blocked using 1% $H_2O_2$/methanol for 30 minutes, and slides were then subjected to antigen retrieval by incubating with proteinase K for 30 minutes at room temperature. Anti-mouse CD31 antibody was diluted 1:20 in PBS containing 0.1% TWEEN-20, and incubated for 2 hours after sections were blocked with 5% normal goat serum/PBS+0.1% TWEEN-20. Normal rat IgG was used as a negative control. Immunoperoxidase staining was carried out using the Vectastain ABC Elite reagent kit. Sections were counterstained with methyl green. MVD was assessed by scanning the tumor at low power magnification, then identifying three areas at the tumor periphery which contained the maximum number of discrete microvessels, and then counting individual microvessels on a 40× field. The mean microvessel density was compared among treatment groups and analyzed using the Student's t-test.

Tumstatin-44-131 intraperitoneal injection significantly inhibited microvessel density in PC-3 xenografts as compared to the vehicle-injected control group. The number of CD31-positive blood vessels per low power (40× field) was 6.33.+-.0.54 for Tumstatin-44-131 treatment, versus 9.44.+-.1.05 for the control (p=0.047). Groups treated with Tum-5-125-C-A or the mini-pump-administered Tumstatin-44-131 showed similar decreases of mean vessel density.

Example 47

Figure 55A:
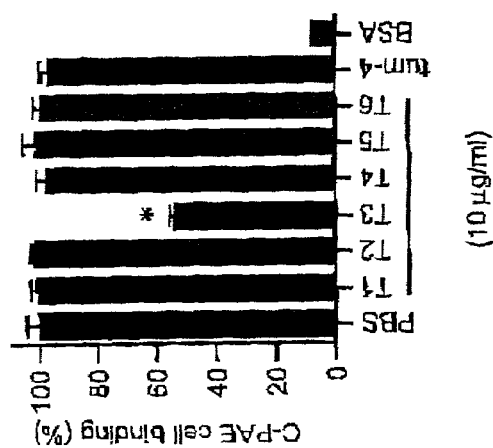
FIGS. 55A and 55B are a pair of histograms showing C-PAE cell binding to tissue culture plates coated with 293-produced Tumstatin, in the presence of various peptide subunits of Tumstatin. PBS and BSA served as positive and negative controls, respectively.
Figure 55B:
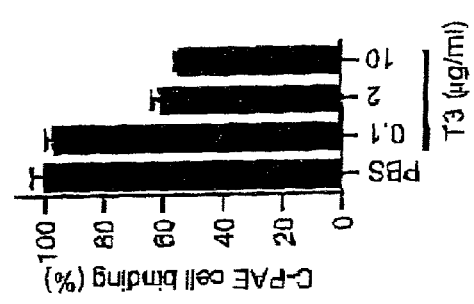

Tumstatin and Tumstatin-44-131 Bind to Endothelial Cells Via the T3 Peptide Sequence Tumstatin produced in 293 human embryonic kidney cells was used to coat tissue culture plates. Attachment of C-PAE cells to the Tumstatin-coated plates in the presence of 10 μg/ml T1, T2, T3, T4, T5, T6, or Tum-4. The results are shown in FIGS. 55A and 55B, which are a pair of histograms showing C-PAE cell binding to tissue culture plates coated with 293-produced Tumstatin, in the presence of various peptide subunits of Tumstatin. PBS and BSA served as positive and negative controls, respectively. FIG. 55A shows cell binding in the presence of 10 μg/ml peptides T1, T2, T3, T4, T5, T6, Tum-4. T3 peptide was found to inhibit cell attachment to Tumstatin-coated plates by 46.4%. FIG. 55B shows cell binding in the presence of 0.1, 2.0 or 10.0 μg/ml T3 peptide. inhibition of the cell attachment was dose-dependent. The other peptides did not inhibit cell attachment.

These results, along with those from Example 40 (FIGS. 44C and 44D), show that endothelial cells bind specifically to the T3 sequence within the Tumstatin-44-131 domain of full-length Tumstatin, and that this binding is likely responsible for the antiangiogenic property of these molecules. Tumstatin and Tumstatin-44-131 have other endothelial cell binding sites, which accounts for the lack of complete inhibition of endothelial cell binding by the T3 peptide, as T3 only inhibits via the $\alpha_v\beta_3$ integrin binding (See Example 40, FIGS. 44E and 44F, above).

Example 48

T3 Peptide Increases the Activity of Caspase-3

The protease activity of Caspase-3 in cells treated with T3 peptide was measured spectrophotometrically by detection of the chromophore (p-nitroanilide) cleaved from the labeled substrate (DEVD-pNA). C-PAE cells treated with 50 μg/ml T3 peptide exhibited a 3.6-fold increase in Caspase-3 activity, whereas the positive control TNF-α (80 ng/ml) gave a comparable (4.5-fold) increase compared with the negative control. T3 peptide at 10 mg/ml slightly increased caspase-3 activity 1.6-fold, suggesting a dose-dependent effect. A specific inhibitor of caspase-3, DEVD-fmk, decreased the protease activity to baseline, indicating that the increase in the measured activity was specific for caspase-3. In PC-3 nonendothelial cells, there was no difference in Caspase-3 activity between control treatments and T3 peptide-treated cells.

Example 49

Synthesis and Activity of T3 Folded Peptide and S—S Bridge Formation

The T3 peptide contains two cysteine residues. S—S bridge formation between two cysteine residues of the T3 peptide was performed by oxidation as follows. T3 peptide was dissolved in 10 ml of 50% acetonitrile and 10 mM ammonium bicarbonate buffer (pH 7.3), to a concentration of 0.25 mg/ml. Aliquots of 30 μl of the oxidizer 2 mg/ml potassium ferricyanide dissolved in 10 mM ammonium bicarbonate buffer (pH 7.3) were added 5 times at room temperature at 5 minute intervals, with brief vortexing after each addition, followed by a two-hour incubation at room temperature. The absence of free thiol groups in the final product was confirmed by using Ellman reagent (DTNB, dithionitrobenzoic acid), and the absence of peptide dimers and higher oligomers was confirmed by SDS-PAGE (16.5%) and silver staining. HPLC was used as the final purification of the T3 peptide. The T3 peptide was applied and run onto a C-18 300A Jupiter column (Phenomenex, Torrance, Calif., USA), using an acetonitrile ($CH_3CN$) gradient (20-60% Buffer B for 30 minutes). Buffer A was 0.1% trifluoroacetic acid, and Buffer B was 0.1%:0.1% trifluoroacetic acid in acetonitrile. A pure monomeric peak was observed with each sample, but at different elution times, suggesting differences in the hydrophobic nature of the peptide. The peak fraction of T3-folded peptide was collected and confirmed by SDS-PAGE and silver staining.

Figure 56:
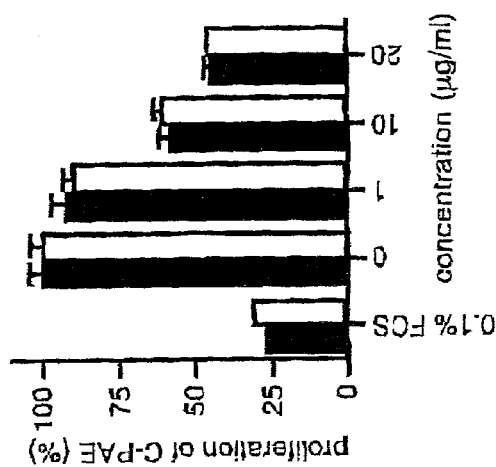
FIG. 56 is a histogram showing the proliferation of C-PAE cells (as a percentage of unstimulated control cells treated with 0.1% FCS) when treated with 0, 1, 10 and 20 µg/ml T3 peptide (black bars), and T3 folded peptide (white bars).

The results are shown in FIG. 56, which is a histogram showing the proliferation of C-PAE cells (as a percentage of unstimulated control cells treated with 0.1% FCS) when treated with 0, 1, 10 and 20 µg/ml T3 peptide (black bars), and T3 folded peptide (white bars). The anti-proliferative effect of T3-unfolded peptide was no different from that of the T3-folded peptide, indicating that, as with Tumstatin and Tumstatin-44-131, disulfide bonding and secondary structure is not a requirement for T3 activity.

Example 50

Comparison of Anti-Angiogenic Activity of Tumstatin and Deletion Mutants

An endothelial cell proliferation assay was used to compare the activity of Tumstatin and some of the deletion mutants. Recombinant Tumstatin (28 kDa), Tumstatin-44-131 (12 kDa) and T3 peptide were used in a methylene blue proliferation assay in equimolar concentrations. At 1 µM, 2.5 µM and 5 µM concentrations, Tumstatin, Tumstatin-44-131 and the T3 peptide exhibited anti-proliferative activity. However, the T3 peptide (either folded or unfolded, see Example 49, supra) was 2.5-fold less active relative to Tumstatin and Tumstatin-44-131 at equimolar concentrations.

Secondary structure does not provide an explanation for the lesser activity of the T3 peptide, and it was possible that there might be additional sequence required for this activity. The T2 peptide did not inhibit $\alpha_v\beta_3$ integrin binding to Tumstatin, nor did it inhibit endothelial cell proliferation, and it seemed likely that this region was not important in enhancing the activity of the T3 peptide. In contrast, although the T4 peptide sequence revealed no inhibitory activity on endothelial cell proliferation, it exhibited weak binding to αvβ3 integrin. Therefore, a new peptide was created, which was extended by nine additional amino acids from the T4 peptide. These nine residues are not contained in the T5 peptide. This new peptide (TMPFLFCNVNDVCNFASRNDYSYWL; SEQ ID NO:37) was named "T7," and it was tested for its effect on proliferation of C-PAE cells.

Figure 57:
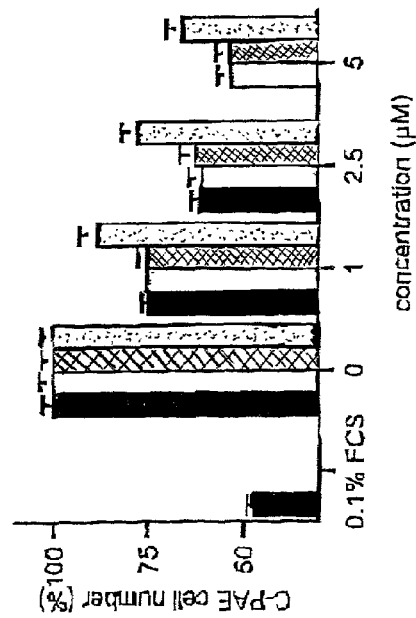
FIG. 57 is a histogram showing the proliferation of C-PAE cells (as a percentage of unstimulated control cells treated with 0.1% FCS) when treated with full-length Tumstatin (black bars), Tumstatin-44-131(white bars), T7 peptide (cross-hatched bars) and T3 peptide (stippled bars). Each column represents the mean ±the SEM of triplicate wells. Tumstatin was not tested at the 5 µM concentration.

The results are shown in FIG. 57, which is a histogram showing the proliferation of C-PAE cells (as a percentage of unstimulated control cells treated with 0.1% FCS) when treated with full-length Tumstatin (black bars), Tumstatin-44-131 (white bars), T7 peptide (cross-hatched bars) and T3 peptide (stippled bars). Each column of FIG. 57 represents the mean ±the SEM of triplicate wells. Tumstatin was not tested at the 5 µM concentration.

7 peptide exhibited a level of activity similar to Tumstatin and Tumstatin-44-131, at equimolar concentrations. Tumstatin, Tumstatin-44-131 and T7 peptide showed anti-proliferative effects with an $ED_{50}$ of 1 µM, while T3 peptide had an $ED_{50}$ of 2.5 µM. These results indicate that while the first nine amino acids of the T4 peptide do not exhibit anti-angiogenic activity, they are important for the optional binding of Tumstatin to the $\alpha_v\beta_3$ integrin, and possibly facilitate better interaction between these molecules and help attain maximal anti-angiogenic activity.

Example 51

In Vivo Anti-Angiogenic Activity of Synthetic Peptides

To evaluate the in vivo effect of T3 on the formation of new capillaries, a matrigel plug assay was performed with Tumstatin-N53 (5 µg/ml), T1 and T3 peptide (10 µg/ml). The number of blood vessels from 4-7 high power fields were counted and averaged. The average number of vessels per high power field after treatment with Tumstatin-N53 was 0.47±0.16, 7.41±0.54 for T1 peptide, and 0.33±0.16 for T3 peptide. Control treatment produced 8.81±0.35 vessels per field, on average. Tumstatin-N53 and T3 inhibited neovascularization by 95% and 96%, respectively, relative to untreated controls, while T1 peptide caused no significant reduction in the number of blood vessels.

Example 52

Tumstatin Peptides Inhibit Total Protein Synthesis in Endothelial Cells

Regulation of protein synthesis is critical for cell proliferation and programmed cell death or apoptosis (McBratney, S. et al., 1993, Curr. Opin. Cell Biol. 5:961-5; Brown, E. J. et al., 1996, Cell 86:517-520; Tan, S. L. et al., 1999, J. Interferon Cytokine. Res. 19:543-54; Gingras, A. C. et al., 2001, Genes Dev. 15:807-826). Tumstatin, a basement membrane-derived α3 type IV collagen peptide fragment, has been shown to be an endothelial cellspecific, pro-apoptotic agent with anti-angiogenic activity (Maeshima, Y. et al., 2000, J. Biol. Chem. 275:21340-8; Maeshima, Y. et al., 2000, J. Biol. Chem. 275:23745-50; Maeshima, Y. et al., 2001, J. Biol. Chem. 276:15240-8; Maeshima, Y. et al., 2001, J. Biol. Chem. 276:31959-68). Tumstatin-induced apoptosis is associated with an increase in caspase-3, an enzyme implicated in the regulation of cap-dependent protein translation (Maeshima, Y. et al., 2000, J. Biol. Chem. 275:23745-50; Maeshima, Y. et al., 2001, J. Biol. Chem. 276:15240-8; Maeshima, Y. et al., 2001, J. Biol. Chem. 276:31959-68; Bushell, M. et al., 1999, FEBS Lett. 451: 332-336).

The potential capacity of tumstatin to inhibit protein synthesis in multiple endothelial cells was therefore explored. Tumstatin and its active subfragments, Tumstatin-44-131, T3 and T7 peptides were used. The amino acids 44-131 of Tumstatin were expressed as recombinant Tumstatin-44-131 in E. Coli as described above and in (Maeshima, Y. et al., 2001, J. Biol. Chem. 276:15240-8). Human endostatin was produced in yeast as described in (Dhanabal, et al., 1999, Cancer Res. 59:189-97). Only soluble protein with a low endotoxin level (less than 50 EU/mg) was used. T3 peptide, T7 peptide, consisting of residues 69-88 and 74-98 of tumstatin, respectively, and T7-mutant peptide (TMPFMFCNINNVCNFASRNDYSYWL; SEQ ID NO:38) were synthesized as described in (Maeshima, Y. et al., 2000, J. Biol. Chem. 275:21340-8; Maeshima, Y. et al., 2001,J. Biol. Chem. 276:31959-68).

Primary human renal epithelial cells (HRE) were purchased from Clonetics (San Diego, Calif., USA) and were maintained in REGM (Clonetics Corp.). Other cell lines were obtained and maintained as described above. Cells were serum-starved for 24 hrs (0.5% FCS), stimulated with 10% FCS in the presence of T3 peptide, Tumstatin-44-131, endostatin or rapamycin for 12-24 hours. After pre-incubation of cells in methionine-free media for 1 hour, cells were labeled with $^{35}$S-methionine for 1 hour and incorporation of radioactivity into trichloracetic acid precipitates was analyzed (Sudhakar, A. et al., 2000, Biochem. 39:12929-38; Maeshima, Y. et al., 1996, J. Amer. Soc. Nephrol. 7:2219-29). ANOVA with a one-tailed Student's t test was used to identify significant differences in multiple comparisons in the present study. A level of P<0.05 was considered statistically significant.

The results are shown in FIGS. 58A-58H, which are a series of eight histograms showing $^{35}$S-methionine incorporation (y-axes) in cells under various treatments α-axes). The experiments were repeated three times and representative data are shown. Each column consists of mean ±SEM of triplicates. In FIG. 58A, C-PAE cells were treated for either 12 hours (black bars) or 24 hours (cross-hatched bars) with T3 peptide (4.5 μM), Tumstatin-44-131 (4.5 μM), endostatin (4.5 μM) or rapamycin (100 ng/ml). HUVECs were also treated for 24 hours (FIG. 58B) with T3 peptide (4.5 μM), Tumstatin-44-131 (4.5 μM), endostatin (4.5 μM) or rapamycin (100 ng/ml). In FIG. 58C, C-PAEs were serum-starved for 12 or 24 hours, and then incubated with medium containing 10% FCS for 24 hours in the presence of T3 peptide at 0 μM (control, black bars), 4.5 μM (bars with horizontal cross-hatching), or 22.7 μM (bars with slanted cross-hatching). In FIGS. 58D-H, PC-3 cells, (FIG. 58D), 786-O cells (FIG. 58E), NIH3T3 cells (FIG. 58F), HRE cells (FIG. 58G) and WM-164 cells (FIG. 59H) were treated for 24 hours with T3 peptide (4.5 μM), Tumstatin-44-131 (4.5 μM), endostatin (4.5 μM) or rapamycin (100 ng/ml).

At molar equivalent concentrations (4.5 μM), all tumstatin peptides inhibit protein synthesis by 25-30% after 24 hours of serum stimulation of bovine and human endothelial cells, as determined by $^{35}$S-methionine incorporation (FIGS. 58A and 58B). In dose responsive studies, tumstatin peptide T3 achieved maximal inhibition of about 45% at a concentration of 22.7 μM (FIG. 58C). In all of these experiments, a positive control, rapamycin (a pan-specific mTOR/protein synthesis inhibitor (Beretta, L. et al 1996, EMBO J. 15:658-64), inhibited protein synthesis, whereas endostatin, another matrix-derived endothelial cell-specific pro-apoptotic agent (O'Reilly, M. S. et al., 1997, Cell 88:277-85; Bergers, G. et al., 1999, Science 284:808-12; Dhanabal, M. et al., 1999, Biochem. Biophys. Res. Commun. 258:345-352), did not inhibit protein synthesis (FIGS. 58A and 58B). The Tumstatin peptides did not inhibit protein synthesis in non-endothelial cells such as PC-3 prostate carcinoma cells, 786-O renal carcinoma cells, N1H-3T3 fibroblasts, primary human renal epithelial cells (HRE) or WM-164 human melanoma cells (FIGS. 58D-58H). In contrast, rapamycin inhibits protein synthesis in all cells tested (FIGS. 58A, 58B, 58D-58H).

Example 53

Tumstatin Peptides Inhibit Cap-Dependent Protein Translation in Endothelial Cells In order to establish the inhibition of protein synthesis by tumstatin as cap-dependent, endothelial cells were transfected with a plasmid expressing dicistronic mRNAs under the control of cytomegalovirus (CMV) promoter and containing the internal ribosomal entry site (IRES) derived from the untranslated region of poliovirus (pcDNA3-LUC/pol/ CAT) (Beretta, L. et al. 1996, EMBO J. 15:658-64; Kumar, V. et al., 2000, J. Biol. Chem. 275:10779-87). The construction of this plasmid is such that, translation of luciferase (LUC) is cap-dependent, while the translation of chloramphenicol acetyltransferase (CAT) is cap-independent (Beretta et al., 1996; Kumar et al., 2000). Briefly, cells were serum-starved for 24 hours and transiently transfected with 1.5 μg pcDNA3-LUC-pol-CAT (Kumar et al., 2000) using Lipofectamine Plus (Life Technologies, Gibco/BRL) (Maeshima, Y. et al., 1998, J. Clin. Invest. 101:2589-97). After 3 hours, cells were then treated in the presence of 10% FCS for 21 hours in the absence (control) or presence of T3 peptide (4.5 μM), Tumstatin-44-131 (4.5 μM), T7 peptide (4.5 μM), endostatin (4.5 μM) or rapamycin (100 ng/ml). Cell lysates were prepared and assayed for luciferase activity using Dual Luciferase Reporter Assay System (Promega, Madison, Wis., USA). CAT activity was determined using CAT Enzyme Assay System (Promega) with $^{14}$C-chloramphenicol. Liquid scintillation counting method was used to determine the level of n-butyryl chloramphenicol.

The results are shown in FIGS. 59A and 59B, which are a pair of histograms showing the reporter activity (y-axis) for translation of luciferase (LUC; cap-dependent translation; black bars) or chloramphenicol acetyltransferase (CAT; cap-independent translation; cross-hatched bars), under treatment by T3 peptide (4.5 μM), Tumstatin-44-131 (4.5 μM), T7 peptide (4.5 μM), endostatin (4.5 μM) or rapamycin (100 ng/ml). Luciferase and CAT activity relative to the control group is shown. These experiments were repeated three times and representative data are shown. Each column consists of mean ±SEM of triplicates.

Tumstatin peptides decreased cap-dependent translation of LUC by 37-39% in bovine endothelial cells, comparable to rapamycin (FIG. 59A). Again, endostatin did not affect cap-dependent translation (FIG. 59B). As observed earlier, tumstatin peptides did not inhibit cap-dependent translation in non-endothelial cells, but rapamycin did (FIG. 59B). Cap-independent translation (CAT activity) was not altered by tumstatin peptides.

Rapamycin induced cap independent translation in endothelial cells (FIG. 59A), which is consistent with previous reports suggesting that rapamycin stimulates the translation of mRNAs containing IRES (poliovirus) (Beretta, L. et al. 1996, EMBO J. 15:658-64; Gingras, A. C. et al., 2001, Genes Dev. 15:807-826). Interestingly, cap-independent translation was decreased by rapamycin in NIH3T3 cells, which is again consistent with previous reports which alluded to this trend (Beretta, L. et al. 1996, EMBO J. 15:658-64). In other experiments, RNA levels in the treated and untreated endothelial cells was unaltered as assessed by Northern analysis, suggesting a specific effect of tumstatin peptides on protein translation and not RNA levels.

Example 54

The Endothelial Cell Specific Inhibitory Effect of Tumstatin Peptides on Cap-Dependent Translation and Protein Synthesis is Mediated Via $α_vβ_3$ Integrin Previous studies suggest that apoptosis of endothelial cells by tumstatin is dependent on its binding to $α_vβ_3$ integrin on endothelial cells Maeshima, Y. et al., 2000, J. Biol. Chem. 275:21340-8; Maeshima, Y. et al., 2001, J. Biol. Chem. 276:15240-8; Maeshima, Y. et al., 2001, J. Biol. Chem. 276:31959-68). Therefore, to evaluate the effect of tumstatin peptides on cap-dependent and independent translation, endothelial cells were isolated from lungs of 12-week-old mice that were deficient in the expression of $α_vβ_3$ integrin (i.e., 3 integrin-deficient mice), and also their wild-type counterparts (Hodivala-Dilke, K. M. et al., 1999, J. Clin. Invest. 103:229-38). Briefly, ICAM-2 expressing MLEC were enriched using rat anti-mouse ICAM-2 (# 01800D, PharMingen, San Diego, Calif., USA) conjugated to magnetic beads (Dynabeads M-450, Dynal, Oslo, Norway). MLEC were maintained in 40% Ham's F-12,40% DME-Low Glucose, 20% FBS supplemented with heparin, endothelial mitogen (Biomedical Technologies, Inc., Cambridge, Mass., USA), glutamine and penicillin/streptomycin. Wild-type and $\beta_3$-integrin-deficient mouse embryonic fibroblasts were prepared (Hodivala-Dilke, K. M. et al., 1999, J. Clin. Invest. 103:229-38). MEFs were maintained in DMEM containing 10% FBS. MLEC were characterized for homogeneity by morphological observations and by immunofluorescence staining for endothelial-specific markers. Cells between passage 3 and 6 were used for the experiments.

Figure 60E:
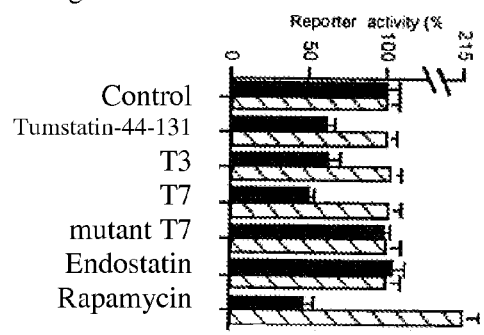
Figure 60F:
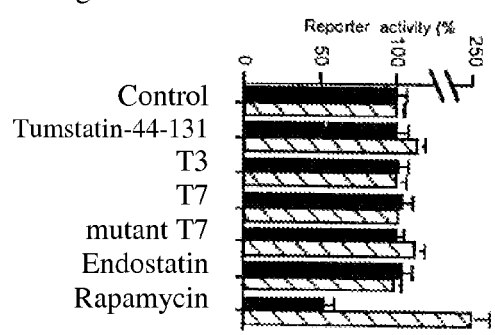
Figure 60G:
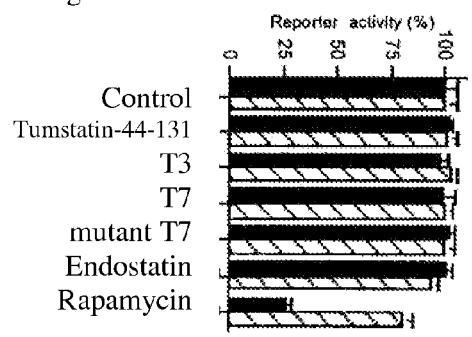
Figure 60H:
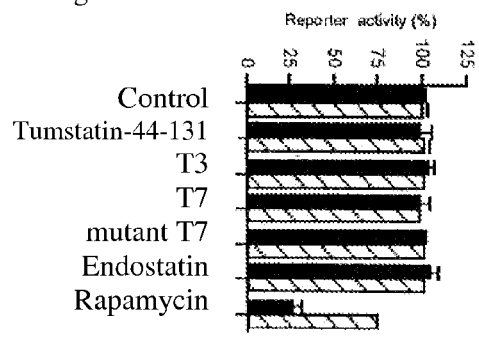

The results are shown in FIGS. 60A-60H, which are a set of eight histograms. FIGS. 60A-60D show total protein synthesis in terms of $^{35}$S-methionine incorporation (y-axis) in endothelial cells (MLEC) (FIGS. 60A and 60B) and embryonic fibroblasts (MEF) (FIGS. 60C and 60D) from wild-type (FIGS. 60A and 60C) and $\beta_3$-integrin knockout (FIGS. 60B and 60D) littermate mice, where the cells were treated (x-axis) with Tumstatin-44-131 (4.5 µM), T3 (4.5 µM), T7 (4.5 µM), mutant T7 peptide (4.5 µM), endostatin (4.5 µM) or rapamycin (100 ng/ml). FIGS. 60E-60G show reporter activity of either luciferase (Luc; black bars) or chloramphenicol acetyltransferase (CAT; cross-hatched bars) as a percentage of control (y-axis) in in endothelial cells (MLEC) (FIGS. 60E and 60F) and embryonic fibroblasts (MEF) (FIGS. 60G and 60H) from wild-type (FIGS. 60E and 60G) and $P_3$-integrin knockout (FIGS. 60F and 60H) littermate mice, where the cells were treated (x-axis) with Tumstatin-44-131 (4.5 µM), T3 (4.5 µM), T7 (4.5 µM), T7-mutant peptide (4.51M), endostatin (4.5 µM) or rapamycin (100 ng/ml). These experiments were repeated three times and the representative data are shown. Each column consists of mean ±SEM of triplicates.

Both wild type and $\beta_3$-integrin deficient MLECs were both positive for the expression of endothelial specific marker, VE-Cadherin, at cell junctions and contact points. Both cell lines were also able to take up diI-Ac-LDL. Tumstatin inhibited protein synthesis in control cells ($\beta_3$+/+ cells), but did not have any effect on cap-dependent protein synthesis in mouse endothelial cells deficient in expression of $\alpha_v\beta_3$ integrin ($\beta_3$-/-) (FIGS. 60A and 60B, 60E and 60F). Rapamycin inhibited cap-dependent protein synthesis in both control and $\alpha_v\beta_3$ integrin-deficient mouse endothelial cells, and under similar experimental conditions endostatin did not exhibit this property (FIGS. 60A and 60B, 60E and 60F). In order to establish the specificity of tumstatin for endothelial cells expressing $\alpha_v\beta_3$ integrin, mouse embryonic fibroblasts expressing $\alpha_v\beta_3$ integrin (Hodivala-Dilke, K. M. et al., 1999, J. Clin. Invest. 103:229-38) were also used in protein synthesis experiments. Tumstatin peptides failed to inhibit protein synthesis in these cells independent of $\alpha_v\beta_3$ integrin expression, whereas rapamycin inhibited protein synthesis and cap-dependent translation in these cells (FIGS. 60C, 60D, 60G and 60H).

Example 55

Tumstatin Peptides Down-Regulate PI3-k-Akt-mTOR Signaling Leading to Decreased Phosphorylation of 4E-BP1

Experiments were performed to elucidate the role of tumstatin on signaling pathways involved in the inhibition of protein synthesis. In different cell types including endothelial cells, ligand binding to integrin induces phosphorylation of focal adhesion kinase (FAK) leading to the activation of various signaling molecules (Vuori, K., 1998, J. Membr. Biol. 165:191-9; Ruoslahti, E., 1999, Adv. Cancer Res. 76:1-20). Phosphorylated FAK is known to interact with and activate phosphatidylinositol 3'-kinase (PI3-kinase) and Akt (downstream of PI3-kinase) leading to cell survival (Chen, H. C. et al., 1994, Proc. Natl. Acad. Sci. USA 91:10148-52; Vuori, K., 1998, J. Membr. Biol. 165:191-9). A previous report showed that inhibition of PI3-K in endothelial cells leads to inhibition of protein synthesis (Vinals, F. et al., 1999, J. Biol. Chem. 274:26776-82).

C-PAEs were serum starved for 30 hours and trypsinized. Cells in suspension were pre-incubated with T3 peptide (50 µg/ml) for 15 minutes, and then allowed to attach onto vitronectin-precoated dishes in serum-free conditions for 30-60 minutes. Total cell extracts were prepared and SDS-PAGE and western blotting (Kalluri, R. et al., 1996, J. Biol. Chem. 271:9062-68; Maeshima, Y. et al., 2000, J. Biol. Chem. 275:23745-50; Sudhakar, A. et al, 1999, Biochem. 38:15398-405; Kalluri, R. et al., 2000, J. Biol. Chem. 275:12719-24) with anti-FAK (Santa Cruz Biotechnology, Santa Cruz, Calif., USA; goat IgG) and anti-phosphorylated FAK (Tyr397; Biosource International, Camarillo, Calif., USA; rabbit IgG) antibody was performed. The same experiments were also performed using WM-164 melanoma cells.

Figure 61A:
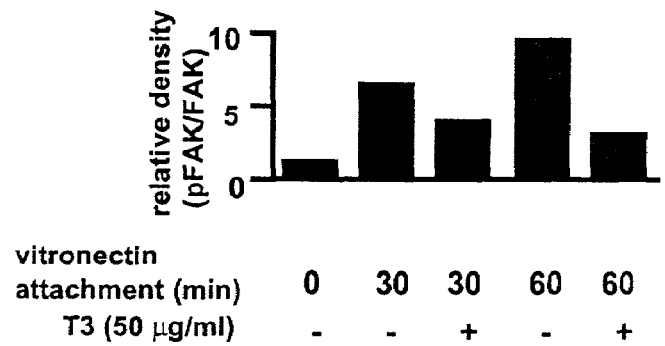
FIGS. 61A-61F are a series of eight histograms.

The results are shown in FIG. 61A, which is a histogram showing the relative density of pFAK/FAK (y-axis) under treatments of (x-axis) no attachment time to vitronectin-coated plates and in the absence of T3 peptide ("0–"bar), 30 minutes' attachment time and no T3 peptide ("30–" bar), 30 minutes attachment time and 50 µg/ml T3 peptide ("30+" bar), 60 minutes attachment time and no T3 peptide ("60–" bar) and 60 minutes attachment time and 50 µg/ml T3 peptide ("60+" bar).

PI3-kinase activities were measured by the in vitro phosphorylation of phosphatidylinositol (PI) (Ueki, K. et al., 2000, J. Clin. Invest. 105:1437-45). C-PAEs were serum-starved (0.5% FCS) for 30 hours, trypsinized and pre-incubated with T3 peptide (50 µg/ml) for 15 minutes. Cells were then allowed to attach on vitronectin-coated dishes for 30-60 minutes and cell lysates were subjected to immunoprecipitation with antiphosphotyrosine antibody (Upstate Biotechnology, Lake Placid, N.Y., USA). After successive washings, the immunoprecipitates were resuspended in 50 µL of P13K reaction buffer (20 mM Tris-HCl, pH 7.4, 100 mM NaCl and 0.5 mM EGTA) containing 0.1 mg/mL of PI (Avanti Polar Lipids, Inc., Alabaster, Ala., USA). The PI3-kinase reactions were initiated by adding 5 µL of 200 µM ATP containing 5 µCi of $\gamma$-$^{32}$P-ATP. After 20 minutes at 25° C., the reactions were terminated, samples were centrifuged, the organic phase was removed and spotted onto a Silicagel 60 plate developing in chloroform-methanol-28% ammonium hydroxide-water (43:38:5:7). The phosphorylated lipids were visualized by autoradiography.

Figure 61B:
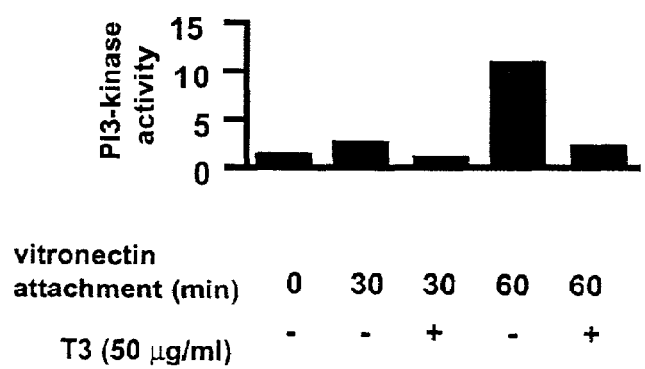

The results are shown in FIG. 61B, which is a histogram showing PI3-kinase activity (y-axis) under treatments of (x-axis) no attachment time to vitronectin-coated plates and in the absence of T3 peptide ("0–" bar), 30 minutes attachment time and no T3 peptide ("30–" bar), 30 minutes attachment time and 50 µg/ml T3 peptide ("30+" bar), 60 minutes attachment time and no T3 peptide ("60–" bar) and 60 minutes attachment time and 50 µg/ml T3 peptide ("60+" bar).

Western blotting with anti-Akt and anti-phosphorylated Akt antibody (Ser473; New England BioLabs, Beverly, Mass., USA; rabbit IgG) was then performed as for FIG.

Figure 61C:
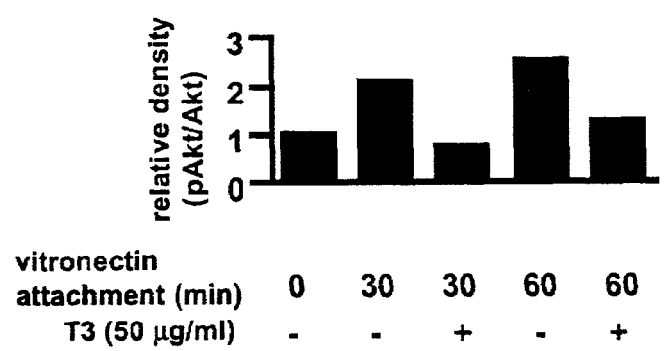

61A, using C-PAE and WM-164 cells. The results are shown in FIG. 61C, which is a histogram showing the relative density of pFAK/FAK (y-axis) under the same treatments as in FIG. 61A (x-axis). mTOR kinase assay was performed as previously described (Kumar, V. et al., 2000, J. Biol. Chem. 275:10779-87). C-PAEs or WM-164 were serum-starved and transiently transfected with HA-mTOR cDNA (Kumar, V. et al., 2000, J. Biol. Chem. 275:10779-87) using Lipofectamine Plus (Life Technologies, Gibco/BRL), and treated with T3 peptide (50 μg/ml) or Tumstatin-44-131 for 24 hours. Cell lysates (150 μg) were subjected to immunoprecipitation with anti-HA antibody (Roche Molecular Biochemicals, Indianapolis, Ind., USA). The beads were incubated with the recombinant GST-4E-BP1 fusion protein (Kumar, V. et al., 2000, J. Biol. Chem. 275:10779-87) in the presence of 10 μCi of γ-$^{32}$P-ATP in kinase buffer (25 mM Tris, 25 mM KCl and 2.5 mM magnesium acetate) containing 30 μM cold ATP at 30° C. for 20 minutes. Reactions were terminated and samples were subjected to SDS-PAGE and analyzed by autoradiography.

Figure 61D:
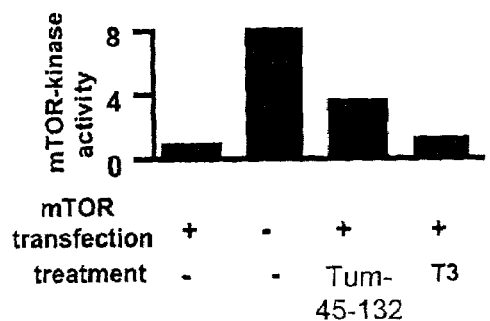

The results are shown in FIG. 61D, which is a histogram showing mTOR-kinase activity (y-axis) under treatments of (x-axis) no mTOR transfection and no peptide treatment ("−−" bar), mTOR transfection and no peptide treatment ("±" bar), mTOR transfection and treatment with Tumstatin-44-131 ("+Tum-5" bar) and mTOR transfection and treatment with peptide T3 ("+T3" bar).

After serum starvation, C-PAEs or WM-164 were treated with T3 peptide, Tumstatin-44-131, rapamycin or endostatin in the presence of 10% FCS for 24 hours. Cell lysates were prepared, and 30 μL of 50% slurry of 7-methyl-GTP-Sepharose (Pharmacia Biotech, Inc., Piscataway, N.J., USA) was added and incubated for 30 minutes at 25° C. After washing the resin twice (washing buffer: 100 mM KCl, 0.2 mM EDTA, 7 mM β-mercaptoethanol, 20 mM Tris-HCl, pH 7.4), bound proteins were resolved by SDS-PAGE, and the level of bound eIF4E and 4E-BP1 was detected by immunoblotting (Kumar et al., supra).

Figure 61E:
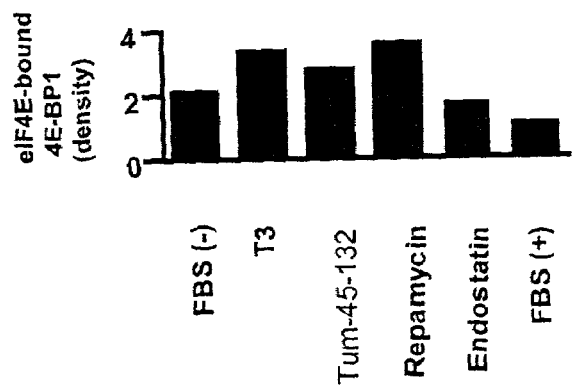

The results are shown in FIG. 61E, which is a histogram of the density of eIF4E-bound 4E-BP1 (y-axis) in C-PAE cells after treatment with no FBS, T3, Tumstatin-44-131, Rapamycin, Endostatin or FBS (x-axis).

To examine the effect of Tumstatin peptides on activation of PI3-kinase and Akt, cDNA of constitutive active Akt (CAAkt, Gag protein fused to N-terminal of wild type Akt) was constructed (Burgering, B. M. et al., 1995, Nature 376:599-602). The recombinant adenoviruses were constructed by homologous recombination between the parental virus genome and the expression cosmid cassette or shuttle vector as described (Ueki, K. et al., 2000, J. Clin. Invest. 105:1437-45). The adenoviruses were applied at a concentration of 1×10$^8$ plaque-forming units/mL, and adenoviruses with the same parental genome carrying lacZ gene was used as controls. After infection of C-PAEs with recombinant adenoviruses for 24 hours, cells were serum-starved for 24 hours and transfected with pcDNA-LUC-pol-CAT. After treating cells with T3 peptide for 21 hours in the presence of medium containing 10% FCS, cell lysates were obtained and luciferase assay and CAT assay were performed.

Figure 61F:
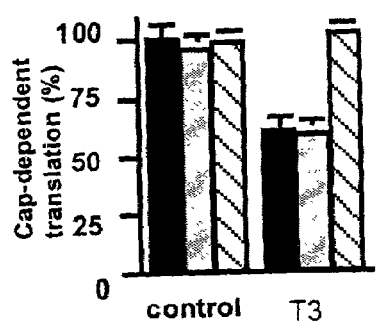

The resulting luciferase activity relative to CAT activity is shown in FIG. 61F, which is a histogram of the percent luciferase activity relative to CAT activity is shown (y-axis) for C-PAEs that were either infected with adenoviral vectors containing cDNAs of control lacZ (shaded bars), constitutive active Akt (cross-hatched bars), or not infected at all (black bars). The cells were then serum starved, transfected with pcDNA-LUC-pol-CAT, and treated with T3 peptide in the presence of medium containing 10% FCS.

Tumstatin peptides inhibit phosphorylation of FAK in endothelial cells induced by attachment to vitronectin (FIG. 61A). Activation of PI3-kinase and Akt were also inhibited by treatment with tumstatin peptides (FIGS. 61B and 61C). Rapamycin/FKBP-target 1 (RAFT 1), also known as FRAP/mTOR, downstream of Akt, directly phosphorylates eukaryotic initiation factor 4E (eIF4E)-binding protein (4EBP1) (Brunn, G. J. et al., 1997, Science 277:99-101; Gingras, A. C. et al., 1998, Genes Dev. 12:502-13). Unphosphorylated 4E-BP1 interacts with eIF4E and inhibits cap-dependent translation (Pause, A. et al., 1994, Nature 371:762-7). Stimulation of cells with growth factors or serum induces phosphorylation of 4E-BP 1 resulting in its dissociation from eIF4E to relieve translational inhibition (Pause, A. et al., 1994, Nature 371:762-7; Gingras, A. C. et al., 1998, Genes Dev. 12:502-13). Tumstatin peptides inactivate mTOR kinase activity, and thus inhibit phosphorylation of 4E-BP1 (FIG. 61D). Inhibition of 4E-BP1 phosphorylation enhances 4E-BP 1 binding to eIF-4E (FIG. 61E), leading to inhibition of cap-dependent translation. When non-endothelial, WM-164 melanoma cells expressing $\alpha_v\beta_3$ integrin, were used for these experiments, no inhibitory effects by tumstatin peptides were observed (FIGS. 61A and 61C-61E). To confirm the importance of this pathway in inhibiting cap-dependent translation in endothelial cells, constitutively active Akt was overexpressed in endothelial cells using recombinant adenoviruses. Inhibition of cap-dependent translation by tumstatin peptides was overcome by overexpression of constitutively active Akt (FIG. 61F).

These data further implicate the involvement of tumstatin peptides in inhibiting protein synthesis of endothelial cells through negative regulation of $\alpha_v\beta_3$ integrin-FAK-PI3-KAkt-mTOR signaling. Tumstatin/$\alpha_v\beta_3$ integrin-induced negative signals may counteract growth factor (vascular endothelial growth factor (VEGF), etc.) initiated cell survival signals via cross-talk between these two pathways.

The role of the MAP-kinase pathway in the regulation of protein synthesis by tumstatin peptides was also examined. Phosphorylation of extracellular regulated kinase (ERK)½ upon vitronectin attachment or stimulation with VEGF was not altered by tumstatin peptides in C-PAEs. Collectively, these results establish that tumstatin peptides as endothelial cell specific inhibitors of cap-dependent protein synthesis, acting via 'outside-in' signaling involving $\alpha_v\beta_3$ integrin, and that the previously reported anti-angiogenic activity of tumstatin can act via $\alpha_v\beta_3$ integrin-mediated inhibition of cap-dependent translation of proteins.

Example 56

Activity of T8 Synthetic Peptide in a MDAMB-435 Tumor Xenograft Model

The activity of the synthetic peptide T8 against the MDAMB-435 human breast orthotopic xenograft model in nude mice was studied.

T8 (KQRFTTMPFLFCNVNDVCNFASRNDYS; SEQ ID NO:39) was synthesized, purified to greater than 90% purity via HPLC (<20 EU/mg). The peptide was neutralized prior to injection with 2× buffer 1:1 (v:v) of 50 mM glycine, 5 mM arginine, 9% D-mannitol (pH 8.0).

Female nude NCRNU mice, 5-6 weeks old, weighing approximately 20 grams, were implanted with 2×10$^6$ MDAMB-435 cells in the subaxillary mammary fat pad. When the tumors were 100 mm$^3$, the animals were pair-matched into treatment and control groups. Each group contained 7 tumored mice, each of which was ear-tagged and followed individually throughout the experiment. Initial doses of T8 peptide or vehicle control were given on the day of pair-matching (Day 0), and were administered via intraperitoneal (i.p.) injection at 1 mg and 2.5 mg per kg animal weight. Mice were weighed twice weekly, and tumor measurements were taken by calipers twice weekly, starting on Day 1. These tumor measurements were converted to tumor volume by the well-known formula V=W2.times.L/2, and mean tumor volumes were plotted against time. Mice were euthenized at the end of the treatment period. Upon termination, the mice were weighed, sacrificed and their tumors were excised. The mean tumor weight per group was calculated, and the value of (mean treated tumor weight/mean control tumor weight×100) was subtracted from 100% to give the tumor growth inhibition (TGI) for each group.

Treatment was initiated when tumor volumes reached 100 mm$^3$. All groups received injections bid, i.p., for 26 days. The results are shown in Table 5, below:

TABLE 5

Summary of in vivo effects of T8 peptide against 100 mm$^3$ pre-existing MDAMB-435 tumor xenografts

| Treatment | Dosage (mg/kg) | Final Tumor Weight ± SEM | % Tumor growth inhibition | t-test (p) |
|---|---|---|---|---|
| Control Vehicle | — | 333.3 ± 39.61 | — | — |
| T8 | 1.9 | 237.8 ± 31.88 | 28.65 | 0.08 |
| T8 | 2.5 | 173.6 ± 23.73 | 47.91 | <0.001** |

No toxicity observed in any groups, as judged by serial weight changes.
**p < 0.01

Figure 62:
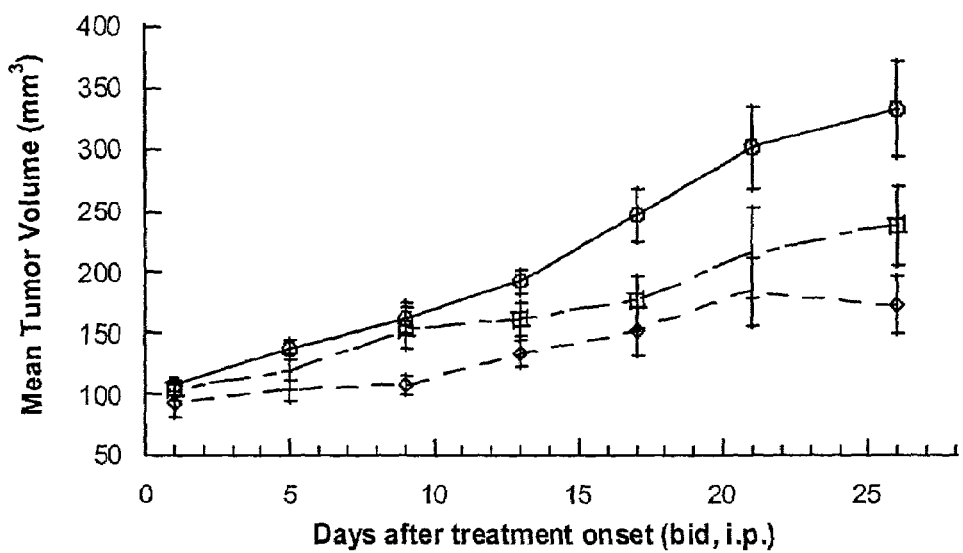
FIG. 62 is a graph showing mean tumor volume ($mm^3$; y-axis) for various days after treatment onset (x-axis) for treatment with control vehicle (○), and treatment with 1 mg/kg (□) or 2.5 mg/kg (◇) T8.

The results are also shown in FIG. 62, which is a graph showing mean tumor volume (mm$^3$; y-axis) for various days after treatment onset (x-axis) for treatment with control vehicle (°), and treatment with 1 mg per kg (□) or 2.5 mg per kg (◇) T8. No toxicity was observed in any groups, as judged by weight change. After 26 days of treatment, our results show that the 27-mer peptide T8, when administered twice daily at a dose of 2.5 mg/kg, significantly inhibited tumor growth by 47.91% (p<0.001). T8 administered twice daily at a dose of 1.0 mg/kg did not significantly inhibit tumor growth. In conclusion, T8, a small synthetic peptide derived from the Tumstatin sequence, is effective at inhibiting tumor growth in the MDAMB-435 orthotopic human breast tumor xenograft model.

Example 57

Activity of T8 and TP3 Synthetic Peptides Against a MDAMB-435 Tumor Xenograft Model The antitumor activity of the Tum5 synthetic peptides T8 and TP3 was evaluated against the MDAMB-435 human breast orthotopic xenograft model in nude mice. The dose schedule with T8 was also varied.

The synthetic peptides T8 and TP3 (KLFCNVNCVCN-FASRNDYS; SEQ ID NO:41), a mutant of the native Tumstatin sequence, were synthesized, purified to greater than 90% purity via HPLC (<20 EU/mg). The peptides were neutralized prior to injection with 2× buffer 1:1 (v:v) of 50 mM glycine, 5 mM arginine, 10 mM Na-acetate, 9% D-mannitol (pH 8.2).

Female nude NCRNU mice, 5-6 weeks old, weighing approximately 20 grams, were implanted with 2×10$^6$ MDAMB-435 cells into the subaxillary mammary fat pad. When the tumors were 100 mm$^3$, the animals were pair-matched into treatment and control groups. Each group contained 6-7 tumored mice, each of which was ear-tagged and followed individually throughout the experiment. Initial doses of T8 or TP3 peptide or vehicle control were given on the day of pair-matching (Day 0), and were administered via intraperitoneal (i.p.) injection at doses indicated. Mice were weighed twice weekly, and tumor measurements were taken by calipers twice weekly, starting on Day 1. These tumor measurements were converted to tumor volume by a well-known formula, (V=W$^2$×L/2) and mean tumor volumes as well as volume ratios (V/Vo) were plotted against time. Mice were euthanized at the end of the treatment period. Upon termination, the mice were weighed, sacrificed and their tumors were excised. The mean tumor weight per group was calculated, and the mean value (treated tumor ratio/mean control tumor ratio.times. 100) was subtracted from 100% to give the tumor growth inhibition (TGI) for each group.

Treatment was initiated when tumor volumes reached 80 mm$^3$. All groups received injections I.P. daily, except for one T8-treated group, which was treated twice per week. The results are shown in Table 6, below.

TABLE 6

Summary of in vivo effects of peptides T8 and TP3 against 100 mm$^3$ pre-existing MDAMB-435 tumor xenografts

| Treatment | Dosage (mg/kg) | Final Tumor Weight (V/Vo) ± SEM | % Tumor growth inhibition | t-test (p) |
|---|---|---|---|---|
| Control Vehicle | — | 3.77 ± 0.38 | — | — |
| T8 | 5.0 | 2.60 ± 0.38 | 31.0 | 0.07 |
| TP3 | 1.0 | 2.62 ± 0.45 | 30.6 | 0.14 |
| TP3 | 5.0 | 1.88 ± 0.29 | 50.0 | 0.005 |
| T8 (2x/week) | 5.0 | 2.21 ± 0.31 | 41.4 | 0.02 |

Figure 63:
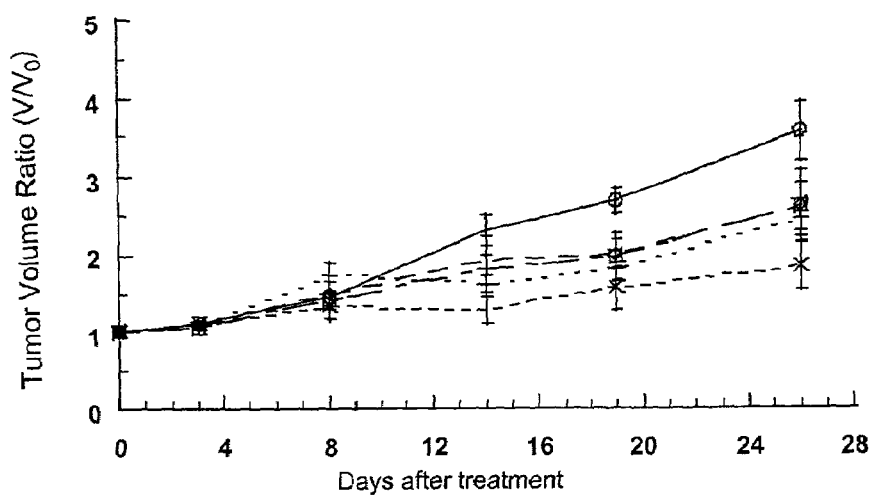
FIG. 63 is a graph showing tumor volume ratio (V/Vo; y-axis) for various days after treatment onset (x-axis) for control treatment (○), and treatment with 1 mg/kg TP3 daily (◇), 5 mg/kg TP3 daily (X), 5 mg/kg T8 daily (□), or 5 mg/kg T8 administered twice weekly (+).

The results are also shown in FIG. 63, which is a graph showing tumor volume ratio (V/Vo; y-axis) for various days after treatment onset (x-axis) for control treatment (°), and treatment with 1 mg per kg TP3 daily (◇), 5 mg per kg TP3 daily (X), 5 mg per kg T8 daily (□), or 5 mg per kg T8 administered twice weekly (+).

No toxicity was observed in any groups, as judged by weight change. After four weeks of treatment, the results show that the 27-mer peptide T8, when administered once daily or twice a week at a dose of 5 mg/kg, inhibited tumor growth by 31.0% (p=0.07) and 41.4% (p=0.02) respectively. In addition, the 18-mer truncated peptide TP3 inhibited tumor growth by 30.6% (P=0.14) at the 1 mg/kg dose, and by 50.0% (p<0.01) at the 5 mg/kg dose. Small synthetic peptides derived from the Tumstatin sequence are therefore effective at inhibiting tumor growth in the MDAMB-435 orthotopic human breast tumor xenograft model.

Example 58

Activity of T7, T8, TP3, SP1 and SP2 Synthetic Peptides in a PC3 Tumor Xenograft Model The antitumor activity of the synthetic peptides T7, T8, TP3, SP 1 and SP2 was evaluated against the PC3 human prostate tumor xenograft model in nude mice.

Peptides T7, T8, TP3, and control scrambled peptide SPI (ANMSRNVFFDCTSFPVCQKFLNDTRNY; SEQ ID NO:43) and SP2 (TFNCVKNYQRLDFTSRFVMDSCAN- FPN; SEQ ID NO:44) were synthesized, purified to greater than 90% purity via HPLC (<20 EU/mg). The peptides were neutralized prior to injection with 2× buffer 1:1 (v:v) of 50 mM glycine, 5 mM arginine, 10 mM Na-acetate, 9% D-mannitol (pH 8.2). Peptide T7 and T8 were stored in different stock vehicles (25% DMSO/PBS for T7 and 2 mM HCl for T8), so the different stock vehicles themselves were also included as controls.

Male nude NCRNU mice, 5-6 weeks old, weighing approximately 25 grams, 6 were implanted with $2\times10^6$ PC3 cells into the dorsal subcutis. When the tumors were 60 mm$^3$, the animals were pair-matched into treatment and control groups. Each group contained 6-7 tumored mice, each of which was ear-tagged and followed individually throughout the experiment. Initial doses of peptide or vehicle control were given on the day of pair-matching (Day 0), and were administered via intraperitoneal (i.p.) injection at doses indicated. Mice were weighed weekly, and tumor measurements were taken by calipers weekly. These tumor measurements were converted to tumor volume by a well-known formula, $(V=W^2\times L/2)$, and mean tumor volumes were plotted against time. Mice were euthenized at the end of the treatment period. Upon termination, the mice were weighed, sacrificed and their tumors were excised. The mean tumor weight per group was calculated, and the value of mean treated tumor volume or volume ratio/mean control tumor volume or volume ratio×100 was subtracted from 100% to give the tumor growth inhibition (TG1) for each group.

All groups received injections I.P. daily, except for two T8-treated groups, which were treated twice per week and once a week, respectively. The results are shown in Table 7, below.

TABLE 7

Summary of in vivo effects of peptides T7, T8, TP3, SP1 and SP2 against 60 mm$^3$ pre-existing PC3 tumor xenografts

| Treatment | Dosage (mg/kg) | Final Tumor Weight (V/Vo) ± SEM | % Tumor growth inhibition | t-test (p) |
| --- | --- | --- | --- | --- |
| T7 Control Vehicle (25% DMSO/PBS) | — | 5.626 ± 0.38 | — | — |
| T7 | 5.0 | 1.868 ± 0755 | 66.8 | 0.0563 |
| T8 Control vehicle (2 mM HCl) | — | 6.278 ± 1.483 | — | — |
| T8 | 5.0 | 3.455 ± 1.228 | 45.0 | 0.1733 |
| TP3 | 5.0 | 2.940 ± 0.636 | 53.2 | 0.0514 |
| SP1 | 5.0 | 4.284 ± 1.244 | 31.7 | 0.3272 |
| SP2 | 5.0 | 5.097 ± 0.185 | 18.7 | 0.6214 |
| T8 | 5.0 (2x/week) | 5.770 ± 1.156 | 8.1 | 0.7926 |
| T8 | 5.0 (2x/week) | 3.800 ± 1.602 | 39.5 | 0.2827 |

No toxicity observed in any groups, as judged by serial weight changes.

Figure 64A:
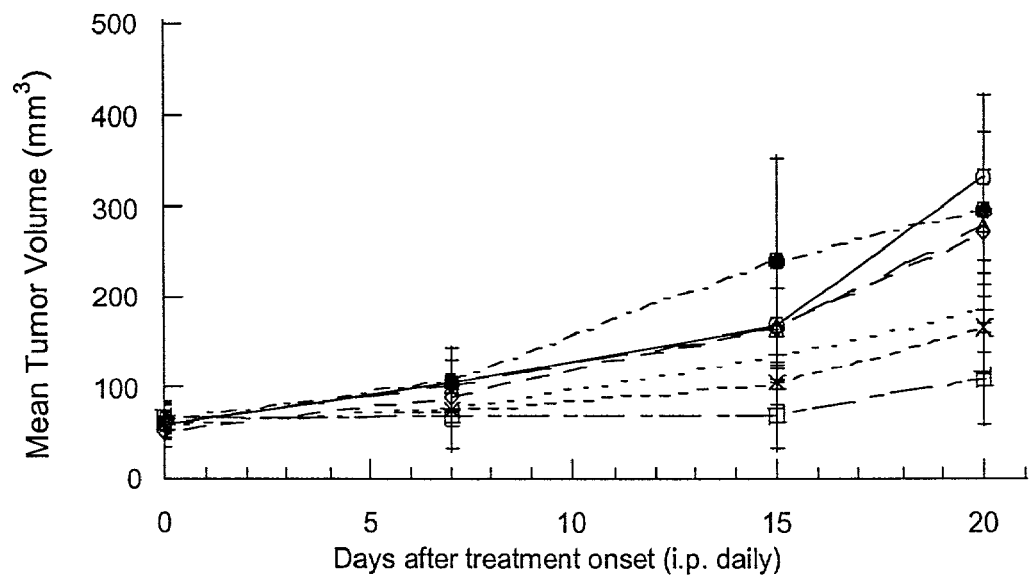
FIGS. 64A and 64B are a pair of graphs showing mean tumor volume ratio (mm$^3$; y-axis) for various days after treatment onset (x-axis) for various treatments.
Figure 64B:
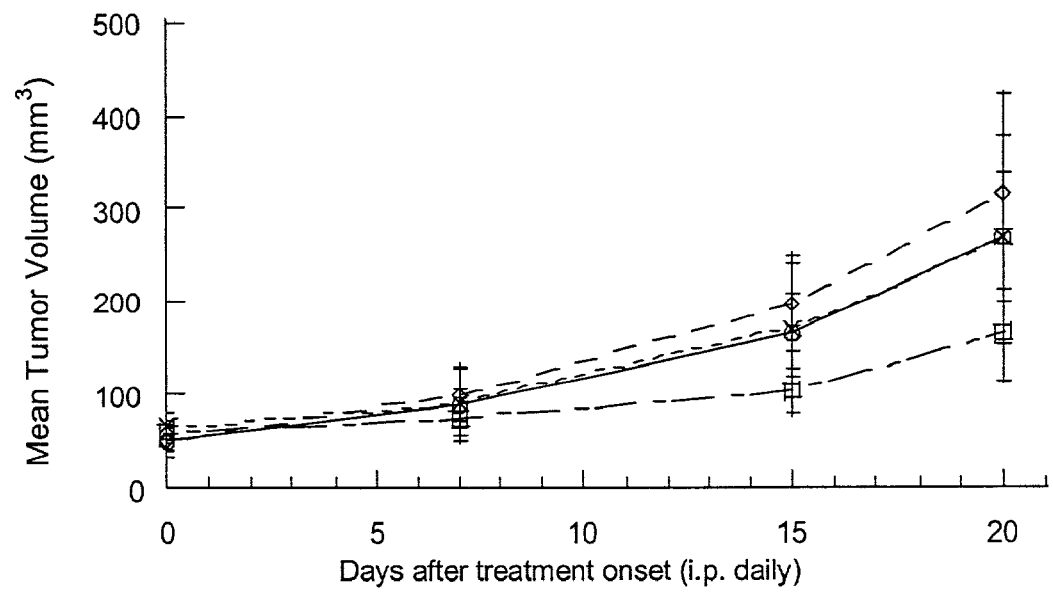

The results are also shown in FIGS. 64A and 64B, which are a pair of graphs showing mean tumor volume ratio (mm$^3$; y-axis) for various days after treatment onset (x-axis) for various treatments. In FIG. 64A, the treatments were: the stock vehicle used for T7 (°), T7 (□), stock vehicle used for T8 (◇), T8 daily (X), TP3 daily (+), SPI daily (Δ) and SP2 daily (●). In FIG. 64B, the treatments were: the stock vehicle for T8 (°), T8 daily (□); T8 twice weekly (◇) and T8 weekly (X).

No toxicity was observed in any groups, as judged by weight change (less than 10% weight loss). After 3 weeks of treatment with peptides administered i.p., daily, the results show that the 27-mer peptide T8, at a dose of 5 mg/kg, inhibited tumor growth by 45%. T7 at the same dose inhibited tumor growth by 66.8%, and TP3 at the same dose inhibited tumor growth by 53.2%. In all cases, the tumor growth inhibition was not quite significant, as determined by the student's t-test. The scrambled peptides SP1 and SP2 inhibited tumor growth to a lesser extent (31.7% and 18.7% respectively), which was not considered significant.

Differences in dose scheduling were also studied. T8, when administered at 5.0 mg/kg, twice or once a week, did not significantly inhibit tumor growth (8.1% and 39.5% respectively). Therefore, peptide TP3 appears to show tumor growth inhibitory activity similar to both T7 and T8 in the PC3 human prostate tumor xenograft model.

Example 59

Activity of T8, T8-3, P2, and SP2 Synthetic Peptides in MDAMB-435 Tumor Xenograft and PC3 Tumor Xenograft Models The antitumor activity of the synthetic peptides T8, T8-3, P2, and SP2 was evaluated against the MDAMB-435 human breast tumor xenograft model and the PC3 human prostate tumor xenograft model in nude mice.

Peptide T8 was synthesized, and also T8-3, which has the same sequence as T8, but in which serine is substituted for each cysteine.

(KQRFTTMPFLFSNVNDVSNFASRNDYS; SEQ ID NO:40), and P2, in which aspartic acid is substituted for each cysteine.

(KQRFTTMPFLFDNVNDVDNFASRNDYS; SEQ ID NO:42). SP2, a scrambled control peptide, was also synthesized. All were purified to greater than 90% purity via HPLC (<20 EU/mg). The peptides were neutralized prior to injection with 2.times.buffer 1:1 (v:v) of 50 mM glycine, 5 mM arginine, 10 mM Na-acetate, 9% D-mannitol (pH 8.2).

For tests involving the MDAMB-435 model, female nude NCRNU mice, 5-6 weeks old, weighing approximately 20 grams, were implanted with $2\times10^6$ MDAMB-435 cells into the subaxillary mammary fat pad. For tests involving the PC3 model, male nude NCRNU mice, 5-6 weeks old, weighing approximately 25 g were implanted with $2\times10^6$ PC3 cells into the dorsal subcutis. When the tumors were 100 mm$^3$ (for the MDAMB-435 model), or 60 mm$^3$ (for the PC3 model), the animals were pair-matched into treatment and control groups.

Each group contained 6-7 tumored mice, each of which was ear-tagged and followed individually throughout the experiment. Initial doses of peptide or vehicle control were given on the day of pair-matching (Day 0), and were administered daily via intraperitoneal (i.p.) injection at doses indicated. Mice were weighed weekly, and tumor measurements were taken by calipers weekly, starting on Day 0. These tumor measurements were converted to tumor volume by a well-known formula, $(V=W^2\times L/2)$ and mean tumor volumes were plotted against time. Mice were euthenized at the end of the treatment period. Upon termination, the mice were weighed, sacrificed and their tumors were excised. The mean tumor weight per group was calculated, and the mean treated tumor volume/control tumor volume×100 was subtracted from 100% to give the tumor growth inhibition (TGI) for each group.

The results for the MDAMB-435 and PC3 models are shown below in Tables 8 and 9, respectively.

TABLE 8

Summary of in vivo effects of peptides T8, T8-3, P2, and SP2 against 100 mm³ pre-existing MDAMB-345 tumor xenografts

| Treatment | Dosage (mg/kg) | Final Tumor Weight (V/Vo) ± SEM | % Tumor growth inhibition | t-test (p) |
|---|---|---|---|---|
| Control | — | 468.5 ± 48.06 | — | — |
| T8 | 5.0 | 231.9 ± 27.03 | 50.5 | 0.002 |
| SP2 | 5.0 | 527.2 ± 57.89 | — | — |
| T8-3 | 1.0 | 370.1 ± 68.17 | 21.0 | 0.278 |
| T8-3 | 5.0 | 272.4 ± 34.86 | 41.9 | 0.008 |
| P2 | 1.0 | 344.7 ± 34.20 | 26.4 | 0.055 |
| P2 | 5.0 | 380.5 ± 25.91 | 18.8 | 0.121 |

TABLE 9

Summary of in vivo effects of peptides T8, T8-3, P2, and SP2 against 60 mm³ pre-existing PC3 tumor xenografts

| Treatment | Dosage (mg/kg) | Final Tumor Weight (V/Vo) ± SEM | % Tumor growth inhibition | t-test (p) |
|---|---|---|---|---|
| Control | — | 1070.0 ± 132.5 | — | — |
| T8 | 5.0 | 691.4 ± 90.52 | 35.4 | 0.036* |
| SP2 | 5.0 | 931.0 ± 112.3 | 13.0 | 0.440 |
| T8-3 | 1.0 | 765.1 ± 133.6 | 28.5 | 0.131 |
| T8-3 | 5.0 | 691.5 ± 130.8 | 35.4 | 0.131 |
| P2 | 1.0 | 732.4 ± 85.96 | 31.6 | 0.054 |
| P2 | 5.0 | 899.7 ± 60.25 | 15.9 | 0.265 |

*p < 0.05

Figure 65A:
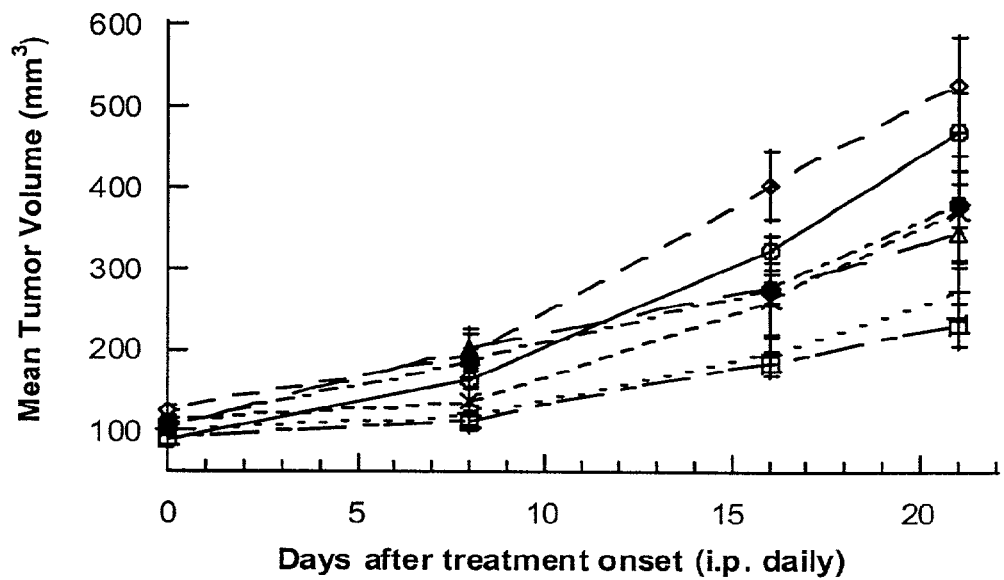
FIGS. 65A and 65B are a pair of graphs showing mean tumor volume (mm$^3$; y-axis) in an MDAMB-435 orthotopic human breast tumor xenograft model in nude mice (FIG. 65A) and PC3 human prostate tumor xenograft model in nude mice (FIG. 65B) for various days after treatment onset (x-axis) for control treatment (○), and daily treatment with T8 peptide at 5 mg/kg (□), SP2 at 5 mg/kg (◇), T8-3 at 1 mg/kg (X) or 5 mg/kg (+), or P2 at 1 mg/kg (Δ) or 5 mg/kg (●).
Figure 65B:
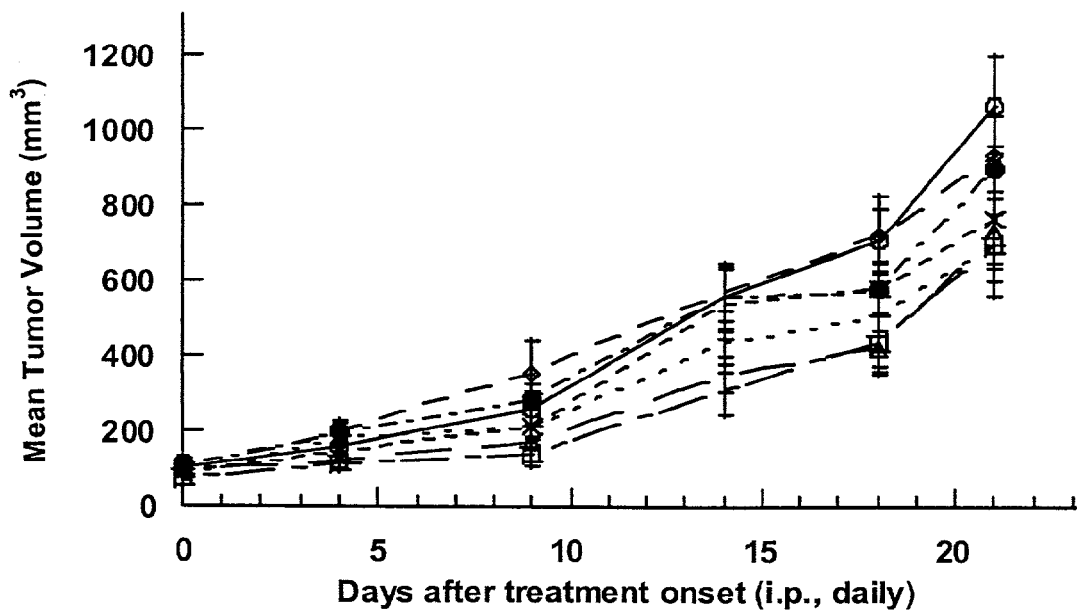

The results are also shown in FIGS. 65A and 65B, which are a pair of graphs showing mean tumor volume (mm³; y-axis) for various days after treatment onset (x-axis) for control treatment (°), and daily treatment with T8 peptide at 5 mg per kg (□), SP2 at 5 mg per kg (◇), T8-3 at 1 mg per kg (X) or 5 mg per kg (+), or P2 at 1 mg per kg (Δ) or 5 mg per kg (●). FIGS. 65A and 65B show the results for the MDAMB-435 and PC3 xenograft models, respectively. No toxicity was observed in any groups, as judged by weight change (less than 10% weight loss).

After 3 weeks of treatment with peptides administered i.p., daily, the results show that in the MDAMB-435 orthotopic human breast tumor xenograft model in nude mice, the 27-mer peptide T8, at a dose of 5 mg/kg, inhibited tumor growth by 50.5% (p=0.002). In addition, the T8-3 peptide at a dose of 5 mg/kg significantly inhibited tumor growth by 41.9% (p=0.008), although it was not effective at the lower dose of 1 mg/kg. The P2 peptide showed 26.4% inhibition of tumor growth at 1 mg/kg (not quite significant, p=0.55), however no significant inhibition was observed at 5 mg/kg. Additionally, the scrambled control peptide, SP2, showed no tumor growth inhibition at a dose of 5 mg/kg. In conclusion, the serine-substituted T8 variant, T8-3 has activity similar to T8 at inhibiting tumor growth in the MDAMB-435 orthotopic human breast tumor xenograft model.

In the PC3 human prostate tumor xenograft model in nude mice, the results show that after 3 weeks of treatment with peptides administered i.p., daily, the 27-mer peptide T8, at a dose of 5 mg/kg, inhibited tumor growth by 35.4% (p=0.036). In addition, the T8-3 peptide at a dose of 5 mg/kg also inhibited tumor growth by 35.4%, although the inhibition was not quite significant (p=0.065). The P2 peptide also showed tumor growth inhibition, although in this case the lower dose appeared more effective: at 1 mg/kg, TGI=31.6%, p=0.54, as opposed to at 5 mg/kg, TGI=15.9%, p=0.265. Additionally, the scrambled control peptide, SP2, showed no significant tumor growth inhibition at a dose of 5 mg/kg. In conclusion, both the serine-substituted T8 variant, T8-3 and the aspartic acid-substituted T8 variant, P2 show some tumor growth inhibitory activity in the PC3 human prostate tumor xenograft model. Although not quite significant, T8-3 appears to approximate T8 in its efficacy.

All references, patents, and patent applications are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated polypeptide consisting of the amino acid sequence Lys Leu Phe Cys Asn Val Asn Cys Val Cys Asn Phe Ala Ser Arg Asn Asp Tyr Ser (SEQ ID NO:41), wherein said polypeptide has the ability to of inhibit angiogenic activity or the ability to inhibit protein synthesis in endothelial cells.

2. An isolated polypeptide consisting of the amino acid sequence Thr Met Pro Phe Leu Phe Cys Ash Val Asn Asp Val Cys Ash Phe Ala Ser Arg Asn Asp Tyr Ser Tyr Trp Leu (SEQ ID NO:37), wherein said polypeptide has the ability to of inhibit angiogenic activity or the ability to inhibit protein synthesis in endothelial cells.

3. An isolated polypeptide consisting of the amino acid sequence Thr Met Pro Phe Met Phe Cys Asn Ile Ash Ash Val Cys Asn Phe Ala Set Arg Ash Asp Tyr Ser Tyr Trp Leu (SEQ ID NO:38).

4. An isolated polypeptide consisting of the amino acid sequence Lys Gln Arg Phe Thr Thr Met Pro Phe Leu Phe Cys Asn Val Asn Asp Val Cys Asn Phe Ala Ser Arg Asn Asp Tyr Ser (SEQ ID NO:39), wherein said polypeptide has the ability to of inhibit angiogenic activity or the ability to inhibit protein synthesis in endothelial cells.

5. An isolated polypeptide consisting of the amino acid sequence Lys Gln Arg Phe Thr Thr Met Pro Phe Leu Phe Ser Asn Val Asn Asp Val Ser Asn Phe Ala Set Arg Asn Asp Tyr Set (SEQ ID NO:40).

6. An isolated polypeptide consisting of the amino acid sequence Lys Gln Arg Phe Thr Tier Met Pro Phe Leu Phe Asp Asn Vat Asn Asp Val Asp Ash Phe Ala Ser Arg Asn Asp Tyr Ser (SEQ ID NO:42).

7. The isolated polypeptide of claim 2, wherein said polypeptide is capable of inhibiting tumor growth.

8. An isolated, mutated Tumstatin polypeptide of SEQ ID NO: 10 comprising one of the following mutations:

(a) wherein the Leu at position 77, Val and position 81 and Asp at position 83 have been substitute for Met, Ile and Asn, respectively;

(b) wherein the Leu at position 68 has been substituted for Lys;

(c) wherein the Leu at position 68, Cys at positions 79 and 85 have been substituted for Lys, Ser and Ser, respectively;

(d) wherein Phe at position 76 and Asp at position 83 have been substituted for Lys and Cys, respectively; or (e) wherein Leu at position 68 and Cys at positions 79 and 85 have been substituted for Lys, Asp and Asp, respectively; and wherein said mutated polypeptide has the ability to inhibit angiogenic activity or the ability to inhibit protein synthesis in endothelial cells.

9. An isolated, mutated Tumstatin polypeptide of SEQ ID NO: 10 having the amino acid sequence of SEQ ID NOs: 37-42, wherein said mutated polypeptide has the ability to inhibit angiogenic activity or the ability to inhibit protein synthesis in endothelial cells.

* * * * *

SEQUENCE LISTING

```
<160> NUMBER OF SEQ ID NOS: 58

<210> SEQ ID NO 1
<211> LENGTH: 690
<212> TYPE: DNA
<213> ORGANISM: Homo sapiens
<220> FEATURE:
<221> NAME/KEY: CDS
<222> LOCATION: (1)..(687)
<223> OTHER INFORMATION:

<400> SEQUENCE: 1 tct gtt gat cac ggc ttc ctt gtg acc agg cat agt caa aca ata gat      48
Ser Val Asp His Gly Phe Leu Val Thr Arg His Ser Gln Thr Ile Asp
1               5                   10                  15 gac cca cag tgt cct tct ggg acc aaa att ctt tac cac ggg tac tct      96
Asp Pro Gln Cys Pro Ser Gly Thr Lys Ile Leu Tyr His Gly Tyr Ser
            20                  25                  30 ttg ctc tac gtg caa ggc aat gaa cgg gcc cat gga cag gac ttg ggc     144
Leu Leu Tyr Val Gln Gly Asn Glu Arg Ala His Gly Gln Asp Leu Gly
        35                  40                  45
```

-continued

```
acg gcc ggc agc tgc ctg cgc aag ttc agc aca atg ccc ttc ctg ttc      192
Thr Ala Gly Ser Cys Leu Arg Lys Phe Ser Thr Met Pro Phe Leu Phe
 50                  55                  60 tgc aat att aac aac gtg tgc aac ttt gca tca cga aat gac tac tcg      240
Cys Asn Ile Asn Asn Val Cys Asn Phe Ala Ser Arg Asn Asp Tyr Ser
 65                  70                  75                  80 tac tgg ctg tcc acc cct gag ccc atg ccc atg tca atg gca ccc atc      288
Tyr Trp Leu Ser Thr Pro Glu Pro Met Pro Met Ser Met Ala Pro Ile
                 85                  90                  95 acg ggg gaa aac ata aga cca ttt att agt agg tgt gct gtg tgt gag      336
Thr Gly Glu Asn Ile Arg Pro Phe Ile Ser Arg Cys Ala Val Cys Glu
            100                 105                 110 gcg cct gcc atg gtg atg gcc gtg cac agc cag acc att cag atc cca      384
Ala Pro Ala Met Val Met Ala Val His Ser Gln Thr Ile Gln Ile Pro
        115                 120                 125 ccg tgc ccc agc ggg tgg tcc tcg ctg tgg atc ggc tac tct ttt gtg      432
Pro Cys Pro Ser Gly Trp Ser Ser Leu Trp Ile Gly Tyr Ser Phe Val
    130                 135                 140 atg cac acc agc gct ggt gca gaa ggc tct ggc caa gcc ctg gcg tcc      480
Met His Thr Ser Ala Gly Ala Glu Gly Ser Gly Gln Ala Leu Ala Ser
145                 150                 155                 160 ccc ggc tcc tgc ctg gag gag ttt aga agt gcg cca ttc atc gag tgt      528
Pro Gly Ser Cys Leu Glu Glu Phe Arg Ser Ala Pro Phe Ile Glu Cys
                165                 170                 175 cac ggc cgt ggg acc tgc aat tac tac gca aac gct tac agc ttt tgg      576
His Gly Arg Gly Thr Cys Asn Tyr Tyr Ala Asn Ala Tyr Ser Phe Trp
            180                 185                 190 ctc gcc acc ata gag agg agc gag atg ttc aag aag cct acg ccg tcc      624
Leu Ala Thr Ile Glu Arg Ser Glu Met Phe Lys Lys Pro Thr Pro Ser
        195                 200                 205 acc ttg aag gca ggg gag ctg cgc acg cac gtc agc cgc tgc caa gtc      672
Thr Leu Lys Ala Gly Glu Leu Arg Thr His Val Ser Arg Cys Gln Val
    210                 215                 220 tgt atg aga aga aca taa                                              690
Cys Met Arg Arg Thr
225
```

<210> SEQ ID NO 2
<211> LENGTH: 229
<212> TYPE: PRT
<213> ORGANISM: Homo sapiens

<400> SEQUENCE: 2

```
Ser Val Asp His Gly Phe Leu Val Thr Arg His Ser Gln Thr Ile Asp
  1               5                  10                  15

Asp Pro Gln Cys Pro Ser Gly Thr Lys Ile Leu Tyr His Gly Tyr Ser
                 20                  25                  30

Leu Leu Tyr Val Gln Gly Asn Glu Arg Ala His Gly Gln Asp Leu Gly
            35                  40                  45

Thr Ala Gly Ser Cys Leu Arg Lys Phe Ser Thr Met Pro Phe Leu Phe
        50                  55                  60

Cys Asn Ile Asn Asn Val Cys Asn Phe Ala Ser Arg Asn Asp Tyr Ser
 65                  70                  75                  80

Tyr Trp Leu Ser Thr Pro Glu Pro Met Pro Met Ser Met Ala Pro Ile
                 85                  90                  95

Thr Gly Glu Asn Ile Arg Pro Phe Ile Ser Arg Cys Ala Val Cys Glu
            100                 105                 110

Ala Pro Ala Met Val Met Ala Val His Ser Gln Thr Ile Gln Ile Pro
```

```
              115                 120                 125
Pro Cys Pro Ser Gly Trp Ser Ser Leu Trp Ile Gly Tyr Ser Phe Val
    130                 135                 140

Met His Thr Ser Ala Gly Ala Glu Gly Ser Gly Gln Ala Leu Ala Ser
145                 150                 155                 160

Pro Gly Ser Cys Leu Glu Glu Phe Arg Ser Ala Pro Phe Ile Glu Cys
                165                 170                 175

His Gly Arg Gly Thr Cys Asn Tyr Tyr Ala Asn Ala Tyr Ser Phe Trp
            180                 185                 190

Leu Ala Thr Ile Glu Arg Ser Glu Met Phe Lys Lys Pro Thr Pro Ser
        195                 200                 205

Thr Leu Lys Ala Gly Glu Leu Arg Thr His Val Ser Arg Cys Gln Val
    210                 215                 220

Cys Met Arg Arg Thr
225
```

<210> SEQ ID NO 3
<211> LENGTH: 27
<212> TYPE: DNA
<213> ORGANISM: Artificial sequence
<220> FEATURE:
<223> OTHER INFORMATION: pET22b(+) forward oligonucleotide primer for Arresten

<400> SEQUENCE: 3
cgggatcctt ctgttgatca cggcttc                                      27

<210> SEQ ID NO 4
<211> LENGTH: 27
<212> TYPE: DNA
<213> ORGANISM: Artificial sequence
<220> FEATURE:
<223> OTHER INFORMATION: pET22b(+) reverse oligonuceotide primer for Arresten

<400> SEQUENCE: 4
cccaagcttt gttcttctca tacagac                                      27

<210> SEQ ID NO 5
<211> LENGTH: 684
<212> TYPE: DNA
<213> ORGANISM: Homo sapiens
<220> FEATURE:
<221> NAME/KEY: CDS
<222> LOCATION: (1)..(681)
<223> OTHER INFORMATION:

<400> SEQUENCE: 5

```
gtc agc atc ggc tac ctc ctg gtg aag cac agc cag acg gac cag gag     48
Val Ser Ile Gly Tyr Leu Leu Val Lys His Ser Gln Thr Asp Gln Glu
1               5                   10                  15 ccc atg tgc ccg gtg ggc atg aac aaa ctc tgg agt gga tac agc ctg     96
Pro Met Cys Pro Val Gly Met Asn Lys Leu Trp Ser Gly Tyr Ser Leu
            20                  25                  30 ctg tac ttc gag ggc cag gag aag gcg cac aac cag gac ctg ggg ctg    144
Leu Tyr Phe Glu Gly Gln Glu Lys Ala His Asn Gln Asp Leu Gly Leu
        35                  40                  45 gcg ggc tcc tgc ctg gcg cgg ttc agc acc atg ccc ttc ctg tac tgc    192
Ala Gly Ser Cys Leu Ala Arg Phe Ser Thr Met Pro Phe Leu Tyr Cys
    50                  55                  60 aac cct ggt gat gtc tgc tac tat gcc agc cgg aac gac aag tcc tac    240
Asn Pro Gly Asp Val Cys Tyr Tyr Ala Ser Arg Asn Asp Lys Ser Tyr
```

```
                65                  70                  75                  80
tgg ctc tct acc act gcg ccg ctg ccc atg atg ccc gtg gcc gag gac          288
Trp Leu Ser Thr Thr Ala Pro Leu Pro Met Met Pro Val Ala Glu Asp
                    85                  90                  95 gag atc aag ccc tac atc agc cgc tgt tct gtg tgt gag gcc ccg gcc          336
Glu Ile Lys Pro Tyr Ile Ser Arg Cys Ser Val Cys Glu Ala Pro Ala
                100                 105                 110 atc gcc atc gcg gtc cac agt cag gat gtc tcc atc cca cac tgc cca          384
Ile Ala Ile Ala Val His Ser Gln Asp Val Ser Ile Pro His Cys Pro
            115                 120                 125 gct ggg tgg cgg agt ttg tgg atc gga tat tcc ttc ctc atg cac acg          432
Ala Gly Trp Arg Ser Leu Trp Ile Gly Tyr Ser Phe Leu Met His Thr
        130                 135                 140 gcg gcg gga gac gaa ggc ggt ggc caa tca ctg gtg tca ccg ggc agc          480
Ala Ala Gly Asp Glu Gly Gly Gly Gln Ser Leu Val Ser Pro Gly Ser
145                 150                 155                 160 tgt cta gag gac ttc cgc gcc aca cca ttc atc gaa tgc aat gga ggc          528
Cys Leu Glu Asp Phe Arg Ala Thr Pro Phe Ile Glu Cys Asn Gly Gly
                165                 170                 175 cgc ggc acc tgc cac tac tac gcc aac aag tac agc ttc tgg ctg acc          576
Arg Gly Thr Cys His Tyr Tyr Ala Asn Lys Tyr Ser Phe Trp Leu Thr
                180                 185                 190 acc att ccc gag cag agc ttc cag ggc tcg ccc tcc gcc gac acg ctc          624
Thr Ile Pro Glu Gln Ser Phe Gln Gly Ser Pro Ser Ala Asp Thr Leu
            195                 200                 205 aag gcc ggc ctc atc cgc aca cac atc agc cgc tgc cag gtg tgc atg          672
Lys Ala Gly Leu Ile Arg Thr His Ile Ser Arg Cys Gln Val Cys Met
    210                 215                 220 aag aac ctg tga                                                          684
Lys Asn Leu
225

<210> SEQ ID NO 6
<211> LENGTH: 227
<212> TYPE: PRT
<213> ORGANISM: Homo sapiens

<400> SEQUENCE: 6

Val Ser Ile Gly Tyr Leu Leu Val Lys His Ser Gln Thr Asp Gln Glu
1               5                   10                  15

Pro Met Cys Pro Val Gly Met Asn Lys Leu Trp Ser Gly Tyr Ser Leu
                20                  25                  30

Leu Tyr Phe Glu Gly Gln Glu Lys Ala His Asn Gln Asp Leu Gly Leu
            35                  40                  45

Ala Gly Ser Cys Leu Ala Arg Phe Ser Thr Met Pro Phe Leu Tyr Cys
    50                  55                  60

Asn Pro Gly Asp Val Cys Tyr Tyr Ala Ser Arg Asn Asp Lys Ser Tyr
65                  70                  75                  80

Trp Leu Ser Thr Thr Ala Pro Leu Pro Met Met Pro Val Ala Glu Asp
                85                  90                  95

Glu Ile Lys Pro Tyr Ile Ser Arg Cys Ser Val Cys Glu Ala Pro Ala
                100                 105                 110

Ile Ala Ile Ala Val His Ser Gln Asp Val Ser Ile Pro His Cys Pro
            115                 120                 125

Ala Gly Trp Arg Ser Leu Trp Ile Gly Tyr Ser Phe Leu Met His Thr
        130                 135                 140

Ala Ala Gly Asp Glu Gly Gly Gly Gln Ser Leu Val Ser Pro Gly Ser
145                 150                 155                 160
```

```
Cys Leu Glu Asp Phe Arg Ala Thr Pro Phe Ile Glu Cys Asn Gly Gly
            165                 170                 175

Arg Gly Thr Cys His Tyr Tyr Ala Asn Lys Tyr Ser Phe Trp Leu Thr
        180                 185                 190

Thr Ile Pro Glu Gln Ser Phe Gln Gly Ser Pro Ser Ala Asp Thr Leu
    195                 200                 205

Lys Ala Gly Leu Ile Arg Thr His Ile Ser Arg Cys Gln Val Cys Met
210                 215                 220

Lys Asn Leu
225

<210> SEQ ID NO 7
<211> LENGTH: 27
<212> TYPE: DNA
<213> ORGANISM: Artificial sequence
<220> FEATURE:
<223> OTHER INFORMATION: pET22b(+) forward oligonucleotide primer for
      Canstatin

<400> SEQUENCE: 7
cgggatcctg tcagcatcgg ctacctc                                         27

<210> SEQ ID NO 8
<211> LENGTH: 27
<212> TYPE: DNA
<213> ORGANISM: Artificial sequence
<220> FEATURE:
<223> OTHER INFORMATION: pET22b(+) reverse oligonucleotide primer for
      Canstatin

<400> SEQUENCE: 8
cccaagcttc aggttcttca tgcacac                                         27

<210> SEQ ID NO 9
<211> LENGTH: 735
<212> TYPE: DNA
<213> ORGANISM: Homo sapiens
<220> FEATURE:
<221> NAME/KEY: CDS
<222> LOCATION: (1)..(732)
<223> OTHER INFORMATION:

<400> SEQUENCE: 9
```

| | | | | | | | | | | | | | | | | |
|---|---|---|---|---|---|---|---|---|---|---|---|---|---|---|---|---|
| ggt | ttg | aaa | gga | aaa | cgt | gga | gac | agt | gga | tca | cct | gca | acc | tgg | aca | 48 |
| Gly | Leu | Lys | Gly | Lys | Arg | Gly | Asp | Ser | Gly | Ser | Pro | Ala | Thr | Trp | Thr | |
| 1 | | | | 5 | | | | | 10 | | | | | 15 | | |
| acg | aga | ggc | ttt | gtc | ttc | acc | cga | cac | agt | caa | acc | aca | gca | att | cct | 96 |
| Thr | Arg | Gly | Phe | Val | Phe | Thr | Arg | His | Ser | Gln | Thr | Thr | Ala | Ile | Pro | |
| | | 20 | | | | | 25 | | | | | 30 | | | | |
| tca | tgt | cca | gag | ggg | aca | gtg | cca | ctc | tac | agt | ggg | ttt | tct | ttt | ctt | 144 |
| Ser | Cys | Pro | Glu | Gly | Thr | Val | Pro | Leu | Tyr | Ser | Gly | Phe | Ser | Phe | Leu | |
| | 35 | | | | | 40 | | | | | 45 | | | | | |
| ttt | gta | caa | gga | aat | caa | cga | gcc | cac | gga | caa | gac | ctt | gga | act | ctt | 192 |
| Phe | Val | Gln | Gly | Asn | Gln | Arg | Ala | His | Gly | Gln | Asp | Leu | Gly | Thr | Leu | |
| | 50 | | | | | 55 | | | | | 60 | | | | | |
| ggc | agc | tgc | ctg | cag | cga | ttt | acc | aca | atg | cca | ttc | tta | ttc | tgc | aat | 240 |
| Gly | Ser | Cys | Leu | Gln | Arg | Phe | Thr | Thr | Met | Pro | Phe | Leu | Phe | Cys | Asn | |
| 65 | | | | | 70 | | | | | 75 | | | | | 80 | |
| gtc | aat | gat | gta | tgt | aat | ttt | gca | tct | cga | aat | gat | tat | tca | tac | tgg | 288 |
| Val | Asn | Asp | Val | Cys | Asn | Phe | Ala | Ser | Arg | Asn | Asp | Tyr | Ser | Tyr | Trp | |
| | | | | 85 | | | | | 90 | | | | | 95 | | |
| ctg | tca | aca | cca | gct | ctg | atg | cca | atg | aac | atg | gct | ccc | att | act | ggc | 336 |

```
Leu Ser Thr Pro Ala Leu Met Pro Met Asn Met Ala Pro Ile Thr Gly
            100                 105                 110 aga gcc ctt gag cct tat ata agc aga tgc act gtt tgt gaa ggt cct      384
Arg Ala Leu Glu Pro Tyr Ile Ser Arg Cys Thr Val Cys Glu Gly Pro
            115                 120                 125 gcg atc gcc ata gcc gtt cac agc caa acc act gac att cct cca tgt      432
Ala Ile Ala Ile Ala Val His Ser Gln Thr Thr Asp Ile Pro Pro Cys
        130                 135                 140 cct cac ggc tgg att tct ctc tgg aaa gga ttt tca ttc atc atg ttc      480
Pro His Gly Trp Ile Ser Leu Trp Lys Gly Phe Ser Phe Ile Met Phe
145                 150                 155                 160 aca agt gca ggt tct gag ggc acc ggg caa gca ctg gcc tcc cct ggc      528
Thr Ser Ala Gly Ser Glu Gly Thr Gly Gln Ala Leu Ala Ser Pro Gly
                165                 170                 175 tcc tgc ctg gaa gaa ttc cga gcc agc cca ttt cta gaa tgt cat gga      576
Ser Cys Leu Glu Glu Phe Arg Ala Ser Pro Phe Leu Glu Cys His Gly
                180                 185                 190 aga gga acg tgc aac tac tat tca aat tcc tac agt ttc tgg ctg gct      624
Arg Gly Thr Cys Asn Tyr Tyr Ser Asn Ser Tyr Ser Phe Trp Leu Ala
            195                 200                 205 tca tta aac cca gaa aga atg ttc aga aag cct att cca tca act gtg      672
Ser Leu Asn Pro Glu Arg Met Phe Arg Lys Pro Ile Pro Ser Thr Val
        210                 215                 220 aaa gct ggg gaa tta gaa aaa ata ata agt cgc tgt cag gtg tgc atg      720
Lys Ala Gly Glu Leu Glu Lys Ile Ile Ser Arg Cys Gln Val Cys Met
225                 230                 235                 240 aag aaa aga cac tga                                                  735
Lys Lys Arg His <210> SEQ ID NO 10
<211> LENGTH: 244
<212> TYPE: PRT
<213> ORGANISM: Homo sapiens

<400> SEQUENCE: 10

Gly Leu Lys Gly Lys Arg Gly Asp Ser Gly Ser Pro Ala Thr Trp Thr
1               5                   10                  15

Thr Arg Gly Phe Val Phe Thr Arg His Ser Gln Thr Thr Ala Ile Pro
            20                  25                  30

Ser Cys Pro Glu Gly Thr Val Pro Leu Tyr Ser Gly Phe Ser Phe Leu
        35                  40                  45

Phe Val Gln Gly Asn Gln Arg Ala His Gly Gln Asp Leu Gly Thr Leu
    50                  55                  60

Gly Ser Cys Leu Gln Arg Phe Thr Thr Met Pro Phe Leu Phe Cys Asn
65                  70                  75                  80

Val Asn Asp Val Cys Asn Phe Ala Ser Arg Asn Asp Tyr Ser Tyr Trp
                85                  90                  95

Leu Ser Thr Pro Ala Leu Met Pro Met Asn Met Ala Pro Ile Thr Gly
            100                 105                 110

Arg Ala Leu Glu Pro Tyr Ile Ser Arg Cys Thr Val Cys Glu Gly Pro
            115                 120                 125

Ala Ile Ala Ile Ala Val His Ser Gln Thr Thr Asp Ile Pro Pro Cys
        130                 135                 140

Pro His Gly Trp Ile Ser Leu Trp Lys Gly Phe Ser Phe Ile Met Phe
145                 150                 155                 160

Thr Ser Ala Gly Ser Glu Gly Thr Gly Gln Ala Leu Ala Ser Pro Gly
                165                 170                 175
```

-continued

```
Ser Cys Leu Glu Glu Phe Arg Ala Ser Pro Phe Leu Glu Cys His Gly
            180                 185                 190

Arg Gly Thr Cys Asn Tyr Tyr Ser Asn Ser Tyr Ser Phe Trp Leu Ala
        195                 200                 205

Ser Leu Asn Pro Glu Arg Met Phe Arg Lys Pro Ile Pro Ser Thr Val
    210                 215                 220

Lys Ala Gly Glu Leu Glu Lys Ile Ile Ser Arg Cys Gln Val Cys Met
225                 230                 235                 240

Lys Lys Arg His

<210> SEQ ID NO 11
<211> LENGTH: 27
<212> TYPE: DNA
<213> ORGANISM: Artificial sequence
<220> FEATURE:
<223> OTHER INFORMATION: pET22b(+) forward oligonucleotide primer for
      Tumstatin

<400> SEQUENCE: 11
cgggatccgg gtttgaaagg aaaacgt                                            27

<210> SEQ ID NO 12
<211> LENGTH: 27
<212> TYPE: DNA
<213> ORGANISM: Artificial sequence
<220> FEATURE:
<223> OTHER INFORMATION: pET22b(+) reverse oligonucleotide primer for
      Tumstatin
<220> FEATURE:
<221> NAME/KEY: misc_feature
<222> LOCATION: (1)..(27)
<223> OTHER INFORMATION: primer

<400> SEQUENCE: 12
cccaagcttt cagtgtcttt tcttcat                                            27

<210> SEQ ID NO 13
<211> LENGTH: 8
<212> TYPE: PRT
<213> ORGANISM: Artificial sequence
<220> FEATURE:
<223> OTHER INFORMATION: Additional vector sequence added to protein

<400> SEQUENCE: 13

Met Asp Ile Gly Ile Asn Ser Asp
1               5

<210> SEQ ID NO 14
<211> LENGTH: 7
<212> TYPE: PRT
<213> ORGANISM: Artificial sequence
<220> FEATURE:
<223> OTHER INFORMATION: Additional vector sequence added to protein

<400> SEQUENCE: 14

Lys Leu Ala Ala Ala Leu Glu
1               5

<210> SEQ ID NO 15
<211> LENGTH: 28
<212> TYPE: DNA
<213> ORGANISM: Artificial sequence
<220> FEATURE:
<223> OTHER INFORMATION: pPICZaA forward oligonucleotide primer for
      Arresten
```

-continued

```
<400> SEQUENCE: 15
ttcggaattc tctgttgatc acggcttc                                              28

<210> SEQ ID NO 16
<211> LENGTH: 35
<212> TYPE: DNA
<213> ORGANISM: Artificial sequence
<220> FEATURE:
<223> OTHER INFORMATION: pPICZaA reverse oligonucleotide primer for
      Arresten

<400> SEQUENCE: 16
tgctctagag gtgttcttct catacagact tggca                                      35

<210> SEQ ID NO 17
<211> LENGTH: 31
<212> TYPE: DNA
<213> ORGANISM: Artificial sequence
<220> FEATURE:
<223> OTHER INFORMATION: pPICZaA forward oligonucleotide primer for
      Canstatin

<400> SEQUENCE: 17
ttcggaattc gtcagcatcg gctacctcct g                                          31

<210> SEQ ID NO 18
<211> LENGTH: 32
<212> TYPE: DNA
<213> ORGANISM: Artificial sequence
<220> FEATURE:
<223> OTHER INFORMATION: pPICZaA reverse oligonucleotide primer for
      Canstatin

<400> SEQUENCE: 18
ggggtacccc caggttcttc atgcacacct gg                                         32

<210> SEQ ID NO 19
<211> LENGTH: 1
<212> TYPE: PRT
<213> ORGANISM: Artificial Sequence
<220> FEATURE:
<223> OTHER INFORMATION: Deleted Sequence

<400> SEQUENCE: 19

Pro
1

<210> SEQ ID NO 20
<211> LENGTH: 124
<212> TYPE: PRT
<213> ORGANISM: Artificial Sequence
<220> FEATURE:
<223> OTHER INFORMATION: Tumstatin 333 (amino acids 1-124 of3
      SEQ ID NO:10)

<400> SEQUENCE: 20

Gly Leu Lys Gly Lys Arg Gly Asp Ser Gly Ser Pro Ala Thr Trp Thr
1               5                   10                  15

Thr Arg Gly Phe Val Phe Thr Arg His Ser Gln Thr Thr Ala Ile Pro
                20                  25                  30

Ser Cys Pro Glu Gly Thr Val Pro Leu Tyr Ser Gly Phe Ser Phe Leu
            35                  40                  45

Phe Val Gln Gly Asn Gln Arg Ala His Gly Gln Asp Leu Gly Thr Leu
        50                  55                  60
```

```
Gly Ser Cys Leu Gln Arg Phe Thr Thr Met Pro Phe Leu Phe Cys Asn
 65                  70                  75                  80

Val Asn Asp Val Cys Asn Phe Ala Ser Arg Asn Asp Tyr Ser Tyr Trp
                 85                  90                  95

Leu Ser Thr Pro Ala Leu Met Pro Met Asn Met Ala Pro Ile Thr Gly
            100                 105                 110

Arg Ala Leu Glu Pro Tyr Ile Ser Arg Cys Thr Val
        115                 120
```

<210> SEQ ID NO 21
<211> LENGTH: 120
<212> TYPE: PRT
<213> ORGANISM: Artificial Sequence
<220> FEATURE:
<223> OTHER INFORMATION: Tumstatin 334 (amino acids 125-244 of
      SEQ ID NO:10)

<400> SEQUENCE: 21

```
Cys Glu Gly Pro Ala Ile Ala Ile Ala Val His Ser Gln Thr Thr Asp
  1               5                  10                  15

Ile Pro Pro Cys Pro His Gly Trp Ile Ser Leu Trp Lys Gly Phe Ser
                 20                  25                  30

Phe Ile Met Phe Thr Ser Ala Gly Ser Glu Gly Thr Gly Gln Ala Leu
             35                  40                  45

Ala Ser Pro Gly Ser Cys Leu Glu Glu Phe Arg Ala Ser Pro Phe Leu
         50                  55                  60

Glu Cys His Gly Arg Gly Thr Cys Asn Tyr Tyr Ser Asn Ser Tyr Ser
 65                  70                  75                  80

Phe Trp Leu Ala Ser Leu Asn Pro Glu Arg Met Phe Arg Lys Pro Ile
                 85                  90                  95

Pro Ser Thr Val Lys Ala Gly Glu Leu Glu Lys Ile Ile Ser Arg Cys
            100                 105                 110

Gln Val Cys Met Lys Lys Arg His
        115                 120
```

<210> SEQ ID NO 22
<211> LENGTH: 191
<212> TYPE: PRT
<213> ORGANISM: Artificial Sequence
<220> FEATURE:
<223> OTHER INFORMATION: Tum-1 (Tumstatin N-53) (amino acids 54-244 of
      SEQ ID NO:10)

<400> SEQUENCE: 22

```
Gln Arg Ala His Gly Gln Asp Leu Gly Thr Leu Gly Ser Cys Leu Gln
  1               5                  10                  15

Arg Phe Thr Thr Met Pro Phe Leu Phe Cys Asn Val Asn Asp Val Cys
                 20                  25                  30

Asn Phe Ala Ser Arg Asn Asp Tyr Ser Tyr Trp Leu Ser Thr Pro Ala
             35                  40                  45

Leu Met Pro Met Asn Met Ala Pro Ile Thr Gly Arg Ala Leu Glu Pro
         50                  55                  60

Tyr Ile Ser Arg Cys Thr Val Cys Glu Gly Pro Ala Ile Ala Ile Ala
 65                  70                  75                  80

Val His Ser Gln Thr Thr Asp Ile Pro Pro Cys Pro His Gly Trp Ile
                 85                  90                  95

Ser Leu Trp Lys Gly Phe Ser Phe Ile Met Phe Thr Ser Ala Gly Ser
            100                 105                 110
```

```
Glu Gly Thr Gly Gln Ala Leu Ala Ser Pro Gly Ser Cys Leu Glu Glu
        115                 120                 125

Phe Arg Ala Ser Pro Phe Leu Glu Cys His Gly Arg Gly Thr Cys Asn
        130                 135                 140

Tyr Tyr Ser Asn Ser Tyr Ser Phe Trp Leu Ala Ser Leu Asn Pro Glu
145                 150                 155                 160

Arg Met Phe Arg Lys Pro Ile Pro Ser Thr Val Lys Ala Gly Glu Leu
                165                 170                 175

Glu Lys Ile Ile Ser Arg Cys Gln Val Cys Met Lys Lys Arg His
        180                 185                 190

<210> SEQ ID NO 23
<211> LENGTH: 132
<212> TYPE: PRT
<213> ORGANISM: Artificial Sequence
<220> FEATURE:
<223> OTHER INFORMATION: Tum-2 (amino acids 1-132 of SEQ ID NO:10)

<400> SEQUENCE: 23

Gly Leu Lys Gly Lys Arg Gly Asp Ser Gly Ser Pro Ala Thr Trp Thr
1               5                   10                  15

Thr Arg Gly Phe Val Phe Thr Arg His Ser Gln Thr Thr Ala Ile Pro
                20                  25                  30

Ser Cys Pro Glu Gly Thr Val Pro Leu Tyr Ser Gly Phe Ser Phe Leu
        35                  40                  45

Phe Val Gln Gly Asn Gln Arg Ala His Gly Gln Asp Leu Gly Thr Leu
    50                  55                  60

Gly Ser Cys Leu Gln Arg Phe Thr Thr Met Pro Phe Leu Phe Cys Asn
65                  70                  75                  80

Val Asn Asp Val Cys Asn Phe Ala Ser Arg Asn Asp Tyr Ser Tyr Trp
                85                  90                  95

Leu Ser Thr Pro Ala Leu Met Pro Met Asn Met Ala Pro Ile Thr Gly
            100                 105                 110

Arg Ala Leu Glu Pro Tyr Ile Ser Arg Cys Thr Val Cys Glu Gly Pro
        115                 120                 125

Ala Ile Ala Ile
    130

<210> SEQ ID NO 24
<211> LENGTH: 112
<212> TYPE: PRT
<213> ORGANISM: Artificial Sequence
<220> FEATURE:
<223> OTHER INFORMATION: Tum-3 (amino acids 133-244 of SEQ ID NO:10)

<400> SEQUENCE: 24

Ala Val His Ser Gln Thr Thr Asp Ile Pro Pro Cys Pro His Gly Trp
1               5                   10                  15

Ile Ser Leu Trp Lys Gly Phe Ser Phe Ile Met Phe Thr Ser Ala Gly
                20                  25                  30

Ser Glu Gly Thr Gly Gln Ala Leu Ala Ser Pro Gly Ser Cys Leu Glu
        35                  40                  45

Glu Phe Arg Ala Ser Pro Phe Leu Glu Cys His Gly Arg Gly Thr Cys
    50                  55                  60

Asn Tyr Tyr Ser Asn Ser Tyr Ser Phe Trp Leu Ala Ser Leu Asn Pro
65                  70                  75                  80

Glu Arg Met Phe Arg Lys Pro Ile Pro Ser Thr Val Lys Ala Gly Glu
                85                  90                  95
```

```
Leu Glu Lys Ile Ile Ser Arg Cys Gln Val Cys Met Lys Lys Arg His
        100                 105                 110
```

<210> SEQ ID NO 25
<211> LENGTH: 64
<212> TYPE: PRT
<213> ORGANISM: Artificial Sequence
<220> FEATURE:
<223> OTHER INFORMATION: Tum-4 (amino acids 181-244 of SEQ ID NO:10)

<400> SEQUENCE: 25

```
Glu Phe Arg Ala Ser Pro Phe Leu Glu Cys His Gly Arg Gly Thr Cys
1               5                   10                  15

Asn Tyr Tyr Ser Asn Ser Tyr Ser Phe Trp Leu Ala Ser Leu Asn Pro
            20                  25                  30

Glu Arg Met Phe Arg Lys Pro Ile Pro Ser Thr Val Lys Ala Gly Glu
        35                  40                  45

Leu Glu Lys Ile Ile Ser Arg Cys Gln Val Cys Met Lys Lys Arg His
    50                  55                  60
```

<210> SEQ ID NO 26
<211> LENGTH: 79
<212> TYPE: PRT
<213> ORGANISM: Artificial Sequence
<220> FEATURE:
<223> OTHER INFORMATION: Tum-5 (amino acids 54-132 of SEQ ID NO:10)

<400> SEQUENCE: 26

```
Gln Arg Ala His Gly Gln Asp Leu Gly Thr Leu Gly Ser Cys Leu Gln
1               5                   10                  15

Arg Phe Thr Thr Met Pro Phe Leu Phe Cys Asn Val Asn Asp Val Cys
            20                  25                  30

Asn Phe Ala Ser Arg Asn Asp Tyr Ser Tyr Trp Leu Ser Thr Pro Ala
        35                  40                  45

Leu Met Pro Met Asn Met Ala Pro Ile Thr Gly Arg Ala Leu Glu Pro
    50                  55                  60

Tyr Ile Ser Arg Cys Thr Val Cys Glu Gly Pro Ala Ile Ala Ile
65                  70                  75
```

<210> SEQ ID NO 27
<211> LENGTH: 19
<212> TYPE: PRT
<213> ORGANISM: Artificial Sequence
<220> FEATURE:
<223> OTHER INFORMATION: T1 (amino acids 1-19 of SEQ ID NO:10)

<400> SEQUENCE: 27

```
Gly Leu Lys Gly Lys Arg Gly Asp Ser Gly Ser Pro Ala Thr Trp Thr
1               5                   10                  15

Thr Arg Gly
```

<210> SEQ ID NO 28
<211> LENGTH: 20
<212> TYPE: PRT
<213> ORGANISM: Artificial Sequence
<220> FEATURE:
<223> OTHER INFORMATION: T2 (amino acids 53-72 of SEQ ID NO:10)

<400> SEQUENCE: 28

```
Asn Gln Arg Ala His Gly Gln Asp Leu Gly Thr Leu Gly Ser Cys Leu
1               5                   10                  15
```

```
Gln Arg Phe Thr
            20

<210> SEQ ID NO 29
<211> LENGTH: 20
<212> TYPE: PRT
<213> ORGANISM: Artificial Sequence
<220> FEATURE:
<223> OTHER INFORMATION: T3 (amino acids 68-87 of SEQ ID NO:10)

<400> SEQUENCE: 29

Leu Gln Arg Phe Thr Thr Met Pro Phe Leu Phe Cys Asn Val Asn Asp
1               5                   10                  15

Val Cys Asn Phe
            20

<210> SEQ ID NO 30
<211> LENGTH: 20
<212> TYPE: PRT
<213> ORGANISM: Artificial Sequence
<220> FEATURE:
<223> OTHER INFORMATION: T4 (amino acids 83-102 of SEQ ID NO:10)

<400> SEQUENCE: 30

Asp Val Cys Asn Phe Ala Ser Arg Asn Asp Tyr Ser Tyr Trp Leu Ser
1               5                   10                  15

Thr Pro Ala Leu
            20

<210> SEQ ID NO 31
<211> LENGTH: 19
<212> TYPE: PRT
<213> ORGANISM: Artificial Sequence
<220> FEATURE:
<223> OTHER INFORMATION: T5 (amino acids 98-116 of SEQ ID NO:10)

<400> SEQUENCE: 31

Ser Thr Pro Ala Leu Met Pro Met Asn Met Ala Pro Ile Thr Gly Arg
1               5                   10                  15

Ala Leu Glu

<210> SEQ ID NO 32
<211> LENGTH: 19
<212> TYPE: PRT
<213> ORGANISM: Artificial Sequence
<220> FEATURE:
<223> OTHER INFORMATION: T6 (amino acids 113-131 of SEQ ID NO:10)

<400> SEQUENCE: 32

Arg Ala Leu Glu Pro Tyr Ile Ser Arg Cys Thr Val Cys Glu Gly Pro
1               5                   10                  15

Ala Ile Ala

<210> SEQ ID NO 33
<211> LENGTH: 88
<212> TYPE: PRT
<213> ORGANISM: Artificial Sequence
<220> FEATURE:
<223> OTHER INFORMATION: Tumstatin-45-132 (amino acids 45-132 of
      SEQ ID NO:10)

<400> SEQUENCE: 33

Phe Ser Phe Leu Phe Val Gln Gly Asn Gln Arg Ala His Gly Gln Asp
1               5                   10                  15
```

```
Leu Gly Thr Leu Gly Ser Cys Leu Gln Arg Phe Thr Thr Met Pro Phe
            20                  25                  30

Leu Phe Cys Asn Val Asn Asp Val Cys Asn Phe Ala Ser Arg Asn Asp
        35                  40                  45

Tyr Ser Tyr Trp Leu Ser Thr Pro Ala Leu Met Pro Met Asn Met Ala
    50                  55                  60

Pro Ile Thr Gly Arg Ala Leu Glu Pro Tyr Ile Ser Arg Cys Thr Val
65                  70                  75                  80

Cys Glu Gly Pro Ala Ile Ala Ile
                85
```

<210> SEQ ID NO 34
<211> LENGTH: 88
<212> TYPE: PRT
<213> ORGANISM: Artificial Sequence
<220> FEATURE:
<223> OTHER INFORMATION: Tumstatin-5-125-C-A (amino acids 45-132 of
      SEQ ID NO:10; alanine has been substituted for the cysteine
      residue at position 125 of the full-length Tumstatin molecule)

<400> SEQUENCE: 34

```
Phe Ser Phe Leu Phe Val Gln Gly Asn Gln Arg Ala His Gly Gln Asp
1               5                   10                  15

Leu Gly Thr Leu Gly Ser Cys Leu Gln Arg Phe Thr Thr Met Pro Phe
            20                  25                  30

Leu Phe Cys Asn Val Asn Asp Val Cys Asn Phe Ala Ser Arg Asn Asp
        35                  40                  45

Tyr Ser Tyr Trp Leu Ser Thr Pro Ala Leu Met Pro Met Asn Met Ala
    50                  55                  60

Pro Ile Thr Gly Arg Ala Leu Glu Pro Tyr Ile Ser Arg Cys Thr Val
65                  70                  75                  80

Ala Glu Gly Pro Ala Ile Ala Ile
                85
```

<210> SEQ ID NO 35
<211> LENGTH: 9
<212> TYPE: PRT
<213> ORGANISM: Artificial Sequence
<220> FEATURE:
<223> OTHER INFORMATION: synthetic blocking peptide

<400> SEQUENCE: 35

```
Cys Asp Cys Arg Gly Asp Cys Phe Cys
1               5
```

<210> SEQ ID NO 36
<211> LENGTH: 5
<212> TYPE: PRT
<213> ORGANISM: Artificial Sequence
<220> FEATURE:
<223> OTHER INFORMATION: synthetic blocking peptide

<400> SEQUENCE: 36

```
Cys Asn Gly Arg Cys
1               5
```

<210> SEQ ID NO 37
<211> LENGTH: 25
<212> TYPE: PRT
<213> ORGANISM: Artificial Sequence
<220> FEATURE:
<223> OTHER INFORMATION: T7 (amino acids 73-97 of SEQ ID NO:10)

```
<400> SEQUENCE: 37

Thr Met Pro Phe Leu Phe Cys Asn Val Asn Asp Val Cys Asn Phe Ala
1               5                   10                  15

Ser Arg Asn Asp Tyr Ser Tyr Trp Leu
            20                  25

<210> SEQ ID NO 38
<211> LENGTH: 25
<212> TYPE: PRT
<213> ORGANISM: Artificial Sequence
<220> FEATURE:
<223> OTHER INFORMATION: T7-mutant (amino acids 73-97 of SEQ ID NO:10;
      methionine has been substituted for the leucine residue at
      position 77 of the full-length Tumstatin molecule, and isoleucine
      has been substituted for valine at position 81, and asparagine has
      been substituted for aspartic acid at position 83)

<400> SEQUENCE: 38

Thr Met Pro Phe Met Phe Cys Asn Ile Asn Asn Val Cys Asn Phe Ala
1               5                   10                  15

Ser Arg Asn Asp Tyr Ser Tyr Trp Leu
            20                  25

<210> SEQ ID NO 39
<211> LENGTH: 27
<212> TYPE: PRT
<213> ORGANISM: Artificial Sequence
<220> FEATURE:
<223> OTHER INFORMATION: T8 (amino acids 68-94 of SEQ ID NO:10; lysine
      has been substituted for the leucine residue at position 68 of the
      full-length Tumstatin molecule)

<400> SEQUENCE: 39

Lys Gln Arg Phe Thr Thr Met Pro Phe Leu Phe Cys Asn Val Asn Asp
1               5                   10                  15

Val Cys Asn Phe Ala Ser Arg Asn Asp Tyr Ser
            20                  25

<210> SEQ ID NO 40
<211> LENGTH: 27
<212> TYPE: PRT
<213> ORGANISM: Artificial Sequence
<220> FEATURE:
<223> OTHER INFORMATION: T8-3 (amino acids 68-94 of SEQ ID NO:10; lysine
      has been substituted for the leucine residue at position 68 of the
      full-length Tumstatin molecule, and serine has been substituted
      for the cysteine residues at positions 79 and 85)

<400> SEQUENCE: 40

Lys Gln Arg Phe Thr Thr Met Pro Phe Leu Phe Ser Asn Val Asn Asp
1               5                   10                  15

Val Ser Asn Phe Ala Ser Arg Asn Asp Tyr Ser
            20                  25

<210> SEQ ID NO 41
<211> LENGTH: 19
<212> TYPE: PRT
<213> ORGANISM: Artificial Sequence
<220> FEATURE:
<223> OTHER INFORMATION: TP3 (amino acids 76-94 of SEQ ID NO:10; lysine
      has been substituted for the phenylalanine residue at position 76
      of the full-length Tumstatin molecule, and cysteine has been
      substituted for the aspartic acid at position 83)

<400> SEQUENCE: 41

Lys Leu Phe Cys Asn Val Asn Cys Val Cys Asn Phe Ala Ser Arg Asn
```

Asp Tyr Ser

<210> SEQ ID NO 42
<211> LENGTH: 27
<212> TYPE: PRT
<213> ORGANISM: Artificial Sequence
<220> FEATURE:
<223> OTHER INFORMATION: P2 (amino acids 68-94 of SEQ ID NO:10; lysine
      has been substituted for the leucine residue at position 68 of the
      full-length Tumstatin molecule, and aspartic acid has been
      substituted for the cysteine residues at positions 79 and 85)

<400> SEQUENCE: 42

Lys Gln Arg Phe Thr Thr Met Pro Phe Leu Phe Asp Asn Val Asn Asp
1               5                   10                  15

Val Asp Asn Phe Ala Ser Arg Asn Asp Tyr Ser
            20                  25

<210> SEQ ID NO 43
<211> LENGTH: 27
<212> TYPE: PRT
<213> ORGANISM: Artificial Sequence
<220> FEATURE:
<223> OTHER INFORMATION: Scrambled peptide SP1

<400> SEQUENCE: 43

Ala Asn Met Ser Arg Asn Val Phe Phe Asp Cys Thr Ser Phe Pro Val
1               5                   10                  15

Cys Gln Lys Phe Leu Asn Asp Thr Arg Asn Tyr
            20                  25

<210> SEQ ID NO 44
<211> LENGTH: 27
<212> TYPE: PRT
<213> ORGANISM: Artificial Sequence
<220> FEATURE:
<223> OTHER INFORMATION: Scrambled peptide SP2

<400> SEQUENCE: 44

Thr Phe Asn Cys Val Lys Asn Tyr Gln Arg Leu Asp Phe Thr Ser Arg
1               5                   10                  15

Phe Val Met Asp Ser Cys Ala Asn Phe Pro Asn
            20                  25

<210> SEQ ID NO 45
<211> LENGTH: 14
<212> TYPE: PRT
<213> ORGANISM: Artificial Sequence
<220> FEATURE:
<223> OTHER INFORMATION: Generic peptide
<220> FEATURE:
<221> NAME/KEY: MISC_FEATURE
<222> LOCATION: (1)..(1)
<223> OTHER INFORMATION: Xaa at position 1 is any amino acid
<220> FEATURE:
<221> NAME/KEY: MISC_FEATURE
<222> LOCATION: (2)..(2)
<223> OTHER INFORMATION: Xaa at position 2 is Phe or Lys
<220> FEATURE:
<221> NAME/KEY: MISC_FEATURE
<222> LOCATION: (5)..(5)
<223> OTHER INFORMATION: Xaa at position 5 is Cys, Ser or Asp
<220> FEATURE:
<221> NAME/KEY: MISC_FEATURE
<222> LOCATION: (9)..(9)
<223> OTHER INFORMATION: Xaa at position 9 is Asp or Cys
<220> FEATURE:

```
<221> NAME/KEY: MISC_FEATURE
<222> LOCATION: (11)..(11)
<223> OTHER INFORMATION: Xaa at position 11 is Cys, Ser or Asp
<220> FEATURE:
<221> NAME/KEY: MISC_FEATURE
<222> LOCATION: (14)..(14)
<223> OTHER INFORMATION: Xaa at position 14 is any amino acid

<400> SEQUENCE: 45

Xaa Xaa Leu Phe Xaa Asn Val Asn Xaa Val Xaa Asn Phe Xaa
 1               5                  10

<210> SEQ ID NO 46
<211> LENGTH: 4
<212> TYPE: PRT
<213> ORGANISM: Artificial Sequence
<220> FEATURE:
<223> OTHER INFORMATION: Generic Peptide

<400> SEQUENCE: 46

Thr Thr Met Pro
 1

<210> SEQ ID NO 47
<211> LENGTH: 5
<212> TYPE: PRT
<213> ORGANISM: Artificial Sequence
<220> FEATURE:
<223> OTHER INFORMATION: Generic Peptide

<400> SEQUENCE: 47

Phe Thr Thr Met Pro
 1               5

<210> SEQ ID NO 48
<211> LENGTH: 6
<212> TYPE: PRT
<213> ORGANISM: Artificial Sequence
<220> FEATURE:
<223> OTHER INFORMATION: Generic Peptide

<400> SEQUENCE: 48

Arg Phe Thr Thr Met Pro
 1               5

<210> SEQ ID NO 49
<211> LENGTH: 7
<212> TYPE: PRT
<213> ORGANISM: Artificial Sequence
<220> FEATURE:
<223> OTHER INFORMATION: Generic peptide

<400> SEQUENCE: 49

Gln Arg Phe Thr Thr Met Pro
 1               5

<210> SEQ ID NO 50
<211> LENGTH: 8
<212> TYPE: PRT
<213> ORGANISM: Artificial Sequence
<220> FEATURE:
<223> OTHER INFORMATION: Generic Peptide

<400> SEQUENCE: 50

Leu Gln Arg Phe Thr Thr Met Pro
 1               5
```

```
<210> SEQ ID NO 51
<211> LENGTH: 8
<212> TYPE: PRT
<213> ORGANISM: Artificial Sequence
<220> FEATURE:
<223> OTHER INFORMATION: Generic Peptide

<400> SEQUENCE: 51

Lys Gln Arg Phe Thr Thr Met Pro
1               5

<210> SEQ ID NO 52
<211> LENGTH: 4
<212> TYPE: PRT
<213> ORGANISM: Artificial Sequence
<220> FEATURE:
<223> OTHER INFORMATION: Generic Peptide

<400> SEQUENCE: 52

Ala Ser Arg Asn
1

<210> SEQ ID NO 53
<211> LENGTH: 5
<212> TYPE: PRT
<213> ORGANISM: Artificial Sequence
<220> FEATURE:
<223> OTHER INFORMATION: Generic Peptide

<400> SEQUENCE: 53

Ala Ser Arg Asn Asp
1               5

<210> SEQ ID NO 54
<211> LENGTH: 6
<212> TYPE: PRT
<213> ORGANISM: Artificial Sequence
<220> FEATURE:
<223> OTHER INFORMATION: Generic Peptide

<400> SEQUENCE: 54

Ala Ser Arg Asn Asp Tyr
1               5

<210> SEQ ID NO 55
<211> LENGTH: 7
<212> TYPE: PRT
<213> ORGANISM: Artificial Sequence
<220> FEATURE:
<223> OTHER INFORMATION: Generic Peptide

<400> SEQUENCE: 55

Ala Ser Arg Asn Asp Tyr Ser
1               5

<210> SEQ ID NO 56
<211> LENGTH: 8
<212> TYPE: PRT
<213> ORGANISM: Artificial Sequence
<220> FEATURE:
<223> OTHER INFORMATION: Generic Peptide

<400> SEQUENCE: 56

Ala Ser Arg Asn Asp Tyr Ser Tyr
1               5

<210> SEQ ID NO 57
```

```
<211> LENGTH: 9
<212> TYPE: PRT
<213> ORGANISM: Artificial Sequence
<220> FEATURE:
<223> OTHER INFORMATION: Generic Peptide

<400> SEQUENCE: 57

Ala Ser Arg Asn Asp Tyr Asp Tyr Trp
1               5

<210> SEQ ID NO 58
<211> LENGTH: 10
<212> TYPE: PRT
<213> ORGANISM: Artificial Sequence
<220> FEATURE:
<223> OTHER INFORMATION: Generic Peptide

<400> SEQUENCE: 58

Ala Ser Arg Asn Asp Tyr Ser Tyr Trp Leu
1               5                   10
```